US 9,029,405 B2

(12) United States Patent
Bombrun et al.

(10) Patent No.: US 9,029,405 B2
(45) Date of Patent: May 12, 2015

(54) 5-(BIPHENYL-4-YL)-3-PHENYL-1,2,4-OXADIAZOLYL DERIVATIVES AS LIGANDS ON THE SPHINGOSINE 1-PHOSPHATE(SIP)RECEPTORS

(75) Inventors: Agnes Bombrun, Chambesy (CH); Anna Quattropani, Geneva (CH); Jerome Gonzalez, Ville la Grand (FR); Jerome Dorbais, Annecy (FR); Chris Knight, Essex (GB); Charles Baker-Glenn, Essex (GB)

(73) Assignee: Merck Serono S.A., Coinsins (CH)

( * ) Notice: Subject to any disclaimer, the term of this patent is extended or adjusted under 35 U.S.C. 154(b) by 75 days.

(21) Appl. No.: 13/809,013

(22) PCT Filed: Jul. 6, 2011

(86) PCT No.: PCT/EP2011/061372
§ 371 (c)(1),
(2), (4) Date: Jan. 8, 2013

(87) PCT Pub. No.: WO2012/004287
PCT Pub. Date: Jan. 12, 2012

(65) Prior Publication Data
US 2013/0116289 A1 May 9, 2013

Related U.S. Application Data

(60) Provisional application No. 61/362,746, filed on Jul. 9, 2010.

(30) Foreign Application Priority Data

Jul. 8, 2010 (EP) .................................... 10168833

(51) Int. Cl.
*A61K 31/4245* (2006.01)
*C07D 271/06* (2006.01)

(52) U.S. Cl.
CPC .......... *C07D 271/06* (2013.01); *A61K 31/4245* (2013.01)

(58) Field of Classification Search
CPC ... A61K 31/4245; A61K 31/70; C07D 271/06
USPC .......................................... 514/364; 548/131
See application file for complete search history.

(56) References Cited

U.S. PATENT DOCUMENTS

| 8,202,865 B2* | 6/2012 | Quattropani et al. ...... 514/236.2 |
| 2008/0200535 A1* | 8/2008 | Ohmori et al. ................. 514/438 |
| 2008/0306124 A1 | 12/2008 | Albert et al. |
| 2010/0087491 A1 | 4/2010 | Albert et al. |
| 2010/0240658 A1 | 9/2010 | Quattropani et al. |
| 2012/0022109 A1 | 1/2012 | Quattropani et al. |
| 2012/0035226 A1 | 2/2012 | Quattropani et al. |

FOREIGN PATENT DOCUMENTS

| WO | 2006131336 A1 | 12/2006 |
| WO | 2008037476 A1 | 4/2008 |
| WO | 2009043889 A2 | 4/2009 |
| WO | WO 2009043889 A2 * | 4/2009 |
| WO | 2010112461 A1 | 10/2010 |

OTHER PUBLICATIONS

International Search Report from PCT/EP2011/061372 dated Jan. 8, 2011.

* cited by examiner

*Primary Examiner* — Yong Chu
(74) *Attorney, Agent, or Firm* — Millen, White, Zelano & Branigan, P.C.

(57) ABSTRACT

The present invention provides compounds of Formula (I), as selective S1P1 inhibitors, as well as their use for treating multiple sclerosis and other diseases.

14 Claims, No Drawings

5-(BIPHENYL-4-YL)-3-PHENYL-1,2,4-OXADIAZOLYL DERIVATIVES AS LIGANDS ON THE SPHINGOSINE 1-PHOSPHATE(S1P)RECEPTORS

The present invention relates to chiral oxadiazoles, their use as medicaments and their use for treating multiple sclerosis and other diseases.

In particular, the invention relates to compounds of formula (I):

[Chemical structure of Formula (I)]

Wherein
$R^1$ denotes H, Hal, $CF_3$, $OCF_3$, CN, or $NO_2$, OH, A, OA
$X^1, X^2, Z^1, Z^2$ independently from one another denote H or A, wherein at least one of $X^1, X^2, Z^1, Z^2$ is A,
$X^1, X^2$, may form together with the $C_1$ a 3-8-membered ring,
$Z^1, Z^2$ may form together with $C_2$ a 4-5-membered ring,
$Y^1, Y^2$ independently from one another denotes H, A, or glucuronide,
$W^1, W^2, W^3$, and $W^4$ independently from one another denote a —$CH_2$-group or a single bond.
$R^a$ denotes Hal or a linear or branched alkyl having 1 to 3 carbon atoms, wherein 1 to 3 H atoms may be replaced by Hal.
$R^b$ denotes Hal, a linear or branched alkyl having 1 to 3 carbon atoms, wherein 1 to 3 H atoms may be replaced by Hal, —$OCH_3$, —$OCH_2CH_3$,
$G^1, G^2$ independently from one another denote H, Hal, A,
A denotes a linear or branched alkyl having 1 to 6 carbon atoms, preferably 1 to 3 carbon atoms, wherein 1 to 3 H atoms may be replaced by Hal, $OCH_3$, OH,
$C_1, C_2$ are carbon atoms,
and the oxidized form wherein the group

[Chemical structure showing $Y^1$—N group]

is oxidized to

[Chemical structure showing $Y^1$—$N^+$—$O^-$ group]

pharmaceutically acceptable derivatives, solvates, tautomers, salts, enantiomers, diastereoisomers thereof, including mixtures thereof in all ratios.

In another embodiment, none of $C_1$ or $C_2$ is chiral. In other words, $X^1$ and $X^2$ are identical and $Z^1$ and $Z^2$ are identical.

In another embodiment, at least one of $C_1$ and $C_2$ is a chiral centre. $X^1$ and $X^2$ and/or $Z^1$ and $Z^2$ are not identical.

In a specific embodiment, the present invention provides compounds of Formula (I) as one diastereoisomer, wherein $C_1$ is (R) and $C_2$ is (R), or wherein $C_1$ is (S) and $C_2$ is (S), or a mixture thereof in all ratios.

In another specific embodiment, the present invention provides compounds of Formula (I) as one diastereoisomer, wherein $C_1$ is (S) and $C_2$ is (R), or wherein $C_1$ is (R) and $C_2$ is (S), or a mixture thereof in all ratios.

In another specific embodiment, the present invention provides compounds of Formula (I) as the enantiomer IA wherein $C_1$ is (S) and $C_2$ is (R).

In another specific embodiment, the present invention provides compounds of Formula (I) as the enantiomer IB wherein $C_1$ is (R) and $C_2$ is (S).

In another specific embodiment, the present invention provides compounds of Formula (I) as the enantiomer IC wherein $C_1$ is (S) and $C_2$ is (S).

In another specific embodiment, the present invention provides compounds of Formula (I) as the enantiomer ID wherein $C_1$ is (R) and $C_2$ is (R).

In case of only one of $C_1$ and $C_2$ is a chiral centre, the present invention may provide compounds of Formula (I) as one enantiomer wherein the chiral center at $C_1$ or $C_2$ is (S).

Alternatively, the present invention may provide compounds of Formula (I) as one enantiomer wherein the chiral center at $C_1$ or $C_2$ is (R). Compounds of Formula (I) wherein one of $C_1$ and $C_2$ is chiral may also be obtained as a mixture of enantiomers in all ratios, including the racemate mixture wherein the ratio is 50/50. When compound of Formula (I) is obtained as an optically active compound, the ratio between one enantiomer and the other is higher than about 60/40, preferably higher than about 80/20, more preferably higher than about 90/10, more preferably higher than about 95/5, even more preferably higher than 98/2.

In another embodiment, the enantiomer IA of compounds of Formula (I) wherein $C_1$ is (S) and $C_2$ is (R) may be mixed in any ratio with the enantiomer IB of compound of Formula (I) wherein $C_1$ is (R) and $C_2$ is (S). When compound of Formula (I) is obtained as a racemate, both enantiomers IA and IB are mixed in equal amount. When compound of Formula (I) is obtained as an optically active compound, the ratio between enantiomer IA and enantiomer IB is higher than about 60/40, preferably higher than about 80/20, more preferably higher than about 90/10, more preferably higher than about 95/5, even more preferably higher than 98/2.

In another embodiment, the enantiomer IC of compounds of Formula (I) wherein $C_1$ is (S) and $C_2$ is (S) may be mixed in any ratio with the enantiomer ID of compounds of Formula (I) wherein $C_1$ is (R) and $C_2$ is (R). When compounds of Formula (I) is obtained as an optically active compound, the ratio between enantiomer IC and enantiomer ID is higher than about 60/40, preferably higher than about 80/20, more preferably higher than about 90/10, more preferably higher than about 95/5, even more preferably higher than 98/2.

In a preferred embodiment the ratio between one enantiomer and the other is higher than 98/2.

In a specific embodiment, the compounds of Formula (I) is one enantiomer wherein:
a) $X^1$, $X^2$ and $Z^1$ are H and $Z^2$ is A,
b) $X^1$, $X^2$ and $Z^2$ are H and $Z^1$ is A,
c) $Z^1$, $Z^2$ and $X^2$ are H and $X^1$ is A, or
d) $Z^1$, $Z^2$ and $X^1$ are H and $X^2$ is A,
either alone or combined in all ratios with one or more of the others.

In another specific embodiment, the compound of Formula (I) is one diastereoisomer wherein:
a) $X^1$ and $Z^1$ are H, $X^2$ and $Z^2$ are A and/or $X^2$ and $Z^2$ are H, $X^1$ and $Z^1$ are A, or
b) $X^1$ and $Z^2$ are H, $X^2$ and $Z^1$ are A and/or $X^2$ and $Z^1$ are H, $X^1$ and $Z^2$ are A,
either alone or combined in all ratios.

An enantiomerically enriched mixture denotes a compound of Formula (I) or related formula having an enantiomeric excess, as measured by methods well known by one skilled in the art, of 10% or more, preferably 50% or more, and more preferably more than 95%. Most preferably an enantiomerically enriched mixture denotes a compound of Formula (I) or related Formulae having an enantiomeric excess of more than 98%.

In another embodiment, the present invention provides compounds of Formula (I) wherein at least 1 or 2 of $W^1$, $W^2$, $W^3$ and $W^4$ is a single bond.

In another embodiment, $W^1$, $W^2$, $W^3$ and $W^4$ all denote a single bond.

In another embodiment, the present invention provide compounds of Formula (I) wherein $Z^1$ and $Z^2$ may form together with $C_2$ a 3-8-membered ring.

In another embodiment, the present invention provides compounds of Formula (Ia)

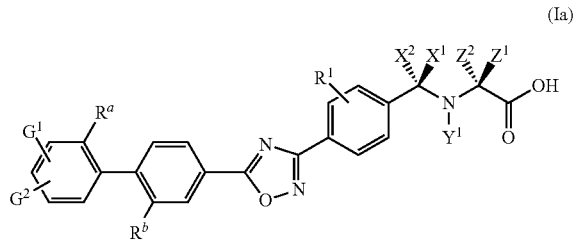

(Ia)

Wherein $G^1$, $G^2$, $R^a$, $R^b$, $R^1$, $X^1$, $X^2$, $Z^1$, $Z^2$ and $Y^1$ are as defined above.

In another embodiment, the present invention provides compounds of Formula (Ib)

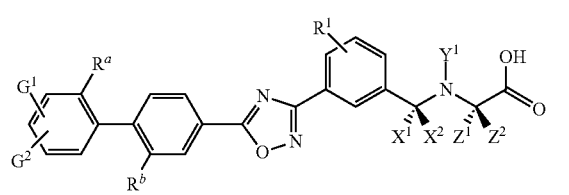

(Ib)

Wherein $G^1$, $R^a$, $R^b$, $R^1$, $X^1$, $X^2$, $Z^1$, $Z^2$ and $Y^1$ are as defined above.

In a specific embodiment, the present invention provides compounds of Formula (I), (Ia) or (Ib) wherein $R^b$ is $CF_3$ or $CH_2OCH_3$ and $R^a$ is $CF_3$ or $CH_3$, preferably, $R^b$ is $CF_3$ and $R^a$ is $CH_3$.

In another specific embodiment, the present invention provides compounds of Formula (I), (Ia) or (Ib) wherein $R^b$ is —$CF_3$ or —$CH_2OCH_3$ and $R^a$ is —$CF_3$ or —$CH_3$, preferably, $R^b$ is —$CF_3$ and $R^a$ is —$CH_3$.

In another specific embodiment, the present invention provides compounds of Formula (I), (Ia) or (Ib) wherein $R^b$ is —$CF_3$ or —$CH_2OCH_3$ and $R^a$ is —$CF_3$ or —$CH_3$, preferably, $R^b$ is —$CF_3$ and $R^a$ is —$CH_3$.

In another specific embodiment, the present invention provides compounds of Formula (I), or (Ia) wherein $R^b$ is —$CF_3$ or —$CH_2OCH_3$ and $R^a$ is —$CF_3$ or —$CH_3$, preferably, $R^b$ is —$CF_3$ and $R^a$ is —$CH_3$, and $Y^2$ is H.

In another specific embodiment, the present invention provides compounds of Formula (I), (Ia), or (Ib) wherein one of $R^a$ and $R^b$ is —$CF_3$.

In another embodiment, the present invention provides compounds of Formula (Ic)

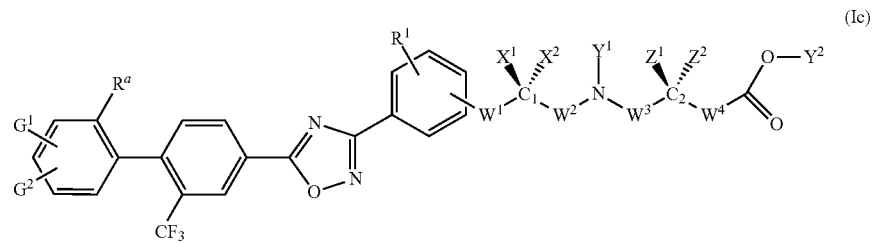

(Ic)

wherein $R^1$, $R^a$, $G^1$, $G^2$, $W^1$, $W^2$, $W^3$, $W^4$, $X^1$, $X^2$, $Z^1$, $Z^2$, $Y^1$ and $Y^2$ are as above defined and pharmaceutically acceptable derivatives, solvates, tautomers, salts and stereoisomers thereof, including mixtures thereof in all ratios.

In another preferred embodiment, the present invention provides compounds of Formula (Id)

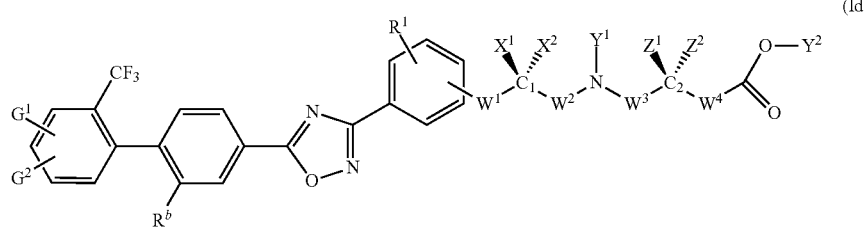

(Id)

Wherein $R^1$, $R^b$, $G^1$, $G^2$, $W^1$, $W^2$, $W^3$, $W^4$, $X^1$, $X^2$, $Z^1$, $Z^2$, $Y^1$ and $Y^2$ are as above defined.

In another specific embodiment, the present invention provides compounds of Formula (I), (Ia), (Ib), (Ic) or (Id) wherein $R^b$ is —$CH_3$, —$CH_2CH_3$, F, Br, Cl, or —$CF_3$, preferably F, —$CH_3$ or —$CF_3$, $G_1$, $G_2$ independently from one another denote H, Hal, or —$CH_3$, preferably H.

And wherein $R^b$, W, $R^1$, $W^1$, $W^2$, $W^3$, $W^4$, $X^1$, $X^2$, $Z^1$, $Z^2$, $Y^1$ and $Y^2$ are as above defined.

In a more preferred embodiment, the present invention provides compounds of Formula (Ie):

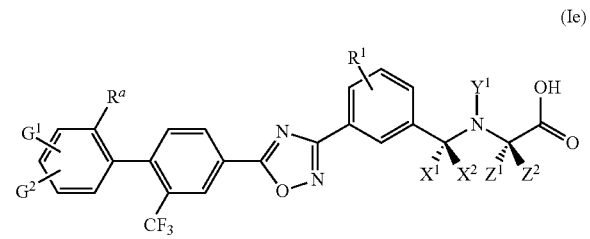

(Ie)

Wherein $R^a$, $G^1$, $G^2$, $X^1$, $X^2$, $Z^1$, $Z^2$, $Y^1$ are as above defined.

In a more preferred embodiment, the present invention provides compounds of Formula (If):

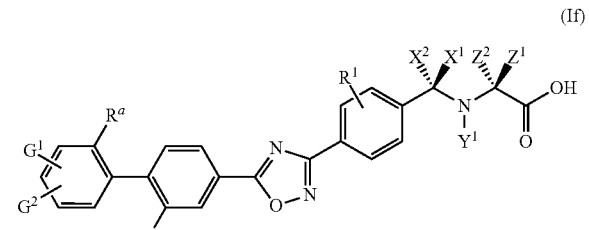

(If)

Wherein $R^a$, $G^1$, $G^2$, $X^1$, $X^2$, $Z^1$, $Z^2$, $Y^1$ are as above defined.

In another preferred embodiment, the present invention provides compounds of Formula (Ig):

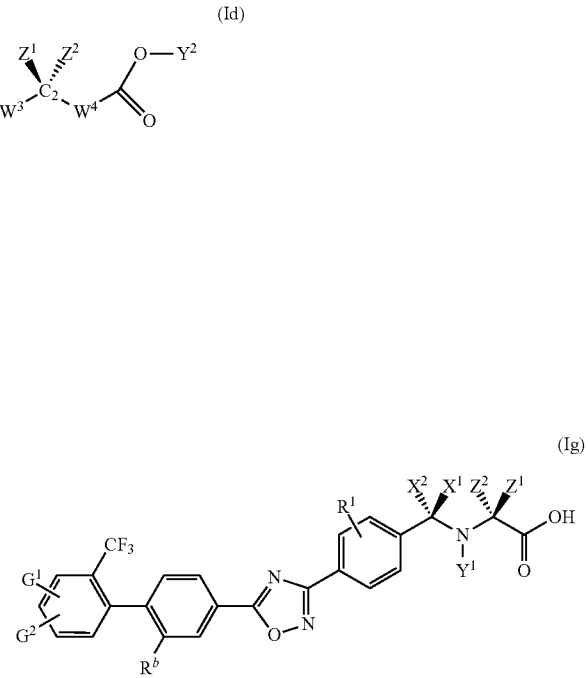

(Ig)

Wherein $R^1$, $R^b$, $G^1$, $G^2$, $X^1$, $X^2$, $Z^1$, $Z^2$, $Y^1$ are as above defined.

In another preferred embodiment, the present invention provides compounds of Formula (Ih):

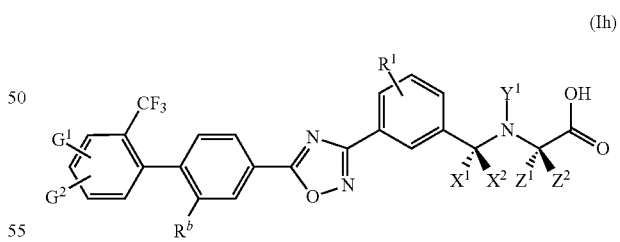

(Ih)

Wherein $R^1$, $R^b$, $G^1$, $G^2$, $X^1$, $X^2$, $Z^1$, $Z^2$, $Y^1$ are as above defined.

In another specific embodiment, the present invention provides compounds of Formula (I), (Ia), (Ib), (Id), (Ig) or (Ih), wherein $R^b$ is —$CH_2OCH_3$.

Compounds of Formula (I) wherein $Y^1$ and/or $Y^2$ is glucuronide may be for instance compounds of Formula (Ik):

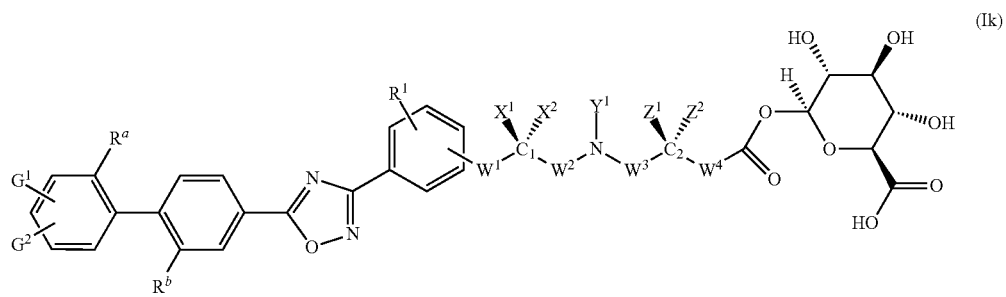

Wherein $G^1$, $G^2$, $R^a$, $R^b$, $R^1$, $W^1$, $W^2$, $W^3$, $W^4$, $X^1$, $X^2$, $Y^1$, $Z^1$, and $Z^2$ are as defined above.

Oxydised forms of the compounds of Formula (I) wherein may be for instance compounds of Formula (IO):

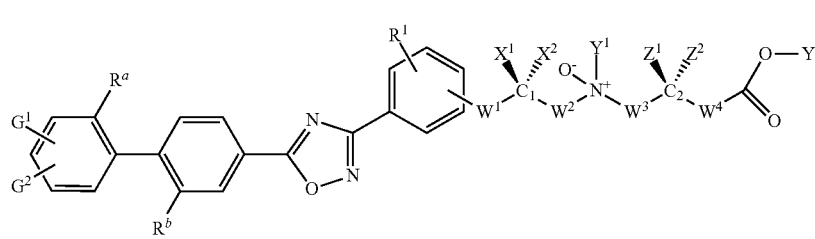

Wherein $G^1$, $G^2$, $R^a$, $R^b$, $R^1$, $W^1$, $W^2$, $W^3$, $W^4$, $X^1$, $X^2$, $Y^1$, $Y^2$, $Z^1$, and $Z^2$ are as defined above.

The compounds of formula (I) and related Formulae are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including multiple sclerosis, systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves' ophthalmopathy, atopic dermatitis and asthma. They are also useful as part of chemotherapeutic regimens for the treatment of cancers, lymphomas and leukemias.

Patent application WO2006/131336 describes oxadiazoles derivatives containing a biphenyl ring. Further oxadiazole derivatives containing a phenyl group substituted with a cycloalkyl group are known from Bioorg Med. Chem. Lett. 16 (2006) 3679-3683.

Other oxadiazole derivatives are described in the patent application EP07117921.2.

It has been found that the compounds of the present invention are selective $S1P_1$ agonists with improved drug-like properties and/or other properties.

The present invention uses compounds of Formula (I) and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

Thus, the present invention preferably comprises compounds which are agonists of the $S1P_1$/Edg1 receptor, especially having selectivity over the $S1P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The present invention further relates to a set or a kit consisting of separate packs of (a) an effective amount of a compound according to Formula (I) or related Formulae and/or pharmaceutically usable derivatives, tautomers, salts, solvates and stereoisomers thereof, including mixtures thereof in all ratios, and (b) an effective amount of a further medicament active ingredient.

The following abbreviations refer respectively to the definitions below:
aq (aqueous), h (hour), g (gram), L (liter), mg (milligram), MHz (Megahertz), µM (micromolar) min. (minute), mm (millimeter), mmol (millimole), mM (millimolar), m.p. (melting point), eq (equivalent), mL (milliliter), µL (microliter), ACN (acetonitrile), BINAP (2,2'-bis(disphenylphosphino)-1,1'-binaphthalene, BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethylamine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (Ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MD Autoprep (Mass directed Autoprep), MeOH (methanol), $MgSO_4$ (magnesium sulfate), MS (mass spectrometry), MTBE (Methyl tert-butyl ether), Mtr. (4-Methoxy-2,3,6-trimethylbenzensulfonyl), MW (microwave), NBS (N-bromo succinimide), $NaHCO_3$ (sodium bicarbonate), $NaBH_4$ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluronium tetrafluoro borate), TEA (triethylamine), TFA (trifluoroacetic acid), THF (tetrahydrofurane), TLC (Thin Layer Chromatography), UV (Ultraviolet).

In general, the chiral oxadiazole compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

Depending on the nature of $R^1$, $R^a$, $R^b$, $G^1$, $G^2$, $W^1$-$W^4$, $X^1$, $X^2$, $Y^1$, $Y^2$, $Z^1$ and $Z^2$, different synthetic strategies may be selected for the synthesis of compounds of Formula (I). In the process illustrated in the following schemes $R^1$, $R^a$, $R^b$, $G^1$, $G^2$, $W^1$-$W^4$, $X^1$, $X^2$, $Y^1$, $Y^2$, $Z^1$ and $Z^2$, are as above-defined in the description unless otherwise mentioned.

Generally, compounds of formula (I'), wherein $R^1$, $R^a$, $R^b$, $G^1$, $G^2$, $W^1$-$W^4$, $X^1$, $X^2$, $Y^1$, $Z^1$ and $Z^2$ are defined as above and $Y^2$ is H, can be prepared by hydrolysis of the ester derivatives of formula (I), wherein $Y^2$ is as above defined and more preferably $Y^2$ is a methyl or tert-butyl group, using conditions well known to those skilled in the art, such as a metal hydroxide, e.g. lithium hydroxide, sodium hydroxide or potassium hydroxide, in a suitable solvent such as THF, methanol, ethanol or water or mixtures thereof, or using an acid, e.g. HCl or TFA, in a suitable solvent such as dioxane, DCM, at a temperature between about 20° C. to about 50° C., preferably at RT, for a few hours, e.g. one hour to 24 h (Scheme 1).

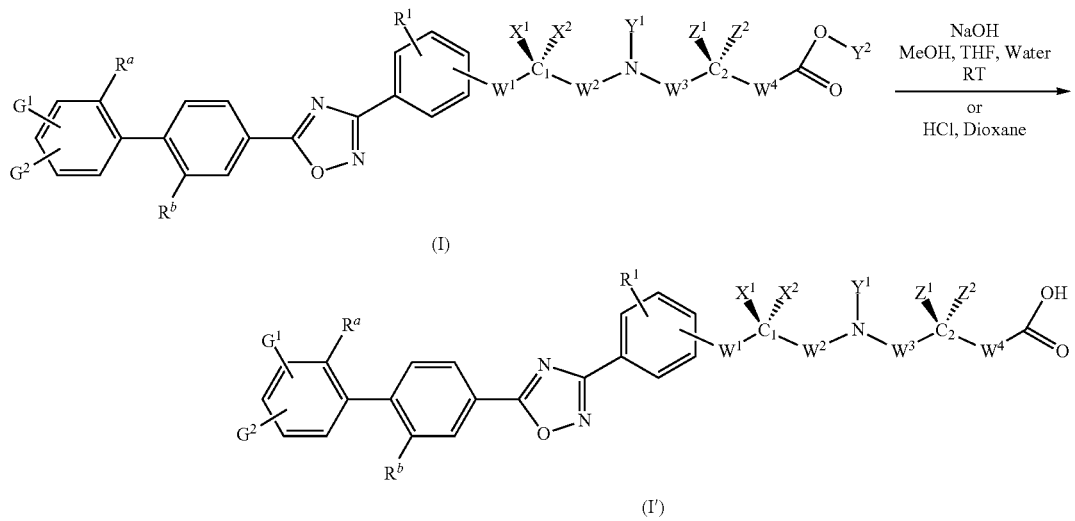

When ester derivatives of Formula (I) are obtained as mixture of enantiomers, they can be separated by chiral HPLC column, such as but not limited to the methods described below in the examples.

The method for preparing ester derivatives of Formula (I) selected below:

Tert-butyl 2-[(2-fluoro-4-{5-[2'-methyl-2-(trifluoromethyl)biphenyl-4-yl]-1,2,4-oxadiazol-3-yl}benzyl)(methyl)amino]butanoate, Methyl N-[(1R)-1-(4-{5-[2'-(difluoromethyl)-2-methylbiphenyl-4-yl]-1,2,4-oxadiazol-3-yl}phenyl)ethyl]-D-alaninate, Methyl N-[(1S)-1-(4-{5-[2-(methoxymethyl)-2'-methylbiphenyl-4-yl]-1,2,4-oxadiazol-3-yl}phenyl)ethyl]-D-alaninate, Methyl N-[(1R)-1-(4-{5-[2-(methoxymethyl)-2'-methylbiphenyl-4-yl]-1,2,4-oxadiazol-3-yl}phenyl)ethyl]-D-alaninate, Tert-butyl N-[(1S)-1-(4-{5-[2-(methoxymethyl)-2'-methylbiphenyl-4-yl]-1,2,4-oxadiazol-3-yl}phenyl)ethyl]glycinate, Methyl N-[(1R)-1-(4-{5-[2-methyl-2'-(trifluoromethyl)biphenyl-4-yl]-1,2,4-oxadiazol-3-yl}phenyl)ethyl]-D-alaninate, Tert-butyl N-[(1R)-1-(4-{5-[2'-(difluoromethyl)-2-methylbiphenyl-4-yl]-1,2,4-oxadiazol-3-yl}phenyl)ethyl]glycinate, Tert-butyl N-[(1R)-1-(4-{5-[2-methyl-2'-(trifluoromethyl)biphenyl-4-yl]-1,2,4-oxadiazol-3-yl}phenyl)ethyl]glycinate, Tert-butyl N-[(1R)-1-(4-{5-[2-(methoxymethyl)-2'-methylbiphenyl-4-yl]-1,2,4-oxadiazol-3-yl}phenyl)ethyl]glycinate, Ethyl (2S)-2-{[(1R)-1-(4-{5-[2'-methyl-2-(trifluoromethyl)biphenyl-4-yl]-1,2,4-oxadiazol-3-yl}phenyl)ethyl]amino}butanoate, Ethyl (2R)-2-{[(1R)-1-(4-{5-[2'-methyl-2-(trifluoromethyl)biphenyl-4-yl]-1,2,4-oxadiazol-3-yl}phenyl)ethyl]amino}butanoate, Tert-butyl N-(3-fluoro-5-{5-[2'-methyl-2-(trifluoromethyl)biphenyl-4-yl]-1,2,4-oxadiazol-3-yl}benzyl)leucinate, Tert-butyl N-(2-fluoro-4-{5-[2'-methyl-2-(trifluoromethyl)biphenyl-4-yl]-1,2,4-oxadiazol-3-yl}benzyl)-N-methylvalinate, Tert-butyl N-methyl-N-[1-(4-{5-[2-methyl-2'-(trifluoromethyl)biphenyl-4-yl]-1,2,4-oxadiazol-3-yl}phenyl)ethyl]glycinate, Tert-butyl N-[1-(4-{5-[2-(methoxymethyl)-2'-methylbiphenyl-4-yl]-1,2,4-oxadiazol-3-yl}phenyl)ethyl]-N-methylglycinate, Tert-butyl N-(2-fluoro-4-{5-[2-(methoxymethyl)-2'-methylbiphenyl-4-yl]-1,2,4-oxadiazol-3-yl}benzyl)-2-methylalaninate, Methyl N-[(1S)-1-(4-{5-[2'-methyl-2-(trifluoromethyl)biphenyl-4-yl]-1,2,4-oxadiazol-3-yl}phenyl)ethyl]-D-alaninate, Methyl N-[(1S)-1-(4-{5-[2'-methyl-2-(trifluoromethyl)biphenyl-4-yl]-1,2,4-oxadiazol-3-yl}phenyl)ethyl]-L-alaninate, Methyl N-[(1R)-1-(4-{5-[2'-methyl-2-(trifluoromethyl)biphenyl-4-yl]-1,2,4-oxadiazol-3-yl}phenyl)ethyl]-L-alaninate, Methyl N-[(1R)-1-(4-{5-[2'-methyl-2-(trifluoromethyl)biphenyl-4-yl]-1,2,4-oxadiazol-3-yl}phenyl)ethyl]-D-alaninate, Tert-butyl N-[(1S)-1-(4-{5-[2'-methyl-2-(trifluoromethyl)biphenyl-4-yl]-1,2,4-oxadiazol-3-yl}phenyl)ethyl]glycinate Tert-butyl N-[(1R)-1-(4-{5-[2'-methyl-2-(trifluoromethyl)biphenyl-4-yl]-1,2,4-oxadiazol-3-yl}phenyl)ethyl]glycinate, Tert-butyl N-[1-(4-{5-[2-methyl-2'-(trifluoromethyl)biphenyl-4-yl]-1,2,4-oxadiazol-3-yl}phenyl)ethyl]glycinate, Methyl N-[(1S)-1-(4-{5-[2-methyl-2'-(trifluoromethyl)biphenyl-4-yl]-1,2,4-oxadiazol-3-yl}phenyl)ethyl]-L-alaninate Methyl N-[(1S)-1-(4-{5-[2-methyl-2'-(trifluoromethyl)biphenyl-4-yl]-1,2,4-oxadiazol-3-yl}phenyl)ethyl]-D-alaninate, Methyl N-[(1R)-1-(4-{5-[2-methyl-2'-(trifluoromethyl)biphenyl-4-yl]-1,2,4-oxadiazol-3-yl}phenyl)ethyl]-L-alaninate, N-methyl-N-[1-(3-{5-[2-methyl-2'-(trifluoromethyl)biphenyl-4-yl]-1,2,4-oxadiazol-3-yl}phenyl)ethyl]alaninate, N-methyl-N-[1-(3-{5-[2'-methyl-2-(trifluoromethyl)biphenyl-4-yl]-1,2,4-oxadiazol-3-yl}phenyl)ethyl]alaninate, Tert-butyl N-methyl-N-[1-(3-{5-[2-methyl-2'-(trifluoromethyl)biphenyl-4-yl]-1,2,4-oxadiazol-3-yl}phenyl)ethyl]glycinate, Tert-butyl N-(2-fluoro-4-{5-[2'-methyl-2-(trifluoromethyl)biphenyl-4-yl]-1,2,4-oxadiazol-3-yl}benzyl)-N,2-dimethylalaninate, Tert-butyl N-[1-(4-{5-[2'-methyl-2-(trifluoromethyl)biphenyl-4-yl]-1,2,4-oxadiazol-3-yl}phenyl)ethyl]glycinate, Tert-butyl N-methyl-N-[(1S)-1-(4-{5-[2-methyl-2'-(trifluoromethyl)biphenyl-4-yl]-1,2,4-oxadiazol-3-yl}phenyl)ethyl]glycinate, Tert-butyl N-methyl-N-[(1S)-1-(4-{5-[2'-methyl-2-(trifluoromethyl)biphenyl-4-yl]-1,2,4-oxadiazol-3-yl}phenyl)ethyl]glycinate, Tert-butyl N-methyl-N-[(1R)-1-(4-{5-[2-methyl-2'-(trifluoromethyl)biphenyl-4-yl]-1,2,4-oxadiazol-3-yl}phenyl)ethyl]glycinate, Tert-butyl N-methyl-N-[(1R)-1-(4-{5-[2'-methyl-2-(trifluoromethyl)biphenyl-4-yl]-1,2,4-oxadiazol-3-yl}phenyl)ethyl]glycinate, Methyl N-[1-(4-{5-[2-(methoxymethyl)-2'-methylbiphenyl-4-yl]-1,2,4-oxadiazol-3-yl}phenyl)ethyl]-N-methylalaninate, Tert-butyl N-[1-(3-{5-[2-methyl-2'-(trifluoromethyl)biphenyl-4-yl]-1,2,4-oxadiazol-3-yl}phenyl)ethyl]glycinate, Methyl N-methyl-N-[1-(4-{5-[2'-methyl-2-(trifluoromethyl)biphenyl-4-yl]-1,2,4-oxadiazol-3-yl}phenyl)ethyl]alaninate, Tert-butyl N-methyl-N-[1-(4-{5-[2'-methyl-2-(trifluoromethyl)biphenyl-4-yl]-1,2,4-oxadiazol-3-yl}phenyl)ethyl]glycinate, Tert-butyl 2-[(2-fluoro-4-{5-[2'-methyl-2-(trifluoromethyl)biphenyl-4-yl]-1,2,4-oxadiazol-3-yl}benzyl)amino]butanoate, Tert-butyl N-[1-(3-{5-[2'-methyl-2-(trifluoromethyl)biphenyl-4-yl]-1,2,4-oxadiazol-3-yl}phenyl)ethyl]glycinate, Tert-butyl N-(2-fluoro-4-{5-[2-(methoxymethyl)-2'-methylbiphenyl-4-yl]-1,2,4-oxadiazol-3-yl}benzyl)-N,2-dimethylalaninate, Tert-butyl N-(2-fluoro-4-{5-[2-(methoxymethyl)-2'-methylbiphenyl-4-yl]-1,2,4-oxadiazol-3-yl}benzyl)-N-methylalaninate, Tert-butyl O-(tert-butyl)-N-(2-fluoro-4-{5-[2'-methyl-2-(trifluoromethyl)biphenyl-4-yl]-1,2,4-oxadiazol-3-yl}benzyl)-N-methylserinate, Tert-butyl N-(3-fluoro-5-{5-[2'-methyl-2-(trifluoromethyl) biphenyl-4-yl]-1,2,4-oxadiazol-3-yl}benzyl)-2-methylalaninate,
tert-butyl N-(2-fluoro-4-{5-[2'-methyl-2-(trifluoromethyl) biphenyl-4-yl]-1,2,4-oxadiazol-3-yl}benzyl)valinate,
Tert-butyl N-(2-fluoro-4-{5-[2-methyl-2'-(trifluoromethyl) biphenyl-4-yl]-1,2,4-oxadiazol-3-yl}benzyl)-2-methylalaninate,
Tert-butyl N-(2-fluoro-4-{5-[2'-methyl-2-(trifluoromethyl) biphenyl-4-yl]-1,2,4-oxadiazol-3-yl}benzyl)-2-methylalaninate,
Tert-butyl N-(2-fluoro-4-{5-[2'-methyl-2-(trifluoromethyl) biphenyl-4-yl]-1,2,4-oxadiazol-3-yl}benzyl)-N-methylalaninate,
Tert-butyl N-[2-methoxy-1-(4-{5-[2'-methyl-2-(trifluoromethyl)biphenyl-4-yl]-1,2,4-oxadiazol-3-yl}phenyl)ethyl]-N-methylglycinate,
Tert-butyl N-[2-hydroxy-1-(4-{5-[2'-methyl-2-(trifluoromethyl)biphenyl-4-yl]-1,2,4-oxadiazol-3-yl}phenyl)ethyl] glycinate,
(2S)-tert-butyl 3-methyl-2-(4-(5-(2'-methyl-2-(trifluoromethyl)biphenyl-4-yl)-1,2,4-oxadiazol-3-yl)phenethylamino)butanoate,
tert-butyl N-[(1R)-1-(4-{5-[2-(methoxymethyl)-2'-methylbiphenyl-4-yl]-1,2,4-oxadiazol-3-yl}phenyl)ethyl]-N-methylglycinate
tert-butyl N-[(1S)-1-(4-{5-[2-(methoxymethyl)-2'-methylbiphenyl-4-yl]-1,2,4-oxadiazol-3-yl}phenyl)ethyl]-N-methylglycinate
tert-butyl N-[2-hydroxy-1-(4-{5-[2'-methyl-2-(trifluoromethyl)biphenyl-4-yl]-1,2,4-oxadiazol-3-yl}phenyl)ethyl]-D-alaninate
tert-butyl N-[2-{[tert-butyl(dimethyl)silyl]oxy}-1-(4-{5-[2'-methyl-2-(trifluoromethyl)biphenyl-4-yl]-1,2,4-oxadiazol-3-yl}phenyl)ethyl]-D-alaninate
is more particularly described in the examples.

According to a preferred synthetic pathway, the compounds of Formula (I), wherein $R^1$, $R^a$, $R^b$, $G^1$, $G^2$, $W^1$-$W^4$, $X^1, X^2, Y^1, Y^2, Z^1$ and $Z^2$ are defined as above, can be obtained in a 2-steps protocol as outlined in Scheme 2. The first step consists in the coupling of a carboxylic acid of Formula (II) wherein $R^a$, $R^b$, $G^1$, and $G^2$ are as above defined, with an amidoxime of Formula (III), wherein $R^1$, $W^1$-$W^4$, $X^1, X^2, Y^1$, $Y^2, Z^1$ and $Z^2$ are defined as above. General protocols for such coupling are given below in the examples, using conditions and methods well known to those skilled in the art. Standard coupling agent, such as HATU, EDC or isobutyl chloroformate can be used in the presence or not of a base such as DIEA, TEA or NMM in a suitable solvent such as DMF, ACN, THF or iPrOAc at a temperature rising from about 0° C. to RT, preferably at 0° C. for a time of 30 minutes to a few hours. Alternatively, a carboxylic acid derivative (e.g. acyl chloride) may be coupled with the amidoxime (III), using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours. The second step consists of the cyclization and dehydration of the O-substituted amidoximes (IV) to form oxadiazole (I). Conditions are given below in the examples, using methods well known to those skilled in the art to prepare oxadiazole, such as thermolysis at temperature rising from 80° C. to about 120° C., typically 90° C., for a time comprised between 12 and 72 hours, preferably for 15 hours, in a suitable solvent or mixture of solvents, such as toluene, pyridine, ACN, THF, DMF or iPrOAc in the presence or not of a base such as DIEA, TEA or NMM.

Scheme 2

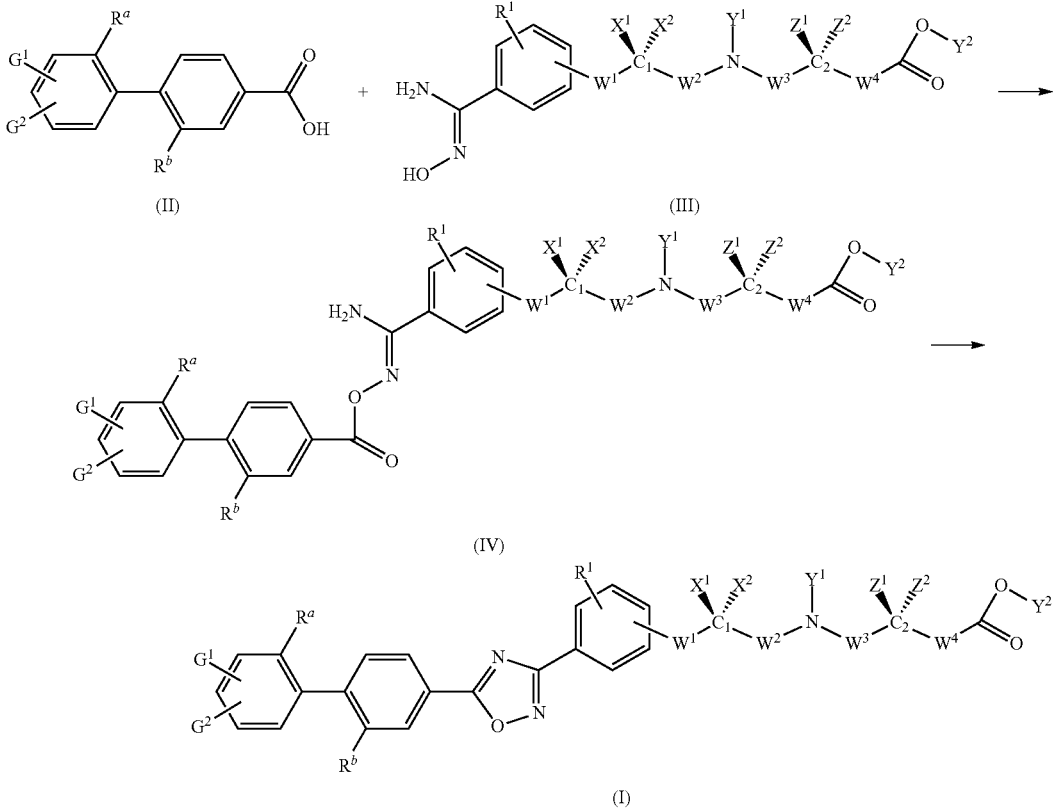

Alternatively, alcohol derivatives of Formula (V) may be converted into the corresponding amine derivatives of Formula (I), as outlined in Scheme 3. Alcohol functionality of compound of Formula (V) may be transformed first into a leaving group, such as a chloride or a sulfonate, using conditions well known to those skilled in the art. As an illustration, alcohol derivatives of Formula (V) may react with methanesulfonyl chloride, in the presence of a base, such as but not limited to a tertiary amine (e.g. TEA or DIEA), in a suitable solvent such as DCM, at a temperature between about 2° C. to about 5° C., preferably at RT, for a few hours. The resulting compound may be then reacted with a suitable amine of Formula $HN(Y^1)W^3C^2(Z^1)(Z^2)W^4COOY^2$, affording compound of Formula (I). Alternatively, alcohol derivatives of Formula (V) may be oxidized into the corresponding aldehyde, using conditions well known to those skilled in the art, such as but not limited to Swern oxidation conditions, or the use of $MnO_2$ as oxidative agent for benzylic alcohols. Reductive amination of the resulting aldehyde with a suitable amine of Formula $HN(Y^1)W^3C^2(Z^1)(Z^2)W^4COOY^2$, in the presence of a reducing agent, such as but not limited to sodium cyanoborohydride, affords compounds of Formula (I).

Alcohol derivatives of Formula (V) may be prepared starting from a carboxylic acid of Formula (II) wherein $R^a$, $R^b$, $G^1$, and $G^2$ are as above defined, with a suitable amidoxime of Formula (III'), wherein $R^1$, $W^1$, $W^2$, $X^1$ and $X^2$ are defined as above.

When alcohol derivatives of Formula (V) are obtained as mixture of enantiomers, they can be separated by chiral HPLC column, such as but not limited to the methods described below in the examples.

The method for preparing alcohol derivatives of Formula (V) selected below:
1-(4-{5-[2'-methyl-2-(trifluoromethyl)biphenyl-4-yl]-1,2,4-oxadiazol-3-yl}phenyl)ethanol,
(4-(5-(2-(methoxymethyl)-2'-methylbiphenyl-4-yl)-1,2,4-oxadiazol-3-yl)phenyl)methanol,
(4-(5-(2'-methyl-2-(trifluoromethyl)biphenyl-4-yl)-1,2,4-oxadiazol-3-yl)phenyl)methanol,
(3-(5-(2'-methyl-2-(trifluoromethyl)biphenyl-4-yl)-1,2,4-oxadiazol-3-yl)phenyl)methanol,
(4-(5-(2'-methyl-2-(trifluoromethyl)biphenyl-4-yl)-1,2,4-oxadiazol-3-yl)phenyl)ethanol,
(3-(5-(2'-methyl-2-(trifluoromethyl)biphenyl-4-yl)-1,2,4-oxadiazol-3-yl)phenyl)ethanol,
is more particularly described in the examples.

Scheme 3

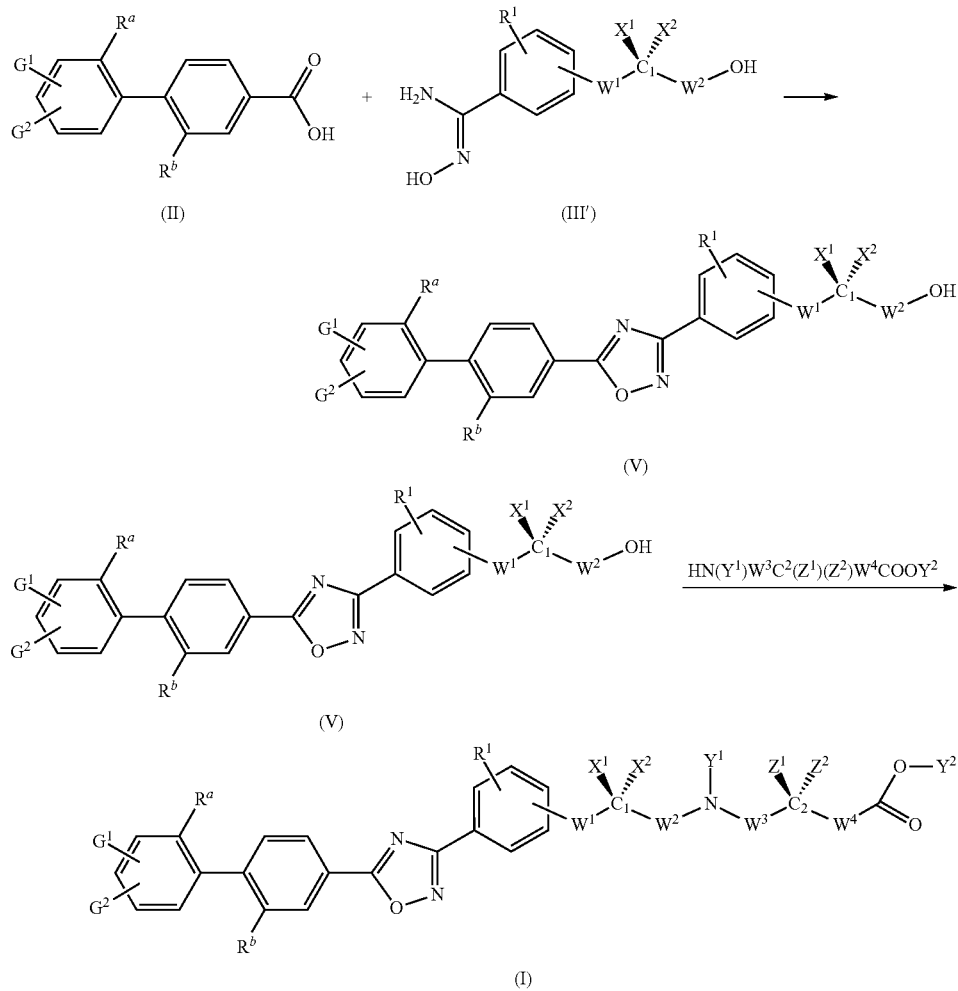

Alternatively, amine derivatives of Formula (V') may be converted into the corresponding amine derivatives of Formula (I), as outlined in Scheme 3a. Amine of Formula (V') may react with a suitable electrophile of Formula LG-(Y$^1$)W$^3$C$^2$(Z$^1$)(Z$^2$)W$^4$COOY$^2$, where LG is a leaving group. Preferred leaving groups are halogens such as but not limited to Br. Such a reaction affords compound of Formula (I).

The method for preparing amine derivatives of Formula (V') selected below:
(1R)-1-(4-{5-[2'-methyl-2-(trifluoromethyl)biphenyl-4-yl]-1,2,4-oxadiazol-3-yl}phenyl)ethanamine
N-methyl-1-(3-{5-[2'-methyl-2-(trifluoromethyl)biphenyl-4-yl]-1,2,4-oxadiazol-3-yl}phenyl)methanamine
is more particularly described in the examples.

Scheme 3a

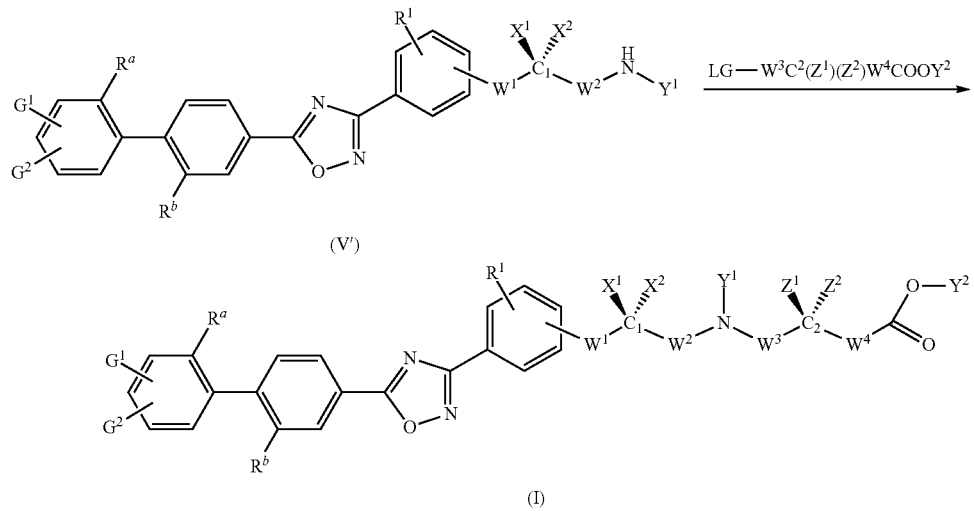

Amine derivatives of Formula (V') may be prepared starting from a carboxylic acid of Formula (II) wherein R$^a$, R$^b$, G$^1$, and G$^2$ are as above defined, with a suitable amidoxime of Formula (III''), wherein R$^1$, W$^1$, W$^2$, X$^1$ and X$^2$ are defined as above, and PG is a protecting group, such as but not limited to boc, as depicted in scheme 3b. The resulting amine derivative of Formula (V'') can be transformed into amine derivative of Formula (V') with one deprotecting step.

The method for preparing derivatives of Formula (V'') selected below:
tert-butyl [(1R)-1-(4-{5-[2'-methyl-2-(trifluoromethyl)biphenyl-4-yl]-1,2,4-oxadiazol-3-yl}phenyl)ethyl]carbamate
tert-butyl methyl(3-{5-[2'-methyl-2-(trifluoromethyl)biphenyl-4-yl]-1,2,4-oxadiazol-3-yl}benzyl)carbamate
is more particularly described in the examples.

Scheme 3b

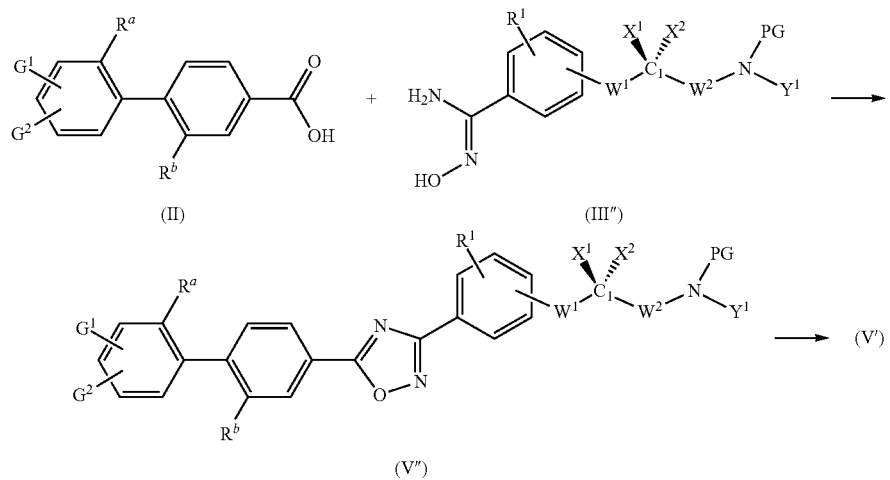

When derivatives of Formula (V') or (V'') are obtained as mixture of enantiomers, they can be separated by chiral HPLC column, such as but not limited to the methods described below in the examples.

The method for preparing amidoxime of Formula (III''), selected below:
tert-butyl ((1R)-1-{4-[amino(hydroxyimino)methyl]phenyl}ethyl)carbamate tert-butyl {3-[amino(hydroxyimino)methyl]benzyl}methylcarbamate
is more particularly described in the examples.

Compounds of Formula (II), wherein $R^a$, $R^b$, $G^1$, and $G^2$ are defined as above, may be prepared by standard synthetic techniques, as hereinafter described in the examples, using conditions and methods well known to those skilled in the art (Scheme 4). In a first synthetic pathway, compounds of Formula (II), wherein $R^a$, $R^b$, $G^1$, and $G^2$ are defined as above, may be obtained by metal catalyzed cross-coupling reaction, followed by hydrolysis of the resulting ester (VI). More particularly, they may be obtained by Suzuki-Miyura coupling reaction between an alkyl benzoate (VII), where $LG_1$ may preferably be Br, I or a sulfonate ester such as triflate, and a boronic acid or ester of Formula (VIII) (Miyaura, N.; Suzuki, A. Chem. Rev. 1995, 95, 2457; Takahiro I. and Toshiaki M., Tetrahedron Lett. 2005, 46, 3573-3577). In a typical procedure, alkyl benzoate (VII) and boronic acid (VIII) are heated in a suitable solvent, such as a mixture of toluene and water, in the presence of a base, such as $K_2CO_3$, and a catalytic amount of a palladium catalyst, such as $Pd(PPh_3)_4$, with the possible addition of a phosphine ligand, such as $PPh_3$. The resulting ester (VI) may be hydrolyzed using a metal hydroxide, such as NaOH, in a suitable solvent, such as MeOH, EtOH, water or mixtures thereof, at a temperature rising from about 20° C. to 60° C., preferably at RT, for a few hours.

Scheme 4

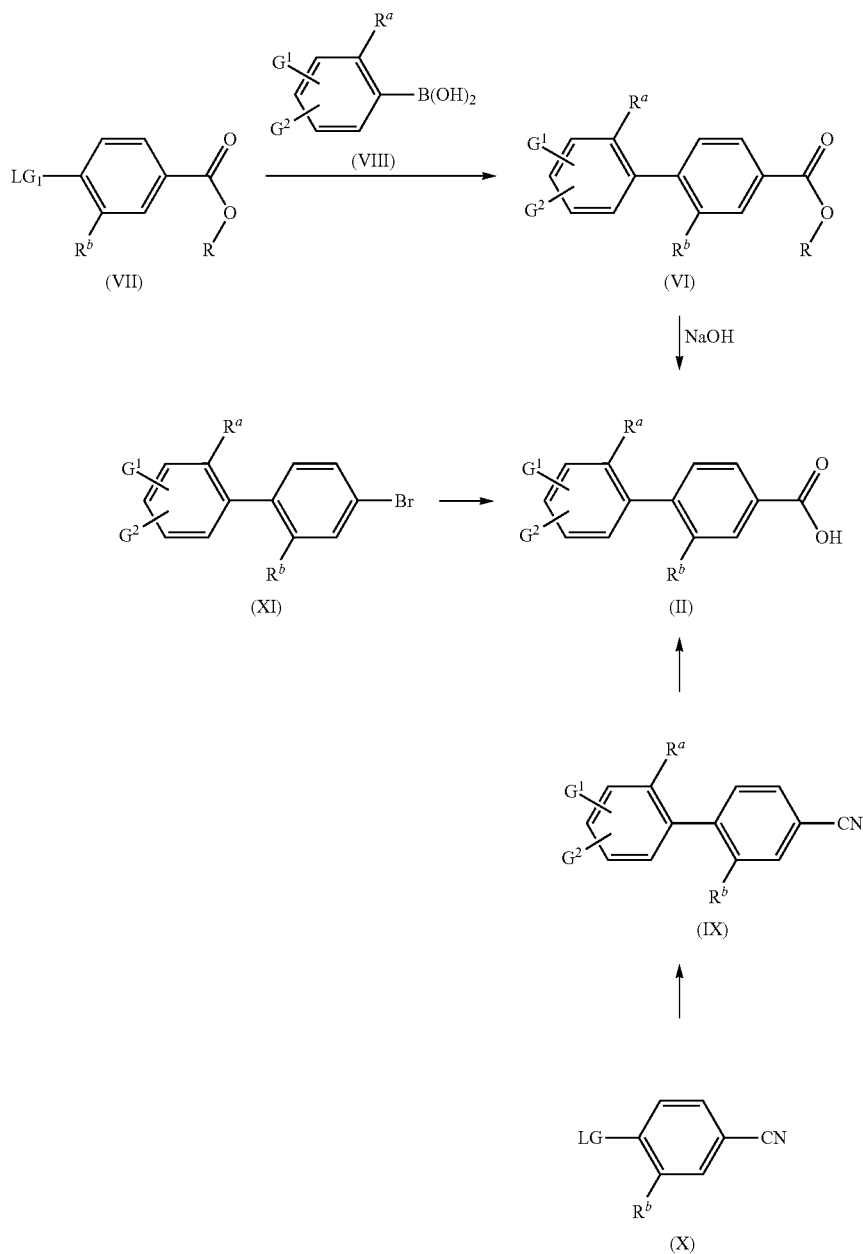

In a second synthetic pathway, compounds of Formula (II), wherein $R^a$, $R^b$, $G^1$, and $G^2$ are defined as above, may be obtained by a coupling reaction, followed by hydrolysis of the resulting nitrile (IX). The resulting benzonitrile of Formula (IX) may be hydrolyzed into the corresponding carboxylic acid (II) by treatment with an aqueous solution of metal hydroxide, such as NaOH, in a suitable solvent, such as MeOH or EtOH, at a temperature rising from RT to reflux, preferably at reflux, for a few hours e.g. from 1 to 24 hours.

In a third synthetic pathway, according to Scheme 4, compounds of Formula (II), wherein $R^a$, $R^b$, $G^1$, and $G^2$ are defined as above, may be prepared from arylbromide of Formula (XI) in a two steps process. The first step is an halogen-metal exchange with a lithiated alkyl, such as nBuLi or tBuLi, in a suitable solvent, such as $Et_2O$, at low temperature, preferably at −78° C. The second step is the quench of the organolithiated derivative by addition of $CO_2$, as gas or in solid state, as electrophile.

When compounds of Formula (II) are obtained as mixture of enantiomers, they can be separated by chiral HPLC column, such as but not limited to the methods described below in the examples.

The method for preparing compounds of formula (II) selected below:
2'-methyl-2-(trifluoromethyl)biphenyl-4-carboxylic acid,
2'-(difluoromethyl)-2-methylbiphenyl-4-carboxylic acid,
2-(methoxymethyl)-2'-methyl biphenyl-4-carboxylic acid,
2-methyl-2'-(trifluoromethyl)biphenyl-4-carboxylic acid,
is more particularly described in the examples.

Compounds of Formula (III) wherein $R^1$, $W^1$-$W^4$, $X^1$, $X^2$, $Y^1$, $Y^2$, $Z^1$ and $Z^2$ are as above defined are either commercially available or may be prepared according to Scheme 5 by addition of aqueous hydroxylamine or hydroxylamine hydrochloride to the corresponding substituted benzonitrile of Formula (XII) in a suitable solvent, such as EtOH, in presence or not of a base, such as TEA, at a temperature ranging from RT to about 80° C., preferably at RT, for a few hours.

Scheme 5

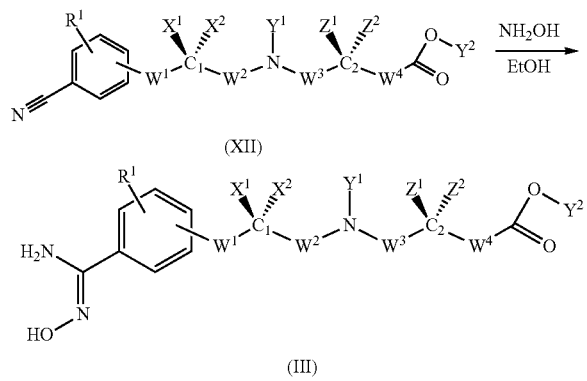

When compounds of Formula (III) are obtained as mixture of enantiomers, they can be separated by chiral HPLC column, such as but not limited to the methods described below in the examples.

The method for preparing compounds of formula (III) selected below:
tert-butyl 2-[{4-[amino(hydroxyimino)methyl]-2-fluorobenzyl}(methyl)amino]butanoate,
methyl N-((1R)-1-{4-[amino(hydroxyimino)methyl]phenyl}ethyl)-D-alaninate,
methyl N-[(1R)-1-(4-cyanophenyl)ethyl]-L-alaninate,
tert-butyl N-((1S)-1-{4-[(hydroxyamino)(imino)methyl]phenyl}ethyl)glycinate,
tert-butyl N-((1R)-1-{4-[(hydroxyamino)(imino)methyl]phenyl}ethyl)glycinate,
methyl N-((1S)-1-{4-[(hydroxyamino)(imino)methyl]phenyl}ethyl)-D-alaninate,
methyl N-((1S)-1-{4-[(hydroxyamino)(imino)methyl]phenyl}ethyl)-L-alaninate,
ethyl (2S)-2-[((1R)-1-{4-[amino(hydroxyimino)methyl]phenyl}ethyl)amino]butanoate,
ethyl (2R)-2-[((1R)-1-{4-[amino(hydroxyimino)methyl]phenyl}ethyl)amino]butanoate,
Ethyl 2-({3-[amino(hydroxyimino)methyl]-5-fluorobenzyl}amino)-4-methylpentanoate,
tert-butyl N-{4-[amino(hydroxyimino)methyl]-2-fluorobenzyl}-N-methylvalinate,
tert-butyl N-(1-{4-[amino(hydroxyimino)methyl]phenyl}ethyl)-N-methylglycinate,
tert-butyl 2-({4-[amino(hydroxyimino)methyl]-2-fluorobenzyl}amino)-2-methylpropanoate,
tert-butyl (1-{4-[amino(hydroxyimino)methyl]phenyl}ethyl)carbamate,
methyl N-(1-{3-[(hydroxyamino)(imino)methyl]phenyl}ethyl)-N-methylalaninate,
methyl tert-butyl N-(1-{3-[amino(hydroxyimino)methyl]phenyl}ethyl)-N-methylglycinate,
tert-butyl 2-[{4-[amino(hydroxyimino)methyl]-2-fluorobenzyl}(methyl)amino]-2-methylpropanoate,
tert-butyl N-(1-{4-[amino(hydroxyimino)methyl]phenyl}ethyl)glycinate,
tert-butyl N-((1S)-1-{4-[amino(hydroxyimino)methyl]phenyl}ethyl)-N-methylglycinate,
tert-butyl N-((1R)-1-{4-[amino(hydroxyimino)methyl]phenyl}ethyl)-N-methylglycinate,
methyl N-(1-{4-[amino(hydroxyimino)methyl]phenyl}ethyl)-N-methylalaninate,
tert-butyl N-(1-{3-[amino(hydroxyimino)methyl]phenyl}ethyl)glycinate,
tert-Butyl 2-({4-[amino(hydroxyimino)methyl]-2-fluorobenzyl}amino)butanoate,
tert-butyl 2-[{4-[amino(hydroxyimino)methyl]-2-fluorobenzyl}(methyl)amino]-2-methylpropanoate,
tert-butyl 2-[{4-[amino(hydroxyimino)methyl]-2-fluorobenzyl}(methyl)amino]propanoate,
tert-butyl N-{4-[(amino(hydroxyimino)methyl]-2-fluorobenzyl}-O-(tert-butyl)-N-methylserinate,
tert-butyl 2-({3-[amino(hydroxyimino)methyl]-5-fluorobenzyl}amino)-2-methylpropanoate,
tert-butyl 2-({4-[amino(hydroxyimino)methyl]-2-fluorobenzyl}amino)-3-methylbutanoate,
tert-butyl 2-({4-[amino(hydroxyimino)methyl]-2-fluorobenzyl}amino)-2-methylpropanoate,
tert-butyl 2-((1-(4-(N'-hydroxycarbamimidoyl)phenyl)-2-methoxyethyl)(methyl)amino)acetate,
tert-butyl 2-(2-(tert-butyldimethylsilyloxy)-1-(4-(N'-hydroxycarbamimidoyl)phenyl)ethylamino)acetate,
N'-hydroxy-4-(hydroxymethyl)benzenecarboximidamide,
N'-hydroxy-3-(hydroxymethyl)benzimidamide,
N'-hydroxy-4-(hydroxyethyl)benzenecarboximidamide,
N'-hydroxy-3-(hydroxyethyl)benzimidamide,
tert-butyl N-(1-{4-[(Z)-amino(hydroxyimino)methyl]phenyl}-2-{[tert-butyl(dimethyl)silyl]oxy}ethyl)-D-alaninate
is more particularly described in the examples.

Compounds of Formula (XII), wherein $R^1$, $W^1$-$W^4$, $X^1$, $X^2$, $Y^1$, $Y^2$, $Z^1$ and $Z^2$ are as above defined, are either commercially available or may be prepared from alternative compounds of Formula (XII), using suitable interconversion procedures such as those described hereinafter in the examples, or conventional interconversion procedures well known by one skilled in the art. Alternatively, but not limited to, compounds of Formula (XII) may be prepared from aldehyde or ketone of formula (XIIa) by reductive amination with a suitable amine of Formula $HN(Y^1)W^3C^2(Z^1)(Z^2)W^4COOY^2$, in the presence of a reducing agent, such as but not limited to sodium cyanoborohydride. Alternatively, aldehyde or ketone of formula (XIIb) can be transformed into chiral imine (XIIc), reacting with a chiral auxiliary, such as but not limited to tert-butanesulfinamide group in the presence of titanium ethoxide (Ellman J. A. et al. *Acc. Chem. Res.* 2002, 35, 984-995). It can be further transformed into sulfinamide (XIId), via reduction or nucleophilic addition, using conditions known by a person skilled in the art. The sulfinyl group is then removed by acidic treatment, such as HCl in a protic solvent, affording the desired chiral amine (XIIe) as hydrochloride salt. The absolute configuration of amine (XIIe) depends on the configuration of the chiral auxiliary and the conditions used for the reduction or nucleophilic addition. As illustration, imine (XIIc) can be reduced diastereoselectively with a reductive agent, such as but not limited to sodium borohydride or L-selectride, yielding chiral amine (XIIe) after removal of the chiral auxiliary (Ellman J. A. et al. *J. Org. Chem.* 2007, 72, 626-629). Chiral amine (XIIe) can be further transformed into compound of formula (XII), either via reductive alkylation with a suitable aldehyde or ketone, or via direct alkylation with a suitable electrophile, such as alkylbromide or alkylsulfonate derivatives.

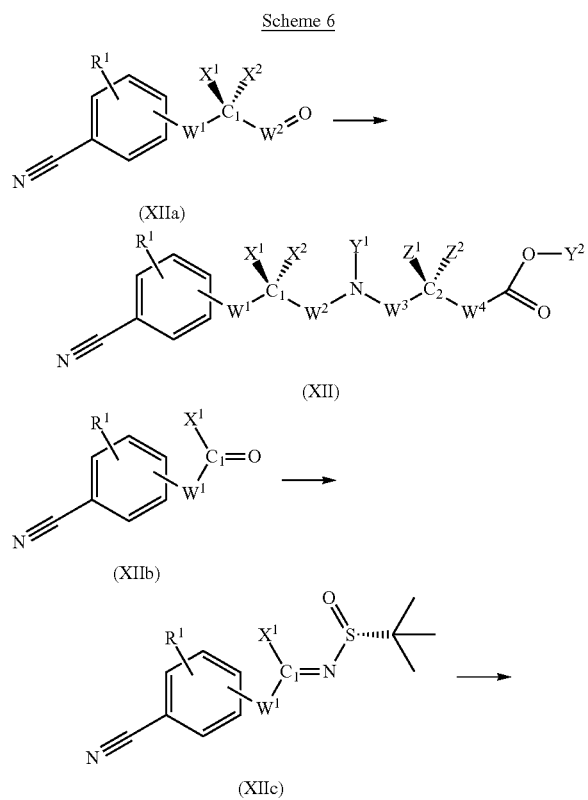

Scheme 6

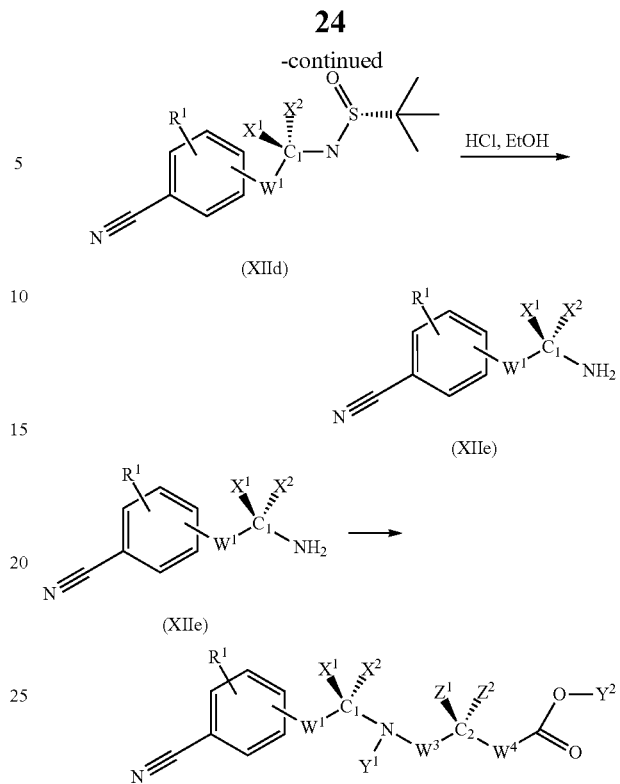

When compounds of Formula (XII) are obtained as mixture of enantiomers, they can be separated by chiral HPLC column, such as but not limited to the methods described below in the examples.

The method for preparing compounds of formula (XII) selected below:

Tert-butyl 2-[(2-fluoro-4-isocyanobenzyl)(methyl)amino]butanoate,
Methyl N-[(1R)-1-(4-cyanophenyl)ethyl]-D-alaninate and methyl N-[(1R)-1-(4-cyanophenyl)ethyl]-L-alaninate,
Tert-butyl N-[(1S)-1-(4-cyanophenyl)ethyl]glycinate,
Tert-butyl N-[(1R)-1-(4-cyanophenyl)ethyl]glycinate,
Methyl N-[(1S)-1-(4-cyanophenyl)ethyl]-D-alaninate and methyl N-[(1S)-1-(4-cyanophenyl)ethyl]-L-alaninate,
Ethyl (2S)-2-{[(1R)-1-(4-cyanophenyl)ethyl]amino}butanoate and ethyl (2R)-2-{[(1R)-1-(4-cyanophenyl)ethyl]amino}butanoate,
Tert-butyl 2-[(3-cyano-5-fluorobenzyl)amino]-4-methylpentanoate,
Tert-butyl 2-[(4-cyano-2-fluorobenzyl)(methyl)amino]-3-methylbutanoate,
Tert-butyl N-[1-(4-cyanophenyl)ethyl]-N-methylglycinate,
Tert-butyl 2-[(4-cyano-2-fluorobenzyl)amino]-2-methylpropanoate,
Tert-butyl [1-(4-cyanophenyl)ethyl]carbamate,
Methyl N-[1-(3-cyanophenyl)ethyl]-N-methylalaninate,
Methyl N-[1-(3-cyanophenyl)ethyl]-N-methylalaninate,
Tert-butyl 2-[(2-fluoro-4-isocyanobenzyl)(methyl)amino]-2-methylpropanoate,
Tert-butyl N-[1-(4-cyanophenyl)ethyl]glycinate,
Tert-butyl N-[1-(4-cyanophenyl)ethyl]-N-methylglycinate,
Methyl N-[1-(4-cyanophenyl)ethyl]-N-methylalaninate,
Tert-butyl N-[1-(3-cyanophenyl)ethyl]glycinate,
Tert-Butyl 2-[(4-cyano-2-fluorobenzyl)amino]butanoate,
Tert-butyl 2-[(2-fluoro-4-isocyanobenzyl)(methyl)amino]-2-methylpropanoate,
Tert-butyl 2-[(4-cyano-2-fluorobenzyl)(methyl)amino]propanoate,
Tert-Butyl 3-tert-butoxy-2-[(4-cyano-2-fluorobenzyl)(methyl)amino]propanoate, Tert-butyl 2-[(3-cyano-5-fluorobenzyl)amino]-2-methylpropanoate,
1-Tert-butyl 2-[(4-cyano-2-fluorobenzyl)amino]-3-methylbutanoate,
Tert-butyl 2-[(4-cyano-2-fluorobenzyl)amino]-2-methylpropanoate,
Tert-butyl 2-((1-(4-cyanophenyl)-2-methoxyethyl)(methyl)amino)acetate,
Tert-butyl 2-(2-(tert-butyldimethylsilyloxy)-1-(4-cyanophenyl)ethylamino)acetate,
is more particularly described in the examples.

Compounds of Formula (I) can be converted to their oxydised form of Formula (IO) using an oxydising agent such as 3-chloroperoxybenzoic acid, as depicted in scheme 7.

a compound of formula B

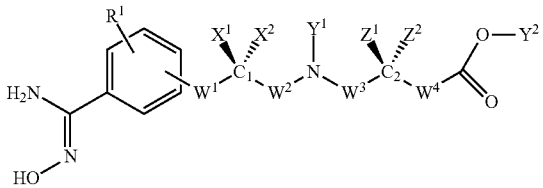

wherein $R^1$, $W_1$-$W_4$, $C_1$, $C_2$, $X_1$, $X_2$, $Y_1$, $Y_2$, $Z_1$ and $Z_2$ have the meanings given above, in the presence of a suitable base, such as an amine like TEA, DIEA or NMM, or in case T is Scheme 7

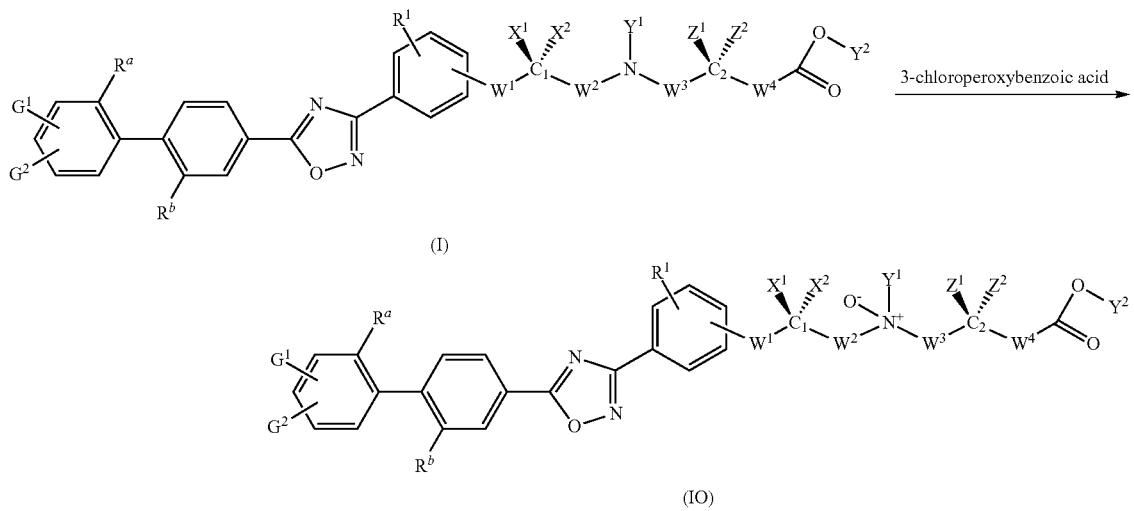

The method for preparing compounds of formula (IO) selected below:
1-[methyl(4-{5-[2'-methyl-2-(trifluoromethyl)biphenyl-4-yl]-1,2,4-oxadiazol-3-yl}benzyl)nitroryl]cyclopentanecarboxylic acid
2-[(2-fluoro-4-{5-[2'-methyl-2-(trifluoromethyl)biphenyl-4-yl]-1,2,4-oxadiazol-3-yl}benzyl)(methyl)nitroryl]propanoic acid
{methyl[1-(4-{5-[2'-methyl-2-(trifluoromethyl)biphenyl-4-yl]-1,2,4-oxadiazol-3-yl}phenyl)ethyl]nitroryl}acetic acid
is more particularly described in the examples.

In a specific embodiment, the present invention provides a process for the preparation of the compounds of formula (I) and salts thereof, characterized in that
a compound of formula A

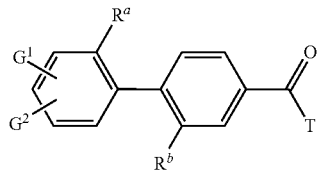

wherein $G_1$, $G_2$, $R^a$ and $R^b$ have the meanings given above, and T is OH, or a leaving group, such as Cl, Br, I, imidazolyl, pentafluorophenoxy or the product of the reaction of isobutyl chloroformate with formula A, wherein T is OH, is reacted with OH, in the presence of a suitable condensation reagent, such as EDC and the resulting product is cyclized, and optionally a base or acid of the formula (I) is converted into one of its salts.

Compounds of Formulae (II) to (XII) may be obtained either from commercial sources or they may be prepared from known compounds using procedures such as those described hereinafter in the examples, or conventional procedures, well known by one skilled in the art.

Compounds of Formulae (II) to (XII), wherein $R^1$, $R^a$, $R^b$, $G^1$, $G^2$, $W^1$-$W^4$, $X^1$, $X^2$, $Y^1$, $Y^2$, $Z^1$, $Z^2$ and $LG_1$ are defined as above, may be converted to alternative compounds of Formulae (II) to (XII), respectively, using suitable interconversion procedures such as those described hereinafter in the examples, or conventional interconversion procedures well known by one skilled in the art.

If the above set of general synthetic methods is not applicable to obtain compounds according to Formula (I) and/or necessary intermediates for the synthesis of compounds of Formula (I), suitable methods of preparation known by a person skilled in the art should be used.

The compounds of invention have been named according the standards used in the program "ACD/Name Batch" from Advanced Chemistry Development Inc., ACD/Labs (7.00 Release). Product version: 7.10, build: 15 Sep. 2003 and the program AUTONOM GOLD v 1.0.1.1.

The formula (I) and related formulae also encompasses the optically active forms (stereoisomers), the enantiomers, the racemates, the diastereomers and the hydrates and solvates of these compounds.

The determination of the stereochemistry (S) or (R) is performed using standard rules of the nomenclature well known by one skilled in the art.

According to a further general process, compounds of formula (I), and any subformulae can be converted to alternative compounds of formula (I) and any subformulae, employing suitable inter-conversion techniques well known by a person skilled in the art.

In general, the synthesis pathways for any individual compounds of formula (I) will depend on the specific substituents of each molecule and upon the ready availability of Intermediates necessary; again such factors being appreciated by those of ordinary skill in the art. For all the protection and de-protection methods, see Philip J. Kocienski, in *"Protecting Groups"*, Georg Thieme Verlag Stuttgart, New York, 1994 and, Theodora W. Greene and Peter G. M. Wuts in *"Protective Groups in Organic Synthesis"*, Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxylprotecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The term "solvates of the compounds" is taken to mean adductions of inert solvent molecules onto the compounds which form owing to their mutual attractive force. Solvates are, for example, mono- or dihydrates or alcoholates.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acyl chloride or anhydride or alkylated using an unsubstituted or substituted alkyl halide or reacted with $CH_3$—C($=$NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt or N-hydroxysuccinimide.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars like glucuronide or oligopeptides and which are rapidly cleaved in the organism to form the active compounds.

These also include biodegradable polymer derivatives of the compounds according to the invention, as described, for example, in Int. J. Pharm. 115, 61-67 (1995).

The metabolites of the compounds of Formula (I) and related Formulae are also part of the present invention. The metabolites of the compounds of Formula (I) may be for instance compounds of Formula (I) wherein $Y^1$ and/or $Y^2$ are glucuronide. Examples of such metabolites are for instance compounds of Formula (Ik).

The metabolites of the compounds of Formula (I) and related Formulae may also be compounds of Formula (I) and related Formulae wherein the bound $NY^1$-$W_3$ has been cleaved, as shown by Formula ($I^M$).

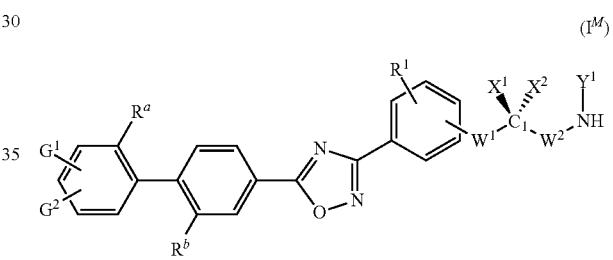

($I^M$)

wherein $G^1, G^2, R^a, R^b, R^1, W^1, X^1, X^2, W^2, Y^1$ are as defined above. Examples of such metabolites are compounds M1 and M2 mentioned in table I below.

Metabolites of the compounds of Formula (I) and related Formules may also be compounds of Formula (I) and related Formulae wherein one or several nitrogen atoms have been oxydised. Compounds of examples 101, 102 and 103 represent examples of such metabolites.

Metabolites of the compounds of Formula (I) and related Formulae may also be compounds of Formula (I) and related formulae wherein one or several aromatic systems, like phenyl rings, are oxidized. Such metabolites may be defined by the following Formula ($I^{M2}$)

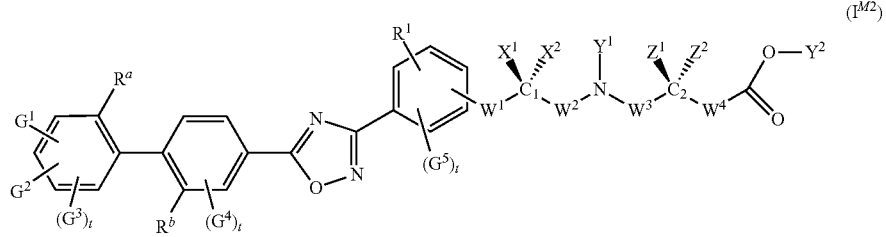

($I^{M2}$)

Wherein $G^3$, $G^4$, $G^5$ independently from each other may denote OH, t is 0, 1, 2 or 3, preferably 1 or 2, $G^1$, $G^2$, $R^a$, $R^b$, $R^1$, $X^1$, $X^2$, $Y^1$, $Y^2$, $Z^1$, $Z^2$, $W^1$, $W^2$, $W^3$, and $W^4$ are as defined above. Examples of such metabolites are compounds M3, M6 and M9 below:

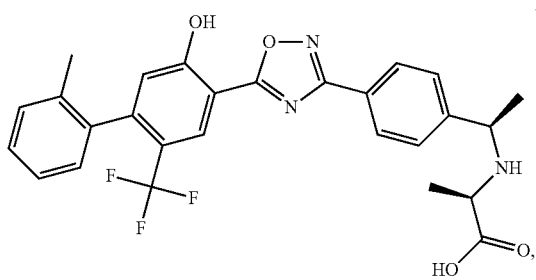

M3

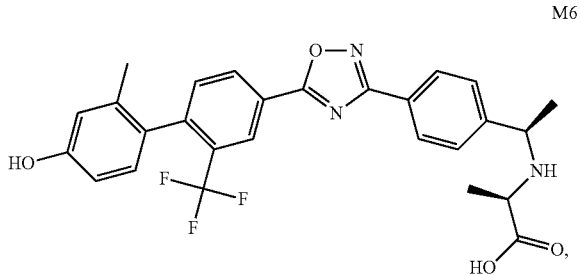

M6

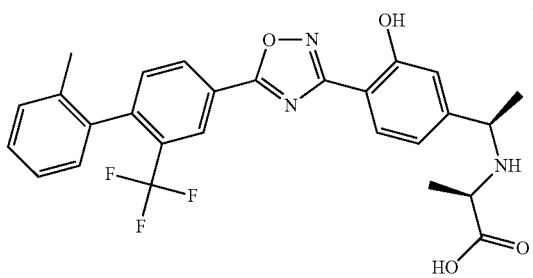

M9

The present invention encompasses compounds of Formula (I) and related Formulae either alone or in combination with one or several metabolites thereof.

The formula (I) also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In another preferred embodiment, compounds of Formula (I) exhibit a selectivity on $S_1P_1$ receptor over $S_1P_3$ receptor, based on the IC50 values as determined in the following examples, of more than 20 fold, preferably more than 50 fold, more preferably more than 100 fold, even more preferably more than 1000 fold.

The preferred compounds of the present invention have a high oral bioavailability and/or a low clearance.

In another preferred embodiment, compounds of the present invention exhibit a selectivity on $S_1P_1$ receptor over $S_1P_3$ receptor, based on the IC50 values as determined in the following examples, of more than 20 fold, preferably more than 50 fold, more preferably more than 100 fold, even more preferably more than 1000 fold and invention have a high oral bioavailability and/or a low clearance.

Preference is given to the compounds of the present invention selected from the following examples 1 to 96:

| Example No | Formula |
|---|---|
| 1 | |
| 2 | |
| 3 | |

-continued
| Example No | Formula |
|---|---|
| 4 | 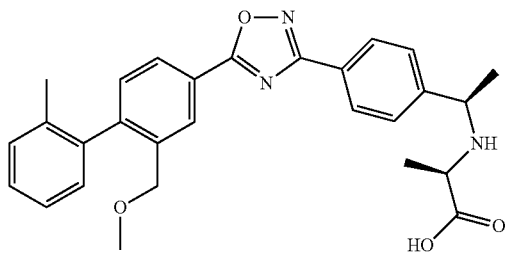 [SMILES: COCc1cc(-c2nc(-c3ccc([C@@H](C)N[C@H](C)C(=O)O)cc3)no2)ccc1-c1ccccc1C] |
| 5 | 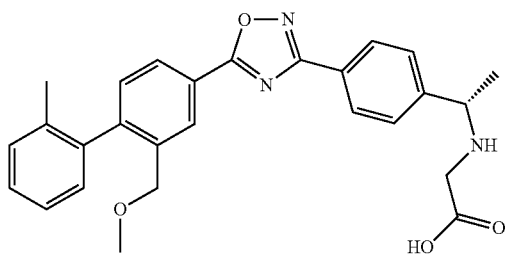 [SMILES: COCc1cc(-c2nc(-c3ccc([C@H](C)NCC(=O)O)cc3)no2)ccc1-c1ccccc1C] |
| 6 | 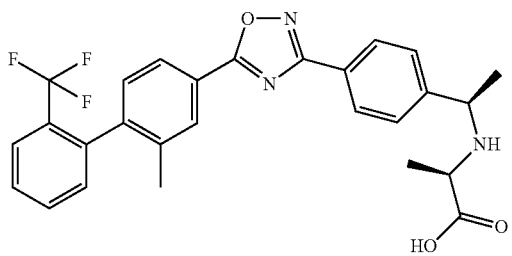 [SMILES: Cc1cc(-c2nc(-c3ccc([C@@H](C)N[C@H](C)C(=O)O)cc3)no2)ccc1-c1ccccc1C(F)(F)F] |
| 7 | 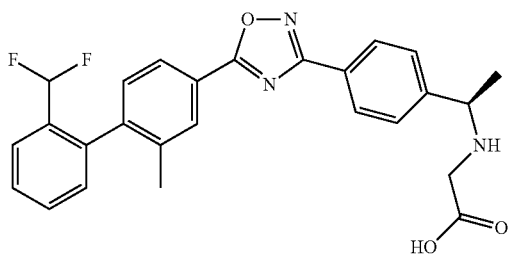 [SMILES: Cc1cc(-c2nc(-c3ccc([C@@H](C)NCC(=O)O)cc3)no2)ccc1-c1ccccc1C(F)F] |
| 8 | 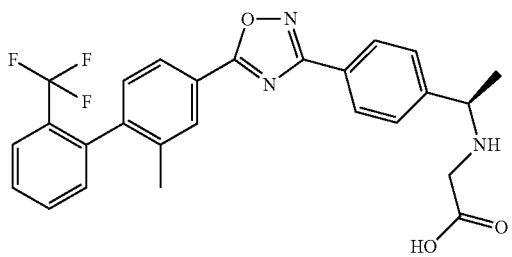 [SMILES: Cc1cc(-c2nc(-c3ccc([C@@H](C)NCC(=O)O)cc3)no2)ccc1-c1ccccc1C(F)(F)F] |
| 9 | 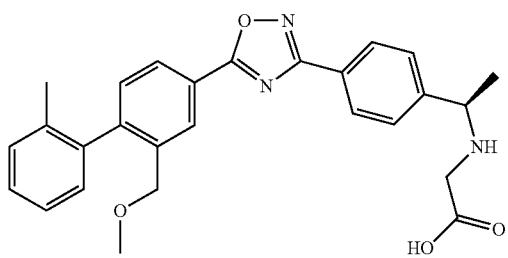 [SMILES: COCc1cc(-c2nc(-c3ccc([C@@H](C)NCC(=O)O)cc3)no2)ccc1-c1ccccc1C] |

| Example No | Formula |
| --- | --- |
| 10 | 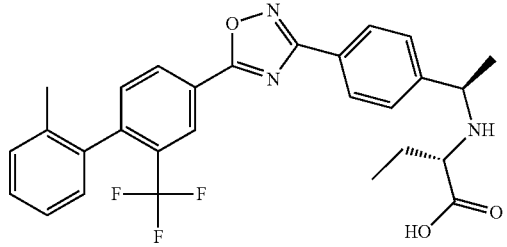 |
| 11 | 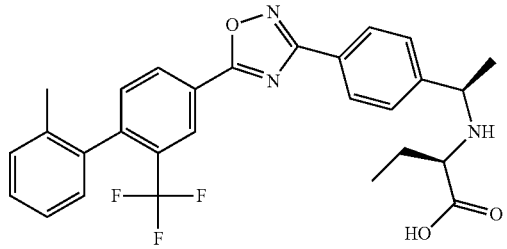 |
| 12 | 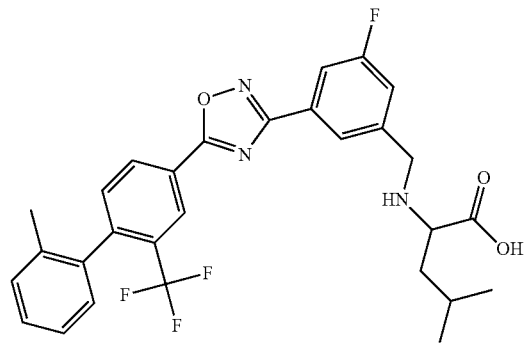 [SMILES: Cc1ccccc1-c1ccc(-c2nc(-c3cc(F)cc(CNC(CC(C)C)C(=O)O)c3)no2)cc1C(F)(F)F] |
| 13 | 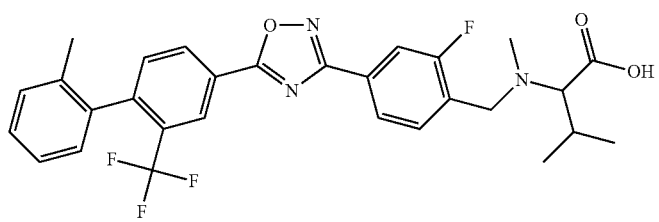 [SMILES: Cc1ccccc1-c1ccc(-c2nc(-c3ccc(CN(C)C(C(=O)O)C(C)C)c(F)c3)no2)cc1C(F)(F)F] |
| 14 | 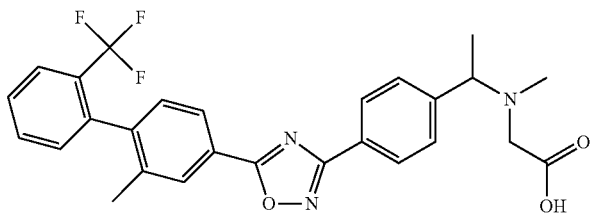 |
| 15 | 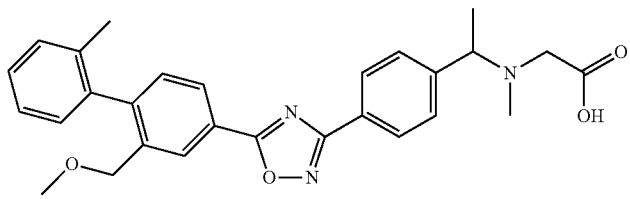 [SMILES: COCc1cc(-c2nc(-c3ccc(C(C)N(C)CC(=O)O)cc3)no2)ccc1-c1ccccc1C] |

| Example No | Formula |
|---|---|
| 16 | 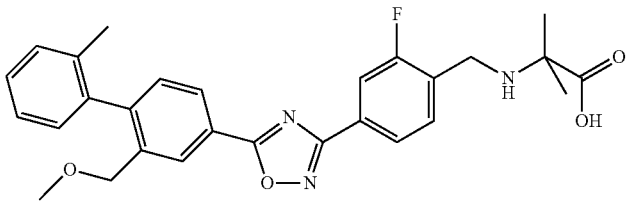 [SMILES: COCc1cc(-c2nc(-c3ccc(CNC(C)(C)C(=O)O)c(F)c3)no2)ccc1-c1ccccc1C] |
| 17 | 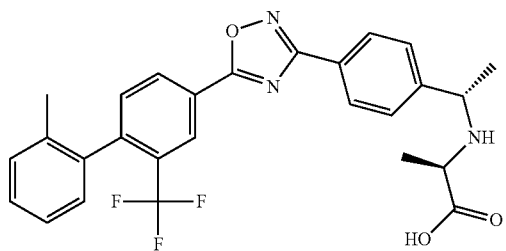 [SMILES: Cc1ccccc1-c1ccc(-c2nc(-c3ccc([C@H](C)N[C@H](C)C(=O)O)cc3)no2)cc1C(F)(F)F] |
| 18 | 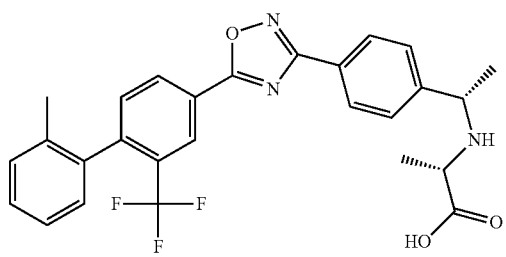 [SMILES: Cc1ccccc1-c1ccc(-c2nc(-c3ccc([C@H](C)N[C@@H](C)C(=O)O)cc3)no2)cc1C(F)(F)F] |
| 19 | 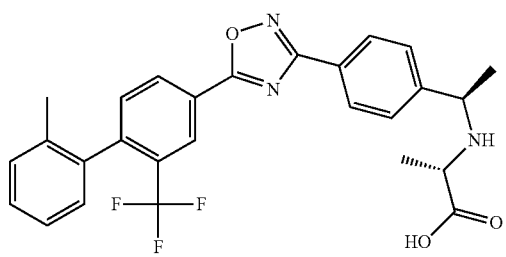 [SMILES: Cc1ccccc1-c1ccc(-c2nc(-c3ccc([C@@H](C)N[C@@H](C)C(=O)O)cc3)no2)cc1C(F)(F)F] |
| 20 | 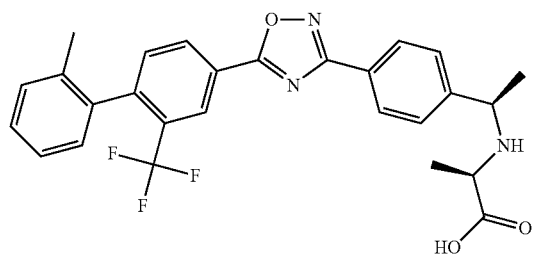 [SMILES: Cc1ccccc1-c1ccc(-c2nc(-c3ccc([C@@H](C)N[C@H](C)C(=O)O)cc3)no2)cc1C(F)(F)F] |
| 21 | 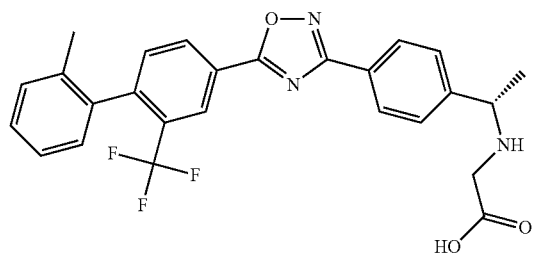 [SMILES: Cc1ccccc1-c1ccc(-c2nc(-c3ccc([C@H](C)NCC(=O)O)cc3)no2)cc1C(F)(F)F] |

| Example No | Formula |
|---|---|
| 22 | |
| 23 | |
| 24 | |
| 25 | |
| 26 | |
| 27 | |
| 28 | |

-continued
| Example No | Formula |
|---|---|
| 29 | 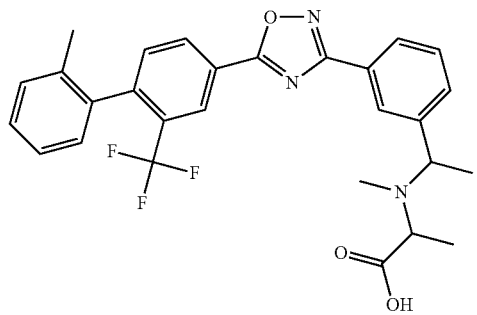 [SMILES: Cc1ccccc1-c1ccc(-c2nc(-c3cccc(C(C)N(C)C(C)C(=O)O)c3)no2)cc1C(F)(F)F] |
| 30 | 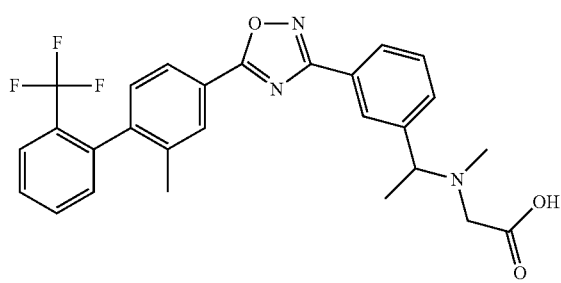 [SMILES: Cc1cc(-c2nc(-c3cccc(C(C)N(C)CC(=O)O)c3)no2)ccc1-c1ccccc1C(F)(F)F] |
| 31 | 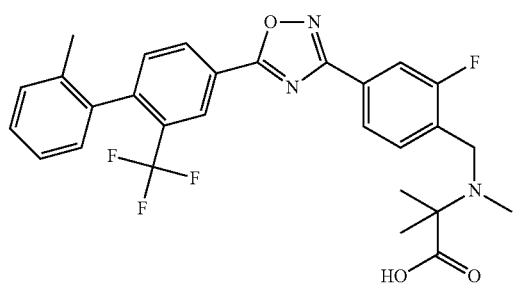 [SMILES: Cc1ccccc1-c1ccc(-c2nc(-c3ccc(CN(C)C(C)(C)C(=O)O)c(F)c3)no2)cc1C(F)(F)F] |
| 32 | 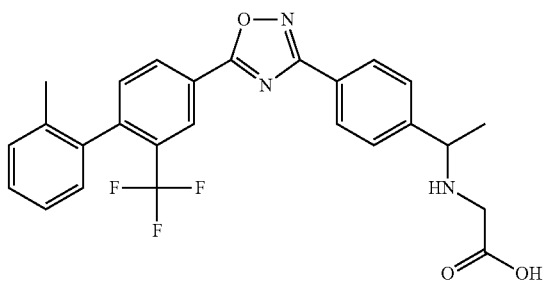 [SMILES: Cc1ccccc1-c1ccc(-c2nc(-c3ccc(C(C)NCC(=O)O)cc3)no2)cc1C(F)(F)F] |
| 33 | 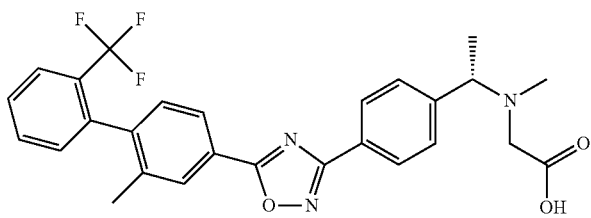 [SMILES: Cc1cc(-c2nc(-c3ccc([C@H](C)N(C)CC(=O)O)cc3)no2)ccc1-c1ccccc1C(F)(F)F] |

-continued
| Example No | Formula |
|---|---|
| 34 | 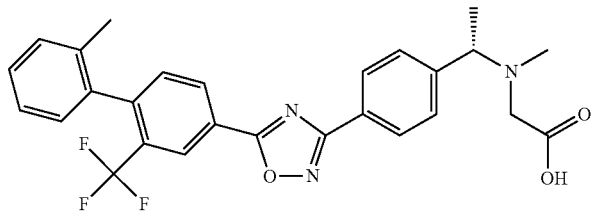 [SMILES: Cc1ccccc1-c1ccc(-c2nc(-c3ccc([C@H](C)N(C)CC(=O)O)cc3)no2)cc1C(F)(F)F] |
| 35 | 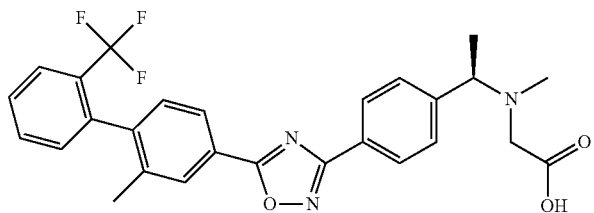 [SMILES: Cc1cc(-c2nc(-c3ccc([C@@H](C)N(C)CC(=O)O)cc3)no2)ccc1-c1ccccc1C(F)(F)F] |
| 36 | 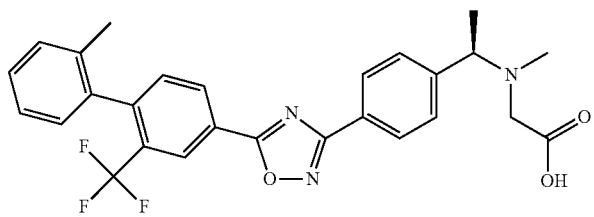 [SMILES: Cc1ccccc1-c1ccc(-c2nc(-c3ccc([C@@H](C)N(C)CC(=O)O)cc3)no2)cc1C(F)(F)F] |
| 37 | 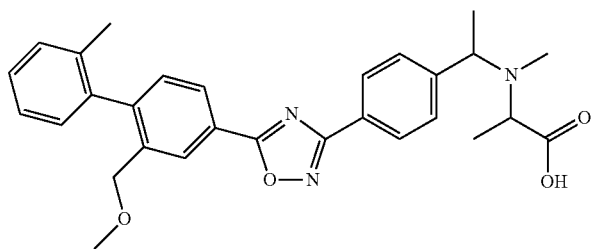 [SMILES: COCc1cc(-c2nc(-c3ccc(C(C)N(C)C(C)C(=O)O)cc3)no2)ccc1-c1ccccc1C] |
| 38 | 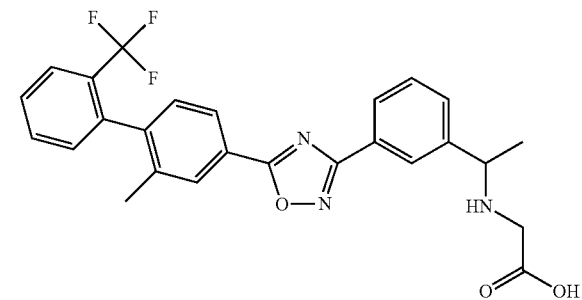 [SMILES: Cc1cc(-c2nc(-c3cccc(C(C)NCC(=O)O)c3)no2)ccc1-c1ccccc1C(F)(F)F] |
| 39 | 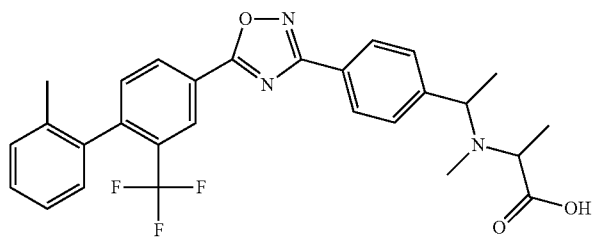 [SMILES: Cc1ccccc1-c1ccc(-c2nc(-c3ccc(C(C)N(C)C(C)C(=O)O)cc3)no2)cc1C(F)(F)F] |

-continued
| Example No | Formula |
|---|---|
| 40 | 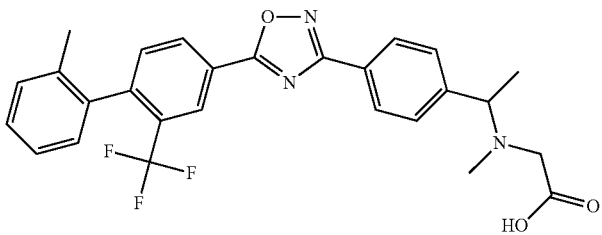 [SMILES: Cc1ccccc1-c1ccc(-c2nc(-c3ccc(C(C)N(C)CC(=O)O)cc3)no2)cc1C(F)(F)F] |
| 41 | 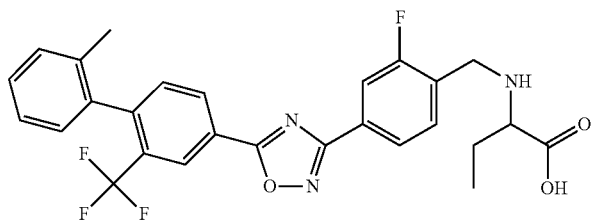 [SMILES: CCC(NCc1ccc(-c2noc(-c3ccc(-c4ccccc4C)c(C(F)(F)F)c3)n2)cc1F)C(=O)O] |
| 42 | 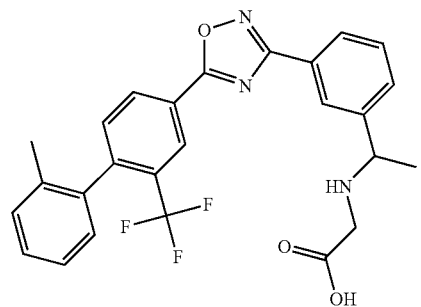 [SMILES: Cc1ccccc1-c1ccc(-c2nc(-c3cccc(C(C)NCC(=O)O)c3)no2)cc1C(F)(F)F] |
| 43 | 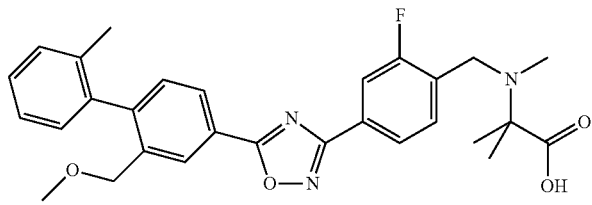 [SMILES: COCc1cc(-c2nc(-c3ccc(CN(C)C(C)(C)C(=O)O)c(F)c3)no2)ccc1-c1ccccc1C] |
| 44 | 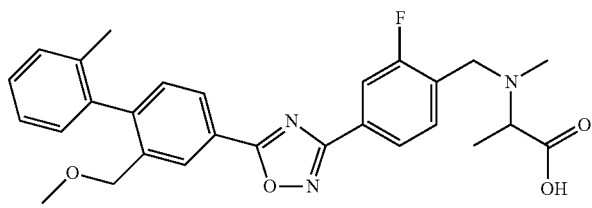 [SMILES: COCc1cc(-c2nc(-c3ccc(CN(C)C(C)C(=O)O)c(F)c3)no2)ccc1-c1ccccc1C] |
| 45 |  |

-continued

| Example No | Formula |
|---|---|
| 46 | |
| 47 | |
| 48 | |
| 49 | |
| 50 | |
| 51 | |

-continued
| Example No | Formula |
|---|---|
| 52 | 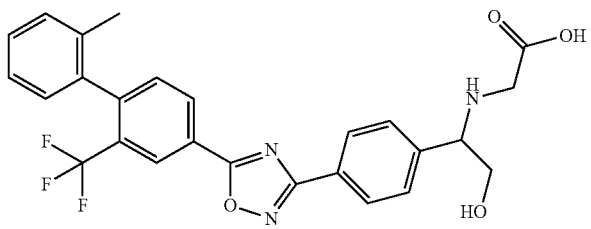 [SMILES: Cc1ccccc1-c1ccc(-c2nc(-c3ccc(C(CO)NCC(=O)O)cc3)no2)cc1C(F)(F)F] |
| 53 | 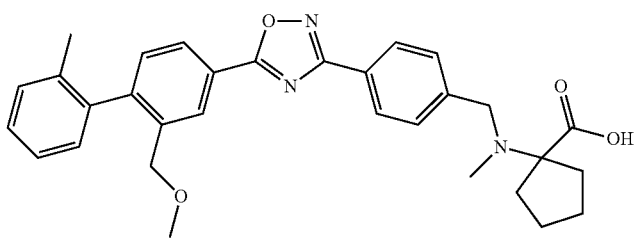 [SMILES: COCc1cc(-c2nc(-c3ccc(CN(C)C4(C(=O)O)CCCC4)cc3)no2)ccc1-c1ccccc1C] |
| 54 | 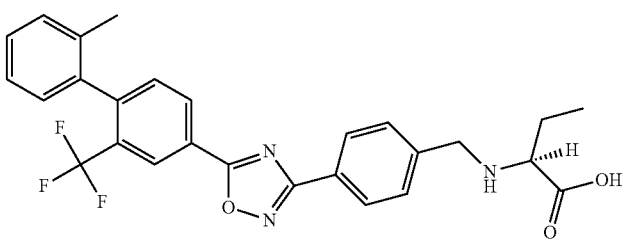 [SMILES: CC[C@H](NCc1ccc(-c2noc(-c3ccc(-c4ccccc4C)c(C(F)(F)F)c3)n2)cc1)C(=O)O] |
| 55 | 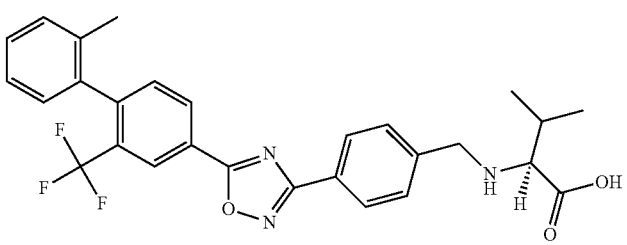 [SMILES: Cc1ccccc1-c1ccc(-c2nc(-c3ccc(CN[C@H](C(=O)O)C(C)C)cc3)no2)cc1C(F)(F)F] |
| 56 | 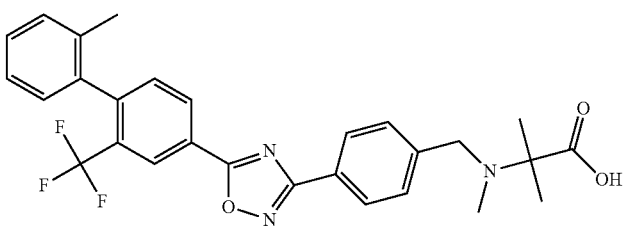 [SMILES: Cc1ccccc1-c1ccc(-c2nc(-c3ccc(CN(C)C(C)(C)C(=O)O)cc3)no2)cc1C(F)(F)F] |
| 57 | 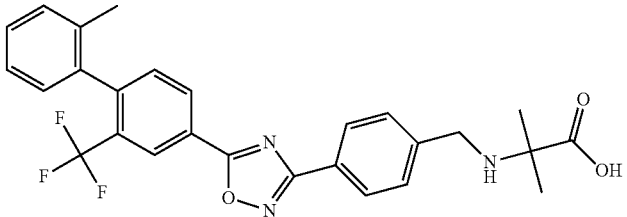 |

-continued

| Example No | Formula |
|---|---|
| 58 | |
| 59 | |
| 60 | |
| 61 | |
| 62 | |
| 63 | |

| Example No | Formula |
|---|---|
| 64 | |
| 65 | |
| 66 | |
| 67 | |
| 68 | |
| 69 | |

| Example No | Formula |
|---|---|
| 70 | |
| 71 | |
| 72 | |
| 73 | |
| 74 | |
| 75 | |

| Example No | Formula |
|---|---|
| 76 | 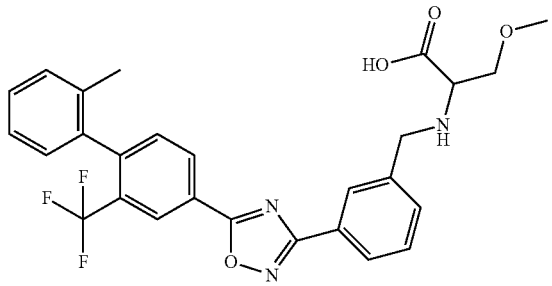 [SMILES: COCC(NCc1cccc(-c2noc(-c3ccc(-c4ccccc4C)c(C(F)(F)F)c3)n2)c1)C(=O)O] |
| 77 | 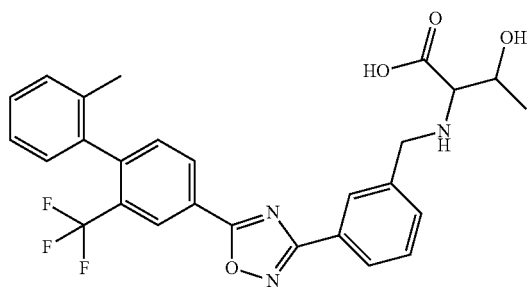 [SMILES: Cc1ccccc1-c1ccc(-c2nc(-c3cccc(CNC(C(=O)O)C(C)O)c3)no2)cc1C(F)(F)F] |
| 78 | 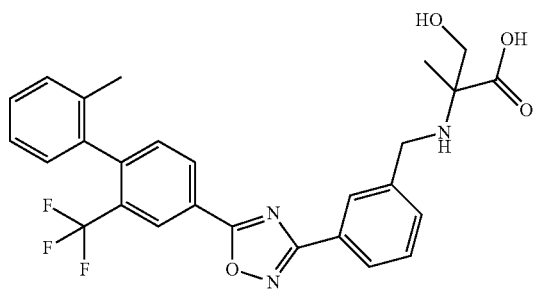 [SMILES: Cc1ccccc1-c1ccc(-c2nc(-c3cccc(CNC(C)(CO)C(=O)O)c3)no2)cc1C(F)(F)F] |
| 79 | 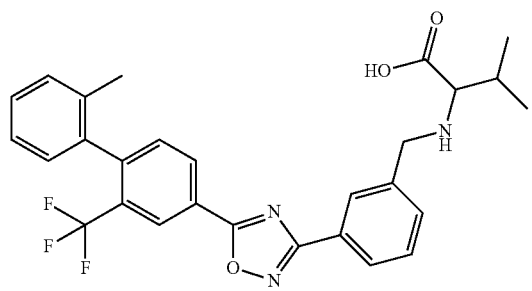 [SMILES: Cc1ccccc1-c1ccc(-c2nc(-c3cccc(CNC(C(=O)O)C(C)C)c3)no2)cc1C(F)(F)F] |
| 80 | 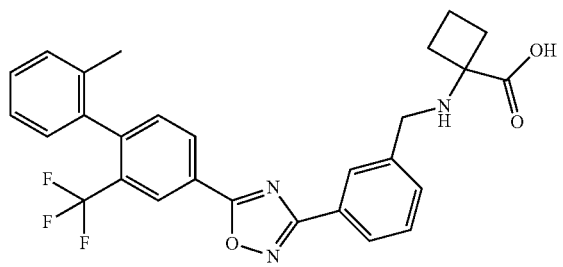 [SMILES: Cc1ccccc1-c1ccc(-c2nc(-c3cccc(CNC4(C(=O)O)CCC4)c3)no2)cc1C(F)(F)F] |

-continued
| Example No | Formula |
|---|---|
| 81 | 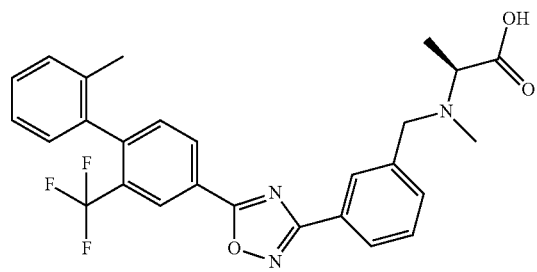 [SMILES: Cc1ccccc1-c1ccc(-c2nc(-c3cccc(CN(C)[C@@H](C)C(=O)O)c3)no2)cc1C(F)(F)F] |
| 82 | 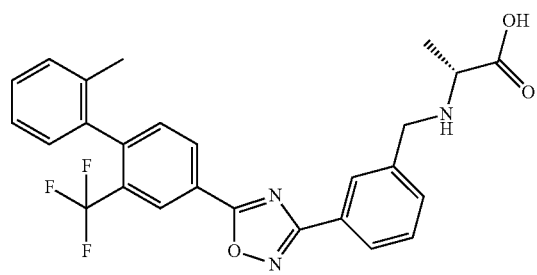 [SMILES: Cc1ccccc1-c1ccc(-c2nc(-c3cccc(CN[C@H](C)C(=O)O)c3)no2)cc1C(F)(F)F] |
| 83 | 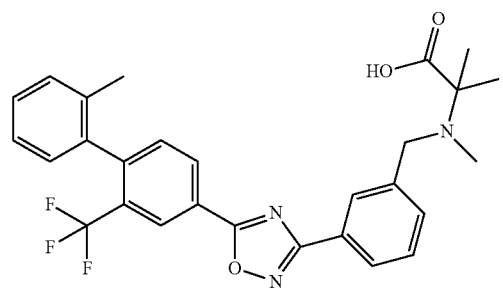 [SMILES: Cc1ccccc1-c1ccc(-c2nc(-c3cccc(CN(C)C(C)(C)C(=O)O)c3)no2)cc1C(F)(F)F] |
| 84 | 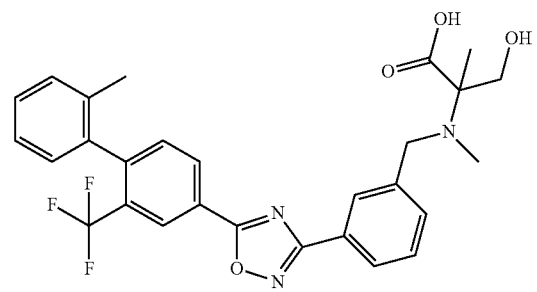 [SMILES: Cc1ccccc1-c1ccc(-c2nc(-c3cccc(CN(C)C(C)(CO)C(=O)O)c3)no2)cc1C(F)(F)F] |
| 85 | 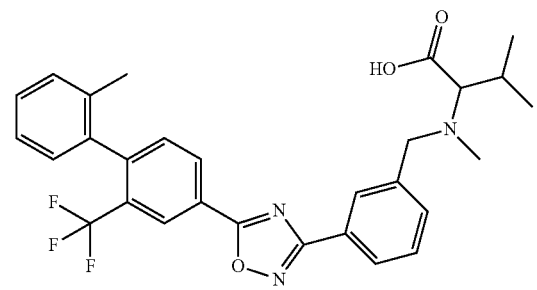 [SMILES: Cc1ccccc1-c1ccc(-c2nc(-c3cccc(CN(C)C(C(=O)O)C(C)C)c3)no2)cc1C(F)(F)F] |

| Example No | Formula |
|---|---|
| 86 | 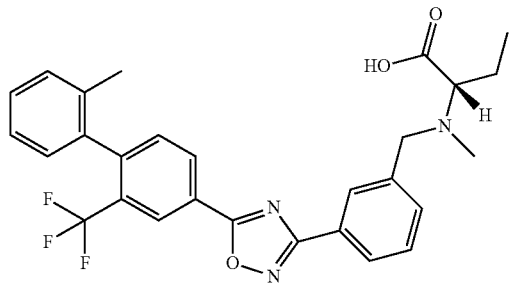 [SMILES: CC[C@@H](C(=O)O)N(C)Cc1cccc(-c2noc(-c3ccc(-c4ccccc4C)c(C(F)(F)F)c3)n2)c1] |
| 87 | 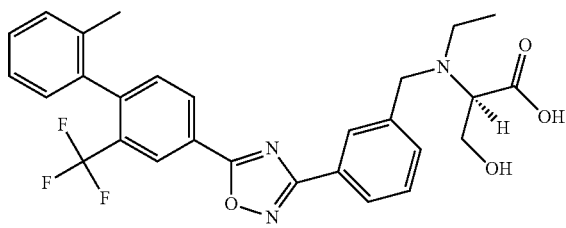 [SMILES: CCN(Cc1cccc(-c2noc(-c3ccc(-c4ccccc4C)c(C(F)(F)F)c3)n2)c1)[C@H](CO)C(=O)O] |
| 88 | 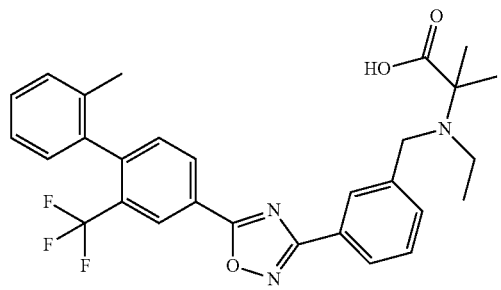 [SMILES: CCN(Cc1cccc(-c2noc(-c3ccc(-c4ccccc4C)c(C(F)(F)F)c3)n2)c1)C(C)(C)C(=O)O] |
| 89 | 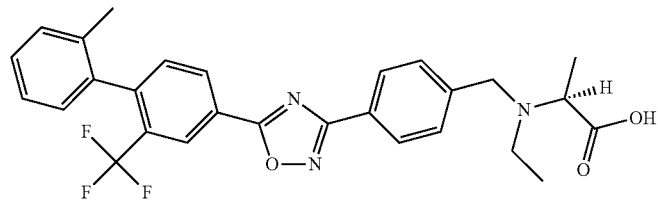 [SMILES: CCN(Cc1ccc(-c2noc(-c3ccc(-c4ccccc4C)c(C(F)(F)F)c3)n2)cc1)[C@@H](C)C(=O)O] |
| 90 | 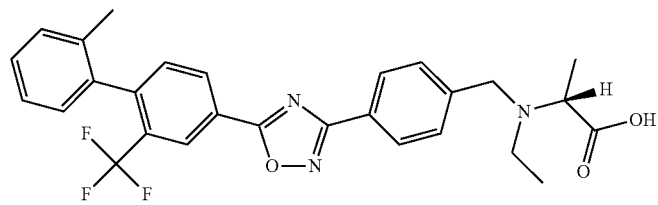 [SMILES: CCN(Cc1ccc(-c2noc(-c3ccc(-c4ccccc4C)c(C(F)(F)F)c3)n2)cc1)[C@H](C)C(=O)O] |
| 91 | 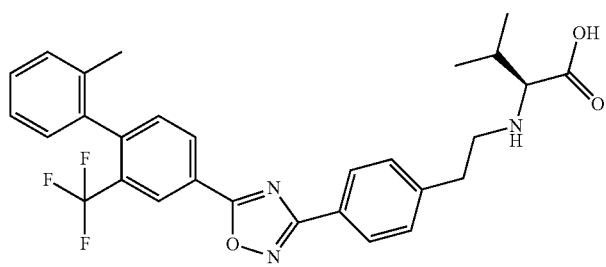 [SMILES: Cc1ccccc1-c1ccc(-c2nc(-c3ccc(CCN[C@H](C(=O)O)C(C)C)cc3)no2)cc1C(F)(F)F] |

-continued
| Example No | Formula |
|---|---|
| 92 | 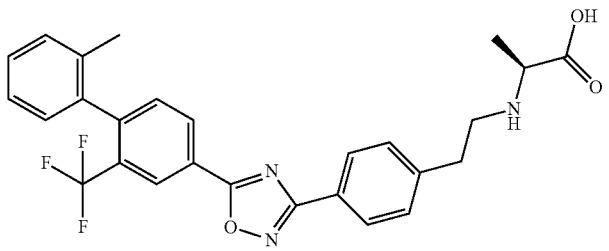 [SMILES: Cc1ccccc1-c1ccc(-c2nc(-c3ccc(CCN[C@@H](C)C(=O)O)cc3)no2)cc1C(F)(F)F] |
| 93 | 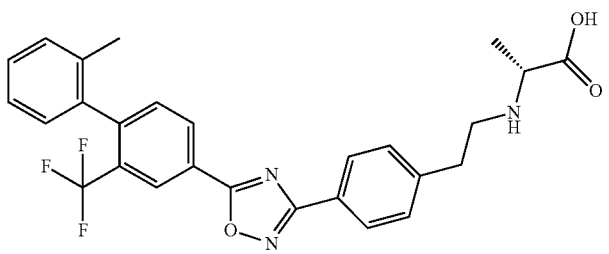 [SMILES: Cc1ccccc1-c1ccc(-c2nc(-c3ccc(CCN[C@H](C)C(=O)O)cc3)no2)cc1C(F)(F)F] |
| 94 | 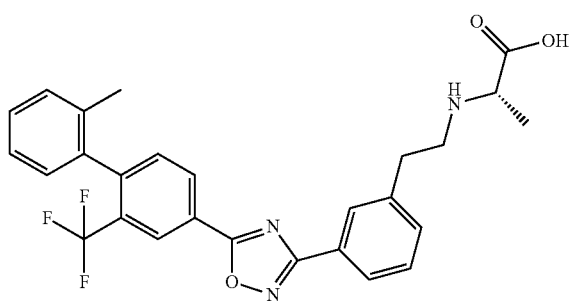 [SMILES: Cc1ccccc1-c1ccc(-c2nc(-c3cccc(CCN[C@@H](C)C(=O)O)c3)no2)cc1C(F)(F)F] |
| 95 | 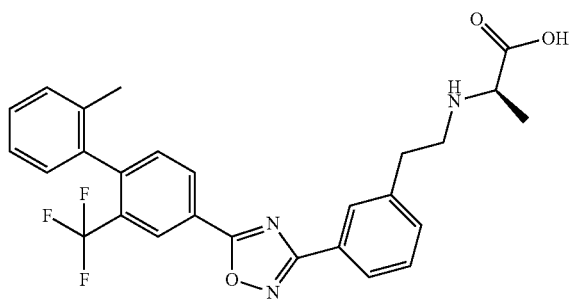 [SMILES: Cc1ccccc1-c1ccc(-c2nc(-c3cccc(CCN[C@H](C)C(=O)O)c3)no2)cc1C(F)(F)F] |
| 96 | 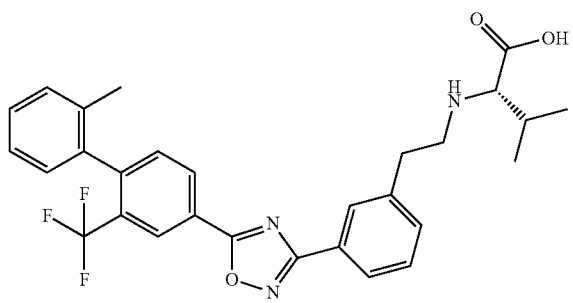 [SMILES: Cc1ccccc1-c1ccc(-c2nc(-c3cccc(CCN[C@H](C(=O)O)C(C)C)c3)no2)cc1C(F)(F)F] |

-continued
| Example No | Formula |
|---|---|
| 97 | 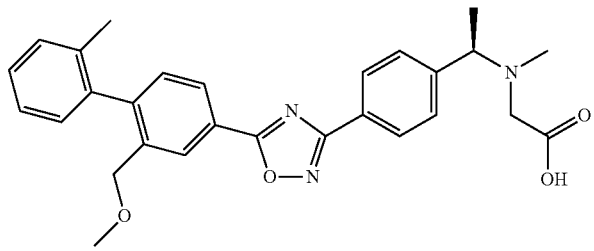 [SMILES: COCc1cc(-c2nc(-c3ccc([C@@H](C)N(C)CC(=O)O)cc3)no2)ccc1-c1ccccc1C] |
| 98 | 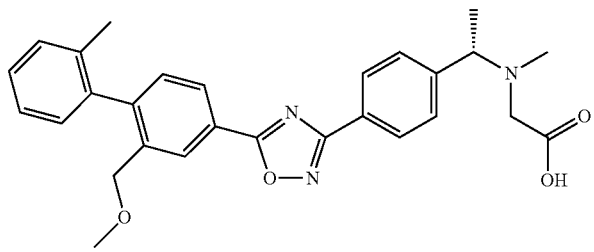 [SMILES: COCc1cc(-c2nc(-c3ccc([C@H](C)N(C)CC(=O)O)cc3)no2)ccc1-c1ccccc1C] |
| 99 | 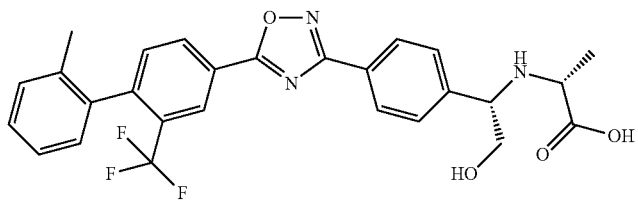 [SMILES: Cc1ccccc1-c1ccc(-c2nc(-c3ccc([C@@H](CO)N[C@H](C)C(=O)O)cc3)no2)cc1C(F)(F)F] |
| 100 | 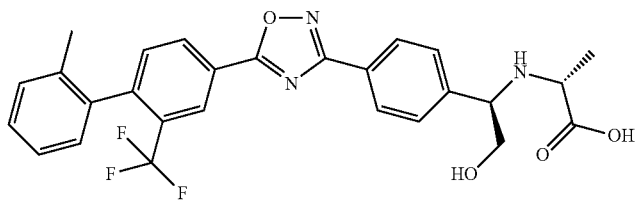 [SMILES: Cc1ccccc1-c1ccc(-c2nc(-c3ccc([C@H](CO)N[C@H](C)C(=O)O)cc3)no2)cc1C(F)(F)F] |
| 101 | 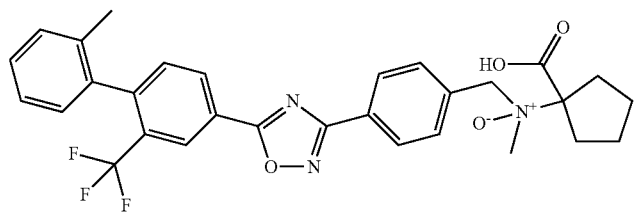 [SMILES: Cc1ccccc1-c1ccc(-c2nc(-c3ccc(C[N+](C)([O-])C4(C(=O)O)CCCC4)cc3)no2)cc1C(F)(F)F] |
| 102 | 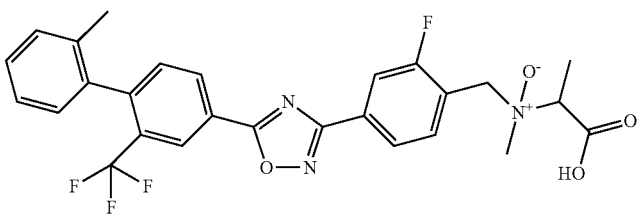 [SMILES: Cc1ccccc1-c1ccc(-c2nc(-c3ccc(C[N+](C)([O-])C(C)C(=O)O)c(F)c3)no2)cc1C(F)(F)F] |

| Example No | Formula |
|---|---|
| 103 | (structure) |
| M1 | (structure) |
| M2 | (structure) | and pharmaceutically usable derivatives, solvates, salts and stereoisomers thereof, including mixtures thereof in all ratios.

The formula (I) also encompasses the optically active forms (stereoisomers), the enantiomers, the racemates, the diastereomers and the hydrates, salts and solvates of these compounds.

In a specific embodiment, when 2 chiral centers or more are present, compounds of Formula (I) are obtained as one diastereoisomer.

A "diastereoisomer" means that each of the chiral centers present in the compound of Formula (I) is defined relatively to the others.

For all radicals and indices which occur more than once within the same chemical structure, their meanings are independent of one another.

Above and below, the radicals or parameters $R^a$, $R^b$, $X^1$, $X^2$, $Y^1$, $Y^2$, $G^1$, A, A, $Z^1$, $Z^2$, $W^1$, $W^2$, $W^3$, $W^4$, have the meaning indicated under the formula (I) and subformulae, unless expressly stated otherwise.

Cycloalkyl is a cyclic alkyl containing 3 to 12 carbon atoms. Cycloalkyl preferably denotes cyclopropyl, cyclobutyl, cyclopentyl, cyclohexyl or cycloheptyl.

Cycloalkylalkylene is a cycloalkyl group bond to the rest of the molecule via a carbon chain and having 1, 2, 3, 4, 5, 6, 7, 8, 9, 10, 11, 12, 13, 14, 15, 16, 17, or 18 carbon atoms. Cycloalkylalkylene preferably denotes cyclopropylmethylene, cyclobutylmethylene, cyclopentylmethylene, cyclohexylmethylene or cycloheptylmethylene.

$R^a$ is preferably —$CH_3$, —$CH_2CH_3$, —$CF_3$, —$CHF_2$,
$R^b$ is preferably —$CF_3$ or —$CH_2OCH_3$.

In a specific embodiment, the present invention provides compounds of Formula (I) wherein one of $R^a$ and $R^b$ is —$CF_3$ or —$CH_2OCH_3$, preferably —$CF_3$.

Hal is preferably F, Cl or Br and especially F or Cl.

$R^1$ preferably denotes F or OA, wherein A is as above defined, especially F or —$OCH_3$, Examples of the group

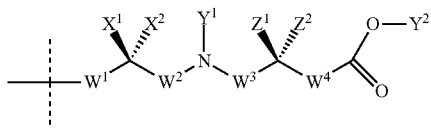

in formula (I)

are selected from the following groups:

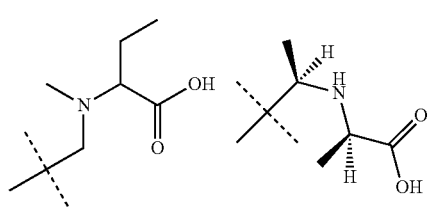

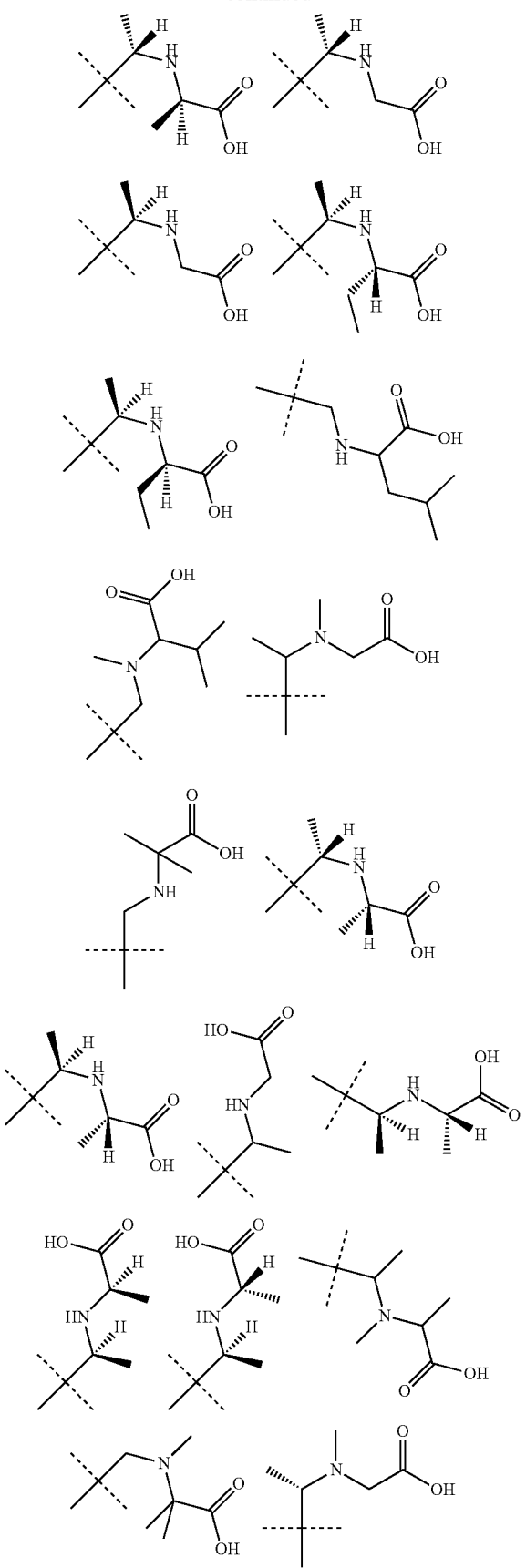
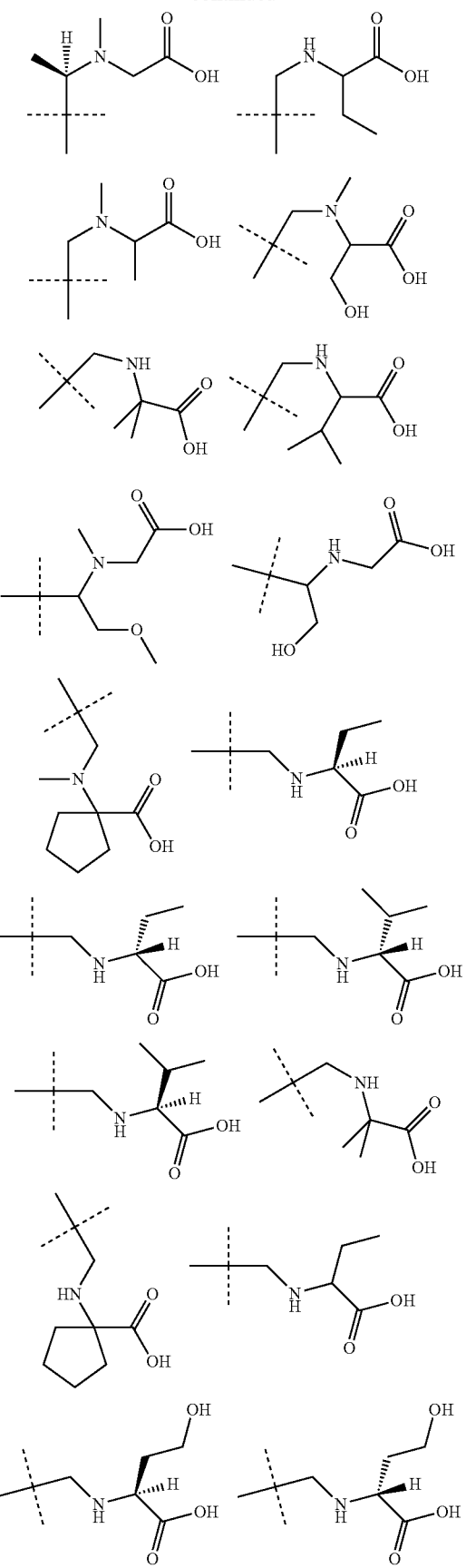

-continued

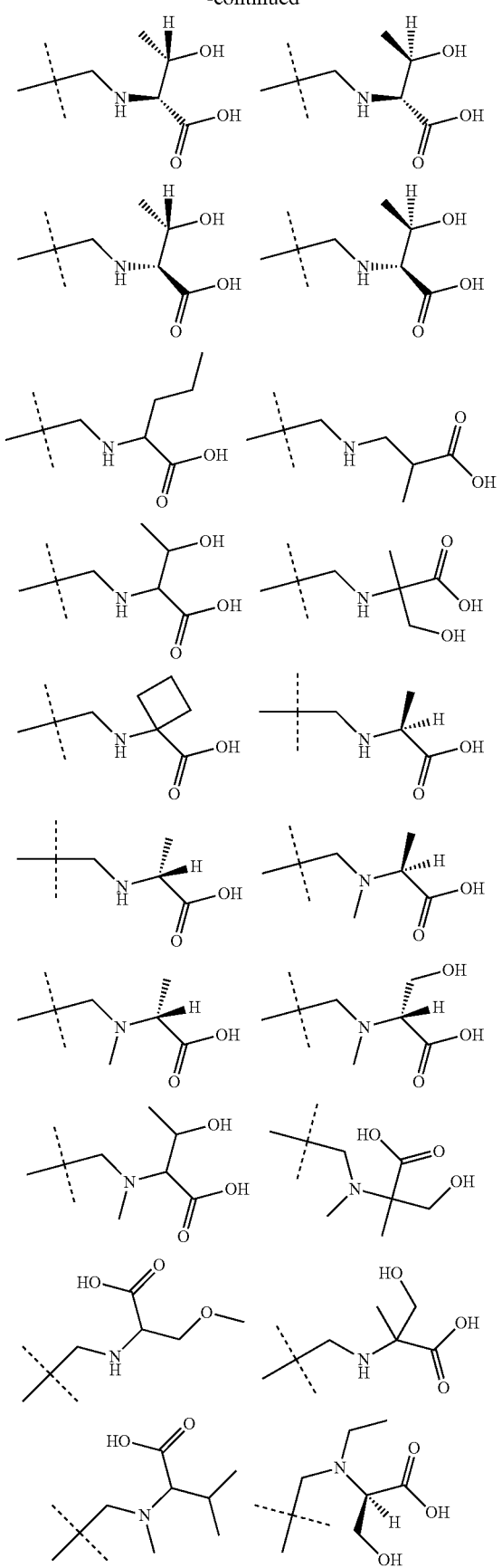
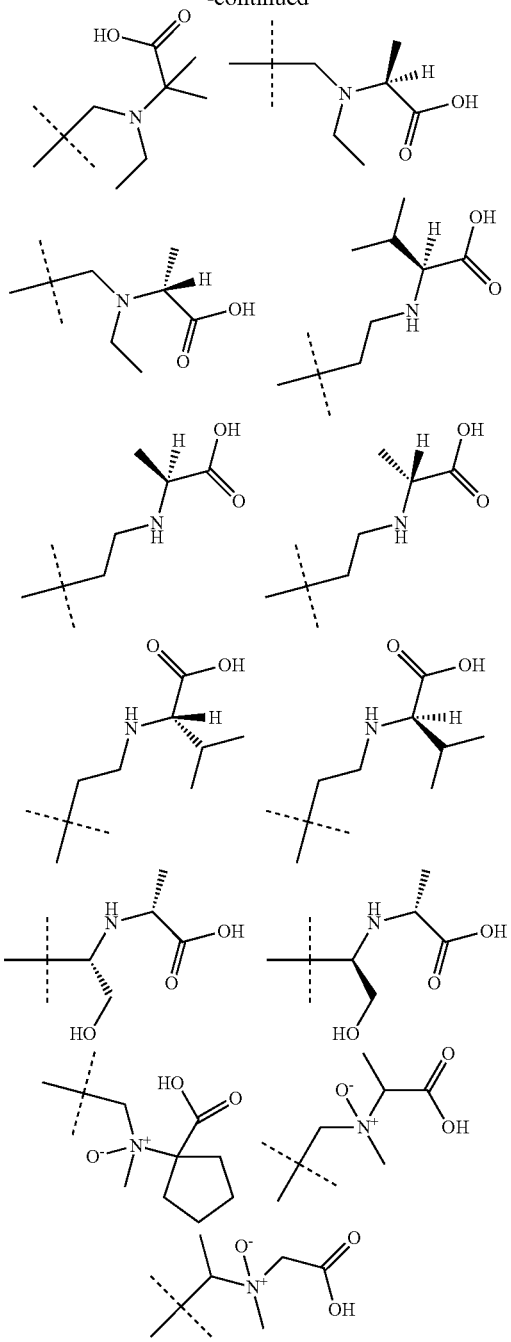

The compounds of formula (I) can have one or more centres of chirality and can therefore occur in various stereoisomeric forms. Formula (I) covers all these forms.

The compounds of the formula (I) and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula (I).

The starting compounds for the preparation of compounds of formula (I) are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or DCM; alcohols, such as methanol, ethanol, isopropanol, n-propanol, n-butanol or tert-butanol; ethers, such as diethyl ether, diisopropyl ether, THF (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylenediamine (benzathine), dicyclohexylamine, diethanol-amine, diethylamine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropylamine and tris(hydroxy-methyl)-methylamine (tromethamine), but this is not intended to represent a restriction.

Compounds of the formula I of the present invention which contain basic $N_2$-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-pie, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula (I). The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnormality, comprising administering to said subject a compounds of formula (I) in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxinshock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, sideriosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

In a preferred embodiment, compounds of the present invention are used in the treatment of multiple sclerosis, including relapsing-remitting multiple sclerosis.

Preferred compounds of formula (I) exhibit a Ki, determined according to the present examples, for the binding to the $S1P_1$ receptor of less than about 10 µM, preferably less than about 5 µM, more preferably less than about 1 µM and even more preferred less than about 0.1 µM. Most preferably, compounds of Formula (I) exhibit a Ki for the binding of $S1P_1$ less than 0.01 µM.

In the following the present invention shall be illustrated by means of some examples, which are not construed to be viewed as limiting the scope of the invention.

EXAMPLES

The oxadiazole compounds according to formula (I) can be prepared from readily available starting materials by several synthetic approaches, using both solution-phase and solid-phase chemistry protocols or mixed solution and solid phase protocols. Examples of synthetic pathways are described below in the examples. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich or Fluka unless otherwise reported.

The HPLC, NMR and MS data provided in the examples described below are obtained as followed:
HPLC Data:
Method A:
HPLC columns: Xbridge™ C8 column 50 mm×4.6 mm at a flow of 2 mL/min; 8 min gradient from 0.1% TFA in $H_2O$ to 0.07% TFA in ACN.

Method B:
HPLC column: CHIRALCEL OJ-H, 250×4.6 mm, 5 µm, 30° C. Gradient: Hexane/ISOH: 80/20 0.1% TEA at a flow of 1 mL/min.

Method C:
HPLC columns: Hichrom, Kromasil Eternity, 2.5 µm C18, 150×4.6 mm at a flow of 1 mL/min; 6.0 min gradient from 95:5 ([10 mM ammonium bicarbonate in $H_2O$]:MeCN) to 5:95 ([10 mM ammonium bicarbonate in $H_2O$]:MeCN) then held for 4.6 minutes at 5:95 ([10 mM ammonium bicarbonate in $H_2O$]:MeCN).

Method D:
HPLC columns: Phenomenex Luna 5 µm C18 (2), 100×4.6 mm (plus guard cartridge) at a flow of 2 mL/min; 3.5 min gradient from 95:5 ([0.1% (V/V) formic acid in $H_2O$]:[0.1% (V/V) formic acid in MeCN]) to 5:95 ([0.1% (V/V) formic acid in $H_2O$]:[0.1% (V/V) formic acid in MeCN]) then held for 2 minutes at 5:95 ([0.1% (V/V) formic acid in $H_2O$]:[0.1% (V/V) formic acid in MeCN]).

Method E:
HPLC columns: Waters Sunfire 5 µm C18, 150×4.6 mm (plus guard cartridge) at a flow of 1 mL/min; 30 min gradient from 95:5 ([0.1% (V/V) formic acid in $H_2O$]:[0.1% (V/V) formic acid in MeOH]) to 0.1% (V/V) formic acid in MeOH then held for 5 minutes at 0.1% (V/V) formic acid in MeOH.

Method F:
HPLC columns: Phenomenex, Gemini NX, 3 µm C18, 100×4.6 mm at a flow of 2 mL/min; 3.5 min gradient from 95:5 ([10 mM ammonium bicarbonate in $H_2O$]:MeCN) to 5:95 ([10 mM ammonium bicarbonate in $H_2O$]:MeCN) then held for 1.5 minutes at 5:95 ([10 mM ammonium bicarbonate in $H_2O$]:MeCN).

Method G:
HPLC columns: Waters Xterra MS 5 µm C18, 100×4.6 mm (plus guard cartridge) at a flow of 2 mL/min; 3.5 min gradient from 95:5 ([10 mM ammonium bicarbonate in $H_2O$]:MeCN) to 5:95 ([10 mM ammonium bicarbonate in $H_2O$]:MeCN) then held for 1.5 minutes at 5:95 ([10 mM ammonium bicarbonate in $H_2O$]:MeCN).

Method H:
Gradient of Method H applied to HPLC columns: Supelco, Ascentis® Express C18 or Hichrom Halo C18, 2.7 µm C18, 100×4.6 mm.

Method I:
HPLC columns: Waters Xbridge 5 µm C18, 150×4.6 mm (plus guard cartridge) at a flow of 1 mL/min; 22 min gradient from 95:5 ([10 mM ammonium bicarbonate in $H_2O$]:MeOH) to MeOH then held for 4 minutes at MeOH.

Method J:
HPLC columns: Chiralpak IC, 5 µm, 250×4.6 mm (Chiral Technologies) at a flow of 1 mL/min; isocratic Hexane-EtOH-TFA-DEA 70:30:0.1:0.1.

Method K:
HPLC columns: Chiralpak OJH, 5 µm, 250×4.6 mm (Chiral Technologies) at a flow of 1 mL/min; isocratic Hexane-EtOH-TFA 97:3:0.1.

Method L:
HPLC columns: Chiralpak AD-RH, 5 µm, 150×4.6 mm (Chiral Technologies) at a flow of 1 mL/min at 40° C.; isocratic Buffer pH 2, 0.1 M $KPF_6$-ACN 65:35.

Method M:

HPLC columns: Chiralpak OD-RH, 5 μm, 150×4.6 mm (Chiral Technologies) at a flow of 1 mL/min; isocratic Buffer pH 2, 0.1 M HClO$_4$/NaClO$_4$-ACN 60:30.

UV Detection (Maxplot) for all Methods.

Mass Spectrum:

Method A: LC/MS Waters ZMD (ESI); GC/MS: GC Agilent 6890N & MS Agilent 5973.

Method B: UPLC/MS: Waters Acquity, column Waters Acquity UPLC BEH C18 1.7 m 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30 V).

$^1$H-NMR Data:

Bruker DPX-300 MHz unless otherwise reported.

Preparative HPLC Purifications:

Preparative HPLC purifications were performed with HPLC waters Prep LC 4000 System equipped with columns ®PrepMS C18 10m, 50×300 mm, unless otherwise reported. All HPLC purifications were performed with a gradient of ACN/H$_2$O or ACN/H$_2$O/TFA (0.1%).

Mass Directed Autoprep (MD Autoprep) Purifications:

Preparative HPLC purifications are performed with a mass directed autopurification Fractionlynx from Waters equipped with a Sunfire Prep C18 OBD column 19×100 mm 5 m, unless otherwise reported. All HPLC purifications were performed with a gradient of ACN/H$_2$O or ACN/H$_2$O/HCOOH (0.1%).

The microwave chemistry was performed on a single mode microwave reactor Emrys™ Optimiser or Initiator™ Sixty from Biotage, or Explorer from CEM.

General Procedures:

General Procedure 1: General Procedure for the Amidoxime Moiety Formation

To a solution of nitrile derivative (1 eq) in EtOH (1-5 mL/mmol of nitrile derivative) was added a 50% aqueous solution of NH$_2$OH (5 eq). The resulting mixture was stirred at a temperature ranging from RT to 80° C. for 1 to 72 hours. In case of precipitation of the expected compound, the precipitate was filtered off and washed with an adequate solvent, such as EtOH, iPrOH or water, and then dried under reduced pressure to give the expected amidoxime derivative. In all other cases, the reaction mixture was concentrated under reduced pressure, diluted with an adequate solvent, such as water or iPrOH, until precipitation. The precipitate was filtered off and washed with an adequate solvent, such as iPrOH or water, and then dried under reduced pressure to give the expected amidoxime derivative. When no precipitation occurred, the concentrated mixture was dissolved in EtOAc and water, the organic layer was washed with water (twice) and brine (twice), then dried over MgSO$_4$, filtered and concentrated under vacuum to give the expected amidoxime derivative.

General Procedure 2: General Procedure for the Amidoxime Moiety Formation

To a solution of nitrile derivative (1 eq) in EtOH (1-5 mL/mmol of nitrile derivative) was added NH$_2$OH.HCl (1.1 eq) and Et$_3$N (1.2 eq). The resulting mixture was stirred at a temperature ranging from RT to 80° C. for 1 to 72 hours. In case of precipitation of the expected compound, the precipitate was filtered off and washed with an adequate solvent, such as EtOH, iPrOH or water, and then dried under reduced pressure to give the expected amidoxime derivative. In all other cases, the reaction mixture was concentrated under reduced pressure, diluted with an adequate solvent, such as water or iPrOH, until precipitation. The precipitate was filtered off and washed with an adequate solvent, such as iPrOH or water, and then dried under reduced pressure to give the expected amidoxime derivative. When no precipitation occurred, the concentrated mixture was dissolved in EtOAc and water, the organic layer was washed with water (twice) and brine (twice), then dried over MgSO$_4$, filtered and concentrated under vacuum to give the expected amidoxime derivative.

General Procedure 3: General Procedure for the Oxadiazole Ring Formation

DIEA (2.0 to 2.2 eq) and HATU (1.0 to 1.1 eq) were added into a solution of the carboxylic acid derivative (1 eq) in anhydrous DMF (4 mL/mmol of carboxylic acid derivative) cooled at 0° C. The resulting mixture was stirred at 0° C. for a period of 5 to 30 minutes. Then the amidoxime derivative (1.0 to 1.2 eq) was added neat or as a DMF solution (2 mL/mmol of amidoxime derivative). The resulting mixture was stirred at 0° C. or RT for a period of 30 minutes to 18 hours. The reaction mixture was diluted with an adequate solvent, such as Et$_2$O, MTBE or EtOAc, and then washed with water and brine. The aqueous layers were extracted once. The organic layers were combined, dried (MgSO$_4$ or Na$_2$SO$_4$) and the solvents were removed under reduced pressure. The residue was either taken up with toluene (6 mL/mmol of carboxylic acid derivative) and pyridine (2 mL/mmol of carboxylic acid derivative) or with ACN (8.5 mL/mmol of carboxylic acid derivative). The resulting mixture was heated at a temperature between 80° C. to reflux for a period of 12 to 72 hours. The reaction mixture was diluted with an adequate solvent, such as Et$_2$O, MTBE or EtOAc, and then washed with water and brine. The aqueous layers were extracted once. The organic layers were combined, dried (MgSO$_4$ or Na$_2$SO$_4$) and the solvents were evaporated under reduced pressure. Purification by flash chromatography or precipitation gave the expected oxadiazole derivative.

General Procedure 4: General Procedure for the Oxadiazole Ring Formation

DIEA (2.0 to 2.2 eq) and HATU (1.0 to 1.1 eq) were added into a solution of the carboxylic acid derivative (1 eq) in anhydrous DMF (4 mL/mmol of carboxylic acid derivative) cooled at 0° C. The resulting mixture was stirred at 0° C. for a period of 5 to 30 minutes. Then the amidoxime derivative (1.0 to 1.2 eq) was added neat or as a DMF solution (2 mL/mmol of amidoxime derivative). The resulting mixture was stirred at 0° C. or RT for a period of 30 minutes to 18 hours. The reaction mixture was diluted with an adequate solvent, such as Et$_2$O, MTBE or EtOAc, and then washed with water and brine. The aqueous layers were extracted once. The organic layers were combined, dried (MgSO$_4$ or Na$_2$SO$_4$) and the solvents were removed under reduced pressure. The residue was taken up with ACN (8.5 mL/mmol of carboxylic acid derivative). The resulting mixture was heated at 150° C. for 30 min under MW irradiation. The reaction mixture was diluted with an adequate solvent, such as Et$_2$O, MTBE or EtOAc, and then washed with water and brine. The aqueous layers were extracted once. The organic layers were combined, dried (MgSO$_4$ or Na$_2$SO$_4$) and the solvents were evaporated under reduced pressure. Purification by flash chromatography or precipitation gave the expected oxadiazole derivative.

General procedure 5: General Procedure for the Oxadiazole Ring Formation

In a microwave vessel was added carboxylic acid derivative (1 eq), amidoxime derivative (1.1 eq), 1-ethyl-3-(3-dimethylaminopropyl)carbodiimide hydrochloride (1.4 eq), and CH3CN (1 mL/mmol of carboxylic acid). The reaction mixture was stirred at RT for 2 to 18 hours. Then pyridine was added (0.3 mL/mmol of carboxylic acid) and the mixture was heated at 150° C. for 30 minutes under microwave irradiation. The solvent was removed in vacuo and the residue partitioned between DCM and H2O. The layers were separated, the organic layer washed with H2O and the mixture passed through a hydrophobic frit. The solvents were removed in vacuo and the residue was purified by recrystallization, precipitation or flash chromatography, affording the expected oxadiazole derivative.

General Procedure 6: Benzylic Alcohol Oxydation

Benzylic Alcohol derivative (1 eq) was dissolved in dioxane (7 mL/mmol of benzylic alcohol) and manganese dioxide (8 eq) was added. The mixture was heated at 70° C. overnight and the solvents were removed in vacuo. The residue was triturated with a mixture of petrol/diethyl ether to give the corresponding benzaldehyde derivative.

General Procedure 7: Reductive Amination with Amino Acid Derivatives

Sodium cyanoborohydride (1.1 eq) was added to a solution of the aldehyde derivative (1 eq); 0.25 mmol) and the appropriate amino acid (2 eq) in a 1:1 methanol/DCM mixture (24 mL/mmol) and acetic acid (2.5 eq). The mixture was stirred at room temperature overnight and was filtered through a frit under positive pressure. To the filtrate was added formaldehyde (37% aqueous solution; 10 eq) followed by addition of AcOH until the pH was in the range of 3-4. To the resulting mixture was added sodium cyanoborohydride (5 eq), the mixture stirred for 16 hours, the solvent removed in vacuo and the residue purified by reverse phase HPLC.

General Procedure 8: Tert-Butyl Ester Hydrolysis

To tert-butyl ester derivative (1 eq) was added hydrochloric acid in dioxane (4N, 20-50 eq) and the reaction mixture was stirred at RT for 1 hour to 24 hours. The solution was then evaporated to dryness and the residue was purified by precipitation from a solvent such as $CH_3CN$, DCM, MTBE or $Et_2O$ to afford the title compound. When no precipitation occurred, the title compound was purified by reverse phase HPLC or Mass Directed Autoprep.

General Procedure 9: Methyl or Ethyl Ester Hydrolysis

To the methyl or ethyl ester derivative (1 eq) in a solution of MeOH or EtOH (5 mL/mmol of ester derivative) or MeOH/THF 1:1 or EtOH/THF 1:1 (5 mL/mmol of ester derivative) was added sodium hydroxide (5M, 5 eq) and the reaction mixture was stirred at RT for 1 hour to 24 hours. The solution was evaporated to dryness. The residue was taken up with EtOAc and washed with a 1N aqueous solution of HCl and brine. The organic layer was dried ($MgSO_4$) and concentrated under vacuum to afford the title compound.

General Procedure 10: Substitution of Benzyl Bromides with Primary and Secondary Amines To a solution of benzyl bromide derivative (1 eq) in $CH_3CN$ or DMF (1.5-3 mL/mmol of benzyl bromide derivative) was added $K_2CO_3$ or $NaHCO_3$ (2-3 eq) and a primary or secondary amine (1.2 eq). The reaction mixture was stirred at RT or at 60° C. overnight. Solvent was removed under vacuum and the resulting mixture was diluted with water, extracted with EtOAc, washed with a saturated solution of NaCl, dried over $MgSO_4$ and concentrated under vacuum. Purification by flash chromatography or recrystallization afforded the expected benzyl amine derivative.

General Procedure 11: Substitution of Benzyl Amines

To a solution of benzyl amine derivative (1 eq) in $CH_3CN$ or DMF (1.5-3 mL/mmol of benzyl amine derivative) was added $K_2CO_3$ or $NaHCO_3$ (2-3 eq) and an electrophile such as an alkyl bromoacetate derivative (1.2 eq). The reaction mixture was stirred at RT or at 60° C. overnight. Solvent was removed under vacuum and the resulting mixture was diluted with water, extracted with EtOAc, washed with a saturated solution of NaCl, dried over $MgSO_4$ and concentrated under vacuum. Purification by flash chromatography or recrystallization afforded the expected benzyl amine derivative.

General Procedure 12: N-oxyde Preparation

Compound of Formula (I) (1 eq) was dissolved in DCM (10 mL/mmol of oxadiazole derivative).

At 0° C., 3-chloroperoxybenzoic acid (1 eq.) was added. The mixture was stirred at room temperature for one hour. It was then evaporated and the crude product was purified on MD autoprep, affording the expected N-oxyde derivative.

Intermediate 1

2'-methyl-2-(trifluoromethyl)biphenyl-4-carboxylic acid

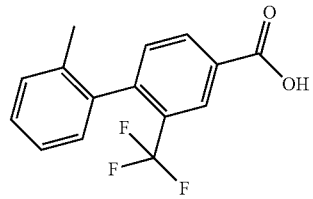 [SMILES: Cc1ccccc1-c1ccc(C(=O)O)cc1C(F)(F)F]

Step 1: Methyl 4-bromo-3-(trifluoromethyl)benzoate

To a suspension of 4-bromo-3-(trifluoromethyl)benzoic acid (Acceledev 000625, 15 g; 56 mmol) in MeOH (300 mL) at RT was added dropwise thionyl chloride (16 mL; 223 mmol) over 15 min. The reaction mixture was stirred at RT for 12 hours. The solvent was concentrated and the crude residue was diluted with EtOAc (500 mL). The organic layer was washed with a saturated aqueous solution of $NaHCO_3$ (200 mL), water (200 mL), brine (200 mL), dried over $MgSO_4$ and concentrated affording the title compound as an orange solid (14.8 g, 94%). $^1H$ NMR (DMSO-$d_6$, 300 MHz) δ 8.26 (m, 1H), 8.14-8.13 (m, 2H), 3.93 (s, 3H). HPLC (Method A) Rt 4.71 min (Purity: 99.0%).

Step 2: Methyl 2'-methyl-2-(trifluoromethyl)biphenyl-4-carboxylate

Methyl 4-bromo-3-(trifluoromethyl)benzoate (6 g; 21 mmol), o-tolylboronic acid (3.2 g; 23 mmol), potassium carbonate (14.7 g; 106 mmol), tetrakis(triphenylphosphine)palladium(0) (2.5 g; 2.12 mmol) were taken up in toluene (30 mL) and water (30 mL) under $N_2$ atmosphere. The reaction mixture was purged with vacuum for 5 minutes, then degassed with $N_2$ and then refluxed for 3 hours. The reaction mixture was cooled to RT, filtered over a pad of celite and washed with toluene (200 mL). The filtrate was concentrated, affording a brown oil which was taken in EtOAc (200 mL). The organic layer was washed with a saturated aqueous solution of $NaHCO_3$ solution (50 mL), water (50 mL) and brine (50 mL), dried over $MgSO_4$ and concentrated affording the title compound as a brown oil (6.4 g, quantitative). HPLC (Method A) Rt 5.33 min (Purity: 60.0%).

Step 3: 2'-methyl-2-(trifluoromethyl)biphenyl-4-carboxylic acid

A solution of methyl 2'-methyl-2-(trifluoromethyl)biphenyl-4-carboxylate (5 g; 17 mmol) in EtOH (150 mL) at RT was treated with sodium hydroxide (10.2 mL; 5 M; 51 mmol). The reaction mixture was stirred at 60° C. for 2 hours. The reaction mixture was concentrated to give a brown solid which was taken up in water (300 mL) and the aqueous phase was washed twice with EtOAc. The aqueous phase was acidified with HCl cc to pH 2, then it was concentrated until precipitation (half of the volume). The suspension was filtered affording the title compound as a beige solid. $^1$H NMR (DMSO-d$_6$, 300 MHz) δ 13.55 (br s, 1H), 8.31 (s, 1H), 8.26-8.23 (d, J=7.9 Hz, 1H), 7.51-7.48 (d, J=7.9 Hz 1H), 7.37-7.12 (m, 4H), 1.99 (s, 3H). LC/MS (Method A): 278.9 (M−H)$^-$. HPLC (Method A) Rt 4.57 min (Purity: 98.7%).

Intermediate 2

2'-(difluoromethyl)-2-methyl biphenyl-4-carboxylic acid

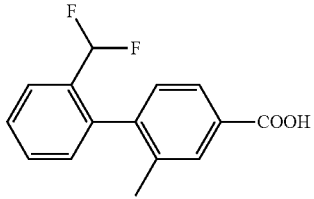 [SMILES: Cc1cc(C(=O)O)ccc1-c1ccccc1C(F)F]

Step 1: methyl 2'-(difluoromethyl)-2-methylbiphenyl-4-carboxylate

A mixture of methyl 3-methyl-4-(4,4,5,5-tetramethyl-1,3,2-dioxaborolan-2-yl)benzoate (Combiblocks PN-8756, 1.9 g, 6.7 mmol), 1-bromo-2-difluoromethyl-benzene (Fluorochem 023878, 1.7 g, 8.1 mmol), cesium fluoride (3.1 g, 20 mmol) and PdCl$_2$(PPh$_3$)$_2$ (142 mg, 0.20 mmol) was prepared in dioxane (20 mL) and water (10 mL) under N$_2$ atmosphere. The resulting mixture was heated at 90° C. for 2 hours. The reaction mixture was diluted with MTBE (60 mL), and then washed with water (2×50 mL) and brine (50 mL). The aqueous layers were extracted with MTBE (50 mL). The organic layers were combined, dried (MgSO$_4$) and concentrated under reduced pressure. After purification by flash chromatography (silica, DCM/heptane), the title compound was obtained as a colorless oil (1.4 g, 76%). HPLC (Method A) Rt 5.0 min (purity: 99.1%). $^1$H NMR (DMSO-d$_6$, 300 MHz) δ 7.93 (s, 1H), 7.84 (dd, J=7.9, 1.4 Hz, 1H), 7.75 (m, 1H), 7.67-7.56 (m, 2H), 7.28 (m, 2H), 6.55 (t, J=55 Hz, 1H), 3.88 (s, 3H), 2.06 (s, 3H).

Step 2: 2'-(difluoromethyl)-2-methylbiphenyl-4-carboxylic acid

A 5 N aqueous solution of NaOH (1.5 mL, 7.5 mmol) was added into a solution of methyl 2'-(difluoromethyl)-2-methylbiphenyl-4-carboxylate (1.4 g, 5.1 mmol) in EtOH (15 mL). The resulting mixture was heated at 70° C. for 1 hour, and then evaporated. The residue was taken up with water (25 mL) and a 5N aqueous solution of HCl (3 mL), and then extracted with MTBE (2×50 mL). The organic layers were washed with brine (25 mL), combined, dried (MgSO$_4$) and concentrated reduced pressure to give the title compound as a white powder (1.3 g, 93%). HPLC (Method A) Rt 4.2 min (purity: 98.9%). LC/MS (Method B): 261.1 (M−H)$^-$. $^1$H NMR (DMSO-d$_6$, 300 MHz) δ 13.1 (s, 1H), 7.90 (s, 1H), 7.82 (dd, J=7.9, 1.4 Hz, 1H), 7.74 (m, 1H), 7.66-7.55 (m, 2H), 7.26 (m, 2H), 6.55 (t, J=55 Hz, 1H), 2.05 (s, 3H).

Intermediate 3

2-(methoxymethyl)-2'-methyl biphenyl-4-carboxylic acid

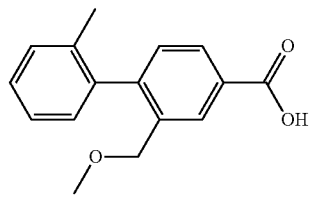 [SMILES: COCc1cc(C(=O)O)ccc1-c1ccccc1C]

Step 1: Methyl 4-bromo-3-(bromomethyl)benzoate

Under N$_2$ atmosphere, to a solution of methyl 4-bromo-3-methylbenzoate (Aldrich 532878, 50 g; 218 mmol) in CHCl$_3$ (1 L) were added NBS (47 g; 262 mmol) in one portion and α,α'-azoisobutyronitrile (720 mg; 4.4 mmol). The mixture was stirred at 70° C. for 2 days. The reaction mixture was cooled to RT and water (500 mL) was added. The organic layer was washed with 50 mL NaHCO$_3$ saturated solution, water (340 mL), then brine (500 mL), dried over MgSO$_4$ and concentrated affording the title compound as a yellow solid. It was washed with pentane (2×500 mL) affording the title compound as a yellow solid. $^1$H NMR (DMSO-d$_6$, 300 MHz) δ 8.24 (d, J=1.9 Hz, 1H), 7.88-7.82 (m, 2H), 4.87 (s, 2H), 3.91 (s, 3H). HPLC (Method A) Rt 4.44 min (Purity: 97.9%).

Step 2: Methyl 4-bromo-3-(methoxymethyl)benzoate

A solution of methyl 4-bromo-3-(bromomethyl)benzoate (38 g; 122 mmol) in MeOH (1.1 L) was refluxed for 4 days. After concentration, the mixture was partitioned between EtOAc (500 mL) and water (200 mL). The organic layer was washed with a 5% NaHCO$_3$ aqueous solution (200 mL), brine (200 mL), dried over MgSO$_4$ and concentrated affording the title compound as a beige solid (30 g, 94%). $^1$H NMR (DMSO-d$_6$, 300 MHz) δ 8.06-8.05 (m, 1H), 7.83 (m, 2H), 4.54 (m, 2H), 3.90 (s, 3H), 3.45 (s, 3H). LC/MS (Method B): 227.2 (M−H)$^-$. HPLC (Method A) Rt 4.42 min (Purity: 93.0%).

Step 3: Methyl 2-(methoxymethyl)-2'-methylbiphenyl-4-carboxylate

Methyl 4-bromo-3-(methoxymethyl)benzoate, (40 g; 154 mmol), o-tolylboronic acid (23 g; 170 mmol), K$_2$CO$_3$ (107 g; 772 mmol), tetrakis(triphenylphosphine)palladium (0) (1.8 g; 1.5 mmol) were taken up in toluene (200 mL) and water (200 mL) under N$_2$ atmosphere. The reaction mixture was purged with vacuum, then degassed with N$_2$ and then refluxed for 1 hour. The reaction mixture was cooled to RT, filtered over a pad of celite and washed with EtOAc (1 L). The filtrate was concentrated, affording a yellow oil which was taken in EtOAc (800 mL). The organic layer was washed with a saturated aqueous solution of NaHCO$_3$ solution (250 mL), water (250 mL) and brine (250 mL), dried over MgSO$_4$ and concentrated affording the title compound as a yellow oil used without further purification (42 g, quantitative). HPLC (Method A) Rt 5.34 min (Purity: 89.4%).

Step 4: 2-(methoxymethyl)-2'-methylbiphenyl-4-carboxylic acid

A solution of methyl 2-(methoxymethyl)-2'-methylbiphenyl-4-carboxylate (40 g; 148 mmol; 1 eq.) in EtOH (1.2 L) at RT was treated with NaOH (89 mL; 5 M; 445 mmol). The reaction mixture was stirred at 60° C. for 1 hour. The reaction mixture was cooled to RT and concentrated to give a yellow solid which was taken up in water (800 mL) and the aqueous phase was washed twice with EtOAc. The aqueous phase was acidified with HCl cc (40 mL) to pH 2 and it was extracted with EtOAc (2×400 mL). The combined organics were washed with brine, dried over MgSO$_4$ and concentrated affording the title compound as a yellow solid (35 g, 92%). $^1$H NMR (DMSO-d$_6$, 300 MHz) δ 12.99 (br s, 1H), 8.09 (s, 1H), 7.92-7.89 (m, 1H), 7.33-7.22 (m, 4H), 7.10-7.08 (m, 1H), 4.11 (m, 2H), 3.18 (s, 3H), 1.99 (s, 3H). LC/MS (Method B): 255.2 (M−H)$^-$. HPLC (Method A) Rt 4.52 min (Purity: 96.4%).

Intermediate 4

2-methyl-2'-(trifluoromethyl)biphenyl-4-carboxylic acid

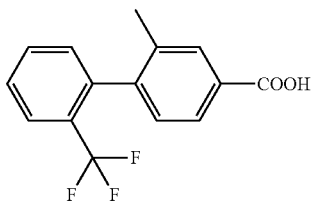 [SMILES: Cc1cc(C(=O)O)ccc1-c1ccccc1C(F)(F)F]

A mixture of methyl 4-bromo-3-methylbenzoate (20 g, 87 mmol), 2-(trifluoromethyl)benzeneboronic acid (24.9 g, 131 mmol), potassium carbonate (24 g, 175 mmol) and bis(tricyclohexylphosphine)palladium (II) dichloride (65 mg, 0.1 mmol) was prepared in dioxane (200 mL) and water (50 mL) under N$_2$ atmosphere. The mixture was heated at 100° C. for 3 hours. A 5N aqueous solution of NaOH (100 mL) was added and the reaction mixture was stirred at 100° C. for one additional hour. The reaction mixture was cooled at RT and the aqueous layer was removed. The organic layer was filtered through a celite pad, concentrated until 75 mL under reduced pressure, diluted with water (125 mL) and washed with MTBE (2×200 mL). The aqueous layer was acidified to pH 1 with a 5N aqueous solution of HCl (25 mL) and extracted with MTBE (2×100 mL). The organic layers were combined, dried (Na$_2$SO$_4$) and filtered through a celite pad. The solution was concentrated until 100 mL, then heptane was added (200 mL). The mixture was concentrated until 100 mL. The precipitate was filtered off and rinsed twice with heptane, then dried under reduced pressure to give the title compound as a white powder (22.5 g, 92%). HPLC (Method A), Rt 4.4 min (purity: 100%). LC/MS (Method B): 279.0 (M−H)$^-$. $^1$H NMR (DMSO-d$_6$, 300 MHz) δ 13.0 (s, 1H), 7.87 (m, 2H), 7.80 (dd, J=7.9, 1.6 Hz, 1H), 7.75 (m, 1H), 7.64 (m, 1H), 7.34 (d, J=7.6 Hz, 1H), 7.23 (d, J=7.9 Hz, 1H), 2.02 (s, 3H).

Intermediate 5 tert-butyl 2-[{4-[amino(hydroxyimino)methyl]-2-fluorobenzyl}(methyl)amino]butanoate

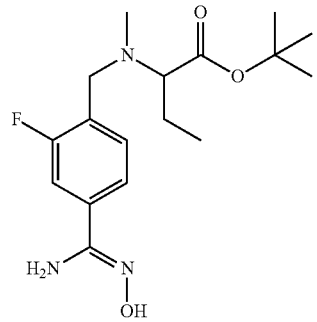 [SMILES: CCC(C(=O)OC(C)(C)C)N(C)Cc1ccc(/C(N)=N/O)cc1F]

Step 1: 3-fluoro-4-[(methylamino)methyl]benzonitrile

A solution of 4-cyano-2-fluoro-benzylbromide (15 g, 0.07 mol) in dry THF (50 mL) was added to the 40% aqueous solution of methyl amine (400 mL) at 5-10° C. and allowed to stir for 5 min. The mixture was extracted with DCM and the organic layer was dried over Na$_2$SO$_4$ and concentrated under vacuum, affording the title compound as a brown liquid (10 g, 89%). $^1$H NMR (DMSO-d$_6$, 400 MHz) δ 7.77 (m, 1H), 7.68-7.61 (m, 2H), 3.71 (s, 2H), 2.24 (s, 3H).

Step 2: tert-butyl 2-[(2-fluoro-4-isocyanobenzyl)(methyl)amino]butanoate

The title compound was prepared following the general procedure 11 starting from 3-fluoro-4-[(methylamino)methyl]benzonitrile and tert-butyl-2-bromo butyrate. It was isolated as a colorless liquid (9.5 g, 71%). $^1$H NMR (DMSO-d$_6$, 400 MHz) δ 7.80 (m, 1H), 7.68 (m, 1H), 7.61 (t, J=7.4 Hz, 1H), 3.85-3.70 (dd, J=14.9, 32.1 Hz, 2H), 3.08-3.04 (t, J=7.6 Hz, 1H), 2.19 (3H, s), 1.70-1.63 (m, 2H), 1.42 (s, 9H), 0.87-0.83 (t, J=7.3 Hz, 3H).

Step 3: tert-butyl 2-[{4-[amino(hydroxyimino)methyl]-2-fluorobenzyl}(methyl)amino]butanoate The title compound was prepared following the general procedure 2 starting from tert-butyl 2-[(2-fluoro-4-isocyanobenzyl)(methyl)amino]butanoate. It was isolated as a white solid. $^1$H NMR (DMSO-d$_6$, 400 MHz) δ 9.72 (s, 1H), 7.49 (m, 1H), 7.39 (m, 2H), 5.85 (s, 2H), 3.77-3.62 (m, 2H), 3.04 (t, J=7.5 Hz, 1H), 2.19 (s, 3H), 1.61 (m, 2H), 1.44 (s, 9H), 0.85 (t, J=7.3 Hz, 3H). LC/MS (Method A) 307.3 (M+H)$^+$. HPLC (Method A) Rt; 2.3 min (Purity: 98.2%).

Intermediate 6 methyl N-((1R)-1-{4-[amino(hydroxyimino)methyl]phenyl}ethyl)-D-alaninate

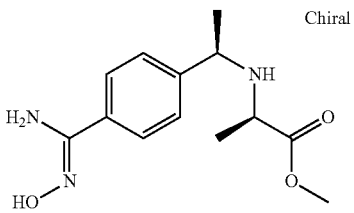 [SMILES: COC(=O)[C@@H](C)N[C@H](C)c1ccc(/C(N)=N/O)cc1]

Step 1: methyl N-[(1R)-1-(4-cyanophenyl)ethyl]-D-alaninate and methyl N-[(1R)-1-(4-cyanophenyl)ethyl]-L-alaninate To 4-[(1R)1-aminoethyl)]benzonitrile (Haoyuan Chemexpress, 3.4 g; 23 mmol) in DMF (34 mL) was added sodium bicarbonate (3.9 g; 46 mmol) and methyl 2-bromopropionate (2.8 mL; 25 mmol). The reaction mixture was stirred at 75° C. overnight. EtOAc was added to the reaction mixture and the organic phase was washed three times with $H_2O$ and once with brine, organic layer was then dried over $MgSO_4$, filtered and concentrated. The crude product was purified by flash chromatography (EtOAc/Heptane gradient from 5:95 to 25:75), affording methyl N-[(1R)-1-(4-cyanophenyl)ethyl]-D-alaninate (first eluting compound) as a white solid (2.1 g, 40%) and methyl N-[(1R)-1-(4-cyanophenyl)ethyl]-L-alaninate (second eluting compound) as an orange solid (2.3 g, 43%).

methyl N-[(1R)-1-(4-cyanophenyl)ethyl]-D-alaninate:

$^1$H NMR (DMSO-$d_6$, 300 MHz) δ 7.78 (d, J=8.4 Hz, 2H), 7.51 (d, J=8.3 Hz, 2H), 3.75 (q, J=6.3 Hz, 1H), 3.62 (s, 3H), 2.95-2.81 (m, 1H), 2.71-2.58 (m, 1H), 1.22 (d, J=6.4 Hz, 3H), 1.14 (d, J=7.0 Hz, 3H). LC/MS (Method B): 233.0 (M+H)$^+$. HPLC (Method A) Rt 1.58 min (Purity: 70.7%).

methyl N-[(1R)-1-(4-cyanophenyl)ethyl]-L-alaninate:

$^1$H NMR (DMSO-$d_6$, 300 MHz) δ 7.77 (d, J=8.4 Hz, 2H), 7.53 (d, J=8.1 Hz, 2H), 3.86 (q, J=6.1 Hz, 1H), 3.46 (s, 3H), 3.26-3.13 (m, 1H), 2.53 (m, 1H), 1.23 (d, J=6.6 Hz, 3H), 1.17 (d, J=6.8 Hz, 3H). LC/MS (Method B): 233.0 (M+H), n.d (M−H). HPLC (Method A) Rt 1.49 min (Purity: 72.4%).

Step 2: methyl N-((1R)-1-{4-[amino(hydroxyimino)methyl]phenyl}ethyl)-D-alaninate The title compound was prepared following the general procedure 1 starting from methyl N-[(1R)-1-(4-cyanophenyl)ethyl]-D-alaninate. It was isolated as a yellowish oil (2.3 g, 93%). $^1$H NMR (DMSO-$d_6$, 300 MHz) δ 9.56 (s, 1H), 7.59 (d, J=8.3 Hz, 2H), 7.28 (d, J=8.3 Hz, 2H), 5.76 (s, 2H), 3.72-3.57 (m, 4H), 3.03-2.82 (m, 1H), 2.49-2.41 (m, 1H), 1.21 (d, J=6.6 Hz, 3H), 1.13 (d, J=7.1 Hz, 3H). LC/MS (Method B): 266.1 (M+H)$^+$.

Intermediate 7 methyl N-[(1R)-1-(4-cyanophenyl)ethyl]-L-alaninate

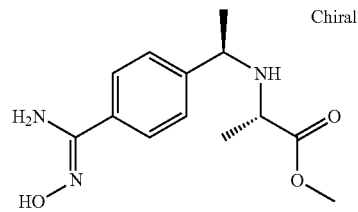 [SMILES: COC(=O)[C@H](C)N[C@H](C)c1ccc(/C(N)=N/O)cc1]

The title compound was prepared following the general procedure 1, starting from methyl N-[(1R)-1-(4-cyanophenyl)ethyl]-L-alaninate (synthesis described under intermediate 6, step 1). It was isolated as a yellow oil (2.1 g, 80%). $^1$H NMR (DMSO-$d_6$, 300 MHz) δ 9.57 (s, 1H), 7.59 (d, J=8.3 Hz, 2H), 7.30 (d, J=8.3 Hz, 2H), 5.76 (s, 2H), 3.82-3.70 (m, 1H), 3.49 (s, 3H), 3.26-3.13 (m, 1H), 2.35-2.26 (m, 1H), 1.23 (d, J=6.6 Hz, 3H), 1.17 (d, J=6.8 Hz, 3H). LC/MS (Method A): 266.1 (M+H)$^+$.

Intermediate 8 tert-butyl N-((1S)-1-{4-[(hydroxyamino)(imino)methyl]phenyl}ethyl)glycinate

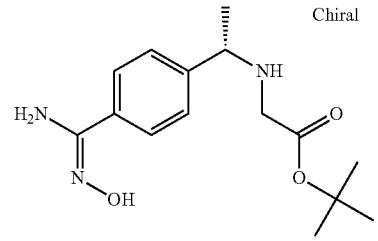 [SMILES: C[C@H](NCC(=O)OC(C)(C)C)c1ccc(/C(N)=N\O)cc1]

Step 1: tert-butyl N-[(1S)-1-(4-cyanophenyl)ethyl]glycinate

The title compound was prepared following the general procedure 11, starting from 4-[(1S)-1-aminoethyl)]benzonitrile (Haoyuan Chemexpress) and tert-butyl bromoacetate. It was isolated as a yellow oil (1.3 g, 73%). $^1$H NMR (DMSO-$d_6$, 300 MHz) δ 7.78 (d, J=8.3 Hz, 2H), 7.51 (d, J=8.3 Hz, 2H), 3.81 (m, 1H), 3.00 (m, 2H), 2.45 (m, 1H), 1.37 (s, 9H), 1.24 (d, J=6.6 Hz, 3H). LC/MS (Method B): 233.0 (M+H)$^+$.

Step 2: tert-butyl N-((1S)-1-{4-[(hydroxyamino)(imino)methyl]phenyl}ethyl)glycinate The title compound was prepared following the general procedure 1 starting from tert-butyl N-[(1S)-1-(4-cyanophenyl)ethyl]glycinate, and was isolated as a white foam (1.3 g, 87%). $^1$H NMR (DMSO-$d_6$, 300 MHz) δ 9.57 (s, 1H), 7.60 (d, J=8.3 Hz, 2H), 7.28 (d, J=8.3 Hz, 2H), 5.76 (brs, 2H), 3.73 (m, 1H), 3.43 (m, 1H), 3.01 (m, 2H), 1.38 (s, 9H), 1.24 (d, J=6.6 Hz, 3H).

Intermediate 9 tert-butyl N-((1R)-1-{4-[(hydroxyamino)(imino)methyl]phenyl}ethyl)glycinate

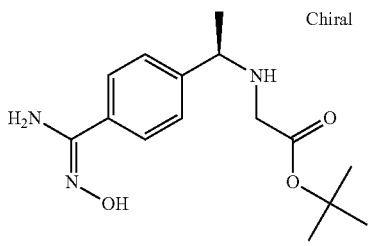 [SMILES: C[C@@H](NCC(=O)OC(C)(C)C)c1ccc(/C(N)=N\O)cc1]

Step 1: tert-butyl N-[(1R)-1-(4-cyanophenyl)ethyl]glycinate

The title compound was prepared following the general procedure 11, starting from 4-[(1R)-1-aminoethyl)]benzonitrile (Haoyuan Chemexpress) and tert-butyl bromoacetate and was isolated as a yellow oil. $^1$H NMR (DMSO-$d_6$, 300 MHz) δ 7.78 (d, J=8.2 Hz, 2H), 7.51 (d, J=8.2 Hz, 2H), 3.82 (m, 1H), 3.00 (m, 2H), 2.47 (m, 1H), 1.37 (s, 9H), 1.24 (d, J=6.6 Hz, 3H). HPLC (Method A) Rt 2.77 min (Purity: 99.4%).

Step 2: tert-butyl N-((1R)-1-{4-[(hydroxyamino)(imino)methyl]phenyl}ethyl)glycinate The title compound was prepared following the general procedure 1 starting from tert-butyl N-[(1R)-1-(4-cyanophenyl)ethyl]glycinate and was isolated as a yellow oil (800 mg, 86%). $^1$H NMR (DMSO-$d_6$, 300 MHz) δ 9.57 (s, 1H), 7.60 (d, J=8.2 Hz, 2H), 7.28 (d, J=8.2 Hz, 2H), 5.76 (brs, 2H), 3.73 (m, 1H), 3.43 (m, 1H), 3.01 (m, 2H), 1.38 (s, 9H), 1.24 (d, J=6.6 Hz, 3H).

Intermediate 10 methyl N-((1S)-1-{4-[(hydroxyamino)(imino)methyl]phenyl}ethyl)-D-alaninate

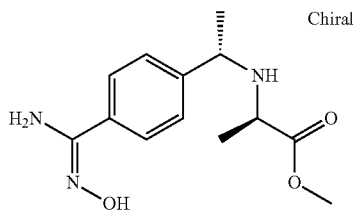 [SMILES: COC(=O)[C@@H](C)N[C@@H](C)c1ccc(/C(N)=N\O)cc1]

Step 1: methyl N-[(1S)-1-(4-cyanophenyl)ethyl]-D-alaninate and methyl N-[(1S)-1-(4-cyanophenyl)ethyl]-L-alaninate To 4-[(1S)-1-aminoethyl)]benzonitrile (Haoyuan Chemexpress, 1 g; 6.8 mmol) in DMF (15 mL) was added sodium bicarbonate (1.2 g; 14 mmol) and methyl 2-bromopropionate (0.84 mL; 7.5 mmol). The reaction mixture was stirred at 75° C. overnight. EtOAc was added and the organic phase was washed with three times with H$_2$O and once with brine, organic layer was then dried over MgSO$_4$, filtered and concentrated. The crude product was purified by flash chromatography (EtOAc/Heptane gradient from 5:95 to 25:75), affording methyl N-[(1S)-1-(4-cyanophenyl)ethyl]-L-alaninate (first eluting compound) as a pale yellow solid (480 mg; 30%) and methyl N-[(1S)-1-(4-cyanophenyl)ethyl]-D-alaninate (second eluting compound) as a yellow solid (470 mg; 30%).

methyl N-[(1S)-(4-cyanophenyl)ethyl]-L-alaninate: $^1$H NMR (DMSO-$d_6$, 300 MHz) δ 7.77 (d, J=8.4 Hz, 2H), 7.51 (d, J=8.3 Hz, 2H), 3.74 (m, 1H), 3.61 (s, 3H), 2.93-2.81 (m, 1H), 2.64 (m, 1H), 1.21 (d, J=6.5 Hz, 3H), 1.13 (d, J=7.0 Hz, 3H). LC/MS (Method B): 233.1 (M+H)$^+$. HPLC (Method A) Rt 1.57 min (Purity: 79%).

methyl N-[(1S)-1-(4-cyanophenyl)ethyl]-D-alaninate: 1H NMR (DMSO-d6, 300 MHz) δ 7.77 (d, J=8.3 Hz, 2H), 7.53 (d, J=8.3 Hz, 2H), 3.85 (q, J=6.1 Hz, 1H), 3.45 (s, 3H), 3.25-3.13 (m, 1H), 2.53 (m, 1H), 1.23 (d, J=6.6 Hz, 3H), 1.16 (d, J=6.8 Hz, 3H). LC/MS (Method B): 233.0 (M+H)$^+$. HPLC (Method A) Rt 1.52 min (Purity: 89.2%).

Step 2: methyl N-((1S)-1-{4-[(hydroxyamino)(imino)methyl]phenyl}ethyl)-D-alaninate The title compound was prepared following the general procedure 1 starting from methyl N-[(1S)-1-(4-cyanophenyl)ethyl]-D-alaninate. It was isolated as a colorless oil (500 mg, 93%). $^1$H NMR (DMSO-$d_6$, 300 MHz) δ 9.57 (s, 1H), 7.59 (d, J=8.3 Hz, 2H), 7.29 (d, J=8.3 Hz, 2H), 5.76 (brs, 2H), 3.76 (m, 1H), 3.49 (s, 3H), 3.27-3.12 (m, 1H), 2.31 (m, 1H), 1.23 (d, J=6.6 Hz, 3H), 1.17 (d, J=6.8 Hz, 3H). LC/MS (Method B): 266.1 (M+H)$^+$.

Intermediate 11 methyl N-((1S)-1-{4-[(hydroxyamino)(imino)methyl]phenyl}ethyl)-L-alaninate

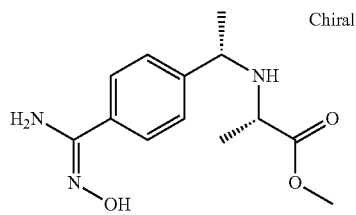 [SMILES: COC(=O)[C@H](C)N[C@@H](C)c1ccc(/C(N)=N\O)cc1]

The title compound was prepared following the general procedure 1, starting from methyl N-[(1S)-1-(4-cyanophenyl)ethyl]-L-alaninate (synthesis described under intermediate 10, step 1). It was isolated as a colorless oil. $^1$H NMR (DMSO-$d_6$, 300 MHz) δ 9.56 (s, 1H), 7.59 (d, J=8.3 Hz, 2H), 7.27 (d, J=8.3 Hz, 2H), 5.75 (brs, 2H), 3.66 (m, 1H), 3.61 (s, 3H), 2.92 (m, 1H), 2.49-2.41 (m, 1H), 1.21 (d, J=6.6 Hz, 3H), 1.13 (d, J=6.9 Hz, 3H). LC/MS (Method A): 266.1 (M+H)$^+$.

Intermediate 12 ethyl (2S)-2-[((1R)-1-{4-[amino(hydroxyimino)methyl]phenyl}ethyl)amino]butanoate

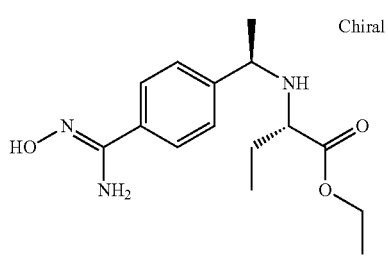 [SMILES: CCOC(=O)[C@H](CC)N[C@H](C)c1ccc(/C(N)=N/O)cc1]

Step 1: Ethyl (2S)-2-{[(1R)-1-(4-cyanophenyl)ethyl]amino}butanoate and ethyl (2R)-2-{[(1R)-1-(4-cyanophenyl)ethyl]amino}butanoate The title compound was prepared following the general procedure 11, starting from 4-[(1R)-1-aminoethyl)]benzonitrile (Haoyuan Chemexpress) and ethyl 2-bromobutyrate. The crude product was purified by flash chromatography (EtOAc/Heptane gradient from 5:95 to 25:75), affording ethyl (2S)-2-{[(1R)-1-(4-cyanophenyl)ethyl]amino}butanoate (second eluting compound) as a colorless oil (345 mg, 19%) and ethyl (2R)-2-{[(1R)-1-(4-cyanophenyl)ethyl]amino}butanoate (first eluting compound) as a colorless oil (460 mg, 26%).

Ethyl (2S)-2-{[(1R)-1-(4-cyanophenyl)ethyl]amino}butanoate:

$^1$H NMR (DMSO-d$_6$, 300 MHz) δ 7.76 (d, J=8.4 Hz, 2H), 7.52 (d, J=8.4 Hz, 2H), 3.86 (m, 2H), 3.05 (m, 1H), 2.42 (m, 1H), 1.51 (m, 2H), 1.23 (d, J=6.7 Hz, 3H), 1.07 (t, J=7.1 Hz, 3H), 0.82 (t, J=7.4 Hz, 3H). LC/MS (Method B): 261.0 (M+H)$^+$.

Ethyl (2R)-2-{[(1R)-1-(4-cyanophenyl)ethyl]amino}butanoate:

$^1$H NMR (DMSO-d$_6$, 300 MHz) δ 7.78 (d, J=8.3 Hz, 2H), 7.51 (d, J=8.3 Hz, 2H), 4.09 (q, J=7.01 Hz, 2H), 3.72 (m, 2H), 2.51 (m, 1H), 1.50 (m, 2H), 1.22 (d, J=6.5 Hz, 3H), 1.17 (t, J=7.1 Hz, 3H), 0.82 (t, J=7.5 Hz, 3H). LC/MS (Method B): 261.0 (M+H)$^+$. HPLC (Method A) Rt 2.17 min (Purity: 99%).

Step 2: Ethyl (2S)-2-[((1R)-1-{4-[amino(hydroxyimino)methyl]phenyl}ethyl)amino]butanoate The title compound was prepared following the general procedure 1, starting from ethyl (2S)-2-{[(1R)-1-(4-cyanophenyl)ethyl]amino}butanoate and was isolated as a colorless oil (330 mg, 85%). $^1$H NMR (DMSO-d$_6$, 300 MHz) δ 9.57 (s, 1H), 7.59 (d, J=8.3 Hz, 2H), 7.29 (d, J=8.3 Hz, 2H), 5.76 (brs, 2H), 3.95-3.85 (m, 2H), 3.71 (m, 1H), 3.07 (m, 1H), 2.19 (m, 1H), 1.55 (m, 2H), 1.24 (d, J=6.6 Hz, 3H), 1.10 (t, J=7.1 Hz, 3H), 0.82 (t, J=7.4 Hz, 3H). LC/MS (Method B): 294.0 (M+H)$^+$.

Intermediate 13 ethyl (2R)-2-[((1R)-1-{4-[amino(hydroxyimino)methyl]phenyl}ethyl)amino]butanoate

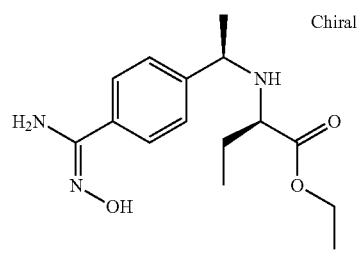 [SMILES: CCOC(=O)[C@@H](CC)N[C@H](C)c1ccc(/C(N)=N\O)cc1]

The title compound was prepared following the general procedure 1 starting ethyl (2R)-2-{[(1R)-1-(4-cyanophenyl)ethyl]amino}butanoate (synthesis described under intermediate 12, step 1) and was isolated as a solid (480 mg, 93%). $^1$H NMR (DMSO-d$_6$, 300 MHz) δ 9.57 (s, 1H), 7.59 (d, J=8.2 Hz, 2H), 7.29 (d, J=8.2 Hz, 2H), 5.76 (brs, 2H), 4.10 (q, 2H, J=7.1 Hz), 3.63 (m, 1H), 2.72 (m, 1H), 2.34 (m, 1H), 1.49 (m, 2H), 1.25-1.13 (m, 6H), 0.81 (t, J=7.5 Hz, 3H). LC/MS (Method B): 294.0 (M+H)$^+$.

Intermediate 14

Ethyl 2-({3-[amino(hydroxyimino)methyl]-5-fluorobenzyl}amino)-4-methylpentanoate

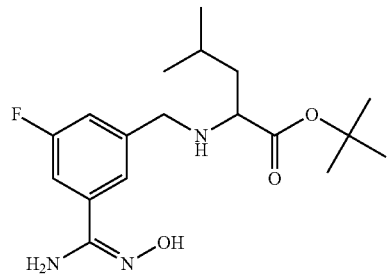 [SMILES: CC(C)CC(NCc1cc(F)cc(/C(N)=N\O)c1)C(=O)OC(C)(C)C]

Step 1: 3-(Bromomethyl)-5-fluorobenzonitrile

3-Fluoro-5-methylbenzonitrile (Hognda Trading; 100 g, 0.74 mol) was taken in acetonitrile (1 L) at 25° C. under nitrogen atmosphere. N-Bromosuccinimide (105 g, 0.59 mol) and AIBN (2.4 g, 0.014 mol) were added and the reaction mixture was heated at 70° C. for 1 h 20 minutes. The reaction mixture was cooled to 25° C. and concentrated. The residue was diluted, cooled to 0-5° C. and stirred for 15 minutes at the same temperature. The precipitated succinimide was filtered and the filtrate was concentrated to get crude product as yellow oil (90 g). It was taken in petroleum ether (200 mL) and cooled to −20° C. stirred for 30 minutes. The precipitated solids were filtered and dried to get the title product as white solid. $^1$H NMR (DMSO-d$_6$; 400 MHz): δ 7.83 (m, 2H), 7.73 (m, 1H), 4.72 (s, 2H). HPLC (Method A) Rt: 4.17 min (Purity: 99.4%).

Step 2: tert-butyl 2-[(3-cyano-5-fluorobenzyl) amino]-4-methylpentanoate

To 3-(bromomethyl)-5-fluorobenzonitrile (4.0 g, 0.02 mol) in dry DMF (40 mL) were added sodium bicarbonate (3.9 g, 0.046 mol) and ethyl D-leucine tert-butyl ester hydrochloride (4.2 g, 0.019 mol). The reaction mixture was stirred at RT for 16 hours. It was diluted with water and extracted with ethyl acetate. The organic phase was washed with water, brine, dried and concentrated. The crude product was purified by chromatography using petroleum ether/ethyl acetate as eluent, affording the title compound as a colorless liquid. $^1$H NMR (DMSO-$d_6$, 400 MHz): δ 7.68 (d, J=9.5 Hz, 1H), 7.63 (s, 1H), 7.53 (d, J=9.8 Hz, 1H), 3.78 (d, 1H), 3.64 (d, 1H), 2.97 (d, 1H), 2.60 (brs, 1H), 1.97-1.71 (m, 1H), 1.36 (m, 11H), 0.86 (d, 3H), 0.80 (d, 3H).

Step 3: Ethyl 2-({3-[amino(hydroxyimino)methyl]-5-fluorobenzyl}amino)-4-methylpentanoate To tert-butyl 2-[(3-cyano-5-fluorobenzyl)amino]-4-methylpentanoate (3.0 g, 9.4 mmol) in ethanol (30 mL) was added hydroxylamine (1.2 mL, 0.019 mol) and it was stirred at 0° C. for 16 hrs. The reaction mixture was diluted with water (250 mL) and extracted with ethyl acetate. The organic layer was separated, washed with brine, dried and concentrated. The crude product was purified by chromatography using petroleum ether/ethyl acetate as eluent, affording the title compound as a white solid (2.3 g, 70%). $^1$H NMR (DMSO-$d_6$, 400 MHz): δ 9.73 (s, 1H), 7.46 (s, 1H), 7.30 (d, J=9.6 Hz, 1H), 7.13 (d, J=9.6 Hz, 1H), 5.84 (s, 2H), 3.75 (d, 1H), 3.55 (d, 1H), 2.98 (s, 1H), 2.38 (brs, 1H), 1.76-1.69 (m, 1H), 1.40 (s, 9H), 1.37 (dd, 2H), 0.96 (d, 3H), 0.87 (d, 3H). LC/MS (Method B) 354.3 (M+H)$^+$. HPLC (Method A) Rt: 2.96 min (Purity 98.3%).

Intermediate 15 tert-butyl N-{4-[amino(hydroximino)methyl]-2-fluorobenzyl}-N-methylvalinate

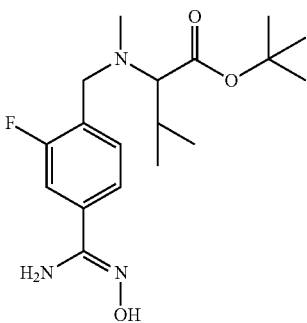 [SMILES: CC(C)C(C(=O)OC(C)(C)C)N(C)Cc1ccc(/C(N)=N/O)cc1F]

Step 1: tert-butyl 2-amino-3-methylbutanoate

To a stirred solution of DL-valine (25 g, 0.213 mol) in tert-butyl acetate (250 mL) at 00° C., was added HClO$_4$ (64.2 g, 0.320 mol) portionwise. The reaction mixture was stirred for 36 h at RT. It was diluted with water and extracted in ethyl acetate (500 mL). The organic layer was washed with a 10% sodium bicarbonate solution (2×150 mL), dried over Na$_2$SO$_4$ and concentrated, affording of the title compound as brown liquid. $^1$H NMR (DMSO-$d_6$, 400 MHz) δ 7.31 (brs, 2H), 3.62 (d, J=4.4 Hz, 1H), 1.98 (d, J=1.7 Hz, 1H), 1.44 (s, 9H), 0.95 (m, 6H).

Step 2: tert-butyl 2-[(4-cyano-2-fluorobenzyl) amino]-3-methylbutanoate

To a stirred solution of tert-butyl 2-amino-3-methylbutanoate (8.5 g, 0.05 mol) in dry DMF (50 mL) under nitrogen, was added 4-cyano-2-fluoro-benzyl bromide (FluoroChem Ltd, 9.4 g, 0.044 mol) and NaHCO$_3$ (10.2 g, 0.12 mol). The resulting mixture was stirred at RT for 16 h. Water (70 mL) was added and the desired product was extracted with ethyl acetate (2×100 mL). The organic layer was washed with water (3×100 mL) and the solvent was dried over Na$_2$SO$_4$ and concentrated under vacuum. The resulted residue was purified by column chromatography using petroleum ether/ethyl acetate as eluent, affording of the title compound as colorless liquid. $^1$H NMR (DMSO-$d_6$, 400 MHz) δ 7.77 (d, J=10.2 Hz, 1H), 7.67 (t, J=1.5 Hz, 1H), 3.85-3.79 (m, 2H), 2.72 (m, 1H), 2.49 (m, 1H), 1.81 (m, 1H), 1.37 (s, 9H), 0.86 (m, 6H).

Step 3: tert-butyl 2-[(4-cyano-2-fluorobenzyl)(methyl)amino]-3-methylbutanoate Tert-butyl 2-[(4-cyano-2-fluorobenzyl)amino]-3-methylbutanoate (7.2 g, 0.023 mol) in DMF (20 mL) was added dropwise to a stirred suspension of sodium hydride (2.2 g, 0.047 mol) in dry DMF (10 mL) at 00° C. The resulting mixture was stirred for 20 min at RT. Methyl iodide (6 mL, 0.094 mol) was then added dropwise at 0° C. and the mixture was allowed to stir for 3 hr at RT. The reaction mixture was quenched in ice water and extracted with ethyl acetate (250 mL). The organic layer was washed with water (3×100 mL) and dried over Na$_2$SO$_4$ and concentrated under reduced pressure. The crude product was purified by column chromatography using petroleum ether and ethyl acetate as eluent, affording the title compound as colorless liquid. $^1$H NMR (DMSO-$d_6$, 400 MHz) δ 7.80 (d, J=10 Hz, 1H), 7.69 (d, J=7.9 Hz, 2H), 7.60 (t, J=7.4 Hz, 1H), 3.79 (d, J=15 Hz, 1H), 3.64 (d, J=15 Hz, 1H), 2.65 (d, J=10.7 Hz, 1H), 2.18 (s, 3H), 1.44 (s, 9H), 0.92-0.83 (m, 6H).

Step 4: tert-butyl N-{4-[amino(hydroxyimino)methyl]-2-fluorobenzyl}-N-methylvalinate To a stirred solution of tert-butyl 2-[(4-cyano-2-fluorobenzyl)(methyl)amino]-3-methylbutanoate (3.4 g, 0.011 mol), in ethanol (30 mL), was added 50% aqueous. hydroxylamine (1.4 mL, 0.021 mol). The mixture was stirred at −20° C., for 12 h. The reaction mixture was diluted with water and extracted in dichloromethane (100 mL), dried over Na$_2$SO$_4$ and concentrated under reduce pressure. The solid was recrystallised with ethyl acetate (5 mL), filtered and dried under vacuum, affording the title compound as a white solid. $^1$H NMR (DMSO-$d_6$, 400 MHz) δ 9.73 (s, 1H), 7.49 (m, 1H), 7.38 (m, 2H), 5.85 (s, 2H), 3.71 (d, J=14.2 Hz, 1H), 3.57 (d, J=14.2 Hz, 1H), 2.66 (d, J=10.7 Hz, 1H), 2.18 (s, 3H), 1.99-1.93 (m, 1H), 1.45 (s, 9H), 0.91-0.81 (m, 6H). LC/MS (Method B) 354.3 (M+H)$^+$. HPLC (Method A) Rt: 2.66 min (Purity 98.6%).

Intermediate 16 tert-butyl N-(1-{4-[amino(hydroximino)methyl]phenyl}ethyl)-N-methylglycinate

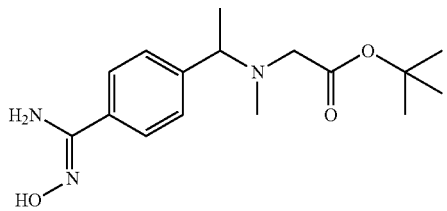 [SMILES: CC(c1ccc(/C(N)=N/O)cc1)N(C)CC(=O)OC(C)(C)C]

Step 1: 4-[1-(methylamino)ethyl]benzonitrile

In THF (50 mL), was added 4-acetylbenzonitrile (5.0 g; 34 mmol), methylamine (20.5 mL; 2 M; 41 mmol) and titanium (IV) isopropoxide (5.6 mL; 18.9 mmol). The mixture was stirred overnight at RT. Sodium borohydride (5.5 g; 145 mmol) was added and the reaction was stirred at RT for 2 h. Ammonium hydroxide solution 25% (100 mL) was added and the reaction was stirred at RT for 1 h30. It was then filtered through a pad of celite which was washed 3 times with EtOAc. The filtrate was poured in a separatory funnel and the organic phase was washed with a saturated solution of $NaHCO_3$ and brine, dried over $MgSO_4$, filtered and concentrated under reduce pressure affording the title compound as a light yellow oil (5.4 g; 97%). It was used in the next step without further purification.

Step 2: tert-butyl N-[1-(4-cyanophenyl)ethyl]-N-methylglycinate

The title compound was prepared following the general procedure 11 starting from 4-[1-(methylamino)ethyl]benzonitrile and tert-butyl bromoacetate. It was isolated as a colorless oil. $^1$H NMR (DMSO-$d_6$, 300 MHz) δ 7.79 (d, J=8.4 Hz, 2H), 7.54 (d, J=8.2 Hz, 2H), 3.89 (q, J=6.7 Hz, 1H), 3.27 (d, J=16.7 Hz, 1H), 3.07 (d, J=16.7 Hz, 1H), 2.21 (s, 3H), 1.41 (s, 9H), 1.26 (d, J=6.8 Hz, 3H). HPLC (Method A) Rt 2.83 min (Purity: 96.8%).

Step 3: tert-butyl N-(1-{4-[amino(hydroxyimino)methyl]phenyl}ethyl)-N-methylglycinate The title compound was prepared following the general procedure 1, starting from tert-butyl N-[1-(4-cyanophenyl)ethyl]-N-methylglycinate and was isolated as a white powder (2.68 g, quantitative). $^1$H NMR (DMSO-$d_6$, 300 MHz) 9.58 (s, 1H), 7.61 (d, J=8.2 Hz, 2H), 7.30 (d, J=8.3 Hz, 2H), 5.78 (s, 2H), 3.80 (q, J=6.7 Hz, 1H), 3.23 (d, J=16.8 Hz, 1H), 3.03 (d, J=16.8 Hz, 1H), 2.22 (s, 3H), 1.41 (s, 9H), 1.26 (d, J=6.8 Hz, 3H). LC/MS (Method B): 308.2 (M+H)$^+$. HPLC (Method A) Rt 1.33 min (Purity: 88.5%).

Intermediate 17 tert-butyl 2-({4-[amino(hydroxyimino)methyl]-2-fluorobenzyl}amino)-2-methylpropanoate

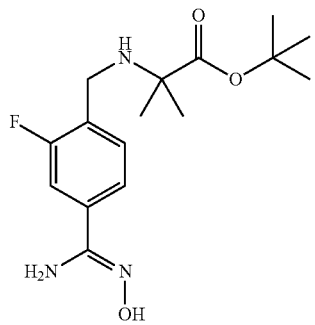 [SMILES: CC(C)(C)OC(=O)C(C)(C)NCc1ccc(/C(N)=N/O)cc1F]

Step 1: tert-butyl 2-(benzylamino)-2-methylpropanoate

The title compound was prepared following general procedure 10 starting from tert-butyl-2-bromo isobutyrate and benzyl amine. It was isolated as a colourless liquid. $^1$H NMR (DMSO-$d_6$, 400 MHz) δ 7.30-7.26 (m, 4H), 7.23-7.20 (m, 1H), 3.55 (s, 2H), 2.10 (s, 1H), 1.42 (s, 9H), 1.20 (s, 6H).

Step 2: tert-butyl 2-amino-2-methylpropanoate

To the solution of tert-butyl 2-(benzylamino)-2-methylpropanoate (20 g, 0.08 mol) in ethyl acetate (1 L), was added the catalyst Palladium-carbon (10%, 2.2 g). The resulting mixture was put under the hydrogen pressure of 5 Kg/cm$^2$, at RT for 18 h. The reaction mixture was filtered. The filtrate was concentrated affording the title compound as pale green liquid. $^1$H NMR (DMSO-$d_6$, 400 MHz) δ 1.38 (brs, 2H), 1.14 (s, 9H), 1.14-1.11 (d, J=10.7 Hz, 6H).

Step 3: tert-butyl 2-[(4-cyano-2-fluorobenzyl)amino]-2-methylpropanoate

The title compound was prepared following general procedure 10 starting from tert-butyl 2-amino-2-methylpropanoate and 4-cyano-2-fluoro benzyl bromide. The title compound was isolated as colorless liquid. $^1$H NMR (DMSO-$d_6$, 400 MHz) δ 7.78-7.75 (d, J=10.0 Hz, 1H), 7.71-7.65 (m, 2H), 3.70-3.68 (d, J=6.9 Hz, 2H), 2.55 (s, 1H), 1.44 (s, 9H), 1.19 (s, 6H).

Step 4: tert-butyl 2-({4-[amino(hydroxyimino)methyl]-2-fluorobenzyl}amino)-2-methylpropanoate The title compound was prepared following general method 1, starting from tert-butyl 2-[(4-cyano-2-fluorobenzyl)amino]-2-methylpropanoate, and was isolated as a white solid. $^1$H NMR (DMSO-$d_6$, 400 MHz) δ 9.71 (s, 1H), 7.49-7.38 (m, 3H), 5.85 (s, 2H), 3.61 (s, 2H), 2.29 (s, 1H), 1.41 (s, 9H), 1.20 (s, 6H). LC/MS (Method B) 326.3 (M+H)$^+$. HPLC (Method A) Rt: 2.25 min (Purity: 99.4%).

Intermediate 18 tert-butyl (1-{4-[amino(hydroxyimino)methyl]phenyl}ethyl)carbamate

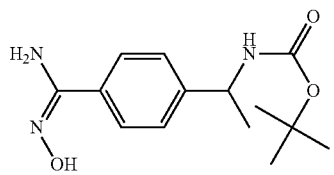 [SMILES: CC(NC(=O)OC(C)(C)C)c1ccc(/C(N)=N\O)cc1]

Step 1: tert-butyl [1-(4-cyanophenyl)ethyl]carbamate

A solution of 4-(1-Amino-ethyl)-benzonitrile (Ukrorgsynthsis Ltd, 2 g; 11 mmol) and N,N-diisopropylethylamine (2.2 mL; 13.1 mmol) was prepared in ACN (30 mL). A solution of di-tert-butyl dicarbonate (2.9 g; 13.1 mmol) in ACN (10 mL) was added at 0° C. and the resulting solution was stirred at RT overnight. Solvents were concentrated and the reaction mixture was diluted with MTBE (100 mL) and washed with $H_2O$ (2×50 mL) and brine (50 mL). Aqueous layers were extracted with MTBE (100 mL). The organic layers were combined, dried over $Na_2SO_4$ and evaporated. Purification by flash chromatography afforded the title compound as a yellow paste (2.2 g, 82%). LC/MS (Method B): 246.9 $(M+H)^+$, 245.2 $(M-H)^-$. HPLC (Method A) Rt 1.20 min (Purity: 100%).

Step 2: tert-butyl (1-{4-[amino(hydroxyimino)methyl]phenyl}ethyl)carbamate

The title compound was prepared following the general procedure 1, starting from tert-butyl [1-(4-cyanophenyl)ethyl]carbamate and was isolated as a white powder (2.3 g, 94%). LC/MS (Method B) 280.3 $(M+H)^+$. HPLC (Method A) Rt 2.11 min (Purity: 99.6%).

Intermediate 19 methyl N-(1-{3-[(hydroxyamino)(imino)methyl]phenyl}ethyl)-N-methylalaninate

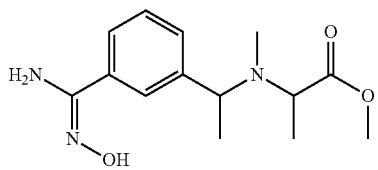 [SMILES: COC(=O)C(C)N(C)C(C)c1cccc(/C(N)=N\O)c1]

Step 1: 3-[1-(methylamino)ethyl]benzonitrile

The title compound was prepared following the procedure used for Intermediate 16, step 1, starting from 3-acetylbenzonitrile. It was isolated as a colorless oil (1 g; 92%). HPLC (Method A) Rt 1.54 min (Purity: 74%).

Step 2: methyl N-[1-(3-cyanophenyl)ethyl]-N-methylalaninate

Compound was prepared following the general procedure 11 starting from 3-[1-(methylamino)ethyl]benzonitrile and methyl 2-bromopropionate, affording the title compound as a colorless oil. HPLC (Method A) Rt 1.54 min (Purity: 74%).

Step 3: methyl N-(1-{3-[(hydroxyamino)(imino)methyl]phenyl}ethyl)-N-methylalaninate The title compound was prepared following the general procedure 1, starting from methyl N-[1-(3-cyanophenyl)ethyl]-N-methylalaninate and was isolated as a colorless oil (330 mg, 88%). LC/MS (Method B): 280.0 $(M+H)^+$.

Intermediate 20 methyl tert-butyl N-(1-{3-[amino(hydroxyimino)methyl]phenyl}ethyl)-N-methylglycinate

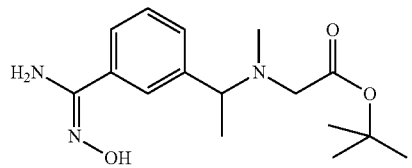 [SMILES: CC(c1cccc(/C(N)=N\O)c1)N(C)CC(=O)OC(C)(C)C]

Step 1: methyl N-[1-(3-cyanophenyl)ethyl]-N-methylalaninate

The title compound was prepared following the general procedure 11 starting from 3-[1-(methylamino)ethyl]benzonitrile (Intermediate 19, step 1) and tert-butyl bromoacetate. It was isolated as a colorless oil. HPLC (Method A) Rt 2.42 min (Purity: 100%).

Step 2: methyl tert-butyl N-(1-{3-[amino(hydroxyimino)methyl]phenyl}ethyl)-N-methylglycinate The title compound was prepared following the general procedure 1, starting from methyl N-[1-(3-cyanophenyl)ethyl]-N-methylalaninate and was isolated as a colorless sticky oil (1.43 g, 98%). LC/MS (Method B): 308.1 $(M+H)^+$. HPLC (Method A): 1.78 min (purity: 78.4%).

Intermediate 21 tert-butyl 2-[{4-[amino(hydroxyimino)methyl]-2-fluorobenzyl}(methyl)amino]-2-methylpropanoate

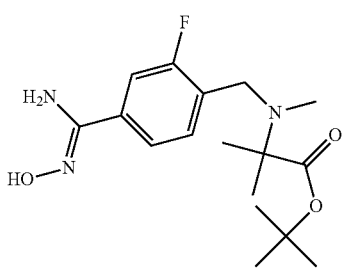 [SMILES: CN(Cc1ccc(/C(N)=N/O)cc1F)C(C)(C)C(=O)OC(C)(C)C]

Step 1: 3-Fluoro-4-[(methylamino)methyl]benzonitrile

A solution of 4-cyano-2-fluoro-benzylbromide (FluoroChem ltd, 16 g, 74 mmol) in dry THF (50 mL) was added to a 40% aqueous solution of methyl amine (700 mL) at 5-10° C. and allowed to stir for 5 min. The reaction mixture was extracted with DCM and the solvent was dried over $Na_2SO_4$ and concentrated under vacuum, affording (12.0 g, 95%) of the title compound as a brown liquid. $^1$H NMR (DMSO-$d_6$, 400 MHz) δ 7.79-7.75 (m, 1H), 7.68-7.61 (m, 2H), 3.71 (s, 2H), 2.24 (s, 3H).

Step 2: tert-butyl 2-[(2-fluoro-4-isocyanobenzyl)(methyl)amino]-2-methylpropanoate The title compound was prepared following the general procedure 11 starting from 3-fluoro-4-[(methylamino)methyl]benzonitrile and tert-butyl-2-bromo isobutyrate. It was isolated as a colorless oil. $^1$H NMR (DMSO-$d_6$, 400 MHz) δ 7.78-7.76 (d, J=10.3 Hz, 1H), 7.73-7.67 (m, 2H), 3.68 (s, 2H), 2.13 (s, 3H), 1.41 (s, 9H), 1.27 (s, 6H).

Step 3: tert-butyl 2-[{4-[amino(hydroxyimino)methyl]-2-fluorobenzyl}(methyl)amino]-2-methylpropanoate The title compound was prepared following the general procedure 1, starting from tert-butyl 2-[(2-fluoro-4-isocyanobenzyl)(methyl)amino]-2-methylpropanoate and was isolated as a white solid. $^1$H NMR (DMSO-$d_6$, 400 MHz) δ 9.71 (s, 1H), 7.49-7.37 (m, 3H), 5.85 (s, 2H), 3.59 (s, 2H), 2.12 (s, 3H), 1.42 (s, 9H), 1.28 (s, 6H). LC/MS (Method B): 340.3 (M+H)$^+$. HPLC (Method A) Rt: 2.14 min (Purity: 98.1%).

Intermediate 22 tert-butyl N-(1-{4-[amino(hydroximino)methyl]phenyl}ethyl)glycinate

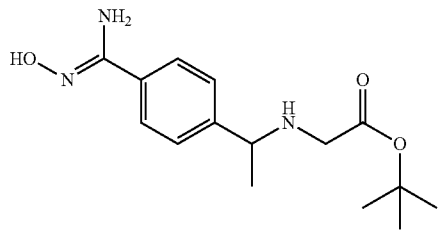 [SMILES: CC(NCC(=O)OC(C)(C)C)c1ccc(/C(N)=N/O)cc1]

Step 1: tert-butyl N-[1-(4-cyanophenyl)ethyl]glycinate 4-acetylbenzonitrile (500 mg; 3.4 mmol; 1 eq.) and tert-butyl glycinate (588 mg; 4.5 mmol) were dissolved in toluene (10 mL). AcOH (103 μl; 1.7 mmol) was added. The mixture was stirred at reflux with a dean stark trap overnight. Solvents were evaporated and the resulting tert-butyl N-[1-(4-cyanophenyl)ethylidene]glycinate (889 mg; 3.4 mmol) was dissolved in MeOH (18 mL). Sodium borohydride (390 mg; 10.3 mmol) was added in portions, resulting in an exothermic reaction (reflux). The reaction was stirred at RT overnight. Solvents were evaporated. The crude residue was suspended in EtOAc, washed with $NH_4Cl$ saturated solution, $NaHCO_3$ saturated solution, brine and dried over $MgSO_4$. After evaporation of the solvents the resulting yellow oil was purified by flash chromatography, affording the title compound as a colorless oil. LC/MS (Method B): 261.0 (M+H)$^+$. HPLC (Method A): 2.77 min (purity: 98.2%).

Step 2: tert-butyl N-(1-{4-[amino(hydroxyimino)methyl]phenyl}ethyl)glycinate

The title compound was prepared following the general procedure 1, starting from tert-butyl N-[1-(4-cyanophenyl)ethyl]glycinate and was isolated as a colorless foam (290 mg, 94%). LC/MS (Method B): 294.1 (M+H)$^+$. HPLC (Method A): 1.31 min (purity: 100%)

Intermediate 23 tert-butyl N-((1S)-1-{4-[amino(hydroxyimino)methyl]phenyl}ethyl)-N-methylglycinate and Intermediate 24: tert-butyl N-((1R)-1-{4-[amino(hydroxyimino)methyl]phenyl}ethyl)-N-methylglycinate

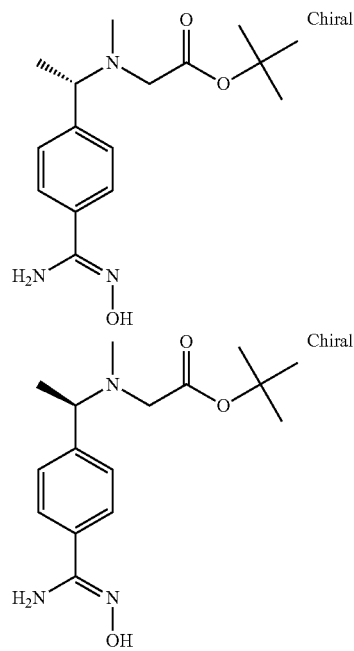

Step 1: tert-butyl N-[1-(4-cyanophenyl)ethyl]-N-methylglycinate

In THF (50 mL) was added 4-acetylbenzonitrile (5.0 g; 34 mmol), methylamine (21 mL; 2.00 M solution in THF; 42 mmol) and titanium isopropoxide (5.6 mL; 19 mmol). The mixture was stirred at RT overnight. Sodium borohydride (5.5 g; 145 mmol) was added and the reaction mixture was let stirred at RT for 2 h. Ammonium hydroxide solution 25% (100 mL) was added and the reaction mixture was stirred at RT for 1 h30. It was then filtered through a pad of celite, which was washed with EtOAc. The organic phase was washed with a saturated solution of $NaHCO_3$, brine, dried over $MgSO_4$, filtered and concentrated under reduced pressure. The crude was then dissolved in $CH_3CN$ (41 mL). Potassium carbonate (10.3 g; 74 mmol) and tert-butyl bromoacetate (5.5 mL; 37 mmol) were added at RT and the reaction mixture was stirred at RT for 1 h30. EtOAc was added and the organic phase was washed with water and brine, dried over $MgSO_4$, filtered and concentrated affording an oil which was purified by Flash Chromatography affording the title compound as a colorless oil. $^1$H NMR (DMSO-d$_6$, 300 MHz) δ 7.79 (d, J=8.4 Hz, 2H), 7.54 (d, J=8.2 Hz, 2H), 3.89 (q, J=6.7 Hz, 1H), 3.27 (d, J=16.7 Hz, 1H), 3.07 (d, J=16.7 Hz, 1H), 2.21 (s, 3H), 1.41 (s, 9H), 1.26 (d, J=6.8 Hz, 3H). LC/MS (Method B): 275.1 (M+H)$^+$. HPLC (Method A) Rt 2.83 min (Purity: 96.8%).

Step 2: tert-butyl N-((1S)-1-{4-[amino(hydroxy-imino)methyl]phenyl}ethyl)-N-methylglycinate and tert-butyl N-((1R)-1-{4-[amino(hydroxyimino)methyl]phenyl}ethyl)-N-methylglycinate The two title compounds were prepared following the general procedure 1 starting from tert-butyl N-[1-(4-cyanophenyl)ethyl]-N-methylglycinate (1.4 g; 5.1 mmol), obtained in step 1 affording 1.6 g (quantitative) as a white solid. It was purified by Chiral HPLC on Chiralcell OJ-H 250 mm×20 mm×5 uM column (eluted with isopropanol/heptane (v:v=15:85) at a rate of 8.0 mL/min) affording tert-butyl N-((1S)-1-{4-[amino(hydroxyimino)methyl]phenyl}ethyl)-N-methylglycinate (second eluting compound) as a white solid (677 mg; 48%) and tert-butyl N-((1R)-1-{4-[amino(hydroxyimino)methyl]phenyl}ethyl)-N-methylglycinate (first eluting compound) as a white solid (606 mg; 43%).

tert-butyl N-((1S)-1-{4-[amino(hydroxyimino)methyl]phenyl}methylglycinate: $^1$H NMR (DMSO-d$_6$, 300 MHz) δ 9.58 (s, 1H), 7.61 (d, J=8.3 Hz, 2H), 7.30 (d, J=8.3 Hz, 2H), 5.78 (s, 2H), 3.80 (q, J=6.7 Hz, 1H), 3.23 (d, J=16.7 Hz, 1H), 3.03 (d, J=16.7 Hz, 1H), 2.22 (s, 3H), 1.41 (s, 9H), 1.26 (d, J=6.7 Hz, 3H). LC/MS (Method B): 308.2 (M+H)$^+$. HPLC (Method B) Rt 12.55 min (Purity: 100.0%). [α]$_D$=−52.8 (c 0.90, EtOH).

tert-butyl N-((1R)-1-{4-[amino(hydroxyimino)methyl]phenyl}ethyl)-N-methylglycinate: $^1$H NMR (DMSO-d6, 300 MHz) δ 9.58 (s, 1H), 7.61 (d, J=8.3 Hz, 2H), 7.30 (d, J=8.3 Hz, 2H), 5.78 (s, 2H), 3.80 (q, J=6.7 Hz, 1H), 3.23 (d, J=16.7 Hz, 1H), 3.03 (d, J=16.7 Hz, 1H), 2.22 (s, 3H), 1.41 (s, 9H), 1.26 (d, J=6.7 Hz, 3H). LC/MS (Method A): 308.2 (M+H)$^+$. HPLC (Method B) Rt 8.99 min (Purity: 100.0%). [α]$_D$=50.5 (c 1.13, EtOH).

Intermediate 25 methyl N-(1-{4-[amino(hydroximino)methyl]phenyl}ethyl)-N-methylalaninate

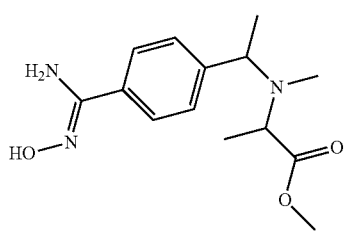 [SMILES: COC(=O)C(C)N(C)C(C)c1ccc(/C(N)=N/O)cc1]

Step 1: methyl N-[1-(4-cyanophenyl)ethyl]-N-methylalaninate

In THF (50 mL), was added 4-acetylbenzonitrile (5.0 g; 34 mmol), methylamine (21 mL; 2.00 M solution in THF; 42 mmol) and titanium isopropoxide (5.6 mL; 19 mmol). The mixture was stirred at RT overnight. Sodium borohydride (5.5 g; 145 mmol) was added and the reaction mixture was let stirred at RT for 2 h. Ammonium hydroxide solution 25% (100 mL) was added and the reaction mixture was let stirred at RT for 1 h30. It was then filtered through a pad of celite, which was washed with EtOAc. The organic phase was washed with a saturated solution of NaHCO$_3$, brine, dried over MgSO$_4$, filtered and concentrated under reduced pressure. The crude was then dissolved in CH$_3$CN (15 mL). Potassium carbonate (3.8 g; 27 mmol) and methyl 2-bromopropionate (1.5 mL; 13.7 mmol) were added at RT and the reaction mixture was stirred at RT for 1 h30. EtOAc was added and the organic phase was washed with water and brine, dried over MgSO$_4$, filtered and concentrated. The resulting oil was purified by Flash Chromatography, affording the title compound as a colorless oil. $^1$H NMR (DMSO-d$_6$, 300 MHz) δ 7.83-7.76 (m, 2H), 7.54 (t, J=8.7 Hz, 2H), 3.94-3.79 (m, 1H), 3.70-3.63 (m, 0.5H), 3.63-3.59 (m, 3H), 3.35-3.26 (m, 0.5H), 2.20 (s, 1.5H), 2.09 (s, 1.5H), 1.30-1.23 (m, 3H), 1.20 (d, J=7.0 Hz, 1.5H), 1.12 (d, J=7.0 Hz, 1.5H). LC/MS (Method B): 247.1 (M+H)$^+$. HPLC (Method A) Rt 1.51 min (Purity: 70.1%).

Step 2: methyl N-(1-{4-[amino(hydroxyimino)methyl]phenyl}ethyl)-N-methylalaninate The title compound was prepared following the general procedure 1 starting from methyl N-[1-(4-cyanophenyl)ethyl]-N-methylalaninate. It was isolated as a colorless oil (113 mg; quantitative). LC/MS (Method B): 280.1 (M+H)$^+$.

Intermediate 26 tert-butyl N-(1-{3-[amino(hydroxyimino)methyl]phenyl}ethyl)glycinate

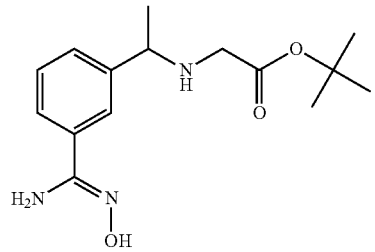 [SMILES: CC(NCC(=O)OC(C)(C)C)c1cccc(/C(N)=N/O)c1]

Step 1: tert-butyl N-[1-(3-cyanophenyl)ethyl]glycinate

4-Acetylbenzonitrile (1.0 g; 6.9 mmol) and tert-butyl glycinate (1.2 g; 9.0 mmol) were dissolved in toluene (20 mL). The mixture was stirred at reflux with a Dean-Stark trap. AcOH (207 μL; 3.4 mmol) was added and the mixture was further heated overnight. Solvents were evaporated. The crude was dissolved in MeOH (35 mL). The solution was cooled down to 0° C. and sodium borohydride (781 mg; 21 mmol) was added in portions. The reaction was stirred at 0° C. for 1 h and was let stirred at RT overnight. Solvents were evaporated. The crude residue was suspended in EtOAc, washed with NH$_4$Cl saturated solution, NaHCO$_3$ saturated solution, brine and dried over MgSO$_4$. After evaporation of the solvents the resulting yellow oil was purified by flash chromatography affording the title compound 716 mg as a colorless oil. LC/MS (Method B): 261.0 (M+H)$^+$. HPLC (Method A) Rt 2.79 min (Purity: 99.2%).

Step 2: tert-butyl N-(1-{3-[amino(hydroxyimino) methyl]phenyl}ethyl)glycinate The title compound was prepared following the general procedure 1 starting from tert-butyl N-[1-(3-cyanophenyl) ethyl]glycinate (716 mg; 2.8 mmol), obtained in step 1. It was isolated as a colorless foam (646 mg; 80%). $^1$H NMR (DMSO-d$_6$, 300 MHz) δ 9.58 (br s, 1H), 7.64-7.58 (m, 1H), 7.56-7.48 (m, 1H), 7.35-7.26 (m, 2H), 5.78 (s, 2H), 3.73 (q, J=6.3 Hz, 1H), 3.06 (d, J=17.1 Hz, 1H), 2.96 (d, J=17.1 Hz, 1H), 1.38 (s, 9H), 1.25 (d, J=6.3 Hz, 3H). LC/MS (Method B): 294.1 (M+H)$^+$. HPLC (Method A) Rt 1.77 min (Purity: 97.3%).

Intermediate 27 tert-Butyl 2-({4-[amino(hydroxyimino)methyl]-2-fluorobenzyl}amino)butanoate

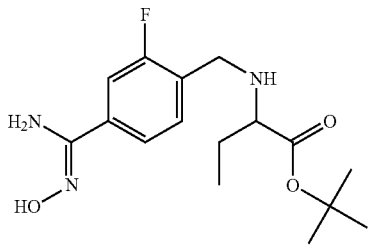 [SMILES: CCC(NCc1ccc(/C(N)=N/O)cc1F)C(=O)OC(C)(C)C]

Step 1: tert-Butyl 2-aminobutanoate

To a solution of tert-butyl-2-bromo butyrate (10 g, 44.8 mmol) in dry THF (50 mL) was added ammonium hydroxide solution 25% (800 mL) at RT. The reaction was stirred at RT for 24 h. The reaction mixture was concentrated under vacuum at low temperature (35-38° C.). It was then extracted with DCM (3×200 mL). The combined organic phases were dried over Na$_2$SO$_4$ and concentrated under vacuum affording the title compound (6.2 g, 85%) as a colorless liquid. $^1$H NMR (DMSO-d$_6$, 400 MHz) δ 3.09-3.06 (t, J=6.1 Hz, 1H), 1.75-1.71 (m, 2H), 1.63-1.57 (m, 2H) 1.46 (s, 9H), 0.96-0.92 (t, J=7.5 Hz, 3H).

Step 2: tert-Butyl 2-[(4-cyano-2-fluorobenzyl)amino]butanoate

The title compound was prepared following the general procedure 10 starting from 4-cyano-2-fluoro-benzylbromide (Fluorochem, 8.2 g, 38 mmol) and tert-butyl 2-aminobutanoate (6.2 g, 38 mmol), obtained in step 1. It was isolated as a colorless liquid. $^1$H NMR (DMSO-d$_6$, 400 MHz) δ 7.79-7.76 (d, J=10.2 Hz, 1H), 7.68-7.67 (t, J=2.1 Hz, 2H), 3.84-3.79 (m, 1H) 3.71-3.66 (m, 1H), 2.95-2.91 (m, 1H), 2.52-2.48 (m, 1H), 1.58-1.53 (m, 2H), 1.49 (s, 9H), 0.87-0.83 (m, 3H).

Step 3: tert-Butyl 2-({4-[amino(hydroxyimino)methyl]-2-fluorobenzyl}amino)butanoate The title compound was prepared following the general procedure 1, starting from tert-butyl 2-[(4-cyano-2-fluorobenzyl)amino]butanoate, obtained in step 2 and was isolated as a white solid. $^1$H NMR (DMSO-d$_6$, 300 MHz) δ 9.72 (s, 1H), 7.49-7.38 (m, 3H) 5.85 (s, 2H), 3.75-3.72 (d, J=14.0 Hz, 1H), 3.64-3.60 (d, J=14 Hz, 1H), 2.94 (m, 1H), 2.31 (m, 1H), 1.55-1.50 (m, 2H), 1.39 (s, 9H), 0.86-0.82 (t, J=7.4 Hz, 3H). LC/MS (Method B): 326.3 (M+H)$^+$. HPLC (Method A) Rt 2.140 min (Purity: 98.6%).

Intermediate 29 tert-butyl 2-[{4-[amino(hydroximino)methyl]-2-fluorobenzyl}(methyl)amino]-2-methylpropanoate

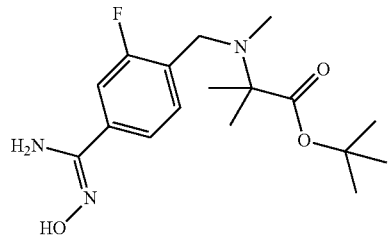 [SMILES: CN(Cc1ccc(/C(N)=N/O)cc1F)C(C)(C)C(=O)OC(C)(C)C]

Step 1: tert-butyl 2-[(2-fluoro-4-isocyanobenzyl)(methyl)amino]-2-methylpropanoate The title compound was prepared following the general procedure 11, starting from 3-Fluoro-4-[(methylamino)methyl]benzonitrile and tert-butyl-2-bromo isobutyrate. It was isolated as a colorless liquid. $^1$H NMR (DMSO-d$_6$, 400 MHz) δ 7.77 (d, J=10.3 Hz, 1H), 7.73-7.67 (m, 2H), 3.68 (s, 2H), 2.13 (s, 3H), 1.41 (s, 9H), 1.27 (s, 6H).

Step 2: tert-butyl 2-[{4-[amino(hydroxyimino)methyl]-2-fluorobenzyl}(methyl)amino]-2-methylpropanoate The title compound was prepared following the general procedure 2, starting from tert-butyl 2-[(2-fluoro-4-isocyanobenzyl)(methyl)amino]-2-methylpropanoate and was isolated as a white solid. $^1$H NMR (DMSO-d$_6$, 400 MHz) δ 9.71 (s, 1H), 7.49-7.37 (m, 3H), 5.85 (s, 2H), 3.59 (s, 2H), 2.12 (s, 3H), 1.42 (s, 9H), 1.28 (s, 6H). LC/MS (Method A) 340.3 (M+H)$^+$. HPLC (Method A) Rt: 2.14 min (Purity: 98%).

Intermediate 30 tert-butyl 2-[{4-[amino(hydroxyimino)methyl]-2-fluorobenzyl}(methyl)amino]propanoate

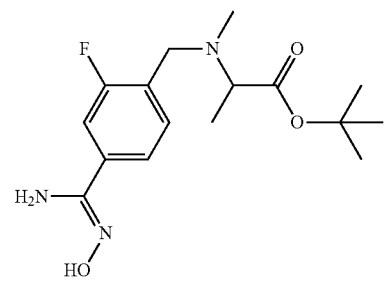 [SMILES: CC(C(=O)OC(C)(C)C)N(C)Cc1ccc(/C(N)=N/O)cc1F]

Step 1: tert-butyl 2-[(4-cyano-2-fluorobenzyl)(methyl)amino]propanoate

The title compound was prepared following the general procedure 11, starting from 3-fluoro-4-[(methylamino)methyl]benzonitrile and tert-butyl-2-bromo propionate. It was isolated as a colorless liquid. $^1$H NMR (DMSO-$d_6$, 400 MHz) δ 7.80-7.77 (t, J=9.9 Hz, 1H), 7.68-7.61 (m, 2H), 3.83-3.70 (dd, 2H), 3.35-3.32 (t, J=7.1 Hz, 1H), 2.19 (s, 3H), 1.42 (s, 9H), 1.19 (d, J=7.1 Hz, 3H).

Step 2: tert-butyl 2-[{4-[amino(hydroxyimino)methyl]-2-fluorobenzyl}(methyl)amino]propanoate The title compound was prepared following the general procedure 2, starting from tert-butyl 2-[(4-cyano-2-fluorobenzyl)(methyl)amino]propanoate and was isolated as a white solid. $^1$H NMR (DMSO-$d_6$, 400 MHz) δ 9.73 (s, 1H), 7.49 (m, 1H), 7.40 (m, 2H), 5.86 (s, 2H), 3.75-3.62 (m, 2H), 3.33-3.10 (t, J=8.7 Hz, 1H), 2.19 (s, 3H), 1.43 (s, 9H), 1.18 (d, J=7.1 Hz, 3H). LC/MS (Method A) 326.3 (M+H)$^+$. HPLC (Method A) Rt: 2.05 min (Purity: 98.3%).

Intermediate 31 tert-butyl N-{4-[(amino(hydroxyimino)methyl]-2-fluorobenzyl}-O-(tert-butyl)-N-methylserinate

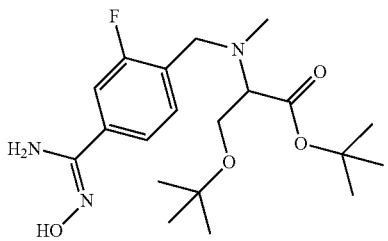 [SMILES: CN(Cc1ccc(/C(N)=N/O)cc1F)C(COC(C)(C)C)C(=O)OC(C)(C)C]

Step 1: tert-Butyl 3-tert-butoxy-2-[(4-cyano-2-fluorobenzyl)amino]propanoate To a stirred solution of 4-cyano-2-fluoro-benzylbromide (5 g, 0.024 mol) and sodium bicarbonate (3.9 g, 0.047 mol) in dry DMF (50 mL), was added o-tert-butyl-L-serine tert-butyl ester hydrochloride (6 g, 0.024 mol). The mixture was stirred at RT for 12 h. The reaction mass was diluted with water (100 mL) and extracted in ethyl acetate (100 mL). The organic layer was washed water (2×100 mL), dried over Na$_2$SO$_4$ and concentrated under reduced pressure. The crude was purified by column chromatography using petroleum ether and ethyl acetate as eluent, affording the title compound as colorless liquid (6.7 g, 82%). $^1$H NMR (DMSO-$d_6$, 400 MHz) δ 7.77 (d, J=10.1 Hz, 1H), 7.67 (t, J=2.2 Hz, 2H), 3.90-3.74 (m, 2H), 3.47 (m, 1H), 3.41 (m, 1H), 3.16 (m, 1H), 1.43 (s, 9H), 1.17 (s, 9H).

Step 2: tert-Butyl 3-tert-butoxy-2-[(4-cyano-2-fluorobenzyl)(methyl)amino]propanoate To a stirred suspension of sodium hydride (1.8 g, 0.038 mol) in dry DMF (10 mL) at 0° C., tert-butyl 3-tert-butoxy-2-[(4-cyano-2-fluorobenzyl)amino]propanoate (6.7 g, 0.019 mol) in DMF (20 mL) was added dropwise. The resulting mixture was allowed to stir for 20 min at RT. Methyl iodide (3.5 mL, 0.0057 mol) was then added dropwise at 000 and the mixture was allowed to stir for 3 hr at RT. The reaction mixture was quenched in ice water and extracted with ethyl acetate (250 mL). The organic layer was washed with water (3×100 mL), dried over sodium sulphate and concentrated under reduced pressure. The crude was purified by column chromatography using petroleum ether and ethyl acetate as eluent, affording the title compound as colorless liquid. $^1$H NMR (DMSO-$d_6$, 400 MHz) δ 7.78 (d, J=9.8 Hz, 1H), 7.67 (t, J=2.5 Hz, 2H), 3.92 (d, J=15.2 Hz, 1H), 3.81-3.70 (d, J=15.0 Hz, 1H), 3.63 (m, 1H), 3.52 (m, 2H), 2.26 (s, 3H), 1.42 (s, 9H), 1.08 (s, 9H).

Step 3: tert-butyl N-{4-[(amino(hydroxyimino)methyl]-2-fluorobenzyl}-O-(tert-butyl)-N-methylserinate The title compound was prepared following the general procedure 2, starting from tert-butyl 3-tert-butoxy-2-[(4-cyano-2-fluorobenzyl)(methyl)amino]propanoate and was isolated as a white solid. $^1$H NMR (DMSO-$d_6$, 400 MHz) δ 9.72 (s, 1H), 7.49 (d, J=8 Hz, 1H), 7.40 (m, 2H), 5.85 (s, 2H), 3.80 (d, J=14.1 Hz, 1H), 3.71-3.63 (m, 2H), 3.47 (m, 1H), 3.26 (t, J=5.5 Hz, 1H), 2.25 (s, 3H), 1.43 (s, 9H), 1.09 (s, 9H). LC/MS (Method A) 398.0 (M+H)$^+$. HPLC (Method A) Rt 3.13 min (Purity 94.9%).

Intermediate 32 tert-butyl 2-({3-[amino(hydroxyimino)methyl]-5-fluorobenzyl}amino)-2-methylpropanoate

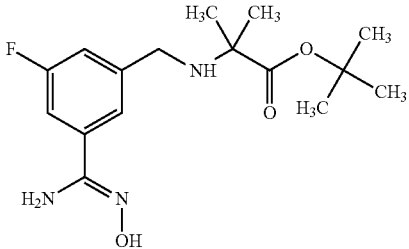 [SMILES: CC(C)(C)OC(=O)C(C)(C)NCc1cc(F)cc(/C(N)=N/O)c1]

Step 1: 3-(Aminomethyl)-5-fluorobenzonitrile

To 3-(bromomethyl)-5-fluorobenzonitrile (Intermediate 14, step 1, 10 g, 0.47 mol) in THF (50 mL) was added ammonium hydroxide solution 25% (2.0 L). The resulting mixture was stirred for 2 h at 85° C. It was then cooled down to RT and extracted with dichloromethane. The organic layer was washed with water, brine, dried and concentrated, affording the title compound as a slight yellow liquid (5 g, 71%). $^1$H NMR (DMSO-$d_6$, 400 MHz): δ 7.6 (d, J=6.6 Hz, 1H), 7.57 (t, J=0.6 Hz, 1H), 7.55 (s, 1H), 3.74 (d, 2H), 1.97 (s, 2H). LC/MS (Method A) 151.0 (M+H)$^+$. HPLC (Method A) Rt: 0.88 min (Purity 98%).

Step 2: tert-butyl 2-[(3-cyano-5-fluorobenzyl)amino]-2-methylpropanoate

The title compound was prepared following the general procedure 11, starting from 3-(aminomethyl)-5-fluorobenzonitrile and 2-bromoisobutyrate, affording the title compound as a light yellow liquid (5 g, 91%). $^1$H NMR (DMSO-$d_6$, 400 MHz): δ 7.67 (d, J=7 Hz, 2H), 7.57 (d, J=9.5 Hz, 1H), 3.67 (d, 2H), 2.67 (t, 1H), 1.40 (s, 9H), 1.19 (s, 6H). LC/MS (Method A) 293.2 (M+H)$^+$. HPLC (Method A) Rt: 2.29 min (Purity: 99.7%).

Step 3: tert-butyl 2-({3-[amino(hydroxyimino)methyl]-5-fluorobenzyl}amino)-2-methylpropanoate The title compound was prepared following the general procedure 2, starting from tert-butyl 2-[(3-cyano-5-fluorobenzyl)amino]-2-methylpropanoate and was isolated as a white solid (5.1 g, 92%). ¹H NMR (DMSO-$d_6$, 400 MHz): δ 9.72 (s, 1H), 7.49 (s, 1H), 7.29 (d, J=10.1 Hz, 1H), 7.15 (d, J=9.7 Hz, 1H), 5.85 (s, 2H), 3.60 (d, 2H), 2.39 (d, 1H), 1.41 (s, 9H), 1.20 (s, 6H). LC/MS (Method A) 326.3 (M−H)⁻. HPLC (Method A) Rt 2.26 min (Purity: 98.7%).

Intermediate 33 tert-butyl 2-({4-[amino(hydroxyimino)methyl]-2-fluorobenzyl}amino)-3-methylbutanoate

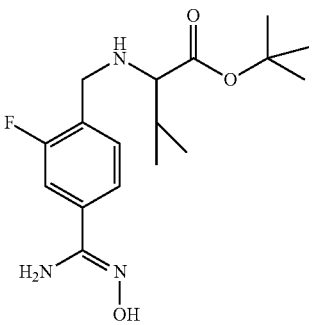 [SMILES: CC(C)C(NCc1ccc(/C(N)=N/O)cc1F)C(=O)OC(C)(C)C]

Step 1: 1-tert-butyl 2-[(4-cyano-2-fluorobenzyl)amino]-3-methylbutanoate

To a stirred solution of tert-butyl 2-amino-3-methylbutanoate (Bachem, 6.3 g, 0.036 mol) in dry DMF (50 mL) under nitrogen, was added 4-cyano-2-fluoro-benzyl bromide (6.2 g, 0.029 mol) and NaHCO₃ (6.09 g, 0.073 mol). The resulting mixture was stirred for 16 h at RT. Water (70 mL) was added and extracted with ethyl acetate (2×100 mL). The organic layer was washed with water (3×100 mL) and the solvent was dried over Na₂SO₄ and concentrated under vacuum. The resulted residue was purified by column chromatography using petroleum ether/ethyl acetate as eluent, affording the title compound as colorless liquid. ¹H NMR (DMSO-$d_6$, 400 MHz) δ 7.78 (d, J=10.2 Hz, 1H), 7.67 (t, J=1.5 Hz, 2H) 3.81 (m, 2H), 2.71 (m, 1H), 2.49 (m 1H), 1.81 (m, 1H), 1.37 (s, 9H), 0.88-0.84 (m, 6H).

Step 2: tert-butyl 2-({4-[amino(hydroxyimino)methyl]-2-fluorobenzyl}amino)-3-methylbutanoate The title compound was prepared following the general procedure 2, starting from tert-butyl 2-[(4-cyano-2-fluorobenzyl)amino]-3-methylbutanoate, and was isolated as a white solid. LC/MS (Method A) 340.3 (M+H)⁺. HPLC (Method A) Rt: 2.47 min (Purity: 98.7%).

Intermediate 34 tert-butyl 2-({4-[amino(hydroxyimino)methyl]-2-fluorobenzyl}amino)-2-methylpropanoate

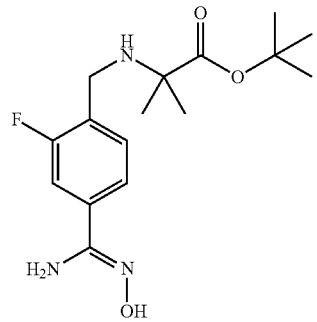 [SMILES: CC(C)(C)OC(=O)C(C)(C)NCc1ccc(/C(N)=N/O)cc1F]

Step 1: tert-butyl 2-[(4-cyano-2-fluorobenzyl)amino]-2-methylpropanoate

To a stirred solution of tert-butyl 2-amino-2-methylpropanoate (Bachem, 7.9 g, 0.05 mol) in dry DMF (50 mL) under nitrogen, was added 4-cyano-2-fluoro benzyl bromide (10.6 g, 0.05 mol) and NaHCO₃ (8.3 g, 0.099 mol) as a solid. The reaction mixture was stirred for 16 h at 70° C. Water (70 mL) was added and extracted with ethyl acetate (100 mL). The organic layer was washed with water (3×100 mL) and the solvent was dried over Na₂SO₄ and concentrated under vacuum. The residue was purified by column chromatography using silica gel (60-120 mesh) and petroleum ether/ethyl acetate as eluent, affording the title compound as colourless liquid. ¹H NMR (DMSO-$d_6$, 400 MHz) δ 7.78 (d, J=10.0 Hz, 1H), 7.71-7.65 (m, 2H), 3.69 (d, J=6.9 Hz, 2H), 2.55 (s, 1H), 1.44 (s, 9H), 1.19 (s, 6H).

Step 2: tert-butyl 2-({4-[amino(hydroxyimino)methyl]-2-fluorobenzyl}amino)-2-methylpropanoate The title compound was prepared following the general procedure 2, starting from tert-butyl 2-[(4-cyano-2-fluorobenzyl)amino]-2-methylpropanoate and was isolated as a white solid. ¹H NMR (DMSO-$d_6$, 400 MHz) δ 9.71 (s, 1H), 7.49-7.38 (m, 3H), 5.85 (s, 2H), 3.61 (s, 2H), 2.29 (s, 1H), 1.41 (s, 9H), 1.20 (s, 6H). LC/MS (Method A) 326.3 (M+H)⁺. HPLC (Method A) Rt: 2.26 min (Purity: 99.4%).

Intermediate 35 tert-butyl 2-((1-(4-(N'-hydroxycarbamimidoyl)phenyl)-2-methoxyethyl)(methyl)amino)acetate

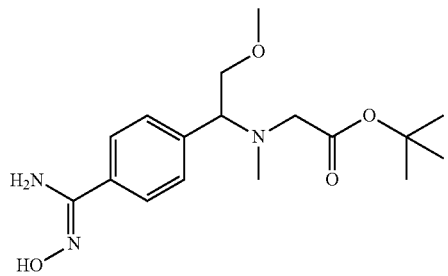 [SMILES: COCC(c1ccc(/C(N)=N/O)cc1)N(C)CC(=O)OC(C)(C)C]

Step 1: 4-(2-methoxyacetoyl)benzonitrile

Iso-propyl magnesium chloride (2 M solution in THF; 3.0 mL; 6.0 mmol) was added to an ice-cooled solution of 4-iodobenzonitrile (1.2 g, 5.0 mmol) in anhydrous THF (10 mL). This solution was stirred at this temperature for 10 minutes and then added dropwise to a cooled (−78° C.) solution of N-2-dimethoxy-N-methylacetamide (0.998 g, 7.50 mmol) in anhydrous THF (5 mL). The reaction mixture was stirred at this temperature for 1 hour and then stirred at RT for 1 hour. The reaction mixture was then treated with 10% aqueous potassium hydrogen sulfate solution and extracted with DCM. The organic phase was passed through a hydrophobic frit and evaporated under reduced pressure. The residue was purified by flash chromatography eluting with iso-hexane/EtOAc (3:2) to afford the title compound. $^1$H NMR (CDCl$_3$, 400 MHz) δ 8.06-8.04 (m, 2H), 7.80-7.77 (m, 2H), 4.67 (s, 2H), 3.50 (s, 3H).

Step 2: tert-butyl 2-((1-(4-cyanophenyl)-2-methoxyethyl)(methyl)amino)acetate

A solution of 4-(2-methoxyacetoyl)benzonitrile (0.338 g; 1.93 mmol) and glycine tert-butyl ester (0.382 mg; 2.90 mmol) in DCM/MeOH (1:1; 10 mL) was stirred at ambient temperature for 1 hour. Sodium cyanoborohydride (0.182 g; 2.90 mmol) and acetic acid (0.166 mL; 2.90 mmol) were added to the reaction mixture and the mixture stirred for 18 hours. Aqueous paraformaldehyde (0.787 mL) and sodium cyanoborohydride (0.182 g; 2.90 mmol) were added and the reaction mixture stirred for a further 72 hours. The reaction mixture was diluted with DCM and water and then poured through a hydrophobic frit. The filtrate was evaporated in vacuo. The residue was purified by flash chromatography eluting with iso-hexane/EtOAc (3:2) to afford the title compound. $^1$H NMR (CDCl$_3$, 400 MHz) δ 7.62-7.61 (m, 2H), 7.51-7.49 (m, 2H), 4.09-4.06 (m, 1H), 3.62 (m, 2H), 3.42-3.37 (m, 1H), 3.29 (s, 3H), 3.21-3.17 (m, 1H), 2.39 (s, 3H), 1.47 (s, 9H).

Step 3: tert-butyl 2-((1-(4-(N'-hydroxycarbamimidoyl)phenyl)-2-methoxyethyl)(methyl)amino)acetate A solution of tert-butyl 2-((1-(4-cyanophenyl)-2-methoxyethyl)(methyl)amino)acetate (0.136 g; 0.45 mmol) and 50% aqueous hydroxylamine (0.137 mL; 2.24 mmol) in ethanol (2 mL) was heated at 80° C. for 18 hours. The solvent was evaporated in vacuo. The residue was partitioned between DCM and water. The organic phase was poured through a hydrophobic frit and evaporated in vacuo to afford the title compound (0.141 g, 93%). $^1$H NMR (CDCl$_3$, 400 MHz) δ 7.78 (d, J=8.4 Hz, 2H), 7.59-7.57 (m, 2H), 6.70 (br s, 1H), 4.84 (br s, 2H), 4.05-4.02 (m, 1H), 3.71-3.67 (m, 1H), 3.63-3.60 (m, 1H), 3.40-3.35 (m, 1H), 3.34 (s, 3H), 3.21-3.16 (m, 1H), 2.40 (s, 3H), 1.49 (s, 9H).

Intermediate 36 tert-butyl 2-(2-(tert-butyldimethylsilyloxy)-1-(4-(N'-hydroxycarbamimidoyl)phenyl)ethylamino)acetate

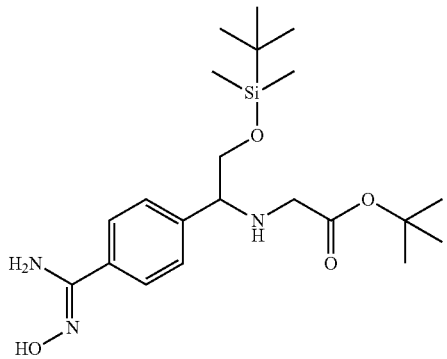 [SMILES: CC(C)(C)OC(=O)CNC(CO[Si](C)(C)C(C)(C)C)c1ccc(/C(N)=N/O)cc1]

Step 1: 4-(2-hydroxyacetoyl)benzonitrile

Trifluoroacetic acid (3.5 mL; 47.1 mmol) was added to a solution of 4-acetylbenzonitrile (3.40 g; 23.4 mmol) and [bis-(trifluoroacetoxy)iodo]benzene (20.1 g; 46.7 mmol) in acetonitrile/water (5:1; 300 mL). The reaction mixture was heated under reflux for 18 hours. The solvent was removed in vacuo and the residue partitioned between DCM and 10% aqueous potassium carbonate. The organic phase was poured through a hydrophobic frit and the solvent evaporated in vacuo. The residue was purified by flash chromatography eluting with iso-hexane/EtOAc (10:1 to 4:1) to afford the title compound. $^1$H NMR (CDCl$_3$, 400 MHz) δ 8.04 (d, J=8.4 Hz, 2H), 7.84 (d, J=8.4 Hz, 2H), 4.91 (d, J=2 Hz, 2H), 3.37 (t, J=2.0 Hz, 2H).

Step 2: tert-butyl 2-(1-(4-cyanophenyl)-2-hydroxyethylamino)acetate

A solution of 4-(2-hydroxyacetoyl)benzonitrile (0.730 g; 4.53 mmol) and glycine tert-butyl ester (0.896 mg; 6.80 mmol) in DCM/MeOH (1:1; 12 mL) was stirred at ambient temperature for 1 hour. Sodium cyanoborohydride (0.342 g; 6.80 mmol) and acetic acid (0.389 mL; 6.80 mmol) were added to the reaction mixture and the mixture stirred for 18 hours. The reaction mixture was diluted with DCM and water and then poured through a hydrophobic frit. The filtrate was evaporated in vacuo. The residue was purified by flash chromatography eluting with iso-hexane/EtOAc (3:2) to afford the title compound. $^1$H NMR (CDCl$_3$, 400 MHz) δ 7.65 (d, J=8.4 Hz, 2H), 7.49 (d, J=8.4 Hz, 2H), 3.88-3.85 (m, 1H), 3.76-3.72 (m, 1H), 3.59-3.55 (m, 1H), 3.32 (d, J=17.6 Hz, 1H), 3.15 (d, J=17.6 Hz, 1H), 1.49 (s, 9H).

Step 3: tert-butyl 2-(2-(tert-butyldimethylsilyloxy)-1-(4-cyanophenyl)ethylamino)acetate t-Butyldimethyl silyl chloride (0.579 g; 3.84 mmol) and imidazole (0.261 g; 3.83 mmol) were added to a solution of tert-butyl 2-(1-(4-cyanophenyl)-2-hydroxyethylamino)acetate (0.709 g; 2.56 mmol) in DMF (10 mL). The reaction mixture was stirred at ambient temperature for 18 hours. The mixture was diluted with EtOAc and washed sequentially with water and brine. The organic phase was poured through a hydrophobic frit and the solvent evaporated in vacuo. The residue was purified by flash chromatography eluting with iso-hexane/EtOAc (10:1) to afford the title compound. $^1$H NMR (CDCl$_3$, 400 MHz) δ 7.63-7.61 (m, 2H), 7.48 (d, J=8.4 Hz, 2H), 3.86-3.83 (m, 1H), 3.66-3.55 (m, 2H), 3.23 (d, J=16.8 Hz, 1H), 3.06 (d, J=16.8 Hz, 1H), 2.53 (br s, 1H), 1.47 (s, 9H), 0.90 (s, 9H), 0.10 (s, 3H), 0.09 (s, 3H).

Step 4: tert-butyl 2-(2-(tert-butyldimethylsilyloxy)-1-(4-(N'-hydroxycarbamimidoyl)phenyl)ethylamino)acetate A solution of tert-butyl 2-(2-(tert-butyldimethylsilyloxy)-1-(4-cyanophenyl)ethylamino)acetate (0.496 g; 1.27 mmol) and 50% aqueous hydroxylamine (0.389 mL; 6.49 mmol) in ethanol (5 mL) was heated at 70° C. for 18 hours. The solvent was evaporated in vacuo. The residue was partitioned between DCM and water. The organic phase was poured through a hydrophobic frit and evaporated in vacuo to afford the title compound (0.566 g, 100%). $^1$H NMR (CDCl$_3$, 400 MHz) δ 7.59 (d, J=8.4 Hz, 2H), 7.39 (d, J=8.0 Hz, 2H), 7.00 (br s, 1H), 4.84 (br s, 2H), 3.84-3.81 (m, 1H), 3.68-3.57 (m, 2H), 3.25 (d, J=17.2 Hz, 1H), 3.08 (d, J=16.8 Hz, 1H), 2.60 (br s, 1H), 1.44 (s, 9H), 0.88 (s, 9H), 0.03 (s, 3H), 0.01 (s, 3H).

Intermediate 37

N'-hydroxy-4-(hydroxymethyl)benzenecarboximidamide

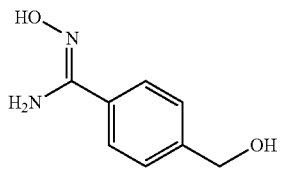 [SMILES: N/C(=N\O)c1ccc(CO)cc1]

To a solution of 4-(hydroxymethyl)benzonitrile (11.05 g; 83.08 mmol) in EtOH (100 mL) was added hydroxylamine (27.4 mL; 415 mmol) (50% in water) and the mixture was heated to 74° C. for 16 hours. The mixture was poured into a crystallizing dish and the solvent were evaporated. The residue was washed with copious amounts of EtOAc, dry MeOH and dry MeCN which was filtered through a hydrophobic frit and the solvent removed in vacuo to give the title compound as a white solid (13.1 g, 95%). $^1$H NMR (DMSO-$d_6$, 400 MHz) δ 9.58 (s, 1H), 7.70-7.62 (m, 2H), 7.34 (d, J=8.1 Hz, 2H), 5.79 (s, 2H), 5.23 (t, J=5.6 Hz, 1H), 4.54 (d, J=5.6 Hz, 2H).

Intermediate 38

N'-hydroxy-3-(hydroxymethyl)benzimidamide

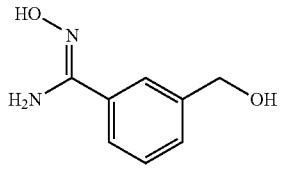 [SMILES: N/C(=N\O)c1cccc(CO)c1]

The title compound was prepared following the procedure described for Intermediate 37, but starting from 3-(hydroxymethyl)benzonitrile (8.4 g; 63.4 mmol), to give the title compound as a white solid (9.2 g, 86%). $^1$H NMR (DMSO-$d_6$, 400 MHz) δ 9.63 (s, 1H), 7.67 (s, 1H), 7.58-7.54 (m, 1H), 7.35 (d, J=4.7 Hz, 2H), 5.82 (s, 2H), 5.27 (t, J=5.7 Hz, 1H), 4.54 (d, J=5.7 Hz, 2H).

Intermediate 39

N'-hydroxy-4-(hydroxyethyl)benzenecarboximidamide

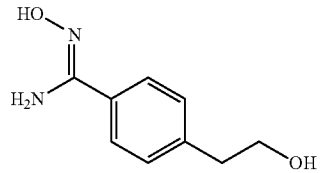 [SMILES: N/C(=N\O)c1ccc(CCO)cc1]

The title compound was prepared following the procedure described for Intermediate 37, but starting from 4-(hydroxyethyl)benzonitrile (2.4 g; 16.5 mmol), to give the title compound as a white solid (3.0 g, 99%). $^1$H NMR (DMSO-$d_6$, 400 MHz) δ 9.58 (s, 1H), 7.60 (d, J=7.9 Hz, 2H), 7.24 (d, J=7.9 Hz, 2H), 5.75 (s, 2H), 4.75-4.69 (m, 1H), 3.64 (d, J=6.5 Hz, 2H), 2.80-2.72 (m, 2H). LC/MS (Method B): 181 (M+H)$^+$. HPLC (Method I) Rt 8.15 min (Purity: 98.7%).

Intermediate 40

N'-hydroxy-3-(hydroxyethyl)benzenecarboximidamide

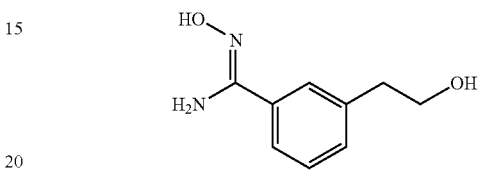

The title compound was prepared following the procedure described for Intermediate 37, but starting from 3-(hydroxyethyl)benzonitrile (9.1 g, 6.2 mmol), to give the title compound as a white solid (1.1 g; 94%). $^1$H NMR (DMSO-$d_6$, 400 MHz) δ 9.59 (s, 1H), 7.55 (s, 1H), 7.51 (d, J=7.7 Hz, 1H), 7.33-7.21 (m, 2H), 5.77 (s, 2H), 4.66 (t, J=5.2 Hz, 1H), 3.65 (q, J=6.2 Hz, 2H), 2.77 (t, J=7.1 Hz, 2H). LC/MS (Method B): 181 (M+H)$^+$. HPLC (Method I) Rt 8.26 min (Purity: 99.9%).

Intermediate 41 tert-butyl ((1R)-1-{4-[amino(hydroxyimino)methyl]phenyl}ethyl)carbamate

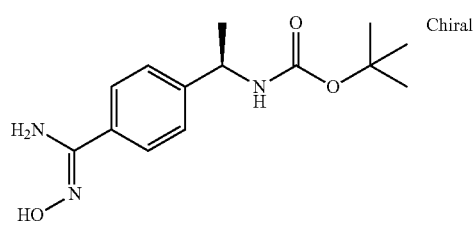 [SMILES: C[C@@H](NC(=O)OC(C)(C)C)c1ccc(/C(N)=N/O)cc1]

Step 1: tert-butyl [(1R)-1-(4-cyanophenyl)ethyl]carbamate

In 5 necked round bottom flask (2.5 L), put under nitrogen atmosphere, equipped with mechanical stirrer, thermometer and addition funnel, a solution of 4-((R)-1-Amino-ethyl)-benzonitrile (81.30 g; 556.13 mmol; 1.0 eq.) in DCM (500 ml) was prepared and cooled at 5° C. A solution of di-tert-butyl dicarbonate (121.38 g; 556.13 mmol; 1.0 eq.) in DCM (400 ml) was added dropwise over minutes, keeping the temperature between 5° C. and 10° C. A precipitate appeared after 20 minutes, but redissolved later. The cooling bath was removed after 2 hr. After 5.5 hr, the reaction mixture was washed with HCl 0.1N aq (300 ml), water (300 ml) and a mixture of water (250 ml)/NaHCO3 aq sat (50 ml). The organic layer was dried (MgSO4) and concentrated under vacuum to give title compound as a pale yellow oil (139.43 g, quantitative yield). LC/MS (Method B): 246.9 (M+H)$^+$, 244.9 (M−H)$^-$. HPLC (Method A) Rt 3.89 min (Purity: 98.8%).

Step 2: tert-butyl ((1R)-1-{4-[amino(hydroxyimino) methyl]phenyl}ethyl)carbamate The title compound was prepared following the general procedure 1, starting from tert-butyl [(1R)-1-(4-cyanophenyl)ethyl]carbamate and was isolated as a white powder (139.2 g, 89%). LC/MS (Method B) 279.9 (M+H)⁺. HPLC (Method A) Rt 2.10 min (Purity: 99.7%).

Intermediate 42 tert-butyl {3-[amino(hydroxyimino)methyl] benzyl}methylcarbamate

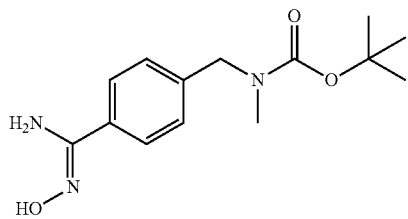 [SMILES: CN(Cc1ccc(/C(N)=N/O)cc1)C(=O)OC(C)(C)C]

Step 1: 3-[(methylamino)methyl]benzonitrile

In a 3 necked round bottom flask (250 ml), put under nitrogen atmosphere, a solution of 3-(bromomethyl)benzonitrile (5 g; 25.5 mmol; 1 eq.) in anhydrous THF (20 ml) was added dropwise into methylamine (63.76 ml; 2 M; 127.52 mmol; 5 eq.) (2M solution in THF) over 1 hour. The reaction mixture was stirred at RT for 2 hours. Some bis-benzylation was observed (7%). The reaction mixture was filtered to remove the salt. The filtrate was evaporated under reduced pressure. The residue was taken up with DCM and evaporated again to give the title compound as a yellow oil (3.78 g, quantitative yield). It was used in the next step without any further purification. LC/MS (Method B) 146.8 (M+H)⁺.

Step 2: tert-butyl (3-cyanobenzyl)methylcarbamate

In a round bottom flask (100 ml), put under nitrogen atmosphere, a solution of crude 3-[(methylamino)methyl]benzonitrile (3.78 g; 23.79 mmol; 1 eq.) in DCM (37.80 ml) was prepared and cooled in an ice bath, then a solution of di-tert-butyl dicarbonate (5.19 g; 23.79 mmol; 1 eq.) in DCM (18.90 ml) was added over 2 minutes. The reaction mixture was stirred between 0° C. and RT during 30 min. The reaction mixture was concentrated under reduced pressure to give a yellow oil (6.87 g). It was purified by flash chromatography (heptane/EtOAc gradient from 90:10 up to 70:30), affording the title compound as a colorless oil (5.13 g, 88%). $^1$H NMR (DMSO-$d_6$, 300 MHz) δ 7.76 (ddd, J=6.9, 1.9, 1.8, 1H), 7.65 (s, 1H), 7.62-7.48 (m, 2H), 4.41 (s, 2H), 2.79 (s, 3H), 1.62-1.16 (m, 9H). HPLC (Method A) Rt 4.28 min (Purity: 100.0%).

Step 3: tert-butyl {3-[(Z)-amino(hydroxyimino)methyl]benzyl}methylcarbamate

The title compound was prepared following the general procedure 1, starting from tert-butyl (3-cyanobenzyl)methylcarbamate and was isolated as a white powder (4.95 g, 87%). $^1$H NMR (DMSO-$d_6$, 300 MHz) δ 9.63 (s, 1H), 7.62-7.48 (m, 2H), 7.42-7.29 (m, 1H), 7.21 (d, J=7.6, 1H), 5.79 (s, 2H), 4.38 (s, 2H), 2.76 (s, 3H), 1.59-1.24 (m, 9H). LC/MS (Method B): 280.3 (M+H)⁺. HPLC (Method A) Rt 2.73 min. (Purity: 99.9%).

Intermediate 43 tert-butyl [{3-[amino(hydroximino)methyl]benzyl}(methyl)amino]acetate

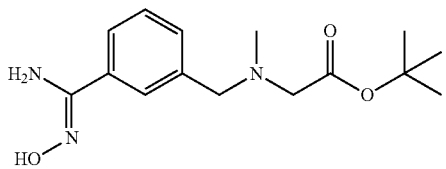 [SMILES: CN(CC(=O)OC(C)(C)C)Cc1cccc(/C(N)=N/O)c1]

Step 1: tert-butyl [(3-cyanobenzyl)(methyl)amino]acetate

To a stirred solution of sarcosine tert-butyl ester hydrochloride (8.1 g, 44.9 mmol) and triethylamine (17 mL, 122.4 mmol) in ACN (100 mL) was added 3-(bromomethyl)benzonitrile (8.0 g, 40.8 mmol) portionwise over a period of 10 minutes at 0° C. After being stirred at RT for 3 hours, the reaction mixture was poured into water and extracted with DCM. Then the organic layer was washed with brine, dried over sodium sulphate and concentrated under reduced pressure to afford the title compound as a pale green liquid (9.0 g, 85%). $^1$H NMR (DMSO-$d_6$, 400 MHz) δ 7.72 (2H, m), 7.64 (1H, m), 7.54 (1H, m), 3.66 (2H, s), 3.18 (2H, s), 2.22 (3H, s), 1.41 (9H, s).

Step 2: tert-butyl [{3-[amino(hydroxyimino)methyl]benzyl}(methyl)amino]acetate The title compound was prepared according the general procedure 1, starting from tert-butyl [(3-cyanobenzyl)(methyl)amino]acetate. It was obtained as a white powder (8.5 g, 84%). $^1$H NMR (DMSO-$d_6$, 400 MHz) δ 9.57 (1H, s), 7.59 (1H, s), 7.53 (1H, m), 7.30 (2H, m), 5.75 (2H, s), 3.61 (2H, s), 3.15 (2H, s), 2.23 (3H, s), 1.41 (9H, s). LC/MS (Method B): 294.0 (M+H)⁺. HPLC (Method A) Rt 3.31 min (Purity: 97.5%).

Intermediate 44

(1R)-1-(4-{5-[2'-methyl-2-(trifluoromethyl)biphenyl-4-yl]-1,2,4-oxadiazol-3-yl}phenyl)ethanamine

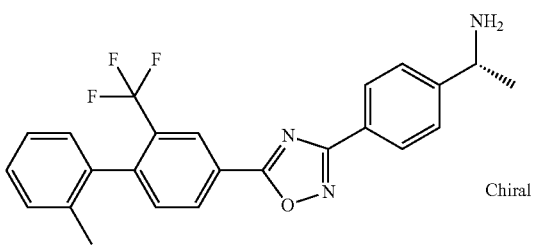 [SMILES: Cc1ccccc1-c1ccc(-c2nc(-c3ccc([C@@H](C)N)cc3)no2)cc1C(F)(F)F]

Step 1: tert-butyl [(1R)-1-(4-{5-[2'-methyl-2-(trifluoromethyl)biphenyl-4-yl]-1,2,4-oxadiazol-3-yl}phenyl)ethyl]carbamate In a 3 necked round bottom flask (250 ml), put under nitrogen atmosphere, a solution of Intermediate 1 (10.03 g; 35.8 mmol; 1.0 eq.) and N-methylmorpholine (4.13 ml; 37.59 mmol; 1.05 eq.) in anhydrous THF (100 ml) was prepared and cooled at 5° C. with an ice bath. Isobutyl chloroformate (4.66 ml; 35.8 mmol; 1.0 eq.) was added dropwise over 2-3 minutes, keeping the temperature between 5° C. and 9° C. After 1 hr at 5° C., Intermediate 41 was added over 2-3 minutes. After 2.5 hr, the reaction mixture was diluted with MTBE (200 ml), then washed with water (2×100 ml), NaOH 0.1N aq (100 ml), water (100 ml) and brine (100 ml). The organic layer was dried (MgSO₄) and concentrated under vacuum until 35 g (a few crystals appeared). The mixture was diluted successively with MTBE (30 ml, quick crystallization), pentane (45 ml), MTBE (15 ml) and pentane (15 ml). The precipitate was filtered off, washed with MTBE/pentane 1:1 (1×, 75 ml)) and pentane (2×). Dried under vacuum (40° C., 45 minutes). Tert-butyl [(1R)-1-(4-{(Z)-amino[({[2'-methyl-2-(trifluoromethyl)biphenyl-4-yl]carbonyl}oxy)imino]methyl}phenyl)ethyl]carbamate was isolated as a white powder (17.55 g, 91%). LC/MS (Method B): 542.3 (M+H)⁺. 540.4 (M−H)⁻. HPLC (Method A) Rt 5.58 min (Purity: 99.6%)

In a round bottom flask (500 ml), put under nitrogen atmosphere, tert-butyl [(1R)-1-(4-{(Z)-amino[({[2'-methyl-2-(trifluoromethyl)biphenyl-4-yl]carbonyl}oxy)imino]methyl}phenyl)ethyl]carbamate (17 g; 31.39 mmol; 1.0 eq.) was suspended in toluene (170 ml), and then heated at 100° C. After one night, the reaction mixture was concentrated under reduced pressure to give the title compound as a pale yellow oil (19.06 g, quantitative yield). This compound was used in the next step without further purification. LC/MS (Method B): 582.4 (M+AcO)⁻. HPLC (Method A) Rt 6.57 min (Purity: 99.1%)

Step 2: (1R)-1-(4-{5-[2'-methyl-2-(trifluoromethyl)biphenyl-4-yl]-1,2,4-oxadiazol-3-yl}phenyl)ethanamine In a round bottom flask (500 ml), a solution of tert-butyl [(1R)-1-(4-{5-[2'-methyl-2-(trifluoromethyl)biphenyl-4-yl]-1,2,4-oxadiazol-3-yl}phenyl)ethyl]carbamate (19 g; 30.85 mmol; 1 eq.) in AcOH (95 ml) was prepared. Then hydrogen chloride (9.09 ml; 92.54 mmol; 3 eq.) (32% aq) was added. The reaction mixture was stirred at RT for 1 hour. The reaction mixture was concentrated under vacuum to remove most of AcOH. The residue was taken up with MTBE (300 ml) and washed with NaOH 3N aq (300 ml), water (150 ml) and brine (150 ml). The aq layers were extracted with MTBE (100 ml). The organic layers were combined, dried (MgSO₄) and concentrated to give the title compound as a pale yellow oil (13.13 g, quantitative yield). ¹H NMR (DMSO-d₆, 300 MHz) δ 8.51 (d, J=1.4, 1H), 8.47 (dd, J=8.0, 1.4, 1H), 8.10-8.01 (m, 2H), 7.69-7.55 (m, 3H), 7.44-7.22 (m, 3H), 7.16 (d, J=7.4, 1H), 4.08 (q, J=6.6, 1H), 2.01 (s, 3H), 1.91 (s, 2H), 1.29 (d, J=6.6, 3H). LC/MS (Method B): 407.1 (M-NH₂)⁺. HPLC (Method A) Rt 4.37 min (Purity: 99.8%)

Intermediate 45

N-methyl-1-(3-{5-[2'-methyl-2-(trifluoromethyl)biphenyl-4-yl]-1,2,4-oxadiazol-3-yl}phenyl)methanamine, hydrochloride salt

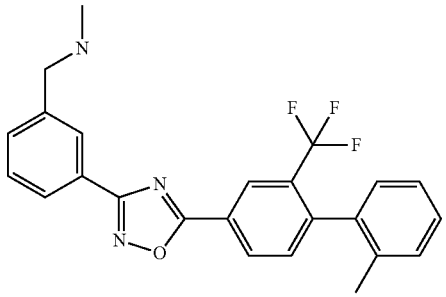 [SMILES: CNCc1cccc(-c2noc(-c3ccc(-c4ccccc4C)c(C(F)(F)F)c3)n2)c1]

Step 1: tert-butyl methyl(3-{5-[2'-methyl-2-(trifluoromethyl)biphenyl-4-yl]-1,2,4-oxadiazol-3-yl}benzyl)carbamate In a round bottom flask (50 ml), put under nitrogen atmosphere, a solution of Intermediate 1 (2.01 g; 7.16 mmol; 1 eq.) in anhydrous THF (20 ml) was prepared and cooled in an ice bath. N-Methylmorpholine (0.83 ml; 7.52 mmol; 1.05 eq.) was added, followed by isobutyl chloroformate (0.93 ml; 7.16 mmol; 1 eq.). The mixture was stirred in ice bath for 1 hour. Intermediate 42 (2.0 g; 7.16 mmol; 1 eq.) was added as one portion and the cooling bath was removed. The reaction mixture was stirred at RT for 1 hour. It was then diluted with MTBE (40 ml) and washed with water (30 ml), NaOH 0.1N (20 ml), water (20 ml) and brine (20 ml). The organic layer was dried (MgSO₄) and concentrated under vacuum to give 3.97 g of a white foam. The foam was taken up with Toluene (30 ml) and the resulting solution was heated at 95° C. for 24 hours. The reaction mixture was concentrated under vacuum to give a yellow glue, which was purified by flash chromatography (Heptane/EtOAc gradient from 95:5 to 80:20). The title compound was isolated as colorless oil (3.25 g, 87%). ¹H NMR (DMSO-d₆, 300 MHz) δ 8.53 (d, J=1.4, 1H), 8.48 (dd, J=8.0, 1.4, 1H), 8.15-7.96 (m, 2H), 7.66 (d, J=8.0, 1H), 7.64-7.56 (m, 1H), 7.56-7.46 (m, 1H), 7.41-7.33 (m, 2H), 7.32-7.25 (m, 1H), 7.17 (d, J=7.3, 1H), 4.49 (s, 2H), 2.81 (s, 3H), 2.02 (s, 3H), 1.47 (s, 9H). LC/MS (Method B): 541.4 (M+NH₄⁺). HPLC (Method A) Rt 6.95 min. (Purity: 98.7%).

Step 2: N-methyl-1-(3-{5-[2'-methyl-2-(trifluoromethyl)biphenyl-4-yl]-1,2,4-oxadiazol-3-yl}phenyl)methanamine, hydrochloride salt In a round bottom flask (100 ml), a solution of tert-butyl methyl(3-{5-[2'-methyl-2-(trifluoromethyl)biphenyl-4-yl]-1,2,4-oxadiazol-3-yl}benzyl)carbamate (3.12 g; 5.96 mmol; 1 eq.) in AcOH (18.72 ml) was prepared, and then aqueous hydrochloric acid solution (2.93 ml of 32% aqueous solution; 29.80 mmol; 5.00 eq.) was added. The reaction mixture was stirred at RT for 2 hours. The reaction mixture was concentrated under vacuum to give a colorless oil. Et₂O (40 ml) was added slowly and the resulting precipitate was filtered off, washed with Et₂O (3×), then pentane (3×) and dried under vacuum (4000, overnight). The title compound was isolated as a white powder (2.44 g, 89%). ¹H NMR (DMSO-d₆, 300

MHz) δ 9.34 (s, 2H), 8.55 (s, 1H), 8.50 (d, J=8.0, 1H), 8.33 (s, 1H), 8.18 (d, J=7.8, 1H), 7.83 (d, J=7.8, 1H), 7.77-7.62 (m, 2H), 7.44-7.33 (m, 2H), 7.32-7.23 (m, 1H), 7.17 (d, J=7.4, 1H), 4.27 (s, 2H), 2.58 (s, 3H), 2.02 (s, 3H). LC/MS (Method B): 424.3 (M+H)⁺. HPLC (Method A) Rt 4.45 min (Purity: 99.7%). Elemental Analysis: [C24H20N3OF3-HCl] Corrected: C, 62.68%; H, 4.60%; N, 9.14%; Cl, 7.71%. Found: C, 62.56%; H, 4.76%; N, 8.81%; Cl, 7.45%.

Intermediate 46 tert-butyl N-(1-{4-[(Z)-amino(hydroxyimino)methyl]phenyl}-2-{[tert-butyl(dimethyl)silyl]oxy}ethyl)-D-alaninate

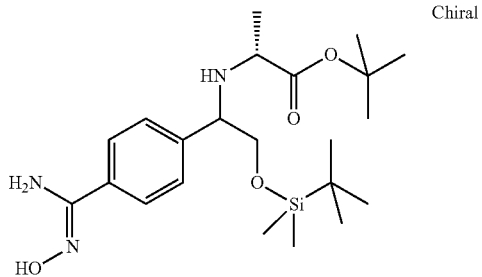 [SMILES: C[C@@H](NC(CO[Si](C)(C)C(C)(C)C)c1ccc(/C(N)=N/O)cc1)C(=O)OC(C)(C)C]

Step 1: 2-Hydroxy-1-(4-cyanophenyl)ethanone

To a solution of 2-Bromo-1-(4-cyanophenyl)ethanone (15 g, 0.067 mol) in methanol (200 ml) was added sodium formate (13.6 g, 0.201 mol) at RT. The reaction mixture was refluxed for 15 h and filtered. The filtrate was concentrated under reduced pressure. The residue was dissolved with ethyl acetate, washed with water and brine solution, dried over Na₂SO₄ and evaporated. The crude material was purified by column chromatography using petroleum ether and ethyl acetate (60:40) as an eluent to afford (5.4 g, 50%) of title compound as an off white solid. ¹H NMR: (DMSO-d₆, 400 MHz) δ 8.06-8.04 (dd, J=1.9, 6.7 Hz, 2H), 8.00-7.98 (dd, J=1.9, 6.7 Hz, 2H), 5.27-5.24 (t, J=5.9 Hz, 1H), 4.82-4.80 (d, J=5.9 Hz, 2H).

Step 2: tert-butyl N-[1-(4-cyanophenyl)-2-hydroxyethyl]-D-alaninate

To a solution of 2-Hydroxy-1-(4-cyanophenyl)ethanone (3.2 g, 0.0198 mol) in methanol and DCM (1:1) (100 ml) were added D-Alanine t-butyl ester hydrochloride (3.6 g, 0.0198 mol) and triethylamine (6.9 ml, 0.0495 mol) at RT. The reaction mixture was heated at 70° C. for 18 h. The reaction mixture was cooled to 0° C. and NaBH₄ (0.9 g, 0.0237 mol) was added in portions and stirred at RT for 1 h. The reaction mixture was quenched with ice, extracted with DCM (2×100 ml), dried over sodium sulphate and evaporated. The crude material was purified by column chromatography using chloroform and methanol (90:10) as an eluent to afford (2.5 g, 43%) of title compound as brown oil. ¹H NMR: (CD₃OD, 400 MHz) δ 7.71-7.69 (d, J=8.36 Hz, 2H), 7.59-7.56 (d, J=8.08 Hz, 2H), 4.76-4.74 (t, J=6.32 Hz, 1H), 3.64-3.61 (q, 4H), 3.44-3.42 (d, J=7.04 Hz, 1H), 1.47 (s, 9H), 1.30-1.28 (d, J=7.04 Hz, 3H). LC/MS (Method A): 291.3 (M+H)⁺. HPLC (Method A) Rt 2.95 min. (Purity: 76.8%).

Step 3: tert-butyl N-[2-{[tert-butyl(dimethyl)silyl]oxy}-1-(4-cyanophenyl)ethyl]-D-alaninate To a solution of tert-butyl N-[1-(4-cyanophenyl)-2-hydroxyethyl]-D-alaninate (2 g, 0.0068 mol) in DCM (30 ml) were added imidazole (0.92 g, 0.0136 mol) and tert-Butyldimethylsilylchloride (1.25 g, 0.0082 mol) at RT. The reaction mixture was stirred at RT for 6 h and portioned between DCM and water, separated the layer and concentrated under reduced pressure. The crude material was purified by column chromatography using petroleum ether and ethyl acetate (80:20) as an eluent to afford (2 g, 74%) of the title compound as brown oil. ¹H NMR: (DMSO-d₆, 400 MHz) δ 7.80-7.77 (m, 2H), 7.53-7.50 (m, 2H), 4.86-4.85 (t, J=3.9 Hz, 1H), 3.17-3.13 (m, 1H), 2.61-2.55 (m, 1H), 1.95-1.89 (m, 1H), 1.39 (s, 9H), 1.09-1.07 (d, J=7.1 Hz, 3H), 0.80 (s, 9H), 0.04 (s, 3H), −0.12 (s, 3H). LC/MS (Method A): 405.3 (M+H)⁺. HPLC (Method A) Rt 5.13 min. (Purity: 73.7%).

Step 4: tert-butyl N-(1-{4-[(Z)-amino(hydroxyimino)methyl]phenyl}-2-{[tert-butyl(dimethyl)silyl]oxy}ethyl)-D-alaninate To a solution of tert-butyl N-[2-{[tert-butyl(dimethyl)silyl]oxy}-1-(4-cyanophenyl)ethyl]-D-alaninate (2 g, 0.0049 mol) in Ethanol (40 ml) was added 50% aqueous Hydroxylamine (1.63 ml, 0.0247 mol) at RT. The reaction mixture was heated at 70° C. for 6 h, cooled to RT and concentrated under reduced pressure. The residue was dissolved in ethyl acetate, washed with water, brine, dried over Na₂SO₄ and evaporated to afford (2 g, 90%) of the title compound as brown oil. ¹H NMR: (DMSO-d₆, 400 MHz) δ 9.57 (s, 1H), 7.61-7.59 (d, J=8.3 Hz, 2H), 7.30-7.28 (d, J=8.3 Hz, 2H), 5.76-5.74 (d, J=5.00 Hz, 2H), 4.77-4.74 (m, 1H), 3.21-3.19 (m, 1H), 2.69-2.59 (m, 1H), 1.95-1.72 (m, 1H), 1.39 (s, 9H), 1.10-1.06 (m, 3H), 0.86-0.82 (m, 9H), 0.03 (s, 3H), −0.12 (s, 3H). LC/MS (Method A): 438.3 (M+H)⁺. HPLC (Method A) Rt 3.82 min. (Purity: 71.1%).

Example 1

2-[(2-fluoro-4-{5-[2'-methyl-2-(trifluoromethyl)biphenyl-4-yl]-1,2,4-oxadiazol-3-yl}benzyl)(methyl)amino]butanoic acid, hydrochloride salt

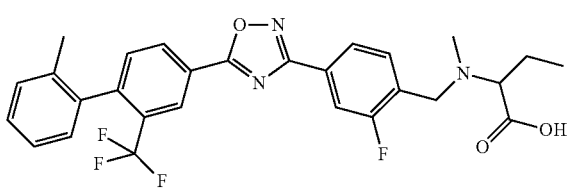 [SMILES: CCC(C(=O)O)N(C)Cc1ccc(-c2noc(-c3ccc(-c4ccccc4C)c(C(F)(F)F)c3)n2)cc1F]

tert-butyl 2-[(2-fluoro-4-{5-[2'-methyl-2-(trifluoromethyl)biphenyl-4-yl]-1,2,4-oxadiazol-3-yl}benzyl)(methyl)amino]butanoate was prepared following the general procedure 3 starting from intermediate 1 and intermediate 5. It was hydrolyzed following general procedure 8, affording the title compound as a white powder. ¹H NMR: (DMSO-d₆, 300 MHz) δ 8.55 (brs, 1H), 8.51 (m, 1H), 8.07 (d, J=8.0 Hz, 1H), 8.00 (d, J=10.4 Hz, 1H), 7.93 (m, 1H), 7.68 (d, J=8 Hz, 1H), 7.43-7.33 (m, 2H), 7.29 (m, 1H), 7.17 (d, J=7.5 Hz, 1H), 4.41 (m, 2H), 3.91 (m, 1H), 2.71 (brs, 3H), 2.02 (s, 3H), 1.97 (m, 2H), 1.00 (t, J=6.9 Hz, 3H). LC/MS (Method B): 528.3 (M+H)+, 526.3 (M−H)−. HPLC (Method A) Rt 4.48 min (Purity: 99.7%).

Example 2

N-[(1R)-1-(4-{5-[2'-(difluoromethyl)-2-methylbiphenyl-4-yl]-1,2,4-oxadiazol-3-yl}phenyl)ethyl]-D-alanine, hydrochloride salt

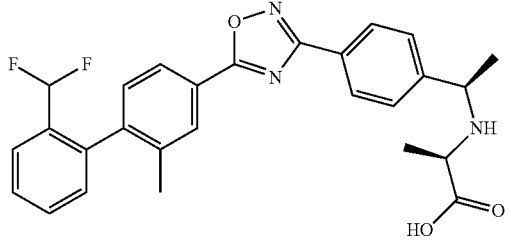 [SMILES: Cc1cc(-c2nc(-c3ccc([C@@H](C)N[C@H](C)C(=O)O)cc3)no2)ccc1-c1ccccc1C(F)F]

Methyl N-[(1R)-1-(4-{5-[2'-(difluoromethyl)-2-methylbiphenyl-4-yl]-1,2,4-oxadiazol-3-yl}phenyl)ethyl]-D-alaninate was prepared following the general procedure 3, starting from Intermediate 2 and intermediate 6. It was hydrolyzed following general procedure 9, affording the title compound as a white powder. $^1$H NMR: (DMSO-$d_6$, 300 MHz) δ 8.17 (m, 3H), 8.08 (m, 1H), 7.76 (m, 3H), 7.65 (m, 2H), 7.44 (d, 1H, J=7.9 Hz), 7.33 (m, 1H), 6.64 (t, 1H, J=54.6 Hz), 4.50 (m, 1H), 3.51 (m, 1H), 2.14 (s, 3H), 1.59 (m, 3H), 1.40 (m, 3H). LC/MS (Method B): 479.4 (M+H)+, 477.5 (M−H)−. HPLC (Method A) Rt 4.15 min (Purity: 98.3%).

Example 3

N-[(1S)-1-(4-{5-[2-(methoxymethyl)-2'-methylbiphenyl-4-yl]-1,2,4-oxadiazol-3-yl}phenyl)ethyl]-D-alanine, hydrochloride salt

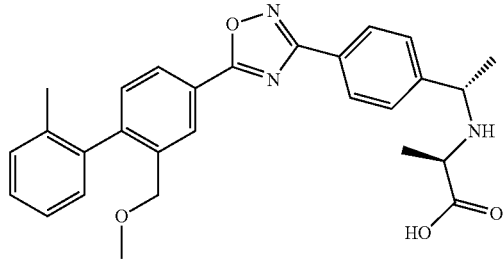 [SMILES: COCc1cc(-c2nc(-c3ccc([C@H](C)N[C@H](C)C(=O)O)cc3)no2)ccc1-c1ccccc1C]

Methyl N-[(1S)-1-(4-{5-[2-(methoxymethyl)-2'-methylbiphenyl-4-yl]-1,2,4-oxadiazol-3-yl}phenyl)ethyl]-D-alaninate was prepared following the general procedure 3, starting from intermediate 3 and Intermediate 10. It was hydrolyzed following general procedure 9, affording the title compound as a white foam. $^1$H NMR: (DMSO-$d_6$, 300 MHz) δ 8.33 (m, 1H), 8.18 (m, 3H), 7.80 (m, 2H), 7.43 (d, 1H, J=7.9 Hz), 7.39-7.23 (m, 3H), 7.14 (m, 1H), 4.53 (m, 1H), 4.20 (m, 2H), 3.66 (m, 1H), 3.25 (s, 3H), 2.03 (s, 3H), 1.62 (m, 3H), 1.44 (m, 3H). LC/MS (Method B): 471.9 (M+H)+, 469.9 (M−H)−. HPLC (Method A) Rt 4.08 min (Purity: 99.2%).

Example 4

N-[(1R)-1-(4-{5-[2-(methoxymethyl)-2'-methylbiphenyl-4-yl]-1,2,4-oxadiazol-3-yl}phenyl)ethyl]-D-alanine, hydrochloride salt

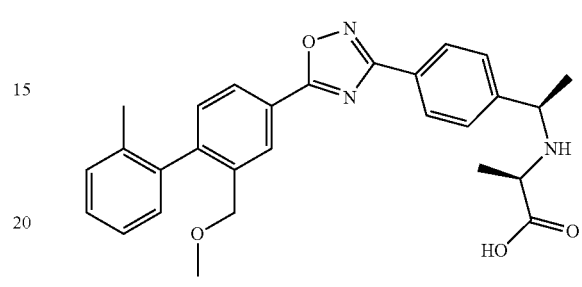

Methyl N-[(1R)-1-(4-{5-[2-(methoxymethyl)-2'-methylbiphenyl-4-yl]-1,2,4-oxadiazol-3-yl}phenyl)ethyl]-D-alaninate was prepared following the general procedure 3, starting from intermediate 3 and intermediate 6. It was hydrolyzed following general procedure 9, affording the title compound as white solid. $^1$H NMR: (DMSO-$d_6$, 300 MHz) δ 8.32 (m, 1H), 8.18 (m, 3H), 7.77 (m, 2H), 7.43 (d, 1H, J=7.9 Hz), 7.39-7.25 (m, 3H), 7.14 (m, 1H), 4.57 (m, 1H), 4.20 (m, 2H), 3.59 (m, 1H), 3.25 (s, 3H), 2.03 (s, 3H), 1.62 (m, 3H), 1.43 (m, 3H). LC/MS (Method B): 472.2 (M+H)+, 470.2 (M−H)−. HPLC (Method A) Rt 4.07 min (Purity: 99.3%).

Example 5

N-[(1S)-1-(4-{5-[2-(methoxymethyl)-2'-methylbiphenyl-4-yl]-1,2,4-oxadiazol-3-yl}phenyl)ethyl]glycine, hydrochloride salt

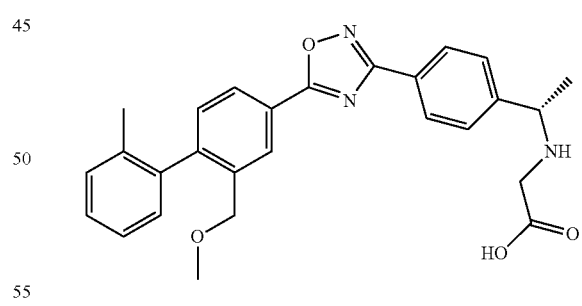

Tert-butyl N-[(1S)-1-(4-{5-[2-(methoxymethyl)-2'-methylbiphenyl-4-yl]-1,2,4-oxadiazol-3-yl}phenyl)ethyl]glycinate was prepared following the general procedure 3, starting from intermediate 3 and intermediate 8. It was hydrolyzed following general procedure 8, affording the title compound as a white powder. $^1$H NMR: (DMSO-$d_6$, 300 MHz) δ 8.32 (m, 1H), 8.18 (m, 3H), 7.78 (m, 2H), 7.44 (d, 1H, J=7.9 Hz), 7.39-7.25 (m, 3H), 7.14 (m, 1H), 4.51 (m, 1H), 4.20 (m, 2H), 3.84 (m, 1H), 3.59 (m, 1H), 3.25 (s, 3H), 2.03 (s, 3H), 1.64 (m, 3H). LC/MS (Method B): 456.0 (M−H)−. HPLC (Method A) Rt 4.05 min (Purity: 97.1%).

Example 6

N-[(1R)-1-(4-{5-[2-methyl-2'-(trifluoromethyl)biphenyl-4-yl]-1,2,4-oxadiazol-3-yl}phenyl)ethyl]-D-alanine, hydrochloride salt

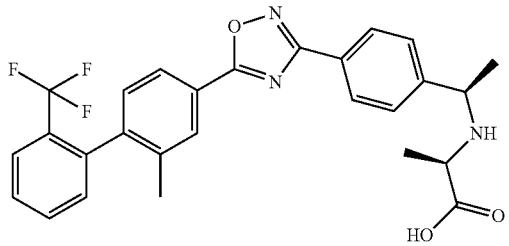 [SMILES: Cc1cc(-c2nc(-c3ccc([C@@H](C)N[C@H](C)C(=O)O)cc3)no2)ccc1-c1ccccc1C(F)(F)F]

Methyl N-[(1R)-1-(4-{5-[2-methyl-2'-(trifluoromethyl)biphenyl-4-yl]-1,2,4-oxadiazol-3-yl}phenyl)ethyl]-D-alaninate was prepared following the general procedure 3, starting from intermediate 4 and intermediate 6. It was hydrolyzed following general procedure 9, affording the title compound as a white powder. $^1$H NMR: (DMSO-$d_6$, 300 MHz) δ 8.18 (m, 3H), 8.06 (m, 1H), 7.91 (m, 1H), 7.83-7.65 (m, 4H), 7.14 (m, 2H), 4.52 (m, 1H), 3.51 (m, 1H), 2.11 (s, 3H), 1.60 (m, 3H), 1.41 (m, 3H). LC/MS (Method B): 496.0 (M+H)$^+$, 494.0 (M−H)$^−$. HPLC (Method A) Rt 4.76 min (Purity: 97.6%).

Example 7

N-[(1R)-1-(4-{5-[2'-(difluoromethyl)-2-methylbiphenyl-4-yl]-1,2,4-oxadiazol-3-yl}phenyl)ethyl]glycine, hydrochloride salt

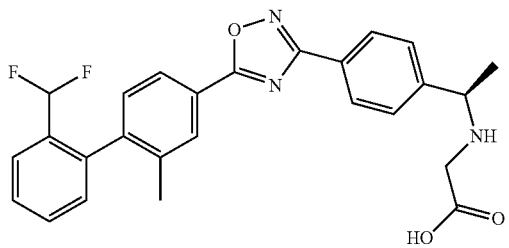 [SMILES: Cc1cc(-c2nc(-c3ccc([C@@H](C)NCC(=O)O)cc3)no2)ccc1-c1ccccc1C(F)F]

Tert-butyl N-[(1R)-1-(4-{5-[2'-(difluoromethyl)-2-methylbiphenyl-4-yl]-1,2,4-oxadiazol-3-yl}phenyl)ethyl]glycinate was prepared following the general procedure 3, starting from intermediate 2 and intermediate 9. It was hydrolyzed following general procedure 8, affording the title compound as a white powder. $^1$H NMR: (DMSO-$d_6$, 300 MHz) δ 8.19 (m, 3H), 8.09 (m, 1H), 7.78 (m, 3H), 7.65 (m, 2H), 7.44 (d, 1H, J=7.9 Hz), 7.33 (m, 1H), 6.64 (t, 1H, J=54.6 Hz), 4.51 (m, 1H), 3.84 (m, 1H), 3.59 (m, 1H), 2.14 (s, 3H), 1.64 (m, 3H). LC/MS (Method B): 462.0 (M−H)$^−$. HPLC (Method A) Rt 4.10 min (Purity: 99.3%).

Example 8

N-[(1R)-1-(4-{5-[2-methyl-2'-(trifluoromethyl)biphenyl-4-yl]-1,2,4-oxadiazol-3-yl}phenyl)ethyl]glycine, hydrochloride salt

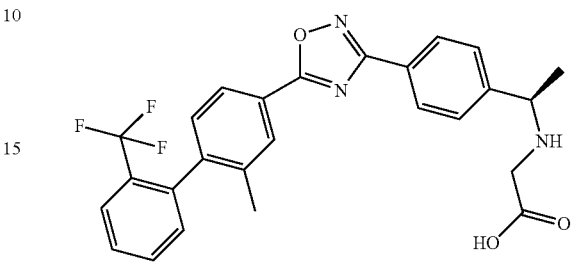

Tert-butyl N-[(1R)-1-(4-{5-[2-methyl-2'-(trifluoromethyl)biphenyl-4-yl]-1,2,4-oxadiazol-3-yl}phenyl)ethyl]glycinate was prepared following the general procedure 3 starting from intermediate 4 and intermediate 9. It was hydrolyzed following general procedure 8, affording the title compound as a white powder. $^1$H NMR: (DMSO-$d_6$, 300 MHz) δ 8.18 (m, 3H), 8.08 (m, 1H), 7.91 (m, 1H), 7.78 (m, 3H), 7.69 (m, 1H), 7.42 (m, 2H), 4.51 (m, 1H), 3.83 (m, 1H), 3.58 (m, 1H), 2.12 (s, 3H), 1.63 (m, 3H). LC/MS (Method B): 480.0 (M−H)$^−$. HPLC (Method A) Rt 4.24 min (Purity: 99.6%).

Example 9

N-[(1R)-1-(4-{5-[2-(methoxymethyl)-2'-methylbiphenyl-4-yl]-1,2,4-oxadiazol-3-yl}phenyl)ethyl]glycine, hydrochloride salt

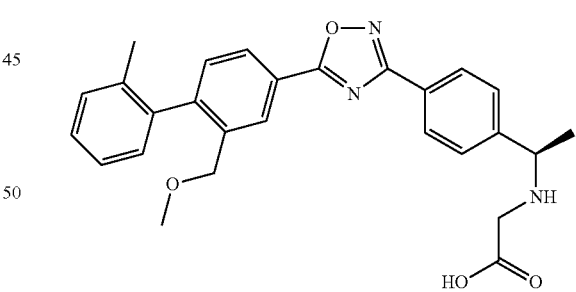

Tert-butyl N-[(1R)-1-(4-{5-[2-(methoxymethyl)-2'-methylbiphenyl-4-yl]-1,2,4-oxadiazol-3-yl}phenyl)ethyl]glycinate was prepared following the general procedure 3, starting from intermediate 3 and intermediate 9. It was hydrolyzed following general procedure 8, affording the title compound as a white powder. $^1$H NMR: (DMSO-$d_6$, 300 MHz) δ 8.32 (m, 1H), 8.18 (m, 3H), 7.79 (m, 2H), 7.43 (d, 1H, J=7.9 Hz), 7.38-7.26 (m, 3H), 7.14 (m, 1H), 4.51 (m, 1H), 4.20 (m, 2H), 3.81 (m, 1H), 3.57 (m, 1H), 3.25 (s, 3H), 2.03 (s, 3H), 1.64 (m, 3H). LC/MS (Method B): 456.0 (M−H)$^−$. HPLC (Method A) Rt 3.87 min (Purity: 95.1%).

Example 10

(2S)-2-{[(1R)-1-(4-{5-[2'-methyl-2-(trifluoromethyl)biphenyl-4-yl]-1,2,4-oxadiazol-3-yl}phenyl)ethyl]amino}butanoic acid, hydrochloride salt

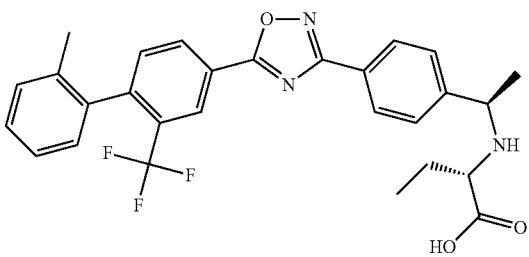 [SMILES: CC[C@H](N[C@H](C)c1ccc(-c2noc(-c3ccc(-c4ccccc4C)c(C(F)(F)F)c3)n2)cc1)C(=O)O]

Ethyl (2S)-2-{[(1R)-1-(4-{5-[2'-methyl-2-(trifluoromethyl)biphenyl-4-yl]-1,2,4-oxadiazol-3-yl}phenyl)ethyl]amino}butanoate was prepared following the general procedure 3, starting from intermediate 1 and intermediate 12. It was hydrolyzed following general procedure 9, affording the title compound as a white foam. $^1$H NMR: (DMSO-$d_6$, 300 MHz) δ 8.54 (brs, 1H), 8.50 (m, 1H), 8.17 (m, 2H), 7.75 (m, 2H), 7.67 (m, 1H), 7.42-7.25 (m, 3H), 7.17 (m, 1H), 4.35 (m, 1H), 3.52 (m, 1H), 2.02 (s, 3H), 1.92-1.72 (m, 2H), 1.56 (m, 3H), 0.91 (t, 3H, J=7.4 Hz). LC/MS (Method B): 510.0 (M+H)$^+$, 508.0 (M−H)$^−$. HPLC (Method A) Rt 4.42 min (Purity: 97.5%).

Example 11

(2R)-2-{[(1R)-1-(4-{5-[2'-methyl-2-(trifluoromethyl)biphenyl-4-yl]-1,2,4-oxadiazol-3-yl}phenyl)ethyl]amino}butanoic acid, hydrochloride salt

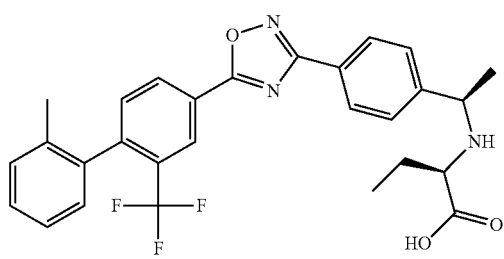 [SMILES: CC[C@@H](N[C@H](C)c1ccc(-c2noc(-c3ccc(-c4ccccc4C)c(C(F)(F)F)c3)n2)cc1)C(=O)O]

Ethyl (2R)-2-{[(1R)-1-(4-{5-[2'-methyl-2-(trifluoromethyl)biphenyl-4-yl]-1,2,4-oxadiazol-3-yl}phenyl)ethyl]amino}butanoate was prepared following the general procedure 3, starting from intermediate 1 and intermediate 13. It was hydrolyzed following general procedure 9, affording the title compound as a white powder. $^1$H NMR: (DMSO-$d_6$, 300 MHz) δ 8.54 (brs, 1H), 8.50 (m, 1H), 8.20 (m, 2H), 7.75 (m, 2H), 7.68 (m, 1H), 7.42-7.33 (m, 2H), 7.29 (m, 1H), 7.17 (m, 1H), 4.48 (m, 1H), 2.02 (s, 3H), 1.92-1.72 (m, 2H), 1.62 (m, 3H), 0.90 (t, 3H, J=7.4 Hz). LC/MS (Method B): 510.0 (M+H)$^+$, 508.0 (M−H)$^−$. HPLC (Method A) Rt 4.43 min (Purity: 99.3%).

Example 12

N-(3-fluoro-5-{5-[2'-methyl-2-(trifluoromethyl)biphenyl-4-yl]-1,2,4-oxadiazol-3-yl}benzyl)leucine, hydrochloride salt

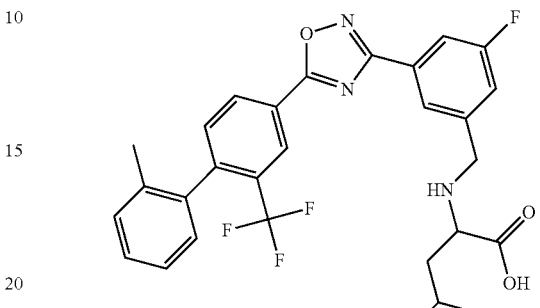

Tert-butyl N-(3-fluoro-5-{5-[2'-methyl-2-(trifluoromethyl)biphenyl-4-yl]-1,2,4-oxadiazol-3-yl}benzyl)leucinate was prepared following the general procedure 3, starting from intermediate 1 and intermediate 14. It was hydrolyzed following general procedure 8, affording the title compound as a white powder. $^1$H NMR: (DMSO-$d_6$, 300 MHz) δ 8.55 (brs, 1H), 8.51 (m, 1H), 8.20 (m, 1H), 7.98 (m, 1H), 7.70 (m, 2H), 7.45-7.22 (m, 3H), 7.17 (m, 1H), 4.35 (m, 2H), 3.94 (m, 1H), 2.02 (s, 3H), 1.85-1.68 (m, 3H), 0.93 (m, 6H). LC/MS (Method B): 542.3 (M+H)$^+$, 540.3 (M−H)$^−$. HPLC (Method A) Rt 5.29 min (Purity: 98.9%).

Example 13

N-(2-fluoro-4-{5-[2'-methyl-2-(trifluoromethyl)biphenyl-4-yl]-1,2,4-oxadiazol-3-yl}benzyl)-N-methylvaline, hydrochloride salt

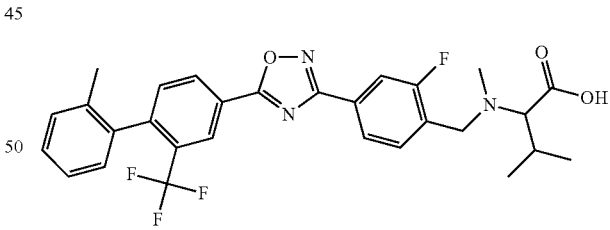

Tert-butyl N-(2-fluoro-4-{5-[2'-methyl-2-(trifluoromethyl)biphenyl-4-yl]-1,2,4-oxadiazol-3-yl}benzyl)-N-methylvalinate was prepared following the general procedure 3 starting from intermediate 1 and intermediate 15. It was hydrolyzed following general procedure 8, affording the title compound as a white powder. $^1$H NMR: (CD$_3$OD, 300 MHz) δ 8.63 (brs, 1H), 8.50 (m, 1H), 8.15 (m, 1H), 8.08 (m, 1H), 7.81 (m, 1H), 7.58 (m, 1H), 7.39-7.20 (m, 3H), 7.14 (m, 1H), 4.54 (m, 2H), 4.01 (m, 1H), 2.89 (s, 3H), 2.58 (m, 1H), 2.06 (s, 3H), 1.24 (m, 3H), 1.09 (m, 3H). LC/MS (Method B): 540.4 (M−H)$^−$. HPLC (Method A) Rt 5.16 min (Purity: 97%).

Example 14

N-methyl-N-[1-(4-{5-[2-methyl-2'-(trifluoromethyl)biphenyl-4-yl]-1,2,4-oxadiazol-3-yl}phenyl)ethyl]glycine, hydrochloride salt

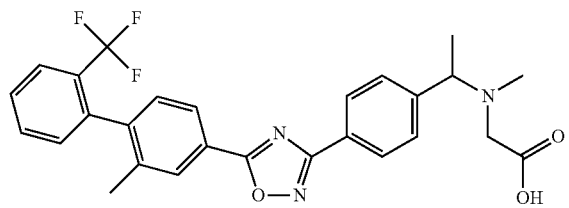

tert-butyl N-methyl-N-[1-(4-{5-[2-methyl-2'-(trifluoromethyl)biphenyl-4-yl]-1,2,4-oxadiazol-3-yl}phenyl)ethyl]glycinate was prepared following the general procedure 3 starting from intermediate 4 and intermediate 16. It was hydrolyzed following general procedure 8, affording the title compound as a white powder. $^1$H NMR: (DMSO-$d_6$, 300 MHz) δ 8.19 (m, 3H), 8.07 (m, 1H), 7.91 (m, 1H), 7.87-7.75 (m, 3H), 7.69 (m, 1H), 7.42 (m, 2H), 4.78 (m, 1H), 4.02 (m, 2H), 2.80 (s, 3H), 2.11 (s, 3H), 1.71 (m, 3H). LC/MS (Method B): 496.2 (M+H)$^+$, 494.3 (M−H)$^−$. HPLC (Method A) Rt 4.78 min (Purity: 99%).

Example 15

N-[1-(4-{5-[2-(methoxymethyl)-2'-methylbiphenyl-4-yl]-1,2,4-oxadiazol-3-yl}phenyl)ethyl]-N-methylglycine, hydrochloride salt

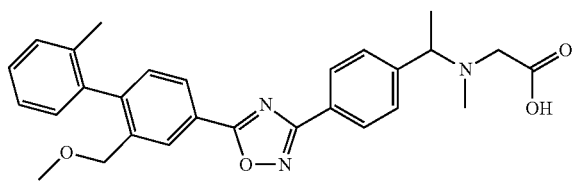 [SMILES: COCc1cc(-c2nc(-c3ccc(C(C)N(C)CC(=O)O)cc3)no2)ccc1-c1ccccc1C]

Tert-butyl N-[1-(4-{5-[2-(methoxymethyl)-2'-methylbiphenyl-4-yl]-1,2,4-oxadiazol-3-yl}phenyl)ethyl]-N-methylglycinate was prepared following the general procedure 3, starting from intermediate 3 and intermediate 16. It was hydrolyzed following general procedure 8, affording the title compound as a colorless oil. $^1$H NMR: (DMSO-$d_6$, 300 MHz) δ 8.33 (brs, 1H), 8.19 (m, 3H), 7.82 (m, 2H), 7.43 (m, 1H), 7.39-7.25 (m, 3H), 7.14 (m, 1H), 4.74 (m, 1H), 4.19 (m, 2H), 3.98 (m, 2H), 3.25 (s, 3H), 2.76 (s, 3H), 2.04 (s, 3H), 1.69 (m, 3H). LC/MS (Method B): 472.2 (M+H)$^+$, 470.3 (M−H)$^−$. HPLC (Method A) Rt 4.05 min (Purity: 98.8%).

Example 16

N-(2-fluoro-4-{5-[2-(methoxymethyl)-2'-methylbiphenyl-4-yl]-1,2,4-oxadiazol-3-yl}benzyl)-2-methylalanine, hydrochloride salt

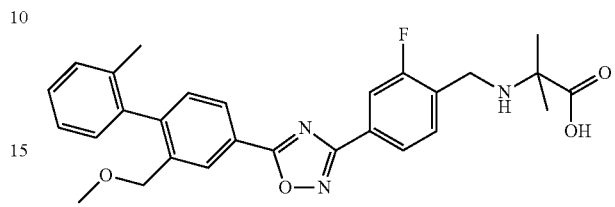

Tert-butyl N-(2-fluoro-4-{5-[2-(methoxymethyl)-2'-methylbiphenyl-4-yl]-1,2,4-oxadiazol-3-yl}benzyl)-2-methylalaninate was prepared following the general procedure 3, starting from intermediate 3 and intermediate 17. It was hydrolyzed following general procedure 8, affording the title compound as a white powder. $^1$H NMR: (DMSO-$d_6$, 300 MHz) δ 8.33 (brs, 1H), 8.18 (m, 1H), 8.08 (m, 1H), 7.98 (m, 1H), 7.89 (m, 1H), 7.44 (m, 1H), 7.39-7.25 (m, 3H), 7.14 (m, 1H), 4.28 (m, 2H), 4.19 (m, 2H), 3.25 (s, 3H), 2.04 (s, 3H), 1.61 (s, 6H). LC/MS (Method B): 490.2 (M+H)$^+$, 488.3 (M−H)$^−$. HPLC (Method A) Rt 4.08 min (Purity: 98.7%).

Example 17

N-[(1S)-1-(4-{5-[2'-methyl-2-(trifluoromethyl)biphenyl-4-yl]-1,2,4-oxadiazol-3-yl}phenyl)ethyl]-D-alanine, hydrochloride salt

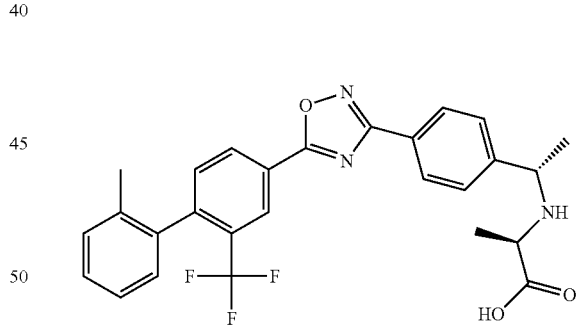

Methyl N-[(1S)-1-(4-{5-[2'-methyl-2-(trifluoromethyl)biphenyl-4-yl]-1,2,4-oxadiazol-3-yl}phenyl)ethyl]-D-alaninate was prepared following the general procedure 3, starting from intermediate 1 and methyl Intermediate 10. It was hydrolyzed following general procedure 9, affording the title compound as a white foam. $^1$H NMR: (DMSO-$d_6$, 300 MHz) δ 8.54 (brs, 1H), 8.50 (m, 1H), 8.21 (m, 2H), 7.83 (m, 2H), 7.67 (m, 1H), 7.36 (m, 2H), 7.29 (m, 1H), 7.17 (m, 1H), 4.54 (m, 1H), 3.67 (m, 1H), 2.02 (s, 3H), 1.63 (d, J=6.8 Hz, 3H), 1.46 (d, J=7.1 Hz, 3H). LC/MS (Method B): 496.4 (M+H)$^+$. HPLC (Method A) Rt 4.85 min (Purity: 98.4%).

Example 18

N-[(1S)-1-(4-{5-[2'-methyl-2-(trifluoromethyl)biphenyl-4-yl]-1,2,4-oxadiazol-3-yl}phenyl)ethyl]-L-alanine, hydrochloride salt

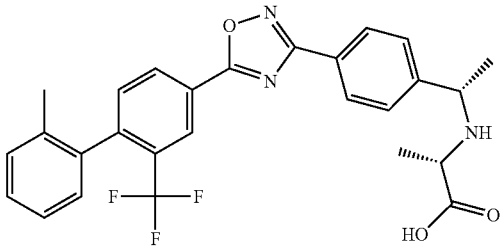 [SMILES: Cc1ccccc1-c1ccc(-c2nc(-c3ccc([C@H](C)N[C@@H](C)C(=O)O)cc3)no2)cc1C(F)(F)F]

Methyl N-[(1S)-1-(4-{5-[2'-methyl-2-(trifluoromethyl)biphenyl-4-yl]-1,2,4-oxadiazol-3-yl}phenyl)ethyl]-L-alaninate was prepared following the general procedure 3, starting from intermediate 1 and intermediate 11. It was hydrolyzed following general procedure 9, affording the title compound as a white foam. $^1$H NMR: (DMSO-$d_6$, 300 MHz) δ 8.54 (brs, 1H), 8.50 (m, 1H), 8.21 (m, 2H), 7.80 (m, 2H), 7.66 (m, 1H), 7.42-7.33 (m, 2H), 7.29 (m, 1H), 7.16 (m, 1H), 4.59 (m, 1H), 3.57 (m, 1H), 2.02 (s, 3H), 1.63 (d, J=6.9 Hz, 3H), 1.45 (d, J=7.0 Hz, 3H). LC/MS (Method B): 496.4 (M+H)$^+$. HPLC (Method A) Rt 4.86 min (Purity: 96.9%).

Example 19

N-[(1R)-1-(4-{5-[2'-methyl-2-(trifluoromethyl)biphenyl-4-yl]-1,2,4-oxadiazol-3-yl}phenyl)ethyl]-L-alanine, hydrochloride salt

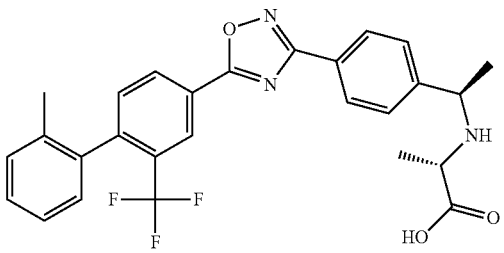 [SMILES: Cc1ccccc1-c1ccc(-c2nc(-c3ccc([C@@H](C)N[C@@H](C)C(=O)O)cc3)no2)cc1C(F)(F)F]

Methyl N-[(1R)-1-(4-{5-[2'-methyl-2-(trifluoromethyl)biphenyl-4-yl]-1,2,4-oxadiazol-3-yl}phenyl)ethyl]-L-alaninate was prepared following the general procedure 3, starting from intermediate 1 and intermediate 7. It was hydrolyzed following general procedure 9, affording the title compound as a white foam. $^1$H NMR: (DMSO-$d_6$, 300 MHz) δ 8.54 (brs, 1H), 8.50 (m, 1H), 8.21 (m, 2H), 7.80 (m, 2H), 7.67 (m, 1H), 7.42-7.33 (m, 2H), 7.29 (m, 1H), 7.17 (m, 1H), 4.53 (m, 1H), 3.65 (m, 1H), 2.02 (s, 3H), 1.61 (d, J=6.8 Hz, 3H), 1.44 (d, J=7.0 Hz, 3H). LC/MS (Method B): 496.5 (M+H)$^+$, 494.5 (M−H)$^−$. HPLC (Method A) Rt 4.89 min (Purity: 100%).

Example 20

N-[(1R)-1-(4-{5-[2'-methyl-2-(trifluoromethyl)biphenyl-4-yl]-1,2,4-oxadiazol-3-yl}phenyl)ethyl]-D-alanine, hydrochloride salt

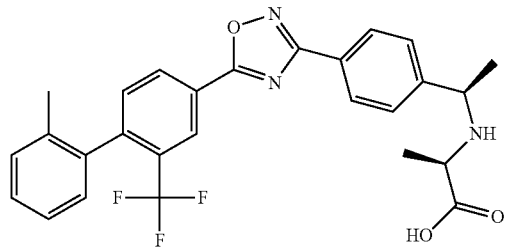 [SMILES: Cc1ccccc1-c1ccc(-c2nc(-c3ccc([C@@H](C)N[C@H](C)C(=O)O)cc3)no2)cc1C(F)(F)F]

Methyl N-[(1R)-1-(4-{5-[2'-methyl-2-(trifluoromethyl)biphenyl-4-yl]-1,2,4-oxadiazol-3-yl}phenyl)ethyl]-D-alaninate was prepared following the general procedure 3, starting from intermediate 1 and intermediate 6. It was hydrolyzed following general procedure 9, affording the title compound as a white solid. $^1$H NMR: (DMSO-$d_6$, 300 MHz) δ 8.55 (d, J=1.5 Hz, 1H), 8.50 (dd, J=8.0, 1.6 Hz, 1H), 8.21 (d, J=8.5 Hz, 2H), 7.80 (d, J=8.3 Hz, 2H), 7.68 (d, J=8.1 Hz, 1H), 7.44-7.25 (m, 3H), 7.17 (d, J=7.5 Hz, 1H), 4.59 (q, J=6.8 Hz, 1H), 3.59 (q, J=7.0 Hz, 1H), 2.02 (s, 3H), 1.64 (d, J=6.8 Hz, 3H), 1.45 (d, J=7.1 Hz, 3H). LC/MS (Method B): 496.5 (M+H)$^+$, 494.4 (M−H)$^−$. HPLC (Method A) Rt 4.88 min (Purity: 100%).

Example 21

N-[(1S)-1-(4-{5-[2'-methyl-2-(trifluoromethyl)biphenyl-4-yl]-1,2,4-oxadiazol-3-yl}phenyl)ethyl]glycine, hydrochloride salt

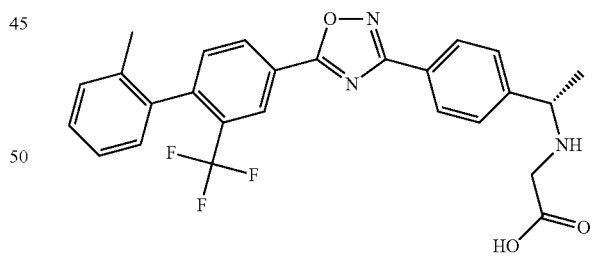

Tert-butyl N-[(1S)-1-(4-{5-[2'-methyl-2-(trifluoromethyl)biphenyl-4-yl]-1,2,4-oxadiazol-3-yl}phenyl)ethyl]glycinate was prepared following the general procedure 3 starting from intermediate 1 and intermediate 8. It was hydrolyzed following general procedure 8, affording the title compound as a pale yellow powder. $^1$H NMR: (DMSO-$d_6$, 300 MHz) δ 8.54 (brs, 1H), 8.50 (m, 1H), 8.21 (m, 2H), 7.79 (m, 2H), 7.69 (d, J=7.9 Hz, 1H), 7.44-7.25 (m, 3H), 7.17 (m, 1H), 4.51 (m, 1H), 3.82 (m, 1H), 3.57 (m, 1H), 2.02 (s, 3H), 1.64 (d, J=6.8 Hz, 3H). LC/MS (Method B): 482.4 (M+H)$^+$, 480.4 (M−H)$^−$. HPLC (Method A) Rt 4.28 min (Purity: 96.4%).

Example 22

N-[(1R)-1-(4-{5-[2'-methyl-2-(trifluoromethyl)biphenyl-4-yl]-1,2,4-oxadiazol-3-yl}phenyl)ethyl]glycine, hydrochloride salt

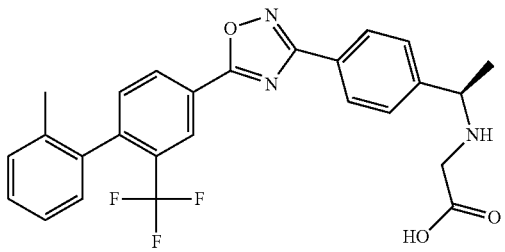 [SMILES: Cc1ccccc1-c1ccc(-c2nc(-c3ccc([C@@H](C)NCC(=O)O)cc3)no2)cc1C(F)(F)F]

Tert-butyl N-[(1R)-1-(4-{5-[2'-methyl-2-(trifluoromethyl)biphenyl-4-yl]-1,2,4-oxadiazol-3-yl}phenyl)ethyl]glycinate was prepared following the general procedure 3, starting from intermediate 1 and intermediate 9. It was hydrolyzed following general procedure 8, affording the title compound as a pale yellow powder. $^1$H NMR: (DMSO-$d_6$, 300 MHz) δ 8.54 (brs, 1H), 8.50 (m, 1H), 8.21 (m, 2H), 7.79 (m, 2H), 7.69 (d, J=7.9 Hz, 1H), 7.43-7.24 (m, 3H), 7.17 (m, 1H), 4.51 (m, 1H), 3.79 (m, 1H), 3.55 (m, 1H), 2.02 (s, 3H), 1.63 (d, J=6.8 Hz, 3H). LC/MS (Method B): n.d (M+H)$^+$, 480.5 (M−H)$^−$. HPLC (Method A) Rt 4.30 min (Purity: 99%).

Example 23

N-[1-(4-{5-[2-methyl-2'-(trifluoromethyl)biphenyl-4-yl]-1,2,4-oxadiazol-3-yl}phenyl)ethyl]glycine, hydrochloride salt

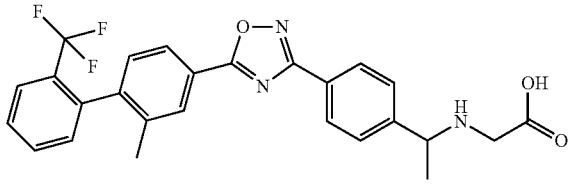 [SMILES: Cc1cc(-c2nc(-c3ccc(C(C)NCC(=O)O)cc3)no2)ccc1-c1ccccc1C(F)(F)F]

Step 1: tert-butyl [1-(4-{5-[2-methyl-2'-(trifluoromethyl)biphenyl-4-yl]-1,2,4-oxadiazol-3-yl}phenyl)ethyl]carbamate The title compound was prepared following the general procedure 3 starting from Intermediate 4 and Intermediate 18. It was isolated as a white foam. LC/MS (Method B): 524.3 (M+H)$^+$. HPLC (Method A) Rt 6.31 min (Purity: 99.6%).

Step 2: 1-(4-{5-[2-methyl-2'-(trifluoromethyl)biphenyl-4-yl]-1,2,4-oxadiazol-3-yl}phenyl)ethanamine, hydrochloride salt The title compound was prepared following the general procedure 8 starting from tert-butyl [1-(4-{5-[2-methyl-2'-(trifluoromethyl)biphenyl-4-yl]-1,2,4-oxadiazol-3-yl}phenyl)ethyl]carbamate and was isolated as a white foam (620 mg, quantitative). $^1$H NMR (DMSO-$d_6$, 300 MHz) δ 8.60 (brs, 3H), 8.18 (m, 3H), 8.07 (m, 1H), 7.91 (d, J=8 Hz, 1H), 7.77 (m, 3H), 7.68 (m, 1H), 7.41 (m, 1H), 4.53 (m, 1H), 2.11 (s, 3H), 1.56 (d, J=6.8 Hz, 3H). LC/MS (Method B): n.dp (M+H), n.dp (M−H). HPLC (Method A) Rt 4.22 min (Purity: 99.7%).

Step 3: N-[1-(4-{5-[2-methyl-2'-(trifluoromethyl)biphenyl-4-yl]-1,2,4-oxadiazol-3-yl}phenyl)ethyl]glycine, hydrochloride salt Tert-butyl N-[1-(4-{5-[2-methyl-2'-(trifluoromethyl)biphenyl-4-yl]-1,2,4-oxadiazol-3-yl}phenyl)ethyl]glycinate was prepared following the general procedure 11 starting from 1-(4-{5-[2-methyl-2'-(trifluoromethyl)biphenyl-4-yl]-1,2,4-oxadiazol-3-yl}phenyl)ethanamine, hydrochloride salt and tert-butyl bromoacetate. It was hydrolyzed following general procedure 8, affording the title compound as a white powder. $^1$H NMR: (DMSO-$d_6$, 300 MHz) δ 8.18 (m, 3H), 8.08 (m, 1H), 7.91 (d, J=7.90 Hz, 1H), 7.77 (m, 3H), 7.69 (m, 1H), 7.41 (m, 2H), 4.74 (m, 1H), 3.74 (m, 1H), 3.52 (m, 1H), 2.11 (s, 3H), 1.61 (d, J=6.8 Hz, 3H). LC/MS (Method B): 482.2 (M+H)$^+$, 480.2 (M−H)$^−$. HPLC (Method A) Rt 4.25 min (Purity: 99.9%).

Example 24

N-[(1S)-1-(4-{5-[2-methyl-2'-(trifluoromethyl)biphenyl-4-yl]-1,2,4-oxadiazol-3-yl}phenyl)ethyl]-L-alanine, hydrochloride salt and N-[(1R)-1-(4-{5-[2-methyl-2'-(trifluoromethyl)biphenyl-4-yl]-1,2,4-oxadiazol-3-yl}phenyl)ethyl]-D-alanine, hydrochloride salt

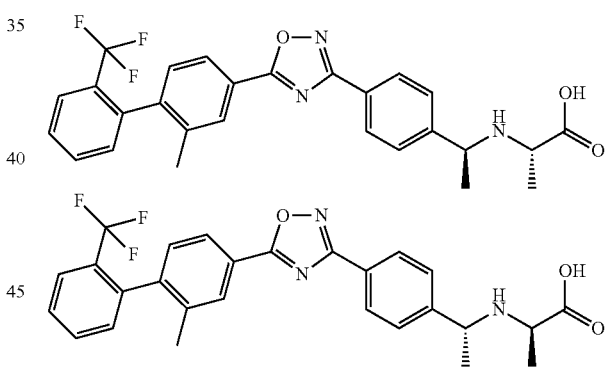

Methyl N-[1-(4-{5-[2-methyl-2'-(trifluoromethyl)biphenyl-4-yl]-1,2,4-oxadiazol-3-yl}phenyl)ethyl]-alaninate was prepared following the general procedure 11 starting from 1-(4-{5-[2-methyl-2'-(trifluoromethyl)biphenyl-4-yl]-1,2,4-oxadiazol-3-yl}phenyl)ethanamine, hydrochloride salt (Example 23, step 2) and methyl 2-bromopropionate. The resulting pair of two diastereomers was separated by flash chromatography (heptane/EtOAc gradient from 95:5 up to 85:15), affording methyl N-[(1S)-1-(4-{5-[2-methyl-2'-(trifluoromethyl)biphenyl-4-yl]-1,2,4-oxadiazol-3-yl}phenyl)ethyl]-D-alaninate and methyl N-[(1R)-1-(4-{5-[2-methyl-2'-(trifluoromethyl)biphenyl-4-yl]-1,2,4-oxadiazol-3-yl}phenyl)ethyl]-L-alaninate (75 mg, 27%) as one fraction and methyl N-[(1S)-1-(4-{5-[2-methyl-2'-(trifluoromethyl)biphenyl-4-yl]-1,2,4-oxadiazol-3-yl}phenyl)ethyl]-L-alaninate and methyl N-[(1R)-1-(4-{5-[2-methyl-2'-(trifluoromethyl)biphenyl-4-yl]-1,2,4-oxadiazol-3-yl}phenyl)ethyl]-D-alaninate (50 mg, 18%) as a second fraction.

The second fraction, containing methyl N-[(1S)-1-(4-{5-[2-methyl-2'-(trifluoromethyl)biphenyl-4-yl]-1,2,4-oxadiazol-3-yl}phenyl)ethyl]-L-alaninate and methyl N-[(1R)-1-(4-{5-[2-methyl-2'-(trifluoromethyl)biphenyl-4-yl]-1,2,4-oxadiazol-3-yl}phenyl)ethyl]-D-alaninate, was hydrolyzed following general procedure 9, affording the title compound as a white powder. $^1$H NMR: (DMSO-$d_6$, 400 MHz) δ 8.15 (m, 3H), 8.07 (m, 1H), 7.91 (m, 1H), 7.83-7.64 (m, 4H), 7.41 (m, 2H), 4.35 (m, 1H), 2.11 (s, 3H), 1.53 (d, J=6.5 Hz, 3H), 1.35 (d, J=7.0 Hz, 3H). LC/MS (Method B): 496.2 (M+H)$^+$, 494.3 (M−H)$^−$. HPLC (Method A) Rt 4.28 min (Purity: 100%). Methyl N-[(1S)-1-(4-{5-[2-methyl-2'-(trifluoromethyl)biphenyl-4-yl]-1,2,4-oxadiazol-3-yl}phenyl)ethyl]-L-alaninate and methyl N-[(1R)-1-(4-{5-[2-methyl-2'-(trifluoromethyl)biphenyl-4-yl]-1,2,4-oxadiazol-3-yl}phenyl)ethyl]-D-alaninate can be separated, by chiral HPLC methods.

Example 25

N-[(1S)-1-(4-{5-[2-methyl-2'-(trifluoromethyl)biphenyl-4-yl]-1,2,4-oxadiazol-3-yl}phenyl)ethyl]-D-alanine and N-[(1R)-1-(4-{5-[2-methyl-2'-(trifluoromethyl)biphenyl-4-yl]-1,2,4-oxadiazol-3-yl}phenyl)ethyl]-L-alanine

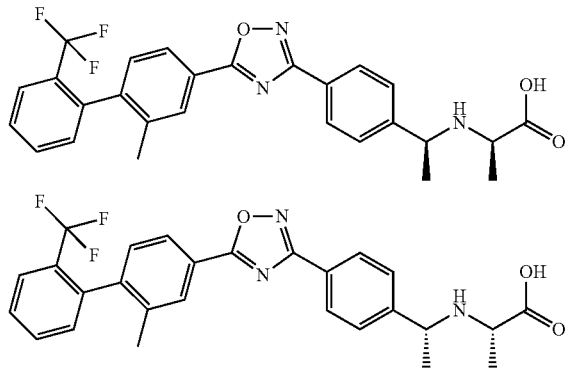 [SMILES: Cc1cc(-c2nc(-c3ccc([C@H](C)N[C@H](C)C(=O)O)cc3)no2)ccc1-c1ccccc1C(F)(F)F ; Cc1cc(-c2nc(-c3ccc([C@@H](C)N[C@@H](C)C(=O)O)cc3)no2)ccc1-c1ccccc1C(F)(F)F]

Methyl N-[(1S)-1-(4-{5-[2-methyl-2'-(trifluoromethyl)biphenyl-4-yl]-1,2,4-oxadiazol-3-yl}phenyl)ethyl]-D-alaninate and methyl N-[(1R)-1-(4-{5-[2-methyl-2'-(trifluoromethyl)biphenyl-4-yl]-1,2,4-oxadiazol-3-yl}phenyl)ethyl]-L-alaninate (prepared in Example 24) were hydrolyzed following general procedure 9, affording the title compound as a white powder. $^1$H NMR: (DMSO-$d_6$, 400 MHz) δ 8.15 (m, 3H), 8.07 (m, 1H), 7.91 (m, 1H), 7.79 (m, 1H), 7.69 (m, 3H), 7.41 (m, 2H), 4.34 (m, 1H), 2.11 (s, 3H), 1.51 (d, J=6.6 Hz, 3H), 1.32 (d, J=7.1 Hz, 3H). LC/MS (Method B): 496.2 (M+H)$^+$, 494.3 (M−H)$^−$. HPLC (Method A) Rt 4.29 min (Purity: 86.5%). N-[(1S)-1-(4-{5-[2-methyl-2'-(trifluoromethyl)biphenyl-4-yl]-1,2,4-oxadiazol-3-yl}phenyl)ethyl]-D-alaninate and methyl N-[(1R)-1-(4-{5-[2-methyl-2'-(trifluoromethyl)biphenyl-4-yl]-1,2,4-oxadiazol-3-yl}phenyl)ethyl]-L-alaninate can be separated, by chiral HPLC method.

Example 26

N-[(1S)-1-(4-{5-[2'-methyl-2-(trifluoromethyl)biphenyl-4-yl]-1,2,4-oxadiazol-3-yl}phenyl)ethyl]-L-alanine, hydrochloride salt and N-[(1R)-1-(4-{5-[2'-methyl-2-(trifluoromethyl)biphenyl-4-yl]-1,2,4-oxadiazol-3-yl}phenyl)ethyl]-D-alanine, hydrochloride salt

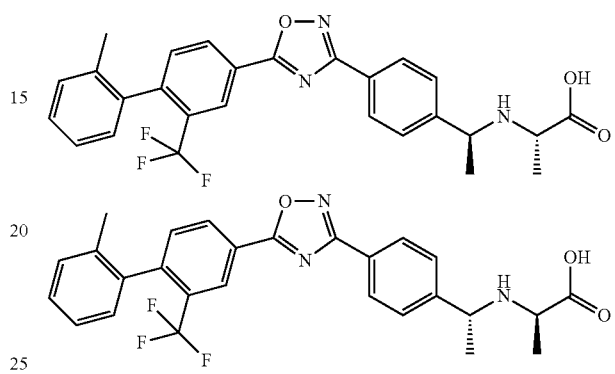

Step 1: tert-butyl [1-(4-{5-[2'-methyl-2-(trifluoromethyl)biphenyl-4-yl]-1,2,4-oxadiazol-3-yl}phenyl)ethyl]carbamate The title compound was prepared following the general procedure 3 starting from Intermediate 1 and Intermediate 18 and was isolated as a white foam. LC/MS (Method B): 524.4 (M+H)$^+$, 522.4 (M−H)$^−$. HPLC (Method A) Rt 6.43 min (Purity: 99.6%).

Step 2: 1-(4-{5-[2'-methyl-2-(trifluoromethyl)biphenyl-4-yl]-1,2,4-oxadiazol-3-yl}phenyl)ethanamine, hydrochloride The title compound was prepared following the general procedure 8 starting from tert-butyl [1-(4-{5-[2'-methyl-2-(trifluoromethyl)biphenyl-4-yl]-1,2,4-oxadiazol-3-yl}phenyl)ethyl]carbamate and was isolated as a yellow foam. (880 mg, 91%). $^1$H NMR: (DMSO-$d_6$, 400 MHz) δ 8.58-8.47 (m, 4H), 8.20 (d, J=8.3 Hz, 2H), 7.76 (d, J=8.3 Hz, 2H), 7.67 (d, J=8.0 Hz, 1H), 7.42-7.25 (m, 3H), 7.17 (d, J=7.3 Hz, 1H), 4.54 (m, 1H), 2.02 (s, 3H), 1.56 (d, J=6.8 Hz, 3H). LC/MS (Method B): 459.2 (M−H)$^−$. HPLC (Method A) Rt 4.32 min (Purity: 98.7%).

Step 3: N-[(1S)-1-(4-{5-[2'-methyl-2-(trifluoromethyl)biphenyl-4-yl]-1,2,4-oxadiazol-3-yl}phenyl)ethyl]-L-alanine, hydrochloride salt and N-[(1R)-1-(4-{5-[2'-methyl-2-(trifluoromethyl)biphenyl-4-yl]-1,2,4-oxadiazol-3-yl}phenyl)ethyl]-D-alanine, hydrochloride salt Methyl N-[1-(4-{5-[2'-methyl-2-(trifluoromethyl)biphenyl-4-yl]-1,2,4-oxadiazol-3-yl}phenyl)ethyl]-alaninate was prepared following the general procedure 11 starting from 1-(4-{5-[2'-methyl-2-(trifluoromethyl)biphenyl-4-yl]-1,2,4-oxadiazol-3-yl}phenyl)ethanamine, hydrochloride salt and methyl 2-bromopropionate. The resulting pair of two diastereomers could be separated by flash chromatography (heptane/EtOAc gradient from 95:5 up to 85:15), affording methyl N-[(1S)-1-(4-{5-[2'-methyl-2-(trifluoromethyl)biphenyl-4-yl]-1,2,4-oxadiazol-3-yl}phenyl)ethyl]-D-alaninate and methyl N-[(1R)-1-(4-{5-[2'-methyl-2-(trifluoromethyl)biphenyl-4-yl]-1,2,4-oxadiazol-3-yl}phenyl)ethyl]-L-alaninate (90 mg, 33%) as a first fraction and methyl N-[(1S)-1-(4-{5-[2'-methyl-2-(trifluoromethyl)biphenyl-4-yl]-1,2,4-oxadiazol-3-yl}phenyl)ethyl]-L-alaninate and methyl N-[(1R)-1-(4-{5-[2'-methyl-2-(trifluoromethyl)biphenyl-4-yl]-1,2,4-oxadiazol-3-yl}phenyl)ethyl]-D-alaninate (85 mg, 31%) as second fraction.

The second fraction, containing methyl N-[(1S)-1-(4-{5-[2'-methyl-2-(trifluoromethyl)biphenyl-4-yl]-1,2,4-oxadiazol-3-yl}phenyl)ethyl]-L-alaninate and methyl N-[(1R)-1-(4-{5-[2'-methyl-2-(trifluoromethyl)biphenyl-4-yl]-1,2,4-oxadiazol-3-yl}phenyl)ethyl]-D-alaninate was hydrolyzed following general procedure 9, affording the title compound as a white powder. $^1$H NMR: (DMSO-$d_6$, 400 MHz) δ 8.54 (brs, 1H), 8.49 (m, 1H), 8.19 (d, J=8.3 Hz, 2H), 7.79 (d, J=8.3 Hz, 2H), 7.67 (d, J=8.3 Hz, 1H), 7.42-7.25 (m, 3H), 7.16 (m, 1H), 4.44 (m, 1H), 3.50 (m, 1H), 2.02 (s, 3H), 1.58 (d, J=6.6 Hz, 3H), 1.40 (d, J=7.0 Hz, 3H). LC/MS (Method B): 496.2 (M+H)$^+$, 494.3 (M−H)$^−$. HPLC (Method A) Rt 4.36 min (Purity: 97.8%). N-[(1S)-1-(4-{5-[2'-methyl-2-(trifluoromethyl)biphenyl-4-yl]-1,2,4-oxadiazol-3-yl}phenyl)ethyl]-L-alaninate and methyl N-[(1R)-1-(4-{5-[2'-methyl-2-(trifluoromethyl)biphenyl-4-yl]-1,2,4-oxadiazol-3-yl}phenyl)ethyl]-D-alaninate can be separated, by chiral HPLC following Method J described above for example.

Example 27

N-[(1S)-1-(4-{5-[2'-methyl-2-(trifluoromethyl)biphenyl-4-yl]-1,2,4-oxadiazol-3-yl}phenyl)ethyl]-D-alanine, hydrochloride salt and N-[(1R)-1-(4-{5-[2'-methyl-2-(trifluoromethyl)biphenyl-4-yl]-1,2,4-oxadiazol-3-yl}phenyl)ethyl]-L-alanine, hydrochloride salt

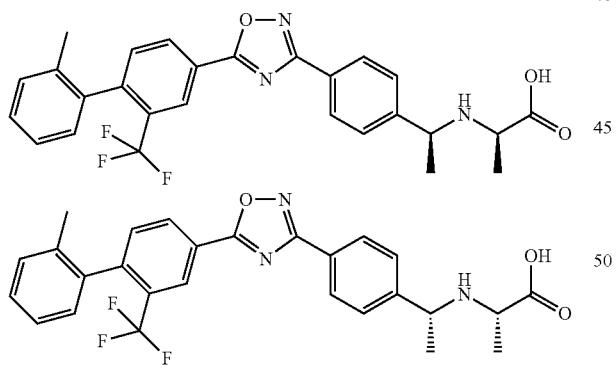

Methyl N-[(1S)-1-(4-{5-[2'-methyl-2-(trifluoromethyl)biphenyl-4-yl]-1,2,4-oxadiazol-3-yl}phenyl)ethyl]-D-alaninate and methyl N-[(1R)-1-(4-{5-[2'-methyl-2-(trifluoromethyl)biphenyl-4-yl]-1,2,4-oxadiazol-3-yl}phenyl)ethyl]-L-alaninate (prepared in Example 26) were hydrolyzed following general procedure 9, affording the title compound as a white powder. $^1$H NMR: (DMSO-$d_6$, 400 MHz) δ 8.54 (brs, 1H), 8.50 (m, 1H), 8.20 (d, J=8.3 Hz, 2H), 7.75 (d, J=8.3 Hz, 2H), 7.67 (d, J=8.3 Hz, 1H), 7.42-7.25 (m, 3H), 7.16 (m, 1H), 4.53 (m, 1H), 3.55 (m, 1H), 2.02 (s, 3H), 1.60 (d, J=6.6 Hz, 3H), 1.41 (d, J=7.0 Hz, 3H). LC/MS (Method B): 496.2 (M+H)$^+$, 494.3 (M−H)$^−$. HPLC (Method A) Rt 4.34 min (Purity: 91.1%). N-[(1S)-1-(4-{5-[2'-methyl-2-(trifluoromethyl)biphenyl-4-yl]-1,2,4-oxadiazol-3-yl}phenyl)ethyl]-D-alaninate and methyl N-[(1R)-1-(4-{5-[2'-methyl-2-(trifluoromethyl)biphenyl-4-yl]-1,2,4-oxadiazol-3-yl}phenyl)ethyl]-L-alaninate can be separated, by chiral HPLC following Method J described above for example.

Example 28

N-methyl-N-[1-(3-{5-[2-methyl-2'-(trifluoromethyl)biphenyl-4-yl]-1,2,4-oxadiazol-3-yl}phenyl)ethyl]alanine, hydrochloride salt

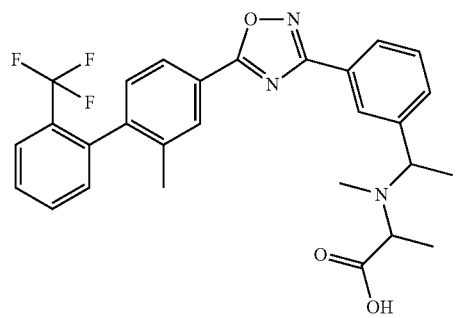 [SMILES: Cc1cc(-c2nc(-c3cccc(C(C)N(C)C(C)C(=O)O)c3)no2)ccc1-c1ccccc1C(F)(F)F]

N-methyl-N-[1-(3-{5-[2-methyl-2'-(trifluoromethyl)biphenyl-4-yl]-1,2,4-oxadiazol-3-yl}phenyl)ethyl]alaninate was prepared following the general procedure 3 starting from intermediate 4 and intermediate 19. It was hydrolyzed following general procedure 9, affording the title compound as a colorless oil. $^1$H NMR: (DMSO-$d_6$, 300 MHz) δ 8.27 (m, 1H), 8.17 (brs, 1H), 8.09 (m, 2H), 7.91 (d, J=8 Hz, 1H), 7.78 (m, 2H), 7.68 (m, 2H), 7.41 (m, 2H), 4.48 (m, 1H), 3.81 (m, 1H), 2.54 (m, 3H), 2.11 (s, 3H), 1.58 (m, 3H), 1.37 (m, 3H). LC/MS (Method B): 510.3 (M+H)$^+$, 508.4 (M−H)$^−$. HPLC (Method A) Rt 4.33 min (Purity: 95.1%).

Example 29

N-methyl-N-[1-(3-{5-[2'-methyl-2-(trifluoromethyl)biphenyl-4-yl]-1,2,4-oxadiazol-3-yl}phenyl)ethyl]alanine, hydrochloride salt

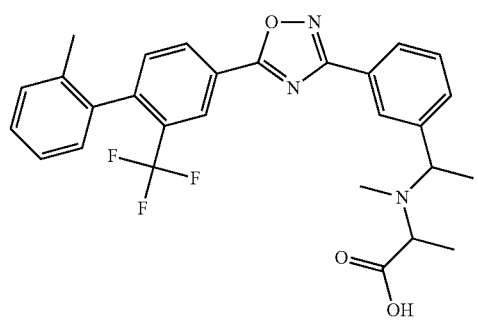 [SMILES: Cc1ccccc1-c1ccc(-c2nc(-c3cccc(C(C)N(C)C(C)C(=O)O)c3)no2)cc1C(F)(F)F]

N-methyl-N-[1-(3-{5-[2'-methyl-2-(trifluoromethyl)biphenyl-4-yl]-1,2,4-oxadiazol-3-yl}phenyl)ethyl]alaninate was prepared following the general procedure 3 starting from intermediate 1 and intermediate 19. It was hydrolyzed following general procedure 9, affording the title compound as a white foam. $^1$H NMR: (DMSO-$d_6$, 300 MHz) δ 8.54 (brs, 1H), 8.51 (m, 1H), 8.30 (m, 1H), 8.14 (m, 1H), 7.80 (m, 1H), 7.68 (m, 2H), 7.43-7.33 (m, 2H), 7.29 (m, 1H), 7.17 (m, 1H), 4.51 (m, 1H), 3.88 (m, 1H), 2.57 (m, 3H), 2.02 (s, 3H), 1.59 (m, 3H), 1.39 (m, 3H). LC/MS (Method B): 510.3 (M+H)$^+$, 508.4 (M−H)$^-$. HPLC (Method A) Rt 4.41 min (Purity: 96.1%).

Example 30

N-methyl-N-[1-(3-{5-[2-methyl-2'-(trifluoromethyl)biphenyl-4-yl]-1,2,4-oxadiazol-3-yl}phenyl)ethyl]glycine, hydrochloride salt

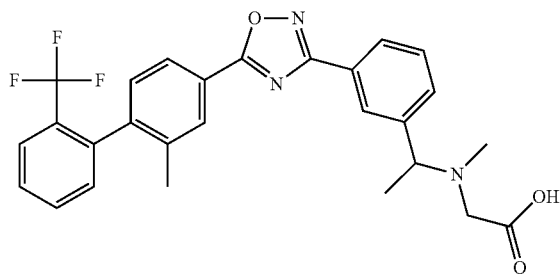

Tert-butyl N-methyl-N-[1-(3-{5-[2-methyl-2'-(trifluoromethyl)biphenyl-4-yl]-1,2,4-oxadiazol-3-yl}phenyl)ethyl]glycinate was prepared following the general procedure 3 starting from intermediate 4 and intermediate 20. It was hydrolyzed following general procedure 8, affording the title compound as a white powder. $^1$H NMR: (DMSO-d$_6$, 300 MHz) δ 8.33 (m, 1H), 8.20 (m, 2H), 8.08 (m, 1H), 7.92 (m, 1H), 7.85 (m, 1H), 7.81-7.65 (m, 3H), 7.42 (m, 2H), 4.76 (m, 1H), 3.95 (m, 2H), 2.77 (s, 3H), 2.12 (s, 3H), 1.71 (m, 3H). LC/MS (Method B): 496.2 (M+H)$^+$, 494.3 (M−H)$^-$. HPLC (Method A) Rt 4.28 min (Purity: 98.6%).

Example 31

N-(2-fluoro-4-{5-[2'-methyl-2-(trifluoromethyl)biphenyl-4-yl]-1,2,4-oxadiazol-3-yl}benzyl)-N,2-dimethylalanine, hydrochloride salt

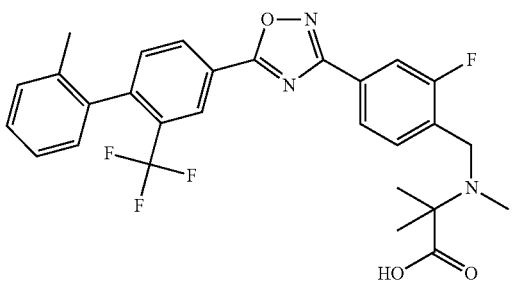 [SMILES: Cc1ccccc1-c1ccc(-c2nc(-c3ccc(CN(C)C(C)(C)C(=O)O)c(F)c3)no2)cc1C(F)(F)F]

Tert-butyl N-(2-fluoro-4-{5-[2'-methyl-2-(trifluoromethyl)biphenyl-4-yl]-1,2,4-oxadiazol-3-yl}benzyl)-N,2-dimethylalaninate was prepared following the general procedure 3 starting from intermediate 1 and intermediate 21. It was hydrolyzed following general procedure 8, affording the title compound as a white powder. $^1$H NMR: (DMSO-d$_6$, 300 MHz) δ 8.56 (m, 1H), 8.52 (m, 1H), 8.11 (m, 1H), 8.03 (m, 1H), 7.93 (m, 1H), 7.69 (d, J=8 Hz, 1H), 7.43-7.33 (m, 2H), 7.29 (m, 1H), 7.17 (m, 1H), 3.48 (m, 2H), 2.66 (brs, 3H), 2.03 (s, 3H), 1.61 (brs, 6H). LC/MS (Method B): 528.1 (M+H)$^+$, 526.3 (M−H)$^-$. HPLC (Method A) Rt 4.45 min (Purity: 97.6%).

Example 32

N-[1-(4-{5-[2'-methyl-2-(trifluoromethyl)biphenyl-4-yl]-1,2,4-oxadiazol-3-yl}phenyl)ethyl]glycine, hydrochloride salt

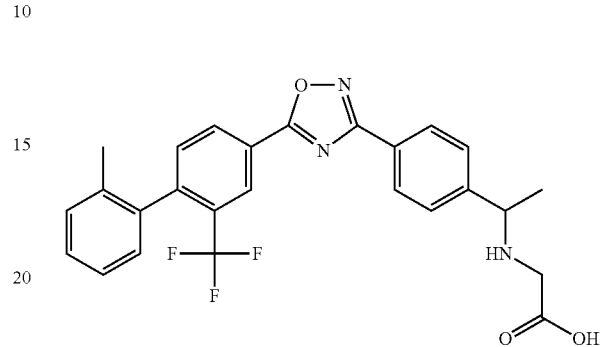

Tert-butyl N-[1-(4-{5-[2'-methyl-2-(trifluoromethyl)biphenyl-4-yl]-1,2,4-oxadiazol-3-yl}phenyl)ethyl]glycinate was prepared following the general procedure 3 starting from intermediate 1 and intermediate 22. It was hydrolyzed following general procedure 8, affording the title compound as a white powder. $^1$H NMR: (DMSO-d$_6$, 300 MHz) δ 8.55 (m, 1H), 8.51 (m, 1H), 8.22 (d, J=8.4 Hz, 2H), 7.77 (d, J=8.4 Hz, 2H), 7.68 (d, J=8 Hz, 1H), 7.43-7.25 (m, 3H), 7.17 (m, 1H), 4.51 (m, 1H), 3.85 (m, 1H), 3.59 (m, 1H), 2.02 (s, 3H), 1.63 (d, J=6.8 Hz, 3H). LC/MS (Method B): 482.0 (M+H)$^+$, 480.1 (M−H)$^-$. HPLC (Method A) Rt 4.82 min (Purity: 99.7%).

Example 33

N-methyl-N-[(1S)-1-(4-{5-[2-methyl-2'-(trifluoromethyl)biphenyl-4-yl]-1,2,4-oxadiazol-3-yl}phenyl)ethyl]glycine, hydrochloride salt

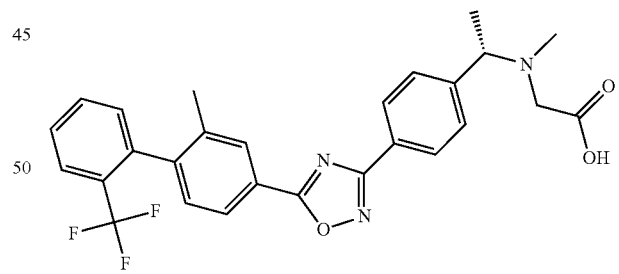

Tert-butyl N-methyl-N-[(1S)-1-(4-{5-[2-methyl-2'-(trifluoromethyl)biphenyl-4-yl]-1,2,4-oxadiazol-3-yl}phenyl)ethyl]glycinate was prepared following the general procedure 4 starting from intermediate 4 and intermediate 23. It was deprotected following the general procedure 8 affording the title compound as a white powder. Melting point: 217° C. [α]$_D$=−28.2 (c 1.47, EtOH). $^1$H NMR (DMSO-d$_6$, 300 MHz) δ 8.25-8.14 (m, 3H), 8.07 (dd, J=8.0, 1.4 Hz, 1H), 7.91 (d, J=7.5 Hz, 1H), 7.86-7.74 (m, 3H), 7.68 (t, J=7.6 Hz, 1H), 7.46-7.35 (m, 2H), 4.76 (q, J=6.9 Hz, 1H), 4.11-3.89 (m, 2H), 2.79 (s, 3H), 2.11 (s, 3H), 1.71 (d, J=7.0 Hz, 3H). LC/MS (Method B): 494.3 (M−H)$^-$, 496.2 (M+H)$^+$. HPLC (Method A) Rt 4.78 min (Purity: 99.7%). Elemental analysis: [C$_{27}$H$_{24}$N$_3$O$_3$F$_3$—HCl-0.2H$_2$O] Corrected: C, 60.55%; H, 4.78%; N, 7.85%; Cl, 6.62%. Found: C, 60.41%; H, 4.83%; N, 7.91%; Cl, 6.71%.

Example 34

N-methyl-N-[(1S)-1-(4-{5-[2'-methyl-2-(trifluoromethyl)biphenyl-4-yl]-1,2,4-oxadiazol-3-yl}phenyl)ethyl]glycine, hydrochloride salt

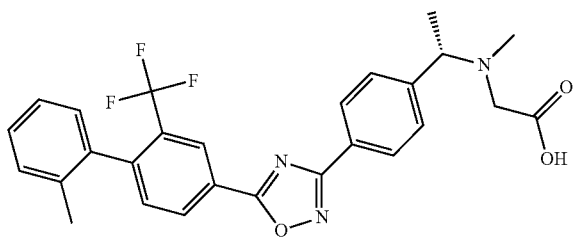 [SMILES: Cc1ccccc1-c1ccc(-c2nc(-c3ccc([C@H](C)N(C)CC(=O)O)cc3)no2)cc1C(F)(F)F]

Tert-butyl N-methyl-N-[(1S)-1-(4-{5-[2'-methyl-2-(trifluoromethyl)biphenyl-4-yl]-1,2,4-oxadiazol-3-yl}phenyl)ethyl]glycinate was prepared following the general procedure 4 starting from intermediate 1 and intermediate 23. It was deprotected following the general procedure 8 affording the title compound as a white powder. Melting point: 221° C. [α]$_D$=−27.4 (c 1.54, EtOH). $^1$H NMR (DMSO-d6, 300 MHz) δ 8.55 (d, J=1.5 Hz, 1H), 8.50 (dd, J=8.0, 1.5 Hz, 1H), 8.23 (d, J=8.6 Hz, 2H), 7.82 (d, J=8.3 Hz, 2H), 7.66 (d, J=8.1 Hz, 1H), 7.41-7.25 (m, 3H), 7.16 (d, J=7.5 Hz, 1H), 4.75 (q, J=6.9 Hz, 1H), 4.10-3.88 (m, 2H), 2.78 (s, 3H), 2.01 (s, 3H), 1.70 (d, J=6.9 Hz, 3H). LC/MS (Method A): 494.3 (M−H)$^-$, 496.2 (M+H)$^+$. HPLC (Method A) Rt 4.85 min (Purity: 99.8%). Elemental Analysis: [C$_{27}$H$_{24}$N$_3$O$_3$F$_3$—HCl-0.2H$_2$O] Corrected: C, 60.55%; H, 4.78%; N, 7.85%; Cl, 6.62%. Found: C, 60.52%; H, 4.63%; N, 7.90%; Cl, 6.65%.

Example 35

N-methyl-N-[(1R)-1-(4-{5-[2-methyl-2'-(trifluoromethyl)biphenyl-4-yl]-1,2,4-oxadiazol-3-yl}phenyl)ethyl]glycine, hydrochloride salt

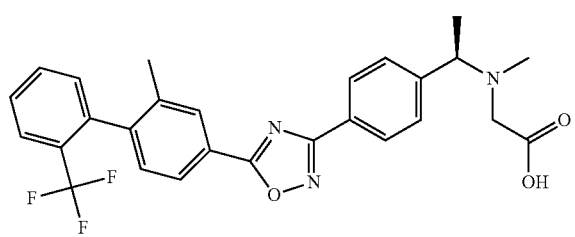 [SMILES: Cc1cc(-c2nc(-c3ccc([C@@H](C)N(C)CC(=O)O)cc3)no2)ccc1-c1ccccc1C(F)(F)F]

Tert-butyl N-methyl-N-[(1R)-1-(4-{5-[2-methyl-2'-(trifluoromethyl)biphenyl-4-yl]-1,2,4-oxadiazol-3-yl}phenyl)ethyl]glycinate was prepared following the general procedure 4 starting from intermediate 4 and intermediate 24. It was deprotected following the general procedure 8 affording the title compound as a white powder. Melting Point: 217° C. [α]D=28.1 (c 1.41, EtOH). $^1$H NMR (DMSO-d$_6$, 300 MHz) δ 8.25-8.14 (m, 3H), 8.07 (dd, J=8.0, 1.4 Hz, 1H), 7.91 (d, J=7.5 Hz, 1H), 7.86-7.74 (m, 3H), 7.68 (t, J=7.6 Hz, 1H), 7.46-7.35 (m, 2H), 4.76 (q, J=6.9 Hz, 1H), 4.11-3.89 (m, 2H), 2.79 (s, 3H), 2.11 (s, 3H), 1.71 (d, J=7.0 Hz, 3H). LC/MS (Method B): 494.3 (M−H)$^-$, 496.2 (M+H)$^+$. HPLC (Method A) Rt 4.79 min (Purity: 99.8%). Elemental Analysis: C$_{27}$H$_{24}$N$_3$O$_3$F$_3$—HCl-0.2H$_2$O] Corrected: C, 60.55%; H, 4.78%; N, 7.85%; Cl, 6.62%. Found: C, 60.44%; H, 4.64%; N, 7.89%; Cl, 6.67%.

Example 36

N-methyl-N-[(1R)-1-(4-{5-[2'-methyl-2-(trifluoromethyl)biphenyl-4-yl]-1,2,4-oxadiazol-3-yl}phenyl)ethyl]glycine, hydrochloride salt

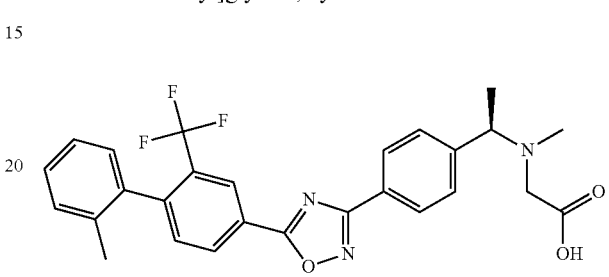

Tert-butyl N-methyl-N-[(1R)-1-(4-{5-[2'-methyl-2-(trifluoromethyl)biphenyl-4-yl]-1,2,4-oxadiazol-3-yl}phenyl)ethyl]glycinate was prepared following the general procedure 4 starting from intermediate 1 and intermediate 24. It was deprotected following the general procedure 8 affording the title compound as a white powder. Melting Point: 221° C. [α]D=26.1 (c 1.44, EtOH). $^1$H NMR (DMSO-d$_6$, 300 MHz) δ 8.55 (d, J=1.5 Hz, 1H), 8.50 (dd, J=8.0, 1.5 Hz, 1H), 8.23 (d, J=8.6 Hz, 2H), 7.82 (d, J=8.3 Hz, 2H), 7.66 (d, J=8.1 Hz, 1H), 7.41-7.25 (m, 3H), 7.16 (d, J=7.5 Hz, 1H), 4.75 (q, J=6.9 Hz, 1H), 4.10-3.88 (m, 2H), 2.78 (s, 3H), 2.01 (s, 3H), 1.70 (d, J=6.9 Hz, 3H). LC/MS (Method B): 494.3 (M−H)$^-$, 496.2 (M+H)$^+$. HPLC (Method A) Rt 4.87 min (Purity: 99.8%). Elemental Analysis [C$_{27}$H$_{24}$N$_3$O$_3$F$_3$—HCl-0.2H$_2$O] Corrected: C, 60.55%; H, 4.78%; N, 7.85%; Cl, 6.62%. Found: C, 60.37%; H, 4.79%; N, 7.84%; Cl, 6.65%.

Example 37

N-[1-(4-{5-[2-(methoxymethyl)-2'-methylbiphenyl-4-yl]-1,2,4-oxadiazol-3-yl}phenyl)ethyl]-N-methylalanine

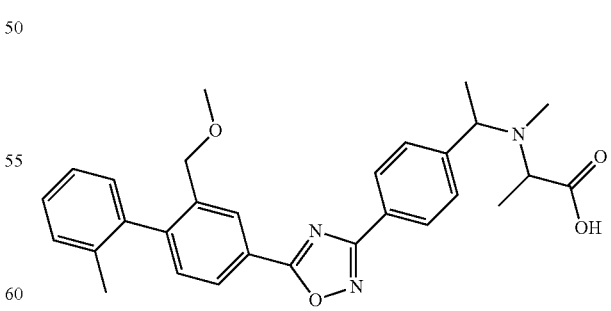

Methyl N-[1-(4-{5-[2-(methoxymethyl)-2'-methylbiphenyl-4-yl]-1,2,4-oxadiazol-3-yl}phenyl)ethyl]-N-methylalaninate was prepared following the general procedure 4 starting from intermediate 3 and intermediate 25. It was deprotected following the general procedure 9 affording the

Example 38

N-[1-(3-{5-[2-methyl-2'-(trifluoromethyl)biphenyl-4-yl]-1,2,4-oxadiazol-3-yl}phenyl)ethyl]glycine, hydrochloride salt

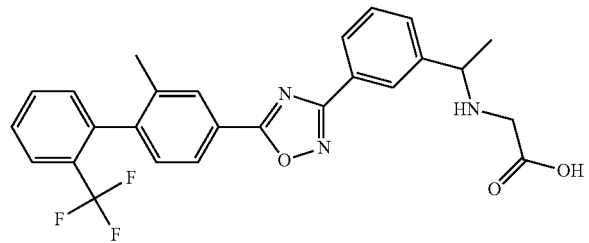 [SMILES: Cc1cc(-c2nc(-c3cccc(C(C)NCC(=O)O)c3)no2)ccc1-c1ccccc1C(F)(F)F]

Tert-butyl N-[1-(3-{5-[2-methyl-2'-(trifluoromethyl)biphenyl-4-yl]-1,2,4-oxadiazol-3-yl}phenyl)ethyl]glycinate was prepared following the general procedure 4 starting from intermediate 4 and intermediate 26. It was deprotected following the general procedure 8 affording the title compound as a slightly yellow powder. Melting Point: 176° C. $^1$H NMR (DMSO-d6, 300 MHz) δ 8.33 (s, 1H), 8.20-8.13 (m, 2H), 8.08 (dd, J=8.0, 1.5 Hz, 1H), 7.92 (d, J=7.7 Hz, 1H), 7.80 (t, J=7.4 Hz, 2H), 7.70 (td, J=7.7, 2.6 Hz, 2H), 7.42 (t, J=8.6 Hz, 2H), 4.54 (q, J=6.7 Hz, 1H), 3.83 (d, J=17.0 Hz, 1H), 3.56 (d, J=16.8 Hz, 1H), 2.12 (s, 3H), 1.65 (d, J=6.8 Hz, 3H). LC/MS (Method A): 484.5 (M−H)$^−$, 486.4 (M+H)$^+$. HPLC (Method A) Rt 4.76 min (Purity: 96.3%).

Example 39

N-methyl-N-[1-(4-{5-[2'-methyl-2-(trifluoromethyl) biphenyl-4-yl]-1,2,4-oxadiazol-3-yl}phenyl)ethyl] alanine

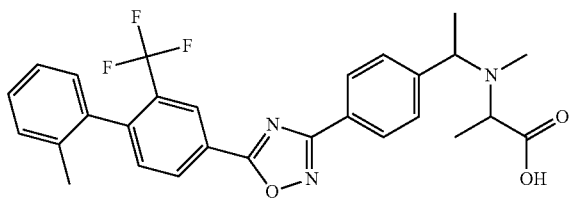 [SMILES: Cc1ccccc1-c1ccc(-c2nc(-c3ccc(C(C)N(C)C(C)C(=O)O)cc3)no2)cc1C(F)(F)F]

Step 1: 4-(1-hydroxyethyl)benzonitrile

4-Acetylbenzonitrile (2.0 g; 13.8 mmol) was dissolved in THF (10 mL) and MeOH (10 mL). Sodium borohydride (782 mg; 20.7 mmol) was added portionwise at 0° C. and the reaction was let stirred at RT for 40 min. Solvents were removed under vacuum, EtOAC was added, and the organic phases were washed with H$_2$O, dried over MgSO$_4$, filtered and concentrated affording the title compound as a colorless oil (2.3 g, quantitative). HPLC (Method A) Rt 4.31 min (Purity: 99.2%).

Step 2: N'-hydroxy-4-(1-hydroxyethyl)benzenecarboximidamide

The title compound was prepared following the general procedure 1 starting from 4-(1-hydroxyethyl)benzonitrile (2.3 g; 16.8 mmol), obtained in step 1 affording 2.5 g (88%) as a colorless foam. LC/MS (Method B): 181.0 (M+H)$^+$.

Step 3: 1-(4-{5-[2'-methyl-2-(trifluoromethyl)biphenyl-4-yl]-1,2,4-oxadiazol-3-yl}phenyl)ethanol 1-(4-{5-[2'-methyl-2-(trifluoromethyl)biphenyl-4-yl]-1,2,4-oxadiazol-3-yl}phenyl)ethanol was prepared following the general procedure 3 starting from intermediate 1 and N'-hydroxy-4-(1-hydroxyethyl)benzenecarboximidamide, obtained in step 2 affording the title compound as a slightly yellow oil (1.9 g, 80%). $^1$H NMR (DMSO-d$_6$, 300 MHz) δ 8.64 (d, J=1.3 Hz, 1H), 8.40 (dd, J=8.0, 1.4 Hz, 1H), 8.19 (d, J=8.4 Hz, 2H), 7.55 (d, J=8.1 Hz, 2H), 7.47 (d, J=8.0 Hz, 1H), 7.38-7.21 (m, 3H), 7.16 (d, J=7.5 Hz, 1H), 5.01 (q, J=6.5 Hz, 2H), 2.07 (s, 3H), 1.56 (d, J=6.6 Hz, 3H). LC/MS (Method B): 425.1 (M+H)$^+$. HPLC (Method A) Rt 5.60 min (Purity: 100.0%).

Step 4: 1-(4-{5-[2'-methyl-2-(trifluoromethyl)biphenyl-4-yl]-1,2,4-oxadiazol-3-yl}phenyl)ethanone To a stirred solution of oxalyl chloride (758 µL; 8.8 mmol in anhydrous DCM (50 mL) at −68° C. a solution of dimethylsulfoxyde (1.3 mL; 17.7 mmol) dissolved in DCM (10 mL) was added over a period of 5 min. The reaction mixture was stirred for 15 min followed by addition of a solution of 1-(4-{5-[2'-methyl-2-(trifluoromethyl)biphenyl-4-yl]-1,2,4-oxadiazol-3-yl}phenyl)ethanol (1.5 g; 3.5 mmol, obtained in step 3 in DCM (10 mL) within 15 min. After being stirred for 1 h at −68° C., the reaction was allowed to reach −30° C., stirred for 15 min and then re-cooled to −68° C. Triethylamine (1.8 mL; 12.7 mmol) was added and the mixture was allowed to reach RT. The clear yellow solution was partioned between saturated aqueous sodium bicarbonate and ethyl acetate, the organic layer was washed with brine, dried over MgSO$_4$, filtered and concentrated. The crude mixture was purified by flash chromatography affording the title compound as a white powder. $^1$H NMR (DMSO-d$_6$, 300 MHz) δ 8.67-8.47 (m, 2H), 8.29 (d, J=7.9 Hz, 2H), 8.19 (d, J=8.3 Hz, 2H), 7.67 (d, J=7.9 Hz, 1H), 7.43-7.25 (m, 3H), 7.17 (d, J=7.7 Hz, 1H), 2.67 (s, 3H), 2.02 (s, 3H). HPLC (Method A) Rt 6.00 min (Purity: 99.0%).

Step 5: N-methyl-1-(4-{5-[2'-methyl-2-(trifluoromethyl)biphenyl-4-yl]-1,2,4-oxadiazol-3-yl}phenyl) ethanamine To a solution of 1-(4-{5-[2'-methyl-2-(trifluoromethyl)biphenyl-4-yl]-1,2,4-oxadiazol-3-yl}phenyl)ethanone (515 mg; 1.2 mmol), obtained in step 4 in THF (5 mL), was added methylamine (732 µL; 2.00 M; 1.5 mmol) and titanium isopropoxide (199 µL; 0.67 mmol). The mixture was stirred overnight at RT. Sodium borohydride (194 mg; 5.1 mmol) was added and the reaction was stirred at RT for 2 h. Then 20 mL of NH$_4$OH was added and the reaction was stirred at RT for 1 h30. It was then filtered through a pad of celite which was washed with EtOAc. The organic phase was washed with a saturated solution of NaHCO$_3$, brine, dried on MgSO$_4$, filtered and concentrated affording after purification by flash chromatography the title compound as a colorless oil. $^1$H NMR (DMSO-d6, 300 MHz) δ 8.66 (s, 1H), 8.43 (d, J=7.6 Hz, 1H), 8.27 (d, J=8.1 Hz, 2H), 7.49 (t, J=8.8 Hz, 3H), 7.42-7.23 (m, 3H), 7.17 (d, J=7.4 Hz, 1H), 3.94-3.80 (m, 1H), 3.61 (br s, 1H), 2.44 (d, J=5.7 Hz, 3H), 2.09 (s, 3H), 1.77 (d, J=6.8 Hz, 3H). LC/MS (Method B): 438.2 (M+H)$^+$. HPLC (Method A) Rt 6.07 min (Purity: 78.6%).

Step 6: methyl N-methyl-N-[1-(4-{5-[2'-methyl-2-(trifluoromethyl)biphenyl-4-yl]-1,2,4-oxadiazol-3-yl}phenyl)ethyl]alaninate The title compound was prepared following the general procedure 10 starting from N-methyl-1-(4-{5-[2'-methyl-2-(trifluoromethyl)biphenyl-4-yl]-1,2,4-oxadiazol-3-yl}phenyl)ethanamine (40 mg, 0.09 mmol), obtained in step 5 affording 46 mg (96%) as a colorless oil. LC/MS (Method B): 524.3 (M+H)$^+$. HPLC (Method A) Rt 4.61 min (Purity: 70.5%).

Step 7: N-methyl-N-[1-(4-{5-[2'-methyl-2-(trifluoromethyl)biphenyl-4-yl]-1,2,4-oxadiazol-3-yl}phenyl)ethyl]alanine The title compound was prepared following the general procedure 9 starting from methyl N-methyl-N-[1-(4-{5-[2'-methyl-2-(trifluoromethyl)biphenyl-4-yl]-1,2,4-oxadiazol-3-yl}phenyl)ethyl]alaninate (40 mg; 0.08 mmol), obtained in step 6. It was isolated after purification with Mass Directed Autoprep as a white solid. LC/MS (Method B): 508.3 (M−H)$^−$, 510.2 (M+H)$^+$. HPLC (Method A) Rt 4.92 min (Purity: 99.8%).

Example 40

N-methyl-N-[1-(4-{5-[2'-methyl-2-(trifluoromethyl)biphenyl-4-yl]-1,2,4-oxadiazol-3-yl}phenyl)ethyl]glycine, hydrochloride salt

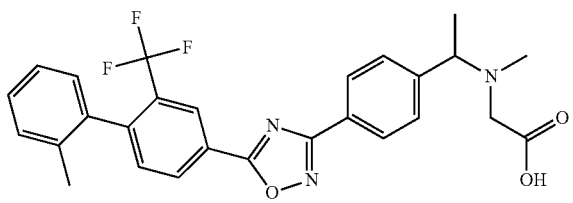 [SMILES: Cc1ccccc1-c1ccc(-c2nc(-c3ccc(C(C)N(C)CC(=O)O)cc3)no2)cc1C(F)(F)F]

Tert-butyl N-methyl-N-[1-(4-{5-[2'-methyl-2-(trifluoromethyl)biphenyl-4-yl]-1,2,4-oxadiazol-3-yl}phenyl)ethyl]glycinate was prepared following the general procedure 4 starting from intermediate 1 and intermediate 16. It was deprotected following the general procedure 8 affording the title compound as a white powder. Melting Point: 204° C. LC/MS (Method B): 494.0 (M−H)$^−$, 496.0 (M+H)$^+$. HPLC (Method A) Rt 4.36 min (Purity: 98.1%).

Example 41

2-[(2-fluoro-4-{5-[2'-methyl-2-(trifluoromethyl)biphenyl-4-yl]-1,2,4-oxadiazol-3-yl}benzyl)amino]butanoic acid, hydrochloride salt

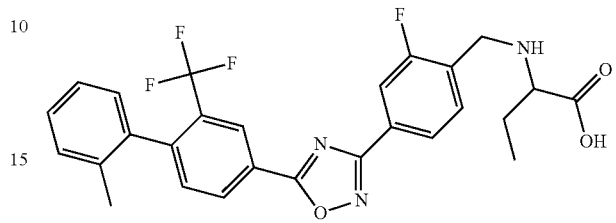

Tert-butyl 2-[(2-fluoro-4-{5-[2'-methyl-2-(trifluoromethyl)biphenyl-4-yl]-1,2,4-oxadiazol-3-yl}benzyl)amino]butanoate was prepared following the general procedure 4 starting from intermediate 1 and intermediate 27. It was deprotected following the general procedure 8 affording the title compound as a white powder. Melting Point: 214° C. $^1$H NMR (DMSO-d$_6$, 300 MHz) δ 8.56 (d, J=1.6 Hz, 1H), 8.51 (dd, J=7.9, 1.5 Hz, 1H), 8.08 (dd, J=7.8, 1.5 Hz, 1H), 7.99 (dd, J=10.2, 1.5 Hz, 1H), 7.91 (t, J=7.8 Hz, 1H), 7.69 (d, J=8.1 Hz, 1H), 7.43-7.25 (m, 3H), 7.17 (d, J=7.3 Hz, 1H), 4.30 (m, 2H), 4.06-3.96 (m, 1H), 2.08-1.87 (m, 5H), 0.97 (t, J=7.4 Hz, 3H). LC/MS (Method B): 512.2 (M−H)$^−$, 514.2 (M+H)$^+$. HPLC (Method A) Rt 4.88 min (Purity: 99.7%).

Example 42

N-[1-(3-{5-[2'-methyl-2-(trifluoromethyl)biphenyl-4-yl]-1,2,4-oxadiazol-3-yl}phenyl)ethyl]glycine, hydrochloride salt

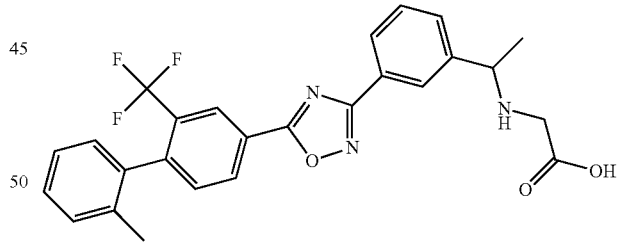

Tert-butyl N-[1-(3-{5-[2'-methyl-2-(trifluoromethyl)biphenyl-4-yl]-1,2,4-oxadiazol-3-yl}phenyl)ethyl]glycinate was prepared following the general procedure 4 starting from intermediate 1 and intermediate 26. It was deprotected following the general procedure 8 affording the title compound as a white powder. Melting Point: 177° C. $^1$H NMR (DMSO-d6, 300 MHz) δ 9.76 (br s, 1H), 8.56 (d, J=1.3 Hz, 1H), 8.51 (dd, J=7.9, 1.7 Hz, 1H), 8.36 (s, 1H), 8.19 (d, J=8.0 Hz, 1H), 7.83 (d, J=8.0 Hz, 1H), 7.75-7.65 (m, 2H), 7.42-7.25 (m, 3H), 7.17 (d, J=7.3 Hz, 1H), 4.58 (q, J=6.5 Hz, 1H), 3.89 (d, J=16.8 Hz, 1H), 3.60 (d, J=17.2 Hz, 1H), 2.03 (s, 3H), 1.66 (d, J=6.8 Hz, 3H). LC/MS (Method B): 480.2 (M−H)$^−$, 482.1 (M+H)$^+$. HPLC (Method A) Rt 4.83 min (Purity: 99.4%).

Example 43

N-(2-fluoro-4-{5-[2-(methoxymethyl)-2'-methylbiphenyl-4-yl]-1,2,4-oxadiazol-3-yl}benzyl)-N,2-dimethylalanine, hydrochloride salt

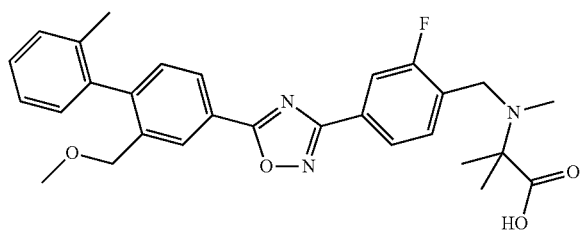 [SMILES: COCc1cc(-c2nc(-c3ccc(CN(C)C(C)(C)C(=O)O)c(F)c3)no2)ccc1-c1ccccc1C]

Tert-butyl N-(2-fluoro-4-{5-[2-(methoxymethyl)-2'-methylbiphenyl-4-yl]-1,2,4-oxadiazol-3-yl}benzyl)-N,2-dimethylalaninate was prepared following the general procedure 3 starting from intermediate 3 and intermediate 29. It was hydrolyzed following general procedure 8, affording the title compound as a white powder. $^1$H NMR: (DMSO-d$_6$, 300 MHz) δ 8.34 (m, 1H), 8.18 (dd, J=8.0 Hz, 1H), 8.09 (dd, J=8.0 Hz, 1H), 8.03-7.91 (m, 2H), 7.45 (d, J=8 Hz, 1H), 7.40-7.26 (m, 3H), 7.15 (d, J=7.3 Hz, 1H), 4.38 (brs, 2H), 4.20 (m, 2H), 3.25 (s, 3H), 2.69 (s, 3H), 2.04 (s, 3H), 1.65 (s, 6H). LC/MS (Method B): 504.3 (M+H)$^+$, 502.4 (M−H)$^−$. HPLC (Method A) Rt 4.16 min (Purity: 99.8%).

Example 44

N-(2-fluoro-4-{5-[2-(methoxymethyl)-2'-methylbiphenyl-4-yl]-1,2,4-oxadiazol-3-yl}benzyl)-N-methylalanine, hydrochloride salt

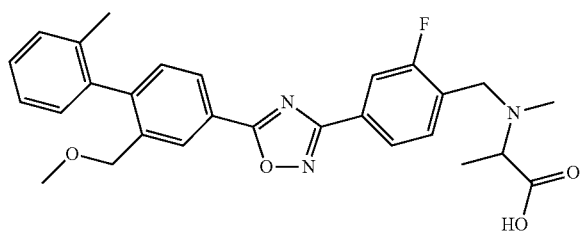 [SMILES: COCc1cc(-c2nc(-c3ccc(CN(C)C(C)C(=O)O)c(F)c3)no2)ccc1-c1ccccc1C]

Tert-butyl N-(2-fluoro-4-{5-[2-(methoxymethyl)-2'-methylbiphenyl-4-yl]-1,2,4-oxadiazol-3-yl}benzyl)-N-methylalaninate was prepared following the general procedure 3 starting from intermediate 3 & intermediate 30. It was hydrolyzed following general procedure 8, affording the title compound as a white powder. $^1$H NMR: (DMSO-d$_6$, 300 MHz) δ 8.33 (m, 1H), 8.17 (dd, J=8.0 Hz, 1H), 8.06 (dd, J=8.0 Hz, 1H), 8.02-7.93 (m, 2H), 7.43 (d, J=8 Hz, 1H), 7.39-7.25 (m, 3H), 7.14 (d, J=7.3 Hz, 1H), 4.47 (m, 2H), 4.33-4.12 (m, 2H), 3.25 (s, 3H), 2.76 (s, 3H), 2.03 (s, 3H), 1.59 (d, J=7.2 Hz, 3H). LC/MS (Method B): 504.3 (M+H)$^+$, 502.4 (M−H)$^−$. HPLC (Method A) Rt 4.10 min (Purity: 99.5%).

Example 45

N-(2-fluoro-4-{5-[2'-methyl-2-(trifluoromethyl)biphenyl-4-yl]-1,2,4-oxadiazol-3-yl}benzyl)-N-methylserine, hydrochloride salt

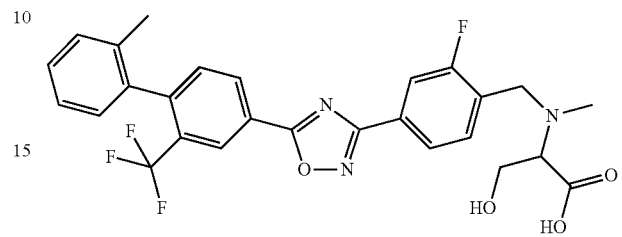

Tert-butyl O-(tert-butyl)-N-(2-fluoro-4-{5-[2'-methyl-2-(trifluoromethyl)biphenyl-4-yl]-1,2,4-oxadiazol-3-yl}benzyl)-N-methylserinate was prepared following the general procedure 3 starting from intermediate 1 and intermediate 31. It was hydrolyzed following general procedure 8, affording the title compound as a white powder. $^1$H NMR: (DMSO-d$_6$, 300 MHz) δ 8.55 (brs, 1H), 8.51 (m, 1H), 8.06 (m, 1H), 7.97 (d, J=10.2 Hz, 1H), 7.91 (t, J=7.7 Hz, 1H), 7.68 (d, J=8 Hz, 1H), 7.37 (m, 2H), 7.29 (m, 1H), 7.17 (d, J=7.7 Hz, 1H), 4.41 (m, 2H), 4.40 (m, 3H), 2.73 (s, 3H), 2.03 (s, 3H). LC/MS (Method B): 530.2 (M+H)$^+$, 528.3 (M−H)$^−$. HPLC (Method A) Rt 4.27 min (Purity: 100%).

Example 46

N-(3-fluoro-5-{5-[2'-methyl-2-(trifluoromethyl)biphenyl-4-yl]-1,2,4-oxadiazol-3-yl}benzyl)-2-methylalanine, hydrochloride salt

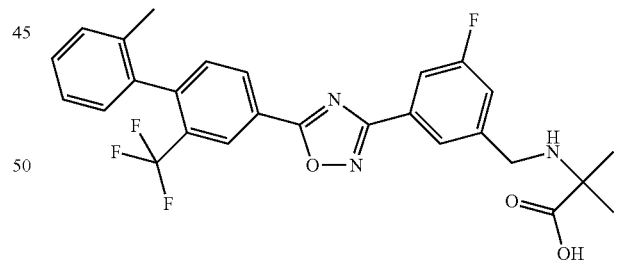

Tert-butyl N-(3-fluoro-5-{5-[2'-methyl-2-(trifluoromethyl)biphenyl-4-yl]-1,2,4-oxadiazol-3-yl}benzyl)-2-methylalaninate was prepared following the general procedure 3 starting from intermediate 1 and intermediate 32. It was hydrolyzed following general procedure 8, affording the title compound as a white powder. $^1$H NMR: (DMSO-d$_6$, 300 MHz) δ 8.51 (brs, 1H), 8.47 (m, 1H), 8.15 (m, 1H), 7.88 (m, 1H), 7.67 (m, 2H), 7.36 (m, 2H), 7.28 (m, 1H), 7.16 (d, J=7.6 Hz, 1H), 4.20 (brs, 2H), 2.02 (s, 3H), 1.51 (s, 6H). LC/MS (Method B): 514.3 (M+H), 512.3 (M−H). HPLC (Method A) Rt 4.44 min (Purity: 99.2%).

Example 47

N-(2-fluoro-4-{5-[2'-methyl-2-(trifluoromethyl)biphenyl-4-yl]-1,2,4-oxadiazol-3-yl}benzyl)valine, hydrochloride salt

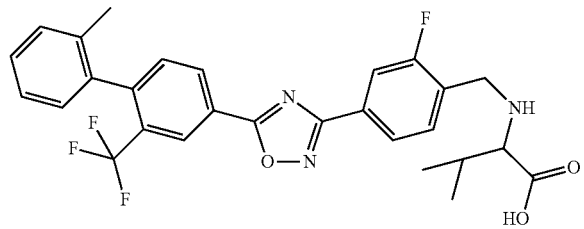 [SMILES: Cc1ccccc1-c1ccc(-c2nc(-c3ccc(CNC(C(=O)O)C(C)C)c(F)c3)no2)cc1C(F)(F)F]

tert-butyl N-(2-fluoro-4-{5-[2'-methyl-2-(trifluoromethyl)biphenyl-4-yl]-1,2,4-oxadiazol-3-yl}benzyl)valinate was prepared following the general procedure 3 starting from intermediate 1 and intermediate 33. It was hydrolyzed following general procedure 8, affording the title compound as a white powder. $^1$H NMR: (DMSO-$d_6$, 300 MHz) δ 8.55 (brs, 1H), 8.50 (m, 1H), 8.07 (m, 1H), 7.96 (m, 2H), 7.68 (d, J=8.2 Hz, 2H), 7.37 (m, 2H), 7.29 (m, 1H), 7.17 (d, J=7.6 Hz, 1H), 4.30 (m, 2H), 3.90 (m, 1H), 2.41 (m, 1H), 2.02 (s, 3H), 1.08 (d, J=7 Hz, 3H), 097 (d, J=6.8 Hz, 3H). LC/MS (Method B): 528.3 (M+H)$^+$, 526.4 (M−H)$^−$. HPLC (Method A) Rt 4.48 min (Purity: 100%).

Example 48

N-(2-fluoro-4-{5-[2-methyl-2'-(trifluoromethyl)biphenyl-4-yl]-1,2,4-oxadiazol-3-yl}benzyl)-2-methylalanine, hydrochloride salt

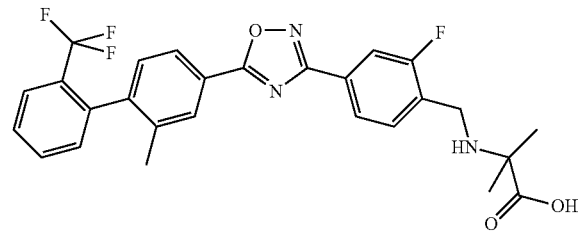 [SMILES: Cc1cc(-c2nc(-c3ccc(CNC(C)(C)C(=O)O)c(F)c3)no2)ccc1-c1ccccc1C(F)(F)F]

Tert-butyl N-(2-fluoro-4-{5-[2-methyl-2'-(trifluoromethyl)biphenyl-4-yl]-1,2,4-oxadiazol-3-yl}benzyl)-2-methylalaninate was prepared following the general procedure 3 starting from intermediate 4 and intermediate 34. It was hydrolyzed following general procedure 8, affording the title compound as a white powder. $^1$H NMR: (DMSO-$d_6$, 300 MHz) δ 8.17 (brs, 1H), 8.06 (m, 2H), 8.01-7.89 (m, 3H), 7.79 (m, 1H), 7.68 (m, 1H), 7.72 (m, 2H), 4.27 (brs, 2H), 2.11 (s, 3H), 1.63 (s, 6H). LC/MS (Method B): 514.3 (M+H)$^+$, 512.4 (M−H)$^−$. HPLC (Method A) Rt 4.31 min (Purity: 99.7%).

Example 49

N-(2-fluoro-4-{5-[2'-methyl-2-(trifluoromethyl)biphenyl-4-yl]-1,2,4-oxadiazol-3-yl}benzyl)-2-methylalanine, hydrochloride salt

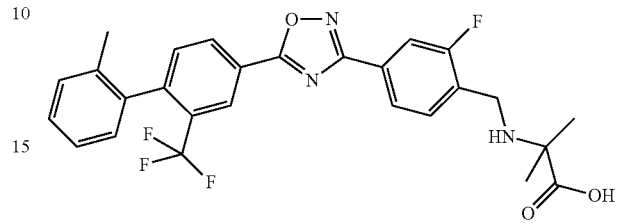

Tert-butyl N-(2-fluoro-4-{5-[2'-methyl-2-(trifluoromethyl)biphenyl-4-yl]-1,2,4-oxadiazol-3-yl}benzyl)-2-methylalaninate was prepared following the general procedure 3 starting from intermediate 1 and intermediate 34. It was hydrolyzed following general procedure 8, affording the title compound as a white powder. $^1$H NMR: (DMSO-$d_6$, 300 MHz) δ 9.87 (m, 1H), 8.55 (brs, 1H), 8.50 (d, J=8.1 Hz, 1H), 8.07 (m, 1H), 7.99 (m, 2H), 7.68 (d, J=8 Hz, 1H), 7.37 (m, 2H), 7.29 (m, 1H), 7.16 (m, 1H), 4.27 (brs, 2H), 2.02 (s, 3H), 1.63 (s, 6H). LC/MS (Method B): 514.4 (M+H)$^+$, 512.4 (M−H)$^−$. HPLC (Method A) Rt 4.37 min (Purity: 100%).

Example 50

N-(2-fluoro-4-{5-[2'-methyl-2-(trifluoromethyl)biphenyl-4-yl]-1,2,4-oxadiazol-3-yl}benzyl)-N-methylalanine, hydrochloride salt

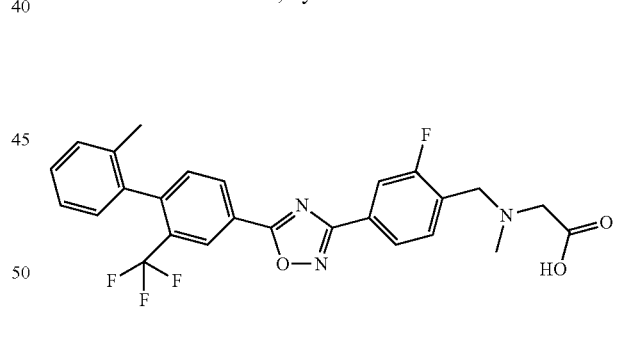

Tert-butyl N-(2-fluoro-4-{5-[2'-methyl-2-(trifluoromethyl)biphenyl-4-yl]-1,2,4-oxadiazol-3-yl}benzyl)-N-methylalaninate was prepared following the general procedure 3 starting from intermediate 1 and intermediate 30. It was hydrolyzed following general procedure 8, affording the title compound as a white powder. $^1$H NMR: (DMSO-$d_6$, 300 MHz) δ 8.55 (brs, 1H), 8.51 (m, 1H), 8.09 (m, 1H), 7.99 (m, 2H), 7.68 (d, J=8.1 Hz, 1H), 7.37 (m, 2H), 7.29 (m, 1H), 7.17 (d, J=7.5 Hz, 1H), 4.47 (m, 2H), 4.26 (brs, 1H), 2.75 (s, 3H), 2.02 (s, 3H), 1.59 (d, J=7.1 Hz, 3H). LC/MS (Method B): 514.4 (M+H)$^+$, 512.4 (M−H)$^−$. HPLC (Method A) Rt 4.40 min (Purity: 100%).

Example 51

2-((2-methoxy-1-(4-(5-(2'-methyl-2-(trifluoromethyl)biphenyl-4-yl)-1,2,4-oxadiazol-3-yl)phenyl)ethyl)(methyl)amino)acetic acid

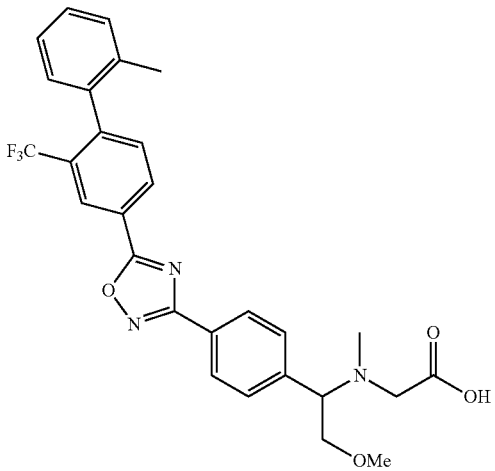 [SMILES: COCC(c1ccc(-c2noc(-c3ccc(-c4ccccc4C)c(C(F)(F)F)c3)n2)cc1)N(C)CC(=O)O]

Step 1: tert-butyl N-[2-methoxy-1-(4-{5-[2'-methyl-2-(trifluoromethyl)biphenyl-4-yl]-1,2,4-oxadiazol-3-yl}phenyl)ethyl]-N-methylglycinate To a solution of Intermediate 35 (0.141 g; 0.42 mmol) and Intermediate 1 (0.129 mg; 0.46 mmol) in MeCN (2 mL) was added EDC (0.121 g; 0.63 mmol). The reaction mixture was stirred at ambient temperature for 18 h. The reaction mixture was diluted with pyridine (2 mL) and heated at 150° C. in the microwave for 30 minutes. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with isohexane/EtOAc (100%/0 to 4:1) to afford the title compound. $^1$H NMR (CDCl$_3$, 400 MHz) δ 8.63 (1H, d, J=1.2 Hz), 8.40 (1H, dd, J=8, 1.7 Hz), 8.17-8.15 (2H, m), 7.55-7.53 (2H, m), 7.48-7.46 (1H, m), 7.34-7.16 (4H, m), 4.11 (1H, m), 3.74-3.68 (2H, m), 3.44 (1H, J=17.2 Hz), 3.33 (3H, s), 3.25 (1H, d, J=17.2 Hz), 2.45 (3H, s), 2.07 (3H, s), 1.47 (9H, s).

Step 2: 2-((2-methoxy-1-(4-(5-(2'-methyl-2-(trifluoromethyl)biphenyl-4-yl)-1,2,4-oxadiazol-3-yl)phenyl)ethyl)(methyl)amino)acetic acid To tert-butyl N-[2-methoxy-1-(4-{5-[2'-methyl-2-(trifluoromethyl)biphenyl-4-yl]-1,2,4-oxadiazol-3-yl}phenyl)ethyl]-N-methylglycinate (0.078 g; 0.13 mmol) was added HCl solution in dioxane (4 M; 4 mL) and the reaction mixture stirred at ambient temperature for 18 hours and at 80° C. for 2 hour. The reaction mixture was allowed to cool and the solvent evaporated in vacuo. The residue was triturated with ether and dried under vacuum. The solid was dissolved in DMSO-d$_6$ and evaporated to afford the title compound as a colourless gum (0.055 g, 75%). $^1$H NMR: (DMSO-d$_6$/D$_2$O, 400 MHz) δ 8.57 (1H, s), 8.54-8.52 (1H, d, J=8 Hz), 8.24 (2H, d, J=8 Hz), 7.79 (2H, d, J=8 Hz), 7.69 (1H, d, J=8 Hz), 7.40-7.37 (2H, m), 7.33-7.31 (1H, m), 7.19 (1H, d, J=7.2 Hz), 4.78 (1H, m), 4.13-4.10 (1H, m), 3.97 (1H, m), 3.87-3.83 (2H, m), 3.36 (3H, s), 2.75 (3H, s), 2.03 (3H, s). LC/MS (Method B): 526 (M+H)$^+$. HPLC (Method C) Rt 9.13 min (Purity: 98.2%).

Example 52

2-(2-Hydroxy-1-(4-(5-(2'-methyl-2-(trifluoromethyl)biphenyl-4-yl)-1,2,4-oxadiazol-3-yl)phenyl)ethylamino)acetic acid

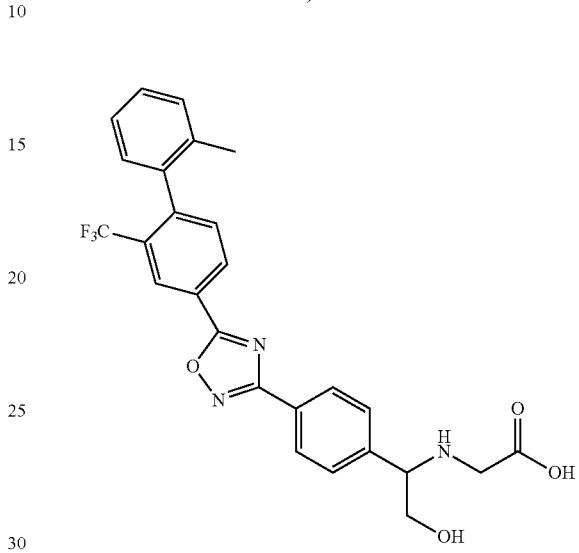

Step 1: tert-butyl N-[2-hydroxy-1-(4-{5-[2'-methyl-2-(trifluoromethyl)biphenyl-4-yl]-1,2,4-oxadiazol-3-yl}phenyl)ethyl]glycinate To a solution of Intermediate 36 (0.563 g; 1.27 mmol) and Intermediate 1 (0.391 mg; 1.40 mmol) in MeCN (3 mL) was added EDC (0.321 g; 1.67 mmol). The reaction mixture was stirred at ambient temperature for 18 h. The reaction mixture was diluted with pyridine (2 mL) and heated at 150° C. in the microwave for 30 minutes. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with isohexane/EtOAc (10:1), affording the title compound. $^1$H NMR (CDCl$_3$, 400 MHz) δ 8.63 (1H, s), 8.41-8.39 (1H, dd, J=7.6, 1.2 Hz), 8.17 (2H, d, J=8.4 Hz), 7.54-7.46 (3H, m), 7.34-7.15 (4H, m), 3.90-3.88 (1H, m), 3.74-3.65 (2H, m), 3.30 (1H, d, J=17.2 Hz), 3.13 (1H, d, J=17.2 Hz), 2.61 (1H, br s), 2.07 (3H, s), 1.46 (9H, s), 0.91 (9H, s), 0.06 (3H, s), 0.05 (3H, s).

Step 2: 2-(2-Hydroxy-1-(4-(5-(2'-methyl-2-(trifluoromethyl)biphenyl-4-yl)-1,2,4-oxadiazol-3-yl)phenyl)ethylamino)acetic acid To tert-butyl N-[2-hydroxy-1-(4-{5-[2'-methyl-2-(trifluoromethyl)biphenyl-4-yl]-1,2,4-oxadiazol-3-yl}phenyl)ethyl]glycinate (0.200 g; 0.13 mmol) was added HCl solution in dioxane (4 M; 4 mL) and the reaction mixture stirred 80° C. for 1 hour. The reaction mixture was allowed to cool and the solvent evaporated in vacuo. The residue was purified by preparative HPLC to afford the title compound. $^1$H NMR: (CDCl$_3$, 400 MHz) δ 8.57 (1H, d, J=1.2 Hz), 8.54-8.52 (1H, m), 8.14 (2H, d, J=8 Hz), 7.70 (1H, d, J=8 Hz), 7.63 (2H, d, J=8.4 Hz), 7.44-7.38 (2H, m), 7.34-7.30 (1H, m), 7.21-7.20

(1H, m), 3.94-3.91 (1H, m), 3.65-3.56 (1H, m), 3.52-3.47 (1H, m), 3.20 (1H, d, J=16.8 Hz), 3.06 (1H, d, J=16.8 Hz), 2.06 (3H, s). LC/MS (Method B): 496 (M+H)+. HPLC (Method D) Rt 3.04 min (Purity: 94.9%).

Example 53

1-((4-(5-(2-(methoxymethyl)-2'-methylbiphenyl-4-yl)-1,2,4-oxadiazol-3-yl)benzyl)(methyl)amino)cyclopentanecarboxylic acid

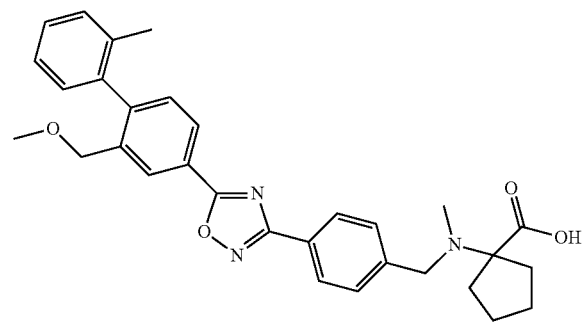 [SMILES: COCc1cc(-c2nc(-c3ccc(CN(C)C4(C(=O)O)CCCC4)cc3)no2)ccc1-c1ccccc1C]

Step 1: (4-(5-(2-(methoxymethyl)-2'-methylbiphenyl-4-yl)-1,2,4-oxadiazol-3-yl)phenyl)methanol The title compound was prepared following the general procedure 5, starting from Intermediate 3 and Intermediate 37. It was isolated as a white solid. $^1$H NMR: (CDCl$_3$, 400 MHz) δ 8.43 (1H, s), 8.22-8.15 (3H, m), 7.53 (2H, d, J=8.0 Hz), 7.36-7.24 (4H, m), 7.13 (1H, d, J=7.4 Hz), 4.81 (2H, d, J=5.6 Hz), 4.23 (2H, d, J=1.8 Hz), 3.33 (3H, s), 2.08 (3H, s), 1.80-1.75 (1H, m). LC/MS (Method B) 387 (M+H)+. HPLC (Method E) Rt=10.9 min (Purity: 96.7%).

Step 2: 4-(5-(2-(methoxymethyl)-2'-methylbiphenyl-4-yl)-1,2,4-oxadiazol-3-yl)benzaldehyde The title compound was prepared following the general procedure 6, starting from (4-(5-(2-(methoxymethyl)-2'-methylbiphenyl-4-yl)-1,2,4-oxadiazol-3-yl)phenyl)methanol (750 mg; 1.94 mmol), obtained in Step 1. It was isolated as a white solid (732 mg; 98%). $^1$H NMR: (CDCl$_3$, 400 MHz) δ 10.12 (1H, s), 8.45 (1H, s), 8.40 (2H, d, J=8.1 Hz), 8.19 (1H, dd, J=7.9, 1.9 Hz), 8.05 (2H, d, J=8.2 Hz), 7.37-7.23 (4H, m), 7.13 (1H, d, J=7.4 Hz), 4.27-4.18 (2H, m), 3.34 (3H, s), 2.09 (3H, s). LC/MS (Method B) 385 (M+H)+. HPLC (Method D) Rt=4.71 min (Purity: 95.9%).

Step 3: 1-((4-(5-(2-(methoxymethyl)-2'-methylbiphenyl-4-yl)-1,2,4-oxadiazol-3-yl)benzyl)(methyl)amino)cyclopentanecarboxylic acid The title compound was prepared following general protocol 7, starting from 4-(5-(2-(methoxymethyl)-2'-methylbiphenyl-4-yl)-1,2,4-oxadiazol-3-yl)benzaldehyde (104 mg; 0.27 mmol), obtained in Step 2, and using 1-aminocyclopentanoic acid (65 mg; 0.50 mmol). It was isolated as a white solid. $^1$H NMR (DMSO-d$_6$, 400 MHz) δ 12.2 (1H, br s), 8.35 (1H, d, J=1.8 Hz), 8.20 (1H, dd, J=7.9, 1.9 Hz), 8.16-8.07 (2H, m), 7.59 (2H, d, J=8 Hz), 7.45 (1H, d, J=8 Hz), 7.40-7.29 (3H, m), 7.18 (1H, d, J=7.4 Hz), 4.27 (1H, d, J=12 Hz), 4.22 (1H, d, J=12 Hz), 3.76 (2H, s), 3.28 (3H, s), 2.26-2.21 (5H, m), 2.07 (3H, s), 1.79-1.76 (4H, m), 1.69-1.65 (2H, m). LC/MS (Method B): 512 (M+H)+. HPLC (Method D) Rt 2.81 min (Purity: 94.0%).

Example 54

(2S)-2-(4-(5-(2'-methyl-2-(trifluoromethyl)biphenyl-4-yl)-1,2,4-oxadiazol-3-yl)benzylamino)butanoic acid

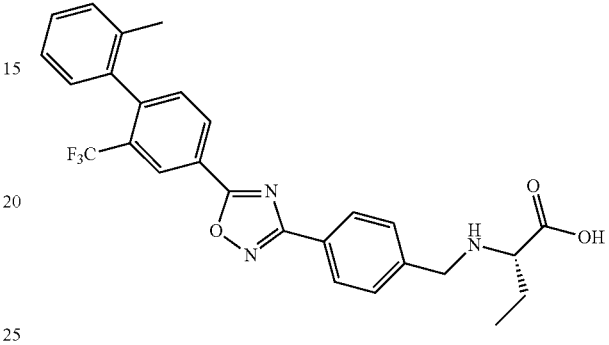

Step 1: (4-(5-(2'-methyl-2-(trifluoromethyl)biphenyl-4-yl)-1,2,4-oxadiazol-3-yl)phenyl)methanol The title compound was prepared following the general procedure 5, starting from Intermediate 1 and Intermediate 37. The crude product was recrystallised from EtOAc and petrol to give the title compound as a white solid. $^1$H NMR: (CDCl$_3$, 400 MHz) δ 8.63 (1H, s), 8.40 (1H, d, J=8.0 Hz), 8.20 (2H, d, J=8.0 Hz), 7.54 (2H, d, J=7.9 Hz), 7.47 (1H, d, J=7.9 Hz), 7.38-7.21 (3H, m), 7.16 (1H, d, J=7.5 Hz), 4.81 (2H, d, J=5.7 Hz), 2.14-1.94 (3H, m). LC/MS (Method B): 411 (M+H)+. HPLC (Method G) Rt=4.50 min (Purity: 97.9%).

Step 2: 4-(5-(2'-methyl-2-(trifluoromethyl)biphenyl-4-yl)-1,2,4-oxadiazol-3-yl)benzaldehyde The title compound was prepared following the general procedure 6, starting from (4-(5-(2'-methyl-2-(trifluoromethyl)biphenyl-4-yl)-1,2,4-oxadiazol-3-yl)phenyl)methanol, obtained in Step 1. The crude product was triturated with a mixture of petrol/diethyl ether to give the title compound as a white solid (5.72 g; 97%). $^1$H NMR (CDCl$_3$, 300 MHz) δ10.13 (1H, s), 8.64 (1H, s), 8.43-8.36 (3H, m), 8.06 (2H, d, J=8.0 Hz), 7.49 (1H, d, J=8.0 Hz), 7.38-7.21 (3H, m), 7.15 (1H, d, J=7.6 Hz), 2.07 (3H, s). LC/MS (Method B): 409 (M+H)+. HPLC (Method G) Rt=4.89 min (Purity: 95.7%).

Step 3: (2S)-2-(4-(5-(2'-methyl-2-(trifluoromethyl)biphenyl-4-yl)-1,2,4-oxadiazol-3-yl)benzylamino)butanoic acid Sodium cyanoborohydride (34.7 mg; 0.55 mmol) was added to a solution of 4-(5-(2'-methyl-2-(trifluoromethyl)biphenyl-4-yl)-1,2,4-oxadiazol-3-yl)benzaldehyde (205 mg; 0.50 mmol), obtained in Step 2, and (S)-2-aminobutanoic acid (103 mg; 1.00 mmol) in a mixture of methanol (3 mL), DCM (3 mL) and acetic acid (75 μl). The mixture was stirred at room temperature overnight and the solvent was then removed in vacuo. The residue was purified by preparative HPLC to give the title compound as a white solid. $^1$H NMR:

(DMSO-d$_6$, 400 MHz) δ 8.58-8.52 (1H, m), 8.53-8.48 (1H, m), 8.12 (2H, d, J=8.0 Hz), 7.67 (1H, d, J=7.9 Hz), 7.62 (2H, d, J=8.0 Hz), 7.41-7.35 (2H, m), 7.33-7.27 (1H, m), 7.18 (1H, d, J=7.5 Hz), 3.96 (1H, d, J=14.1 Hz), 3.78 (1H, d, J=14.0 Hz), 3.07-3.00 (1H, m), 2.03 (3H, s), 1.69-1.58 (2H, m), 0.94-0.88 (3H, m). LC/MS (Method B): 496 (M+H)$^+$. HPLC (Method D) Rt=3.16 min (Purity: 99.6%).

The examples shown in the table below were prepared by the same protocol as Example 54, using the appropriate amino acid for each example:

| Ex No | Structure | HPLC Method | Purity (%) | RT [min] | Mass peak [M]+ | Mass peak [M]− |
|---|---|---|---|---|---|---|
| 55 | 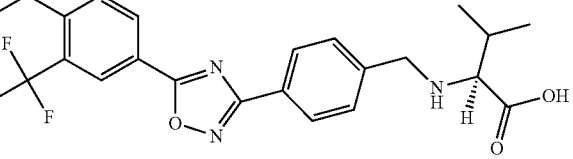 Chiral | Method D | 99.8 | 3.23 | 510 | 508 |
| 56 | 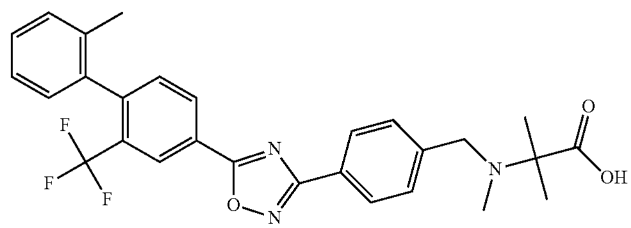 [SMILES: Cc1ccccc1-c1ccc(-c2nc(-c3ccc(CN(C)C(C)(C)C(=O)O)cc3)no2)cc1C(F)(F)F] | Method D | 99.8 | 3.34 | 510 | 508 |
| 57 | 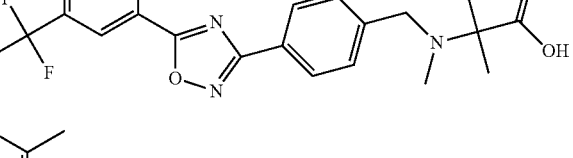 | Method H | 99.4 | 8.94 | 496 | 494 |
| 58 | 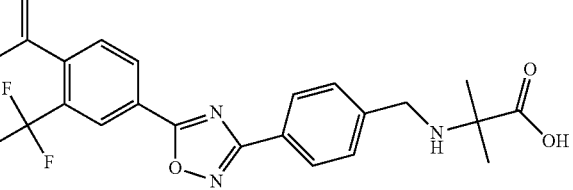 | Method H | 96.3 | 9.03 | 496 | 494 |
| 59 | 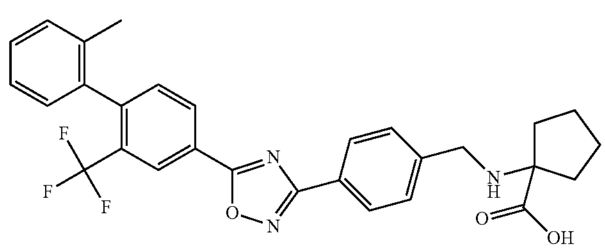 [SMILES: Cc1ccccc1-c1ccc(-c2nc(-c3ccc(CNC4(C(=O)O)CCCC4)cc3)no2)cc1C(F)(F)F] | Method D | 99.1 | 3.13 | 522 | 520 |
| 60 |  Chiral | Method D | 98.1 | 3.11 | 512 | 510 |

-continued

| Ex No | Structure | HPLC Method | Purity (%) | RT [min] | Mass peak [M]+ | Mass peak [M]- |
|---|---|---|---|---|---|---|
| 61 | Chiral | Method D | 96.6 | 3.14 | 512 | 510 |
| 62 | 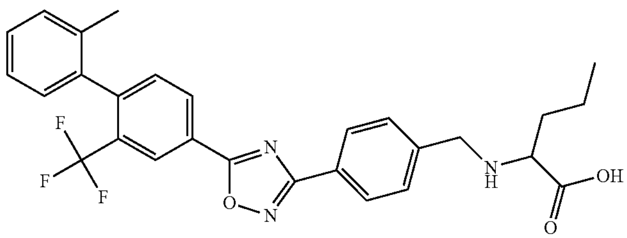 [SMILES: CCCC(NCc1ccc(-c2noc(-c3ccc(-c4ccccc4C)c(C(F)(F)F)c3)n2)cc1)C(=O)O] | Method D | 98.1 | 3.24 | 510 | 508 |
| 63 | 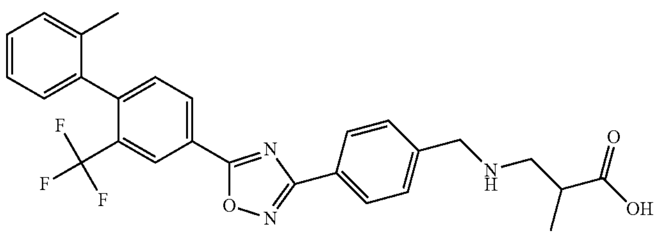 [SMILES: Cc1ccccc1-c1ccc(-c2nc(-c3ccc(CNCC(C)C(=O)O)cc3)no2)cc1C(F)(F)F] | Method H | 99.0 | 8.66 | 496 | 494 |
| 64 | 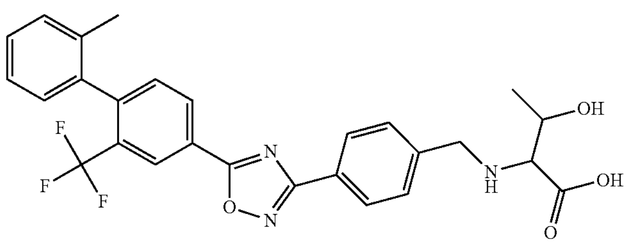 [SMILES: Cc1ccccc1-c1ccc(-c2nc(-c3ccc(CNC(C(=O)O)C(C)O)cc3)no2)cc1C(F)(F)F] | Method D | 98.6 | 3.14 | 512 | 510 |
| 65 | 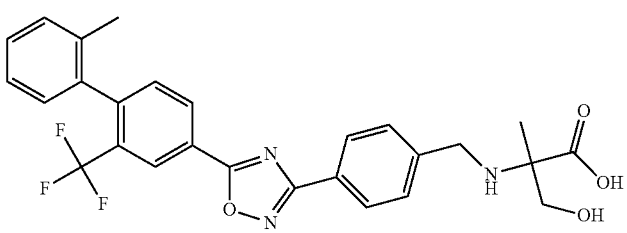 [SMILES: Cc1ccccc1-c1ccc(-c2nc(-c3ccc(CNC(C)(CO)C(=O)O)cc3)no2)cc1C(F)(F)F] | Method H | 99.8 | 3.12 | 512 | 510 |
| 66 | 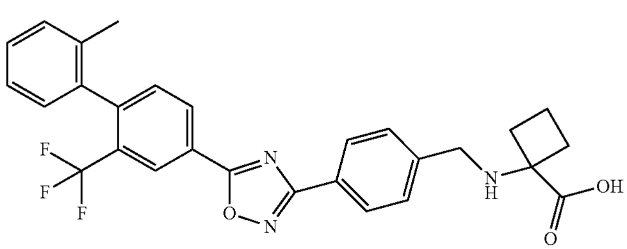 [SMILES: Cc1ccccc1-c1ccc(-c2nc(-c3ccc(CNC4(C(=O)O)CCC4)cc3)no2)cc1C(F)(F)F] | Method D | 98.1 | 3.1 | 508 | 506 |

| Ex No | Structure | HPLC Method | Purity (%) | RT [min] | Mass peak [M]+ | Mass peak [M]- |
|---|---|---|---|---|---|---|
| 67 | 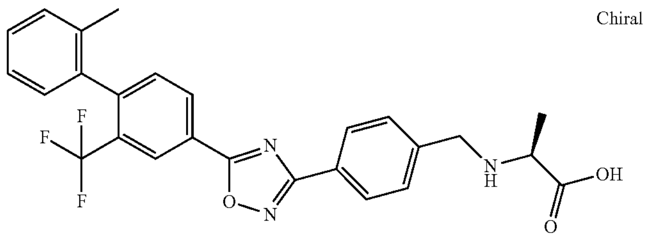 [SMILES: Cc1ccccc1-c1ccc(-c2nc(-c3ccc(CN[C@@H](C)C(=O)O)cc3)no2)cc1C(F)(F)F ; "Chiral"] | Chiral Method H | 95.1 | 3.12 | 482 | 480 |
| 68 | 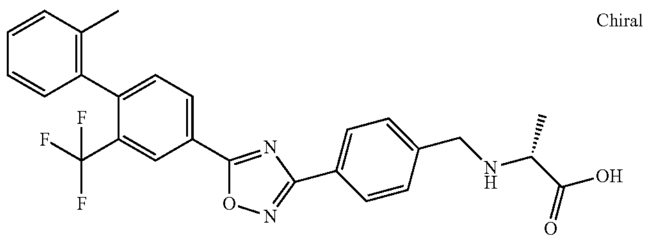 [SMILES: Cc1ccccc1-c1ccc(-c2nc(-c3ccc(CN[C@H](C)C(=O)O)cc3)no2)cc1C(F)(F)F ; "Chiral"] | Chiral Method D | 99.3 | 3.11 | 482 | — |

Example 69

(2S)-2-(methyl(4-(5-(2'-methyl-2-(trifluoromethyl) biphenyl-4-yl)-1,2,4-oxadiazol-3-yl)benzyl)amino) butanoic acid

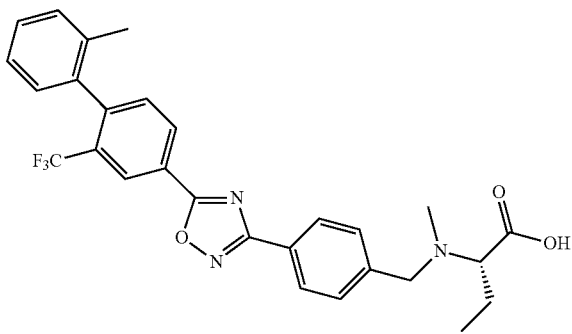 [SMILES: CC[C@@H](C(=O)O)N(C)Cc1ccc(-c2noc(-c3ccc(-c4ccccc4C)c(C(F)(F)F)c3)n2)cc1]

Sodium cyanoborohydride (18 mg; 0.28 mmol) was added to a solution of 4-(5-(2'-methyl-2-(trifluoromethyl)biphenyl-4-yl)-1,2,4-oxadiazol-3-yl)benzaldehyde (Example 54, step 2, 103 mg; 0.25 mmol) and (S)-2-aminobutanoic acid (52 mg; 0.50 mmol) in a mixture of methanol (3 mL), DCM (3 mL) and acetic acid (38 µl). The mixture was stirred at room temperature overnight and was filtered through a frit under positive pressure. To the filtrate was added formaldehyde (37% aqueous solution; 204 mg, 2.51 mmol) followed by addition of AcOH until the pH was in the range of 3-4 (240 mL). To the resulting mixture was added sodium cyanoborohydride (79 mg, 1.26 mmol), the mixture stirred for 16 hours, the solvent removed in vacuo and the residue purified by reverse phase HPLC to give a white solid as the title compound. $^1$H NMR (DMSO-$d_6$, 400 MHz) δ 8.57-8.53 (1H, m), 8.52-8.48 (1H, m), 8.10 (2H, d, J=8.0 Hz), 7.67 (1H, d, J=7.9 Hz), 7.57 (2H, d, J=8.0 Hz), 7.40-7.35 (2H, m), 7.32-7.27 (1H, m), 7.18 (1H, d, J=7.5 Hz), 3.86 (1H, d, J=14.3 Hz), 3.72 (1H, d, J=14.3 Hz), 3.15 (1H, t, J=7.4 Hz), 2.24 (3H, s), 2.03 (3H, s), 1.76-1.60 (2H, m), 0.95 (3H, t, J=7.3 Hz). LC/MS (Method B): 510 (M+H)$^+$. HPLC (Method D) Rt 3.39 min (Purity: 99.8%).

The examples shown in the table below were prepared by the same protocol as Example 69, using the appropriate amino acid for each example:

| Ex No | Structure | Purity Method | Purity | RT | Mass peak [M]+ | Mass peak [M]- |
|---|---|---|---|---|---|---|
| 70 | 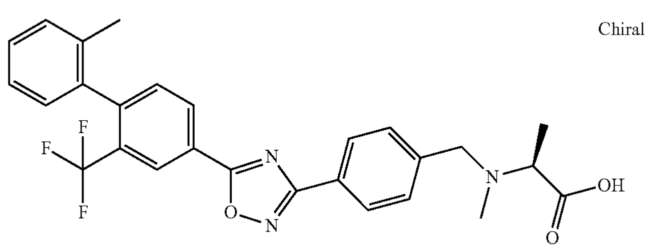 [SMILES: Cc1ccccc1-c1ccc(-c2nc(-c3ccc(CN(C)[C@@H](C)C(=O)O)cc3)no2)cc1C(F)(F)F ; "Chiral"] | Chiral Method G | 98.7 | 3.23 | 496 | 494 |

| Ex No | Structure | Purity Method | Purity | RT | Mass peak [M]+ | Mass peak [M]− |
|---|---|---|---|---|---|---|
| 71 | Chiral | Method D | 99.8 | 3.29 | 496 | 494 |
| 72 | Chiral | Method D | 99.9 | 3.24 | 512 | 510 |
| 73 | 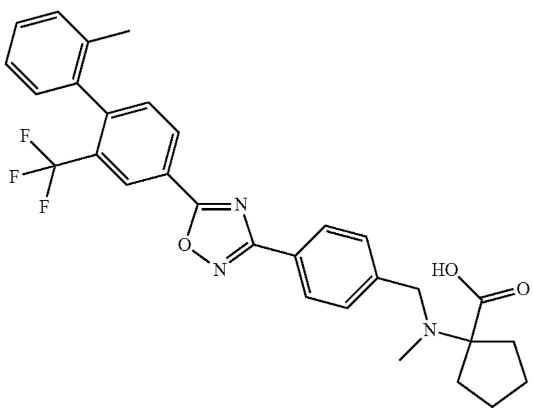 [SMILES: Cc1ccccc1-c1ccc(-c2nc(-c3ccc(CN(C)C4(C(=O)O)CCCC4)cc3)no2)cc1C(F)(F)F] | Method D | 99.8 | 3.46 | 536 | 534 |
| 74 | 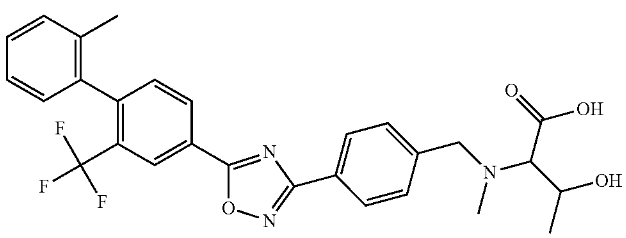 [SMILES: Cc1ccccc1-c1ccc(-c2nc(-c3ccc(CN(C)C(C(=O)O)C(C)O)cc3)no2)cc1C(F)(F)F] | Method G | 90.7 | 2.8 | 526 | 524 |
| 75 | 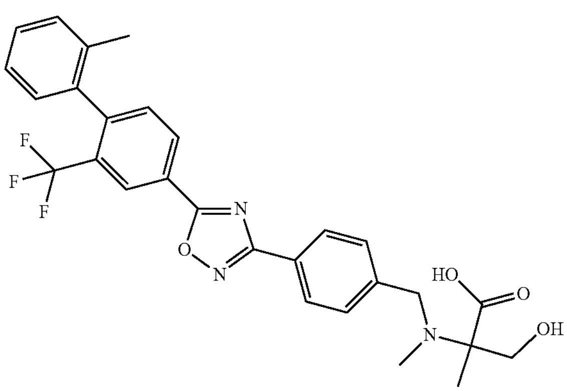 [SMILES: Cc1ccccc1-c1ccc(-c2nc(-c3ccc(CN(C)C(C)(CO)C(=O)O)cc3)no2)cc1C(F)(F)F] | Method D | 99.5 | 3.29 | 526 | 524 |

Example 76

3-Methoxy-2-{3-[5-(2'-methyl-2-trifluoromethyl-biphenyl-4-yl)-[1,2,4]oxadiazol-3-yl]-benzylamino}-propionic acid

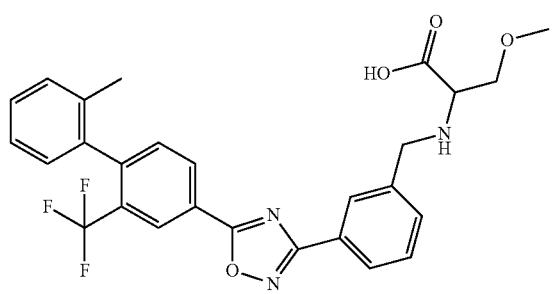 [SMILES: COCC(NCc1cccc(-c2noc(-c3ccc(-c4ccccc4C)c(C(F)(F)F)c3)n2)c1)C(=O)O]

Step 1: (3-(5-(2'-methyl-2-(trifluoromethyl)biphenyl-4-yl)-1,2,4-oxadiazol-3-yl)phenyl)methanol The title compound was prepared following the general procedure 5, starting from Intermediate 1 and Intermediate 38 and was isolated as a white solid. $^1$H NMR (CDCl$_3$, 400 MHz) δ 8.65-8.58 (2H, m), 8.40 (1H, d, J=7.9 Hz), 8.22 (1H, s), 8.13 (1H, d, J=7.3 Hz), 7.60-7.50 (2H, m), 7.47 (1H, d, J=7.9 Hz), 7.37-7.20 (2H, m), 7.15 (1H, d, J=7.5 Hz), 4.83 (2H, d, J=4.2 Hz), 2.07 (3H, s), 1.93-1.81 (1H, m). LC/MS (Method B): 411 (M+H)$^+$. HPLC (Method G) Rt 4.54 min (Purity: 96.8%).

Step 2: 3-(5-(2'-methyl-2-(trifluoromethyl)biphenyl-4-yl)-1,2,4-oxadiazol-3-yl)benzaldehyde The title compound was prepared following the general procedure 6, starting from (3-(5-(2'-methyl-2-(trifluoromethyl)biphenyl-4-yl)-1,2,4-oxadiazol-3-yl)phenyl)methanol (452 mg; 1.10 mmol) and was isolated as a white solid (392 mg; 87%). $^1$H NMR (CDCl$_3$, 400 MHz) δ 10.16 (1H, s), 8.72-8.71 (1H, m), 8.68-8.62 (1H, m), 8.48 (1H, dt, J=7.7, 1.4 Hz), 8.43-8.40 (1H, m), 8.09 (1H, dt, J=7.7, 1.4 Hz), 7.73 (1H, t, J=7.7 Hz), 7.49 (1H, d, J=7.9 Hz), 7.35-7.24 (3H, m), 7.16 (1H, d, J=7.5 Hz), 2.07 (3H, s). LC/MS (Method B): 409 (M+H)$^+$. HPLC (Method G) Rt 4.68 min (Purity: 97.4%).

Step 3: 3-Methoxy-2-{3-[5-(2'-methyl-2-trifluoromethyl-biphenyl-4-yl)-[1,2,4]oxadiazol-3-yl]-benzylamino}-propionic acid The title compound was prepared following the same protocol described for Example 54, step 3, starting from 4-(5-(2'-methyl-2-(trifluoromethyl)biphenyl-4-yl)-1,2,4-oxadiazol-3-yl)benzaldehyde and O-methylserine. It was isolated as an off-white solid. LC/MS (Method B): 512 (M+H)$^+$. HPLC (Method G) Rt 6.75 min (Purity: 97.3%).

The examples shown in the table below were prepared by the same protocol as Example 76, using the appropriate amino acid or amino ester for each example:

| Ex No | Structure | Purity Method | Purity (%) | RT | Mass peak [M]+ | Mass peak [M]− |
|---|---|---|---|---|---|---|
| 77 | 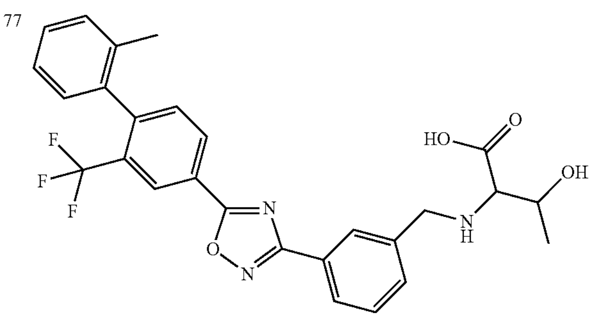 | Method I | 98.2 | 17.21 | 512 | 510 |
| 78 | 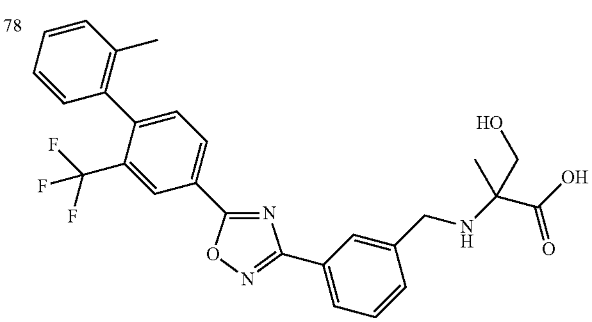 | Method E | 97.2 | 15.97 | 512 | 510 |

| Ex No | Structure | Purity Method | Purity (%) | RT | Mass peak [M]+ | Mass peak [M]- |
|---|---|---|---|---|---|---|
| 79 | 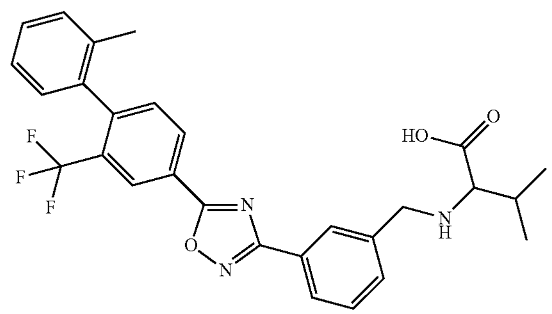 [SMILES: Cc1ccccc1-c1ccc(-c2nc(-c3cccc(CNC(C(=O)O)C(C)C)c3)no2)cc1C(F)(F)F] | Method D | 99.7 | 3.24 | 510 | 508 |
| 80 | 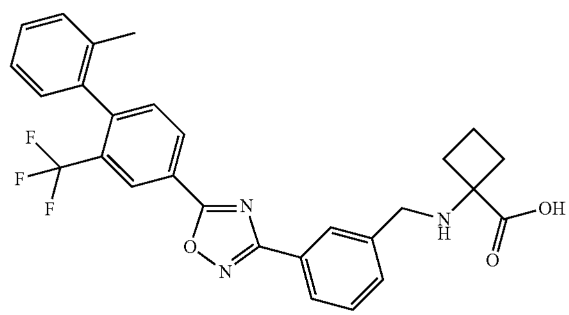 [SMILES: Cc1ccccc1-c1ccc(-c2nc(-c3cccc(CNC4(C(=O)O)CCC4)c3)no2)cc1C(F)(F)F] | Method D | 98.9 | 3.07 | 508 | 506 |
| 81 | Chiral | Method D | 96.5 | 3.28 | 496 | — |
| 82 | 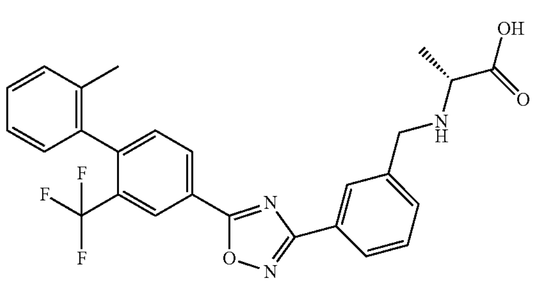 [SMILES: Cc1ccccc1-c1ccc(-c2nc(-c3cccc(CN[C@H](C)C(=O)O)c3)no2)cc1C(F)(F)F] | Method E | 97.5 | 15.89 | 482 | 480 |

Example 83

2-Methyl-2-(methyl-{3-[5-(2'-methyl-2-trifluoromethyl-biphenyl-4-yl)-[1,2,4]oxadiazol-3-yl]-benzyl}-amino)-propionic acid

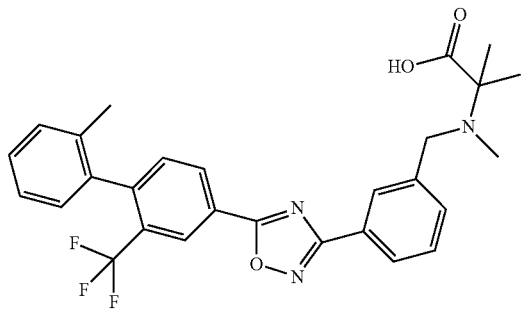 [SMILES: Cc1ccccc1-c1ccc(-c2nc(-c3cccc(CN(C)C(C)(C)C(=O)O)c3)no2)cc1C(F)(F)F]

The title example was prepared following the same protocol described for Example 69, starting from 4-(5-(2'-methyl-2-(trifluoromethyl)biphenyl-4-yl)-1,2,4-oxadiazol-3-yl)benzaldehyde and 2-methylalanine. It was isolated as an off-white solid. LC/MS (Method B): 508 (M−H)⁻. 510 (M+H)⁺. HPLC (Method D) Rt 3.35 min (Purity: 99.8%).

The examples shown in the table below were prepared by the same protocol as Example 83, using the appropriate amino acid or amino ester for each example:

| Ex No | Structure | | Purity Method | Purity (%) | RT | Mass peak [M]+ | Mass peak [M]− |
|---|---|---|---|---|---|---|---|
| 84 | 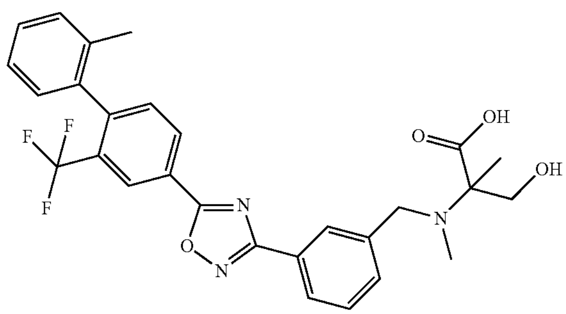 [SMILES: Cc1ccccc1-c1ccc(-c2nc(-c3cccc(CN(C)C(C)(CO)C(=O)O)c3)no2)cc1C(F)(F)F] | | Method D | 99.9 | 3.3 | 526 | 524 |
| 85 | 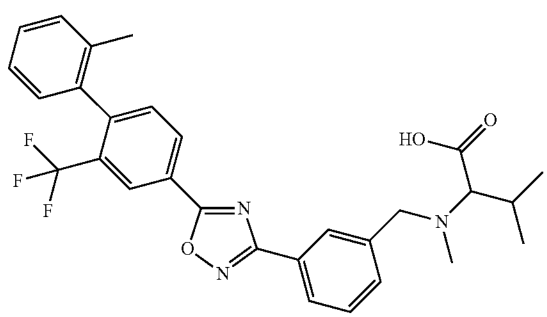 [SMILES: Cc1ccccc1-c1ccc(-c2nc(-c3cccc(CN(C)C(C(=O)O)C(C)C)c3)no2)cc1C(F)(F)F] | | Method D | 97.2 | 4.01 | 524 | 522 |
| 86 | 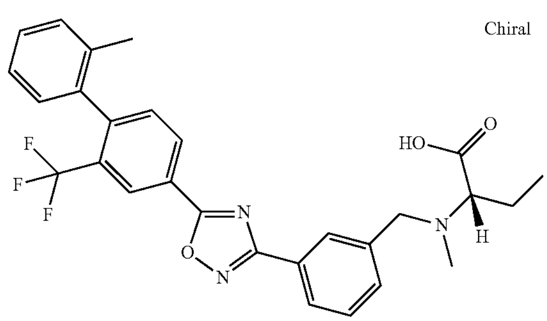 [SMILES: CC[C@@H](C(=O)O)N(C)Cc1cccc(-c2noc(-c3ccc(-c4ccccc4C)c(C(F)(F)F)c3)n2)c1 ; "Chiral"] | Chiral | Method D | 99.2 | 3.4 | 510 | 508 |

Example 87

(R)-2-(Ethyl-{3-[5-(2'-methyl-2-trifluoromethyl-biphenyl-4-yl)-[1,2,4]oxadiazol-3-yl]-benzyl}-amino)-3-hydroxy-propionic acid

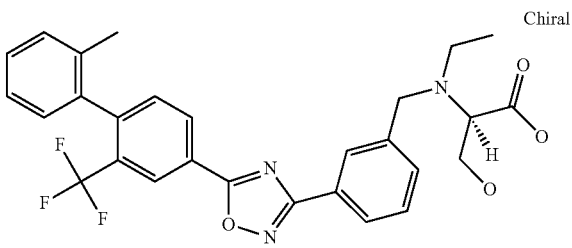 [SMILES: CCN(Cc1cccc(-c2noc(-c3ccc(-c4ccccc4C)c(C(F)(F)F)c3)n2)c1)[C@H](CO)C(=O)O]

The title compound was prepared following the same protocol described for Example 69, starting from 4-(5-(2'-methyl-2-(trifluoromethyl)biphenyl-4-yl)-1,2,4-oxadiazol-3-yl)benzaldehyde, acetaldehyde and D-serine. It was isolated as an off-white solid. LC/MS (Method B): 524 (M−H)⁻. 526 (M+H)⁺. HPLC (Method D) Rt 3.35 min (Purity: 99.0%).

Example 88

2-(Ethyl-{3-[5-(2'-methyl-2-trifluoromethyl-biphenyl-4-yl)-[1,2,4]oxadiazol-3-yl]-benzyl}-amino)-2-methyl-propionic acid

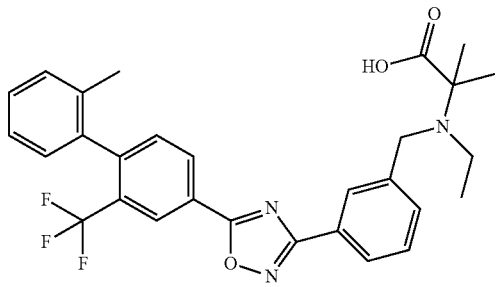 [SMILES: CCN(Cc1cccc(-c2noc(-c3ccc(-c4ccccc4C)c(C(F)(F)F)c3)n2)c1)C(C)(C)C(=O)O]

The title compound was prepared following the same protocol described for Example 87, replacing D-serine with 2-methylalanine. It was isolated as a pale yellow oil. LC/MS (Method B): 522 (M−H)⁻. 524 (M+H)⁺. HPLC (Method D) Rt 3.49 min (Purity: 99.1%).

Example 89

(2S)-2-(ethyl(4-(5-(2'-methyl-2-(trifluoromethyl)biphenyl-4-yl)-1,2,4-oxadiazol-3-yl)benzyl)amino)propanoic acid

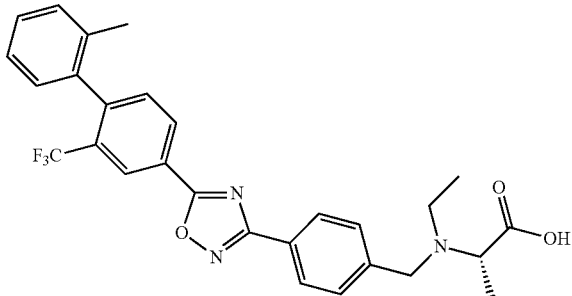 [SMILES: CCN(Cc1ccc(-c2noc(-c3ccc(-c4ccccc4C)c(C(F)(F)F)c3)n2)cc1)[C@@H](C)C(=O)O]

The title compound was prepared following the same protocol described for Example 69, but using acetaldehyde (134 mg; 3.06 mmol) and (S)-2-aminopropanoic acid (55 mg; 0.62 mmol). It was isolated as a white solid. ¹H NMR (DMSO-d₆, 400 MHz) δ 8.56 (1H, s), 8.52 (1H, d, J=8.0 Hz), 8.11 (2H, d, J=7.9 Hz), 7.68 (1H, d, J=7.9 Hz), 7.63 (2H, d, J=8.0 Hz), 7.44-7.37 (2H, m), 7.34-7.29 (1H, m), 7.20 (1H, d, J=7.5 Hz), 3.92 (1H, d, J=15.0 Hz), 3.79 (1H, d, J=15.1 Hz), 3.55-3.44 (1H, m), 2.72-2.57 (2H, m), 2.05 (3H, s), 1.26 (3H, d, J=7.0 Hz), 1.06-0.97 (3H, t, J=7.0 Hz). LC/MS (Method B): 510 (M+H)⁺. HPLC (Method D) Rt 3.38 min (Purity: 98.6%).

Example 90

(R)-2-(Ethyl-{4-[5-(2'-methyl-2-trifluoromethyl-biphenyl-4-yl) [1,2,4]oxadiazol-3-yl]-benzyl}-amino)-propionic acid

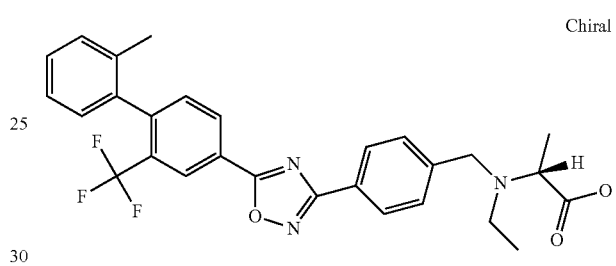

The title compound was prepared following the same protocol described for Example 89, replacing (S)-2-aminopropanoic acid with D-alanine. It was isolated as a colorless oil. LC/MS (Method B): 508 (M−H)⁻. 510 (M+H)⁺. HPLC (Method D) Rt=3.39 min (Purity: 99.08%).

Example 91

(2S)-3-methyl-2-(4-(5-(2'-methyl-2-(trifluoromethyl)biphenyl-4-yl)-1,2,4-oxadiazol-3-yl)phenethylamino)butanoic acid

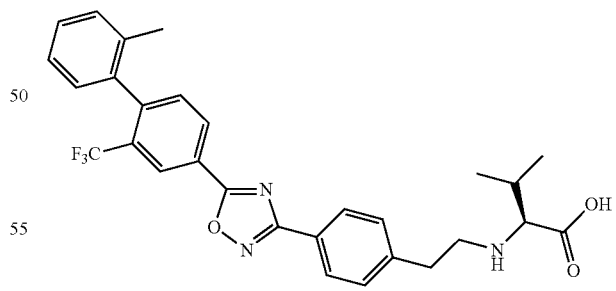

Step 1: (4-(5-(2'-methyl-2-(trifluoromethyl)biphenyl-4-yl)-1,2,4-oxadiazol-3-yl)phenyl)ethanol The title compound was prepared following the general procedure 5, starting from Intermediate 1 and Intermediate 39. It was isolated as a white solid. $^1$H NMR (CDCl$_3$, 400 MHz) δ 8.63 (1H, s), 8.40 (1H, dd, J=8.0, 1.7 Hz), 8.15 (2H, d, J=8.1 Hz), 7.47 (1H, d, J=8.0 Hz), 7.41 (2H, d, J=8.0 Hz), 7.39-7.22 (3H, m), 7.15 (1H, d, J=7.6 Hz), 3.94 (2H, s), 2.97 (2H, t, J=6.5 Hz), 2.06 (3H, s), 1.44 (1H, s). LC/MS (Method B): 425 (M+H)$^+$. HPLC (Method G) Rt 4.31 min (Purity: 99.3%).

Step 2: (2S)-tert-butyl 3-methyl-2-(4-(5-(2'-methyl-2-(trifluoromethyl)biphenyl-4-yl)-1,2,4-oxadiazol-3-yl)phenethylamino)butanoate To (4-(5-(2'-methyl-2-(trifluoromethyl)biphenyl-4-yl)-1,2,4-oxadiazol-3-yl)phenyl)ethanol (84 mg; 0.2 mmol) in DCM (2 mL) was added DIEA (71 μL; 0.4 mmol) and mesyl chloride (17 μL; 0.22 mmol), at 0° C. The resulting mixture was stirred at 0° C. for 10 minutes, allowed to warm to RT and stirred for 2 hours. The mixture was diluted with DCM (20 mL) and saturated aqueous NaHCO$_3$ solution was added. The aqueous layer was extracted with DCM (3×20 mL), the combined organic fractions were dried (MgSO$_4$), filtered and the solvent removed in vacuo. The crude residue was all used in the next step without further purification. It was dissolved in dioxan (2 mL). Potassium carbonate (165 mg, 1.2 mmol) and (S)-tert-butyl 2-amino-3-methylbutanoate (104 mg; 0.60 mmol) were added. The mixture was heated at 130° C. for 72 hours, diluted with DCM (5 mL) and water (5 mL). The aqueous layer was extracted with DCM (3×20 mL), the combined organic fractions were dried (MgSO$_4$), filtered and the solvent removed in vacuo. The residue was purified by flash chromatography eluting with petrol containing increasing amounts of EtOAc to give the title compound as a colourless gum (86 mg; 72%). $^1$H NMR (CDCl$_3$, 400 MHz) δ 8.63 (1H, s), 8.39 (1H, dd, J=8.0, 1.7 Hz), 8.12 (2H, d, J=8.1 Hz), 7.47 (1H, d, J=8.0 Hz), 7.43-7.21 (5H, m), 7.16 (1H, d, J=7.6 Hz), 2.99-2.68 (5H, m), 2.07 (3H, s), 1.94-1.79 (1H, m), 1.46 (9H, s), 0.94 (6H, dd, J=6.8, 3.7 Hz). LC/MS (Method B): 580 (M+H)$^+$. HPLC (Method D) Rt 3.7 min (Purity: 94.9%).

Step 3: (2S)-3-methyl-2-(4-(5-(2'-methyl-2-(trifluoromethyl)biphenyl-4-yl)-1,2,4-oxadiazol-3-yl)phenethylamino)butanoic acid To (2S)-tert-butyl 3-methyl-2-(4-(5-(2'-methyl-2-(trifluoromethyl)biphenyl-4-yl)-1,2,4-oxadiazol-3-yl)phenethylamino)butanoate (86 mg; 0.15 mmol) was added 4M HCl in dioxan and the mixture was heated in a tube at 70° C. for 3 hours. The solvent was then removed in vacuo and the residue was purified by preparative HPLC to give the title compound as a white solid. $^1$H NMR (DMSO-d$_6$, 400 MHz) δ 8.56 (1H, s), 8.50 (1H, d, J=8.1 Hz), 8.08 (2H, d, J=7.8 Hz), 7.65 (1H, d, J=8.1 Hz), 7.51 (2H, d, J=8.0 Hz), 7.40-7.38 (2H, m), 7.31 (1H, td, J=7.0, 2.3 Hz), 7.18 (1H, d, J=7.6 Hz), 3.09-2.80 (5H, m), 2.16 (3H, s), 1.99-1.90 (1H, m), 0.96 (6H, dd, J=6.8, 2.1 Hz). LC/MS (Method B): 524 (M+H)$^+$. HPLC (Method H) Rt 9.20 min (Purity: 97.7%).

The examples shown in the table below were prepared by the same protocol as Example 91, using the appropriate amino acid or amino ester for each example:

| Ex No | Structure | Purity Method | Purity (%) | RT | Mass peak [M]+ | Mass peak [M]− |
|---|---|---|---|---|---|---|
| 92 | 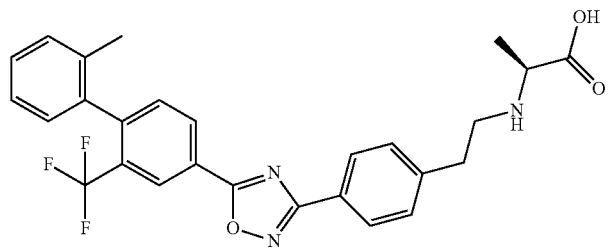 | Chiral Method D | 99.7 | 2.54 | 496 | 494 |
| 93 | 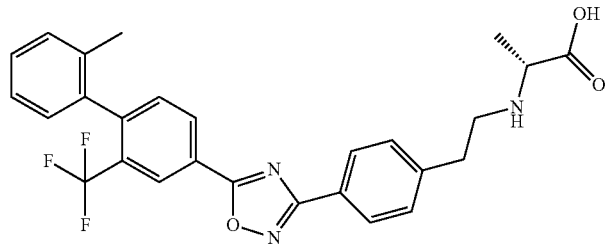 | Chiral Method G | 99.4 | 2.93 | 496 | 494 |

Example 94

(2S)-2-(3-(5-(2'-methyl-2-(trifluoromethyl)biphenyl-4-yl)-1,2,4-oxadiazol-3-yl)phenethylamino)propanoic acid

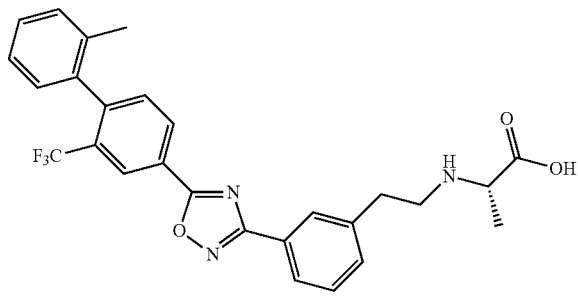 [SMILES: Cc1ccccc1-c1ccc(-c2nc(-c3cccc(CCN[C@@H](C)C(=O)O)c3)no2)cc1C(F)(F)F]

Step 1: (3-(5-(2'-methyl-2-(trifluoromethyl)biphenyl-4-yl)-1,2,4-oxadiazol-3-yl)phenyl)ethanol The title compound was prepared following the general procedure 5, starting from Intermediate 1 and Intermediate 40 and was isolated as a white solid (1.03 g, 80%). $^1$H NMR (CDCl$_3$, 400 MHz) δ 8.66 (s, 1H), 8.42 (dd, J=8.0, 1.7 Hz, 1H), 8.11-8.08 (m, 2H), 7.54-7.21 (m, 6H), 7.17 (d, J=7.7 Hz, 1H), 3.98 (dd, J=12.1, 6.0 Hz, 2H), 3.02 (t, J=6.5 Hz, 2H), 2.08 (s, 3H), 1.50-1.43 (m, 1H). LC/MS (Method B): 425 (M+H)$^+$. HPLC (Method G) Rt 4.30 min (Purity: 95.8%).

Step 2: (2S)-2-(3-(5-(2'-methyl-2-(trifluoromethyl)biphenyl-4-yl)-1,2,4-oxadiazol-3-yl)phenethylamino)propanoic acid The title compound was prepared following the protocol used for Example 91, Steps 2 and 3, but starting from (3-(5-(2'-methyl-2-(trifluoromethyl)biphenyl-4-yl)-1,2,4-oxadiazol-3-yl)phenyl)ethanol (84 mg, 0.2 mmol) and (S)-tert-butyl 2-aminopropanoate (87 mg, 0.6 mmol). It was isolated as a white solid (133 mg, 96%). $^1$H NMR: (DMSO-d$_6$, 400 MHz) δ 8.57 (s, 1H), 8.53 (d, J=8.1 Hz, 1H), 8.07-8.03 (m, 2H), 7.69 (d, J=8.0 Hz, 1H), 7.65-7.53 (m, 2H), 7.44-7.37 (m, 2H), 7.33 (td, J=4.0, 2.1 Hz, 1H), 7.20 (d, J=7.6 Hz, 1H), 3.31 (q, J=7.2 Hz, 2H), 3.18-3.02 (m, 3H), 2.06 (s, 3H), 1.33 (d, J=7.0 Hz, 3H). LC/MS (Method B): 496 (M+H)$^+$. HPLC (Method G) Rt 3.24 min (Purity: 99.1%).

The examples shown in the table below were prepared by the same protocol as Example 94, using the appropriate amino acid or amino ester for each example:

| Ex No | Structure | Purity Method | Purity (%) | RT | Mass peak [M]+ | Mass peak [M]− |
|---|---|---|---|---|---|---|
| 95 | Chiral | Method D | 99.9 | 2.79 | 496 | 494 |
| 96 | Chiral | Method F | 93.5 | 9.07 | 524 | 522 |

Example 97

N-[(1R)-1-(4-{5-[2-(methoxymethyl)-2'-methylbiphenyl-4-yl]-1,2,4-oxadiazol-3-yl}phenyl)ethyl]-N-methylglycine, hydrochloride salt

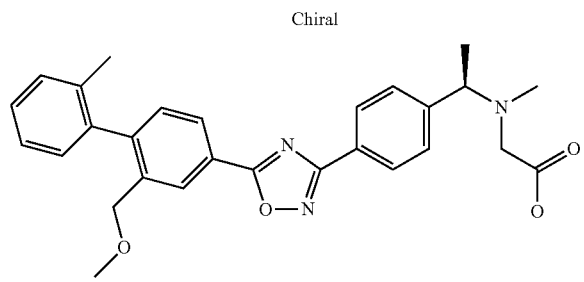 [SMILES: COCc1cc(-c2nc(-c3ccc([C@@H](C)N(C)CC(=O)O)cc3)no2)ccc1-c1ccccc1C]

tert-butyl N-[(1R)-1-(4-{5-[2-(methoxymethyl)-2'-methylbiphenyl-4-yl]-1,2,4-oxadiazol-3-yl}phenyl)ethyl]-N-methylglycinate was prepared following the general procedure 3 starting from intermediate 24 and intermediate 3. It was hydrolyzed following general procedure 8, affording the title compound as a white powder. $^1$H NMR: (DMSO-$d_6$, 400 MHz) δ 8.31 (s, 1H), 8.20-8.14 (m, 3H) 7.81 (d, J=8.2 Hz, 2H), 7.42 (d, J=7.9 Hz, 1H), 7.35 (d, J=3.8 Hz, 2H), 7.29 (q, J=5.5 Hz, 2H), 7.13 (d, J=7.0 Hz, 1H), 4.72 (d, J=6.4 Hz, 1H), 4.17 (dd, J=12.7 Hz, 2H), 4.00-3.92 (m, 2H), 3.24 (s, 3H), 2.75 (s, 3H), 2.02 (s, 3H), 1.68 (d, J=6.7 Hz, 3H). LC/MS (Method A): 472.3 (M+H)$^+$, 526.3 (M−H)$^-$. HPLC (Method A) Rt 4.62 min (Purity: 97.8%).

Example 98

N-[(1S)-1-(4-{5-[2-(methoxymethyl)-2'-methylbiphenyl-4-yl]-1,2,4-oxadiazol-3-yl}phenyl)ethyl]-N-methylglycine, hydrochloride salt

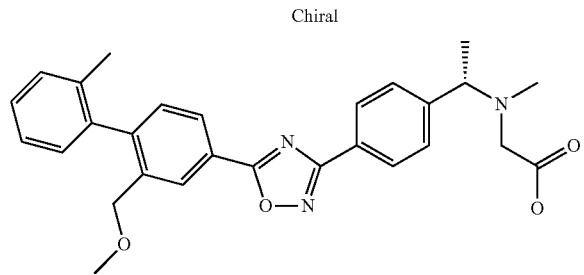 [SMILES: COCc1cc(-c2nc(-c3ccc([C@H](C)N(C)CC(=O)O)cc3)no2)ccc1-c1ccccc1C]

tert-butyl N-[(1S)-1-(4-{5-[2-(methoxymethyl)-2'-methylbiphenyl-4-yl]-1,2,4-oxadiazol-3-yl}phenyl)ethyl]-N-methylglycinate was prepared following the general procedure 3 starting from intermediate 23 and intermediate 3. It was hydrolyzed following general procedure 8, affording the title compound as a white powder. $^1$H NMR: (DMSO-$d_6$, 400 MHz) δ 8.31 (s, 1H), 8.21-8.15 (m, 3H), 7.81 (d, J=8.2 Hz, 2H), 7.42 (d, J=7.9 Hz, 1H), 7.35 (d, J=4.1 Hz, 2H), 7.30-26 (m, 1H), 7.13 (d, J=7.2 Hz, 1H), 4.72 (d, J=5.9 Hz, 1H), 4.23-4.14 (dd, J=12.7 Hz, 2H), 3.97-3.96 (m, 2H), 3.24 (s, 3H), 2.75 (s, 3H), 2.02 (s, 3H), 1.68 (d, J=6.8 Hz, 3H). LC/MS (Method A): 472.3 (M+H)$^+$, 526.3 (M−H)$^-$. HPLC (Method A) Rt 4.64 min (Purity: 98.8%).

Example 99 and Example 100

N-[(1S)-2-hydroxy-1-(4-{5-[2'-methyl-2-(trifluoromethyl)biphenyl-4-yl]-1,2,4-oxadiazol-3-yl}phenyl)ethyl]-D-alanine, hydrochloride salt and N-[(1R)-2-hydroxy-1-(4-{5-[2'-methyl-2-(trifluoromethyl)biphenyl-4-yl]-1,2,4-oxadiazol-3-yl}phenyl)ethyl]-D-alanine, hydrochloride salt

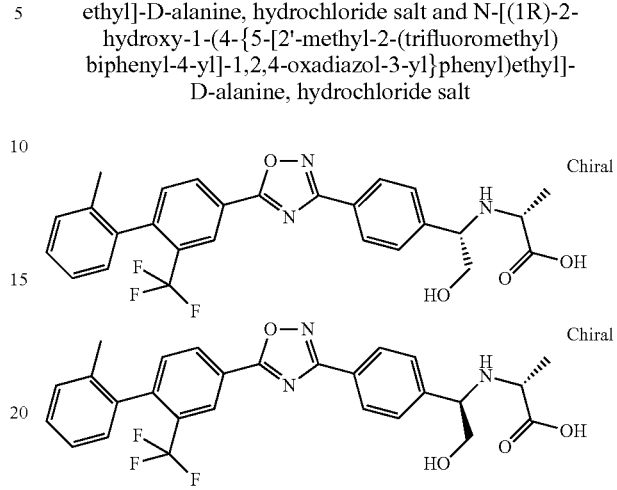

Step 1: tert-butyl N-[2-{[tert-butyl(dimethyl)silyl]oxy}-1-(4-{5-[2'-methyl-2-(trifluoromethyl)biphenyl-4-yl]-1,2,4-oxadiazol-3-yl}phenyl)ethyl]-D-alaninate To a solution of Intermediate 46 (2 g, 0.0045 mol) in DMF (30 ml) were added Intermediate 1 (1.54 g, 0.0054 mol), triethylamine (2.5 ml, 0.018 mol) and T$_3$P (3.57 g, 0.0112 mol) at RT. The reaction mixture was heated at 70° C. for 15 h. The reaction mixture was concentrated under reduced pressure. The residue was dissolved with ethyl acetate, washed with water and 10% NaHCO$_3$ solution, dried over Na$_2$SO$_4$ and evaporated to afford (1.2 g, 38%) of the title compound as brown oil. This crude material was taken for next step without purification. LC/MS (Method A): 682.3 (M+H)$^+$. HPLC (Method A) Rt 7.1 min (Purity: 70.3%).

Step 2: N-[(1S)-2-hydroxy-1-(4-{5-[2'-methyl-2-(trifluoromethyl)biphenyl-4-yl]-1,2,4-oxadiazol-3-yl}phenyl)ethyl]-D-alanine, hydrochloride salt and N-[(1R)-2-hydroxy-1-(4-{5-[2'-methyl-2-(trifluoromethyl)biphenyl-4-yl]-1,2,4-oxadiazol-3-yl}phenyl)ethyl]-D-alanine, hydrochloride salt A solution of tert-butyl N-[2-{[tert-butyl(dimethyl)silyl]oxy}-1-(4-{5-[2'-methyl-2-(trifluoromethyl)biphenyl-4-yl]-1,2,4-oxadiazol-3-yl}phenyl)ethyl]-D-alaninate (1.2 g, 0.0017 mol) in THF (25 ml) was added TBAF (50 mg, 0.1 eq) at RT. The reaction mixture was stirred at RT for 30 min and quenched with water, extracted with ethyl acetate and concentrated under reduced pressure. The crude material was purified by column chromatography using chloroform and methanol (90:10) as an eluent to afford tert-butyl N-[2-hydroxy-1-(4-{5-[2'-methyl-2-(trifluoromethyl)biphenyl-4-yl]-1,2,4-oxadiazol-3-yl}phenyl)ethyl]-D-alaninate as brown oil, as mixture of two diastereomers (0.7 g, 77%). The two diastereomers were separated by chromatography (SFC on Chiralpak ADH, 20% Co-solvent: 0.5% DEA in Ethanol, Total Flow: 3 ml/min), with the first eluting isomer Rt at 4.06 min and the second eluting isomer Rt at 5.25 min.

Each diastereomer was dissolved in HCl 4 M in Dioxane (4 ml). The resulting mixture was stirred at RT for 10 h then heated at 80° C. for 2 h. It was then concentrated under reduced pressure. The crude material was purified by preparative-HPLC, with water/acetonitrile as eluents, affording the title compounds as off-white solid.

First Eluting Diastereomer, after Hydrolysis: 50 mg, 43%
$^1$H NMR: (DMSO-$d_6$, 400 MHz) δ 8.51 (s, 1H), 8.50-8.45 (d, J=7.9 Hz, 1H), 8.12-8.08 (d, J=8.2 Hz, 2H), 7.66-7.58 (m, 3H), 7.38-7.33 (m, 2H), 7.30-7.24 (m, 1H), 7.17-7.13 (d, J=7.9 Hz, 1H), 4.92-4.88 (m, 1H), 3.28-3.24 (m, 1H), 3.03-2.97 (m, 1H), 2.90-2.80 (m, 1H), 2.00 (s, 3H), 1.30-1.26 (d, J=7.2 Hz, 3H). LC/MS (Method A): 512.3 (M+H)$^+$. HPLC (Method A) Rt 4.83 min (Purity: 99.2%).

Second Eluting Diastereomer, after Hydrolysis: 50 mg, 43%
$^1$H NMR: (DMSO-$d_6$, 400 MHz) δ 8.51 (s, 1H), 8.50-8.45 (d, J=7.9 Hz, 1H), 8.12-8.08 (d, J=8.2 Hz, 2H), 7.66-7.58 (m, 3H), 7.38-7.33 (m, 2H), 7.30-7.24 (m, 1H), 7.17-7.13 (d, J=7.9 Hz, 1H), 4.97-4.94 (m, 1H), 3.37-3.33 (m, 1H), 3.08-3.03 (m, 1H), 2.95-2.80 (m, 1H), 2.01 (s, 3H), 1.31-1.27 (d, J=7.2 Hz, 3H). LC/MS (Method A): 512.3 (M+H)$^+$. HPLC (Method A) Rt 4.90 min (Purity: 99.4%).

Example 101

1-[methyl(4-{5-[2'-methyl-2-(trifluoromethyl)biphenyl-4-yl]-1,2,4-oxadiazol-3-yl}benzyl)nitroryl]cyclopentanecarboxylic acid

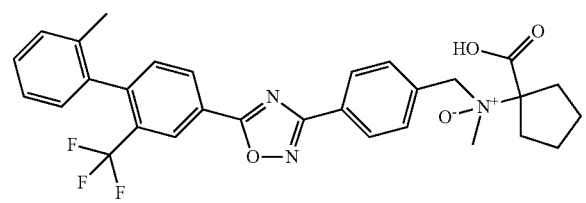 [SMILES: Cc1ccccc1-c1ccc(-c2nc(-c3ccc(C[N+](C)([O-])C4(C(=O)O)CCCC4)cc3)no2)cc1C(F)(F)F]

The title compound was prepared according to the general procedure 12, starting from Example 53 (95.7 mg; 0.18 mmol). After evaporation of the solvents, the crude mixture was triturate in DMSO/MeCN 1:1 mixture (2 mL), filtrated and washed with MeCN, affording the title compound as white solid (69.50 mg; 70.5%). $^1$H NMR: (CDCl$_3$, 300 MHz) δ 8.65 (br d, J=1.4 Hz, 1H), 8.43 (br dd, J=1.4, 8.0 Hz, 1H), 8.35-8.28 (m, 2H), 7.78-7.70 (m, 2H), 7.51 (d, J=8.0 Hz, 1H), 7.41-7.23 (m, 3H), 7.17 (br d, J=7.6 Hz, 1H), 4.97 (br d, J=12.6 Hz, 1H), 4.48 (br d, J=12.6 Hz, 1H), 3.06 (s, 3H), 2.96-2.70 (m, 1H), 2.70-2.32 (m, 2H), 2.20-1.66 (m, 5H), 2.08 (s, 3H). LC/MS (Method A): 552.5 (M+H)$^+$. 550.5 (M+H)$^-$. HPLC (Method A) Rt 5.15 min (Purity: 98.4%).

Example 102

2-[(2-fluoro-4-{5-[2'-methyl-2-(trifluoromethyl)biphenyl-4-yl]-1,2,4-oxadiazol-3-yl}benzyl)(methyl)nitroryl]propanoic acid

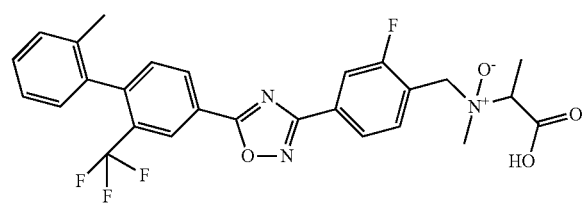 [SMILES: Cc1ccccc1-c1ccc(-c2nc(-c3ccc(C[N+](C)([O-])C(C)C(=O)O)c(F)c3)no2)cc1C(F)(F)F]

Example 50 (100 mg; 0.18 mmol) was dissolved in EtOAc, washed with NaHCO$_3$ sat solution. Glacial acetic acid (1 mL) was added and the resulting solution was washed with water and brine. It was dried over MgSO$_4$, filtrated and evaporated. General procedure 12 was then followed, starting with Example 50 as parent (92.4 mg; 0.18 mmol). After evaporation of the solvents, the crude mixture was dissolved in 1:1 mixture of DMSO/MeCN (1 mL) and was purified by MD-autoprep. The title compound was isolated as white solid as 47:53 diastereomeric mixture (LC/MS Method A). $^1$H NMR: (CDCl$_3$, 300 MHz) δ 8.64 (br d, J=1.5 Hz, 1H), 8.42 (brdd, J=1.5, 8.0 Hz, 1H), 8.18-8.12 (m, 1H), 8.10-8.03 (m, 1H), 7.99-7.84 (m, 1H), 7.51 (d, J=8.1 Hz, 1H), 7.41-7.23 (m, 3H), 7.16 (br d, J=7.4 Hz, 1H), 4.87 and 4.81 (2 br s, 2H), 4.47-4.31 and 4.24-4.07 (2 m, 1H), 3.28 and 3.19 (2 s, 3H), 2.08 (s, 3H), 1.92 and 1.80 (2 d, J=6.9 Hz, 3H). LC/MS (Method A): 2 pairs of diastereomers at Rt 1.87 min (47%) and 1.94 min (53%): 530.4 (M+H)$^+$. HPLC (Method A) Rt 4.84 min (Purity: 94.1%).

Example 103

{methyl[1-(4-{5-[2'-methyl-2-(trifluoromethyl)biphenyl-4-yl]-1,2,4-oxadiazol-3-yl}phenyl)ethyl]nitroryl}acetic acid

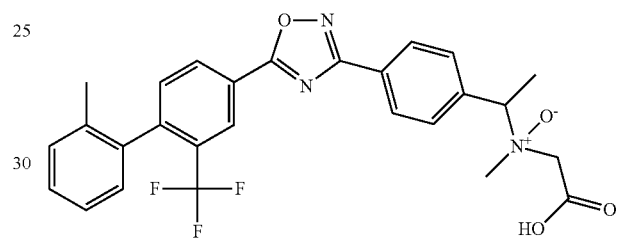

Example 40 (50 mg; 0.09 mmol) was dissolved in EtOAc, washed with NaHCO3 sat solution. Glacial acetic acid (1 mL) was added and the resulting solution was washed with water and brine. It was dried over MgSO$_4$, filtrated and evaporated. General procedure 12 was then followed, starting with Example 40 as parent (44.6 mg; 0.09 mmol). After evaporation of the solvents, the crude mixture was dissolved in 1:1 mixture of DMSO/MeCN (1 mL) and was purified by MD-autoprep. The title compound was isolated as white solid as 22:78 diastereomeric mixture (LC/MS Method A). $^1$H NMR: (CDCl$_3$, 300 MHz) δ 8.68-8.61 (m, 1H), 8.50-8.08 (m, 3H), 7.84-7.56 (m, 2H), 7.55-7.45 (m, 1H), 7.42-7.22 (m, 3H), 7.17 (br d, J=6.7 Hz, 1H), 5.47-5.27 (m, 1H), 4.80 (br d, J=14.2 Hz, 1H), 4.62 (br d, J=14.2 Hz, 1H), 3.90 and 3.48 (2 s, 3H), 2.08 (s, 3H), 2.02-1.88 (m, 3H). LC/MS (Method A): 2 pairs of diastereomers at Rt 1.87 min (22%) and 1.94 min (78%): 512.5 (M+H)$^+$. HPLC (Method A) Rt 5.15 min (Purity: 98.4%).

Example 104

In Vitro Assays

Membranes Preparation:
Membranes were prepared from CHO cells expressing S1P1 or S1P3 for use in ligand binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N2 decompression using a cell disruption bomb (Parr Instrument). Following centrifugation at 1000 RPM for 10 min at 4° C., the supernatant was diluted (2×) in buffer A and centrifuged again at 19000 RPM for 75 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid $N_2$ and stored at −80° C.

Receptor Binding Assay:

[33P]sphingosine 1-phosphate (3000 Ci/mmol; American Radiolabeled Chemicals, Inc.) was added to test compounds in 20% DMSO by competition. Membranes and WGA SPA beads (GE Healthcare) were added to give a final volume of 100 μl in 96-well plates or 50 μl in 384-well plates with assay concentrations of 30 pM or 15 pM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 μg/well of proteins in 96-well plates vs 0.6-1 μg/well of proteins in 384-well plates and 100 μg/well of WGA SPA beads in 96-well plates vs 75 μg/well of WGA SPA beads in 384-well plates. Binding was performed for 60 min at RT on a shaker and bound radioactivity was measured on a PerkinElmer 1450 MicroBeta counter. Triplicate samples were averaged and normalized as percentage of inhibition relative to total binding (only DMSO in well) and non specific binding (1000-fold excess of unlabeled S1P). Binding data were analyzed using the GraphPad Prism program or Genedata software.

Cellular Functional Assays: Internalization of Sphinqosine-1-phosphate Receptor 1 ($S1P_1$) in a Human Cell Line (U2OS) in a 384-Well Format Using a Cell Imaging Analysis.

Jo, E.; Sanna, M. G.; Gonzalez-Cabrera, P. J.; Thangada, S.; Tigyi, S.; Osborne, D. A.; Hla, T.; Parrill, A. L.; Rosen, H. Chem. Biol. 2005, 12, 703

The $S1P_1$ internalization assay was performed in 384 well plates (Corning 384 black with clear bottom 3712) using $S1P_1$-U2OS cells from BioImage (C039A), a human epithelial cell line (Human Bone Osteosarcoma Epithelial Cells). These cells expressed the human $S1P_1$ Receptor fused to the green fluorescent protein (EGFP). A standard CMV promoter (cytomegalovirus promoter) controls the expression of S1P1-EGFP and continuous expression was maintained by addition of geneticin to the culture medium.

$S1P_1$ Receptor desensitization induced the internalization of the membrane-localized S1P-EGFP fusion protein to endosomes, which can be monitored by cell imaging analysis.

The cells are plated in low serum medium (Dulbecco's Modified Eagle Medium (DMEM) with Glutamax-1 and high glucose, 1% Penicillin/Streptomycin, 1% Fetal Calf Serum (FCS), 0.5 mg/ml Geneticin) overnight.

The next day, $S1P_1$-U2OS cells are incubated in 20 μl serum free medium (DMEM with Glutamax-1 and high glucose, 0.1% of fatty-acid free Bovin Serum Albumin (BSA), 10 mM, N'-2-Hydroxyethylpiperazine-N'-2 ethanesulphonic acid (HEPES) 1M) for 2 hours at 37° C./5% $CO_2$. The cells are then treated with 4 μl compounds/agonists (6×/3% DMSO) for a total volume of 24 μl, and plates are incubated for 1 hour at 37° C./5% $CO_2$.

$S1P_1$-U2OS cells are fixed with 25 μl Paraformaldehyde 8% and stained with Hoechst 33345 dye (1:1000) for 20 minutes.

They were then washed 3 times with Phosphate Buffered Saline (PBS) and plates are sealed. The internalization of the receptor $S1P_1$-EGFP is measured on Cellomics by calculating the "spot count per object" ("object" corresponds to nuclear and "spot" corresponds to $S1P_1$-EGFP receptor). Internalization data were observed thanks to vHCS View and analyzed using Genedata® software.

The compounds of formula (I) have utility as immunoregulatory agents as demonstrated by their activity as potent agonists of the $S_1P_1$ receptor, as measured in the assays described above. Ki of the compounds of formula (I) and subformulae for $S_1P_1$ is below 0.1 M. Preferred compounds of formula (I) exhibit an Ki for S1P1 receptor below 0.01 M. More preferred compounds of Formula (I) exhibit Ki for $S_1P1_1$ below 0.001 μM. Compounds of formula (I) exhibit a selectivity for the $S_1P_1$ receptor over the $S_1P_3$ receptor as measured by the ratio of Ki for the $S_1P_1$ receptor to the Ki for the $S_1P_3$ receptor as evaluated in the binding assay described above. The ratio of Ki $S_1P_1$ to Ki $S_1P_3$ is more than 20, preferably more than 50, more preferably more than 100 and even more preferably more than 1000.

The "potency" or the "activity" of the compounds is determined by the Ki values as evaluated in one of the above described binding assay, 96 or 384 well plates. The lowest Ki values characterize the most potent or active compounds, according to the present invention.

The following results have been obtained:

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 1 | 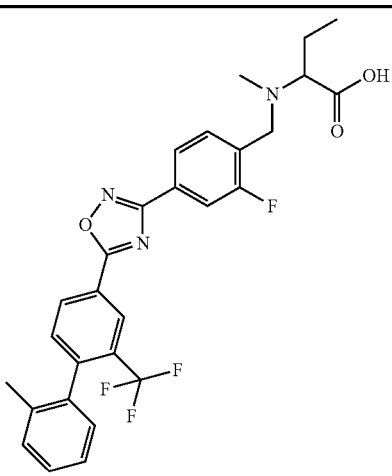 | 4.33E-08 | 2.81E-09 | 1.77E-06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 2 | | 1.03E−08 | 1.42E−09 | >2.000E−05 | 2.800E−10 | — |
| 3 | | 8.19E−09 | 2.00E−09 | 2.59E−06 | 3.400E−10 | — |
| 4 | | 2.00E−09 | 9.18E−10 | 8.63E−07 | 1.450E−10 | 2.200E−06 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 5 | | 4.33E−09 | 1.27E−09 | 1.23E−06 | — | — |
| 6 | | 7.57E−09 | 2.18E−09 | >2.000E−05 | 9.920E−10 | >2.000E−05 |
| 7 | | 1.79E−08 | 1.64E−09 | 5.24E−06 | 3.700E−10 | >2.000E−05 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 8 | | 2.69E−08 | 3.68E−09 | 6.38E−06 | 9.130E−10 | >2.000E−05 |
| 9 | | 4.34E−09 | 1.11E−09 | 4.94E−07 | 1.750E−10 | 7.700E−07 |
| 10 | | 1.87E−07 | 1.94E−08 | — | — | — |

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 11 | | 2.60E−08 | 3.96E−09 | 2.32E−06 | — | — |
| 12 | | 2.89E−08 | 2.58E−09 | 6.43E−07 | — | — |
| 13 | | 2.83E−07 | 5.23E−09 | 1.53E−06 | — | — |

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 14 | | 8.62E−08 | 4.78E−09 | >2.000E−05 | — | — |
| 15 | | 8.93E−08 | 1.98E−09 | 5.68E−07 | — | — |
| 16 | | 8.43E−09 | 1.23E−09 | 7.20E−07 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 17 | | 2.10E−08 | 2.01E−09 | 2.25E−06 | — | — |
| 18 | | 1.16E−07 | 1.03E−08 | 3.65E−06 | — | — |
| 19 | | 4.56E−08 | 3.98E−09 | 2.56E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 20 | | 7.57E-09 | 1.63E-09 | 2.27E-06 | 8.670E-10 | 6.830E-06 |
| 21 | | 1.12E-08 | 2.19E-09 | 1.21E-06 | — | — |
| 22 | | 6.51E-09 | 1.72E-09 | 4.70E-07 | 4.140E-10 | 5.980E-07 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 23 | | 2.13E−08 | 1.71E−09 | 7.05E−06 | — | — |
| 24 | | 8.94E−08 | 4.29E−09 | — | — | — |
| 25 | | 2.81E−08 | 2.59E−09 | >2.000E−05 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 26 | | 2.16E−08 | 2.24E−09 | 1.65E−06 | — | — |
| 27 | | 7.84E−09 | 2.21E−09 | 1.33E−06 | — | — |
| 28 | | 5.17E−06 | 1.38E−08 | | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 29 | | 4.60E−08 | 5.95E−10 | 5.84E−08 | — | — |
| 30 | | 4.10E−07 | 1.43E−08 | — | — | — |
| 31 | | 3.66E−08 | 5.32E−09 | 2.54E−06 | — | — |
| 32 | | 7.58E−09 | 1.69E−09 | 4.33E−07 | — | — |

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 33 | | 9.10E−08 | 5.77E−09 | — | — | — |
| 34 | | 2.63E−08 | 4.47E−09 | 6.00E−06 | — | — |
| 35 | | 2.11E−07 | 6.14E−09 | — | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 36 | | 3.36E−08 | 2.55E−09 | 7.93E−07 | — | — |
| 37 | | 1.51E−08 | 1.44E−09 | 3.40E−06 | — | — |
| 38 | | 7.79E−08 | 2.84E−09 | 1.43E−06 | — | — |
| 39 | | 2.09E−08 | 4.34E−09 | 3.18E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 40 | | 1.78E−08 | 2.17E−09 | 5.32E−07 | — | — |
| 41 | | 1.28E−08 | 4.88E−09 | 8.72E−06 | — | — |
| 42 | | 7.17E−09 | 1.02E−09 | 1.06E−07 | — | — |
| 43 | | 2.41E−08 | 2.32E−09 | 8.40E−07 | 6.300E−10 | 3.150E−06 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 44 | | 6.29E−09 | 1.58E−09 | 8.69E−07 | — | — |
| 45 | | 3.08E−08 | 2.68E−09 | 4.36E−07 | — | — |
| 46 | | 9.34E−09 | 7.94E−10 | 9.55E−08 | — | — |
| 47 | | 3.91E−08 | 4.26E−09 | 1.95E−05 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 48 | | 2.38E−08 | 4.68E−09 | >2.000E−05 | — | — |
| 49 | | 1.38E−08 | 1.06E−09 | 9.71E−07 | — | — |
| 50 | | 2.58E−08 | 3.02E−09 | 6.61E−07 | — | — |
| 51 | | 2.98E−08 | 7.52E−09 | — | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 52 | | 1.02E−08 | 3.76E−09 | 1.08E−06 | — | — |
| 53 | | 4.22E−08 | 3.97E−09 | 3.64E−06 | — | — |
| 54 | | 3.97E−08 | 7.95E−09 | 6.69E−06 | — | — |

-continued
| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 55 | 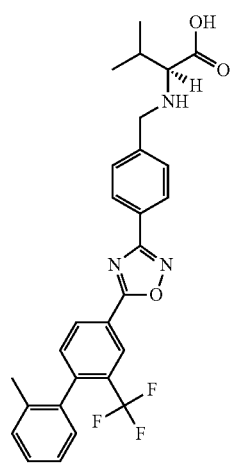 [SMILES: Cc1ccccc1-c1ccc(-c2nc(-c3ccc(CN[C@H](C(=O)O)C(C)C)cc3)no2)cc1C(F)(F)F] | 1.68E−08 | 2.20E−09 | 8.02E−07 | — | — |
| 56 | 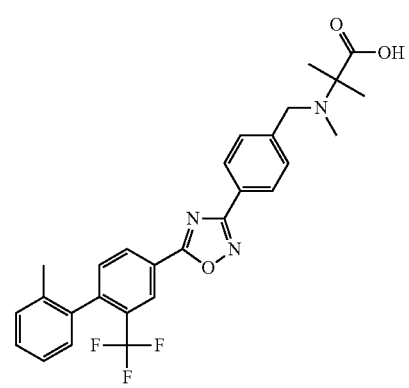 [SMILES: Cc1ccccc1-c1ccc(-c2nc(-c3ccc(CN(C)C(C)(C)C(=O)O)cc3)no2)cc1C(F)(F)F] | 5.78E−08 | 4.13E−09 | 8.54E−06 | — | — |
| 57 | 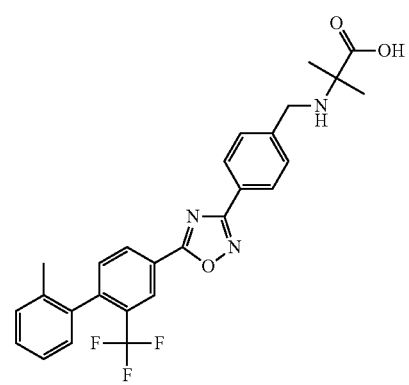 [SMILES: Cc1ccccc1-c1ccc(-c2nc(-c3ccc(CNC(C)(C)C(=O)O)cc3)no2)cc1C(F)(F)F] | 1.99E−08 | 5.69E−09 | >2.000E−05 | — | — |

-continued
| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 58 | 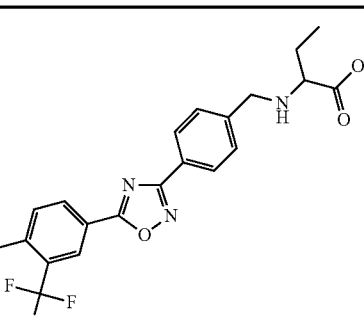 | 4.87E−09 | 3.39E−09 | 5.22E−06 | — | — |
| 59 | 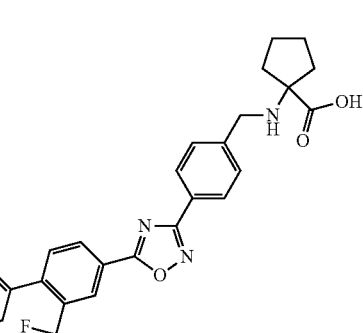 | 4.44E−08 | 6.83E−09 | >2.000E−05 | — | — |
| 60 | 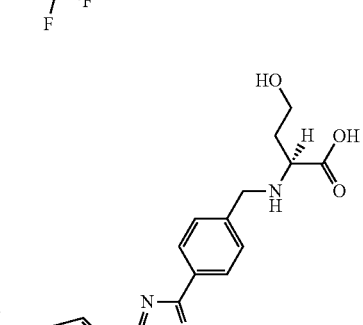 | 2.42E−08 | 3.46E−09 | 1.03E−06 | — | — |
| 61 | 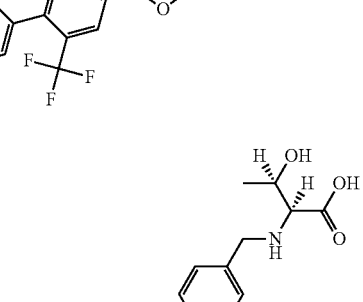 | 2.33E−08 | 4.27E−09 | 1.15E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 62 | | 7.33E−08 | 3.81E−09 | — | — | — |
| 63 | | 3.47E−09 | 1.15E−09 | 2.02E−07 | — | — |
| 64 | | 4.59E−08 | 6.78E−09 | 1.99E−06 | — | — |
| 65 | | 7.53E−09 | 4.82E−09 | 2.56E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 66 | | 2.76E−08 | 3.86E−09 | 9.31E−07 | — | — |
| 67 | | 2.85E−08 | 3.45E−09 | 4.49E−06 | — | — |
| 68 | | 2.05E−08 | 2.47E−09 | 7.57E−06 | — | — |
| 69 | | 4.91E−08 | 5.20E−09 | 4.07E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 70 | | 1.88E−08 | 2.98E−09 | 7.53E−07 | — | — |
| 71 | | 5.66E−09 | 2.00E−09 | 7.70E−07 | — | 7.010E−07 |
| 72 | | 3.19E−08 | 3.94E−09 | 2.66E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 73 | | 2.98E−08 | 2.27E−09 | 5.42E−06 | — | — |
| 74 | | 1.06E−07 | 8.53E−09 | — | — | — |
| 75 | | 3.02E−08 | 5.30E−09 | 2.30E−06 | — | — |

-continued
| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 76 | 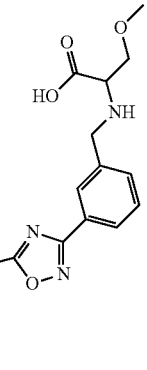 | 1.33E−07 | 1.50E−08 | — | — | — |
| 77 | 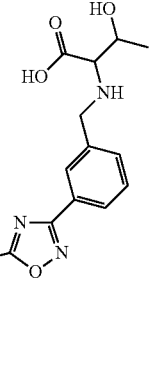 | 3.99E−08 | 5.47E−09 | — | — | — |
| 78 | 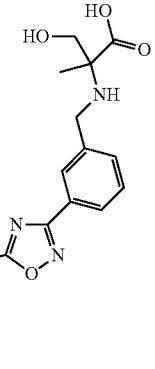 | 2.23E−08 | 2.16E−09 | 2.78E−07 | — | — |
| 79 | 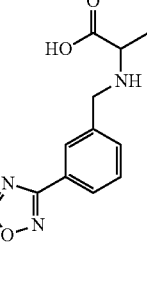 | 1.51E−08 | 1.07E−09 | 2.67E−07 | — | 3.320E−08 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 80 | | 1.22E−09 | 3.18E−10 | 3.51E−08 | — | — |
| 81 | | 4.95E−08 | 1.72E−09 | 1.72E−07 | — | — |
| 82 | | 2.51E−08 | 1.01E−09 | 1.17E−07 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 83 | | 7.55E−08 | 3.56E−09 | — | — | — |
| 84 | | 8.46E−08 | 4.25E−09 | — | — | — |
| 85 | | 4.79E−08 | 5.26E−09 | 7.93E−07 | — | — |

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 86 | 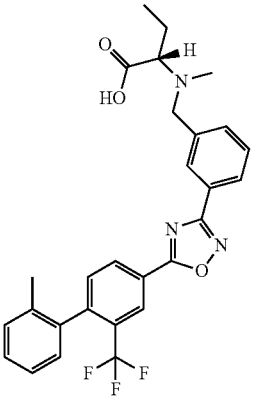 [SMILES: CC[C@@H](C(=O)O)N(C)Cc1cccc(-c2noc(-c3ccc(-c4ccccc4C)c(C(F)(F)F)c3)n2)c1] | 3.97E−08 | 5.88E−09 | 5.55E−07 | — | — |
| 87 | 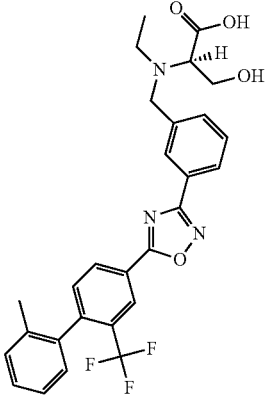 [SMILES: CCN(Cc1cccc(-c2noc(-c3ccc(-c4ccccc4C)c(C(F)(F)F)c3)n2)c1)[C@H](CO)C(=O)O] | 2.49E−08 | 2.29E−09 | 4.68E−07 | — | — |
| 88 | 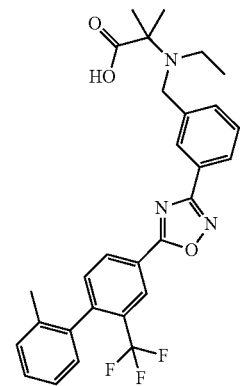 [SMILES: CCN(Cc1cccc(-c2noc(-c3ccc(-c4ccccc4C)c(C(F)(F)F)c3)n2)c1)C(C)(C)C(=O)O] | 6.97E−08 | 2.85E−09 | — | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 89 | | 3.22E−08 | 2.56E−09 | 2.03E−06 | — | — |
| 90 | | 7.92E−09 | 2.48E−09 | 9.48E−07 | — | — |
| 91 | | 3.45E−08 | 8.12E−09 | 7.36E−06 | — | — |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 92 | | 2.95E−08 | 6.94E−09 | 1.24E−06 | — | — |
| 93 | | 2.86E−08 | 1.22E−08 | 4.67E−06 | — | — |
| 94 | | 2.91E−09 | 1.01E−09 | 7.40E−08 | 1.850E−10 | — |

-continued
| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 95 | 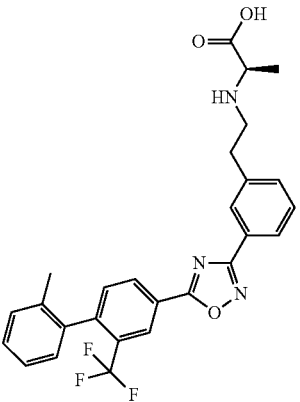 [SMILES: Cc1ccccc1-c1ccc(-c2nc(-c3cccc(CCN[C@H](C)C(=O)O)c3)no2)cc1C(F)(F)F] | 4.25E−09 | 8.46E−10 | 1.12E−07 | 2.150E−10 | — |
| 96 | 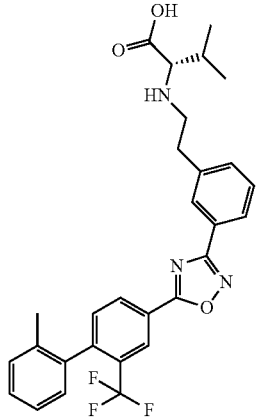 [SMILES: Cc1ccccc1-c1ccc(-c2nc(-c3cccc(CCN[C@H](C(=O)O)C(C)C)c3)no2)cc1C(F)(F)F] | 3.73E−09 | 5.33E−10 | 1.78E−07 | — | — |
| 97 | 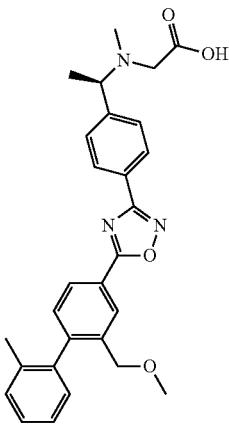 [SMILES: COCc1cc(-c2nc(-c3ccc([C@@H](C)N(C)CC(=O)O)cc3)no2)ccc1-c1ccccc1C] | — | — | — | 7.800E−10 | 4.800E−07 |

-continued
| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| 98 | 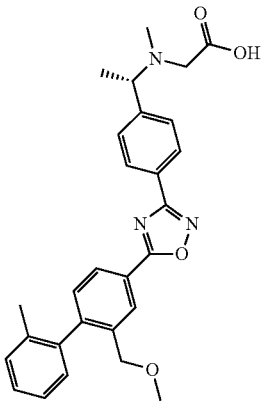 [SMILES: COCc1cc(-c2nc(-c3ccc([C@H](C)N(C)CC(=O)O)cc3)no2)ccc1-c1ccccc1C] | — | — | — | 6.200E−10 | 2.000E−05 |
| 99 | 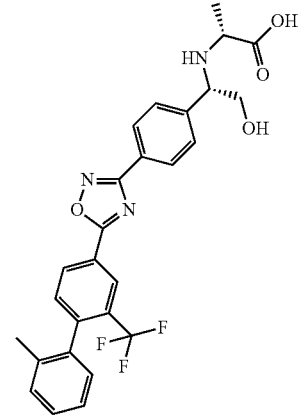 [SMILES: Cc1ccccc1-c1ccc(-c2nc(-c3ccc([C@@H](CO)N[C@H](C)C(=O)O)cc3)no2)cc1C(F)(F)F] | — | — | — | 8.850E−10 | 2.300E−06 |
| 100 | 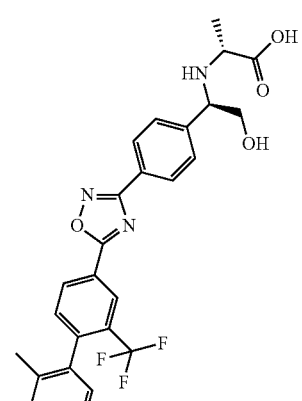 | — | — | — | 1.090E−09 | 2.450E−06 |

-continued

| Ex No | Formula | S1P1 Internalization EC50 | S1P1 Binding Ki [M] (384 well plate) | S1P3 Binding Ki [M] (384 well plate) | S1P1 Binding Ki [M] (96 well plate) | S1P3 Binding Ki [M] (96 well plate) |
|---|---|---|---|---|---|---|
| M1 | *(structure: H₂N-substituted phenyl-oxadiazole-trifluoromethyl-biphenyl-methyl)* | — | — | — | 4.050E−10 | 1.450E−06 |
| M2 | *(structure: methylaminomethyl-phenyl-oxadiazole-trifluoromethyl-biphenyl-methyl)* | — | — | — | 5.600E−10 | 2.400E−08 |

Example 105

Animal Models Evaluating the In Vivo Efficacy of S1P Agonists

Model of S1P Agonists-Induced Lymphopenia in Mice

Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 µl of PBS) by ip route and 100 µl of an emulsion containing MOG35-55 peptide (NeoMPS, 200 µg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 µl of PBS) was done by ip route. After EAE induction, mice were weighed daily and the neurological impairment was quantified using a 15-points clinical scale assessing the paralysis (tail, hind limbs and fore limbs), the incontinency and the death.

Pharmacokinetics Data:

The pharmacokinetic properties of compound of example 31, 2-({2-Fluoro-4-[5-(2'-methyl-2-trifluoromethyl-biphenyl-4-yl)-[1,2,4]oxadiazol-3-yl]-benzyl}-methyl-amino)-2-methyl-propionic acid, are the following:

| % of lymphopenia in mouse at 48 h 67 +/− 6 | |
|---|---|
| PK parameters from lymphopenia (mouse) | PK-PD (30 mpk) |
| Plasma AUC∞ (h*ng/ml) | 74978 |
| Cmax (ng/ml) | 7423 |
| Tmax(h) | 2 |
| T½ (h) | 6.3 |
| Cl/F (L/kg/h) | 0.4 |
| Brain/plasma ratio: AUCZ (h*ng/ml) | 3.5 |
| Lymphe node/plasma ratio: 24 h/48 h | 2.5/2.7 |

Clinical Score

—1— Tail

Score=0 A normal mouse holds its tail erect when moving.

Score=1 If the extremity of the tail is flaccid with a tendency to fall.

Score=2 If the tail is completely flaccid and drags on the table.

—2— Hind Limbs

Score=0 A normal mouse has an energetic walk and doesn't drag his paws.

Score=1 Either one of the following tests is positive:

—a— Flip test: while holding the tail between thumb and index finger, flip the animal on his back and observe the time it takes to right itself. A healthy mouse will turn itself immediately. A delay suggests hind-limb weakness.

—b— Place the mouse on the wire cage top and observe as it crosses from one side to the other. If one or both limbs frequently slip between the bars we consider that there is a partial paralysis.

Score=2 Both previous tests are positive.

Score=3 One or both hind limbs show signs of paralysis but some movements are preserved; for example: the animal can grasp and hold on to the underside of the wire cage top for a short moment before letting go Score=4 When both hind legs are paralyzed and the mouse drags them when moving.

—3— Fore Limbs:

Score=0 A normal mouse uses his front paws actively for grasping and walking and holds his head erect.

Score=1 Walking is possible but difficult due to a weakness in one or both of the paws, for example, the front paws are considered weak when the mouse has difficulty grasping the underside of the wire top cage. Another sign of weakness is head drooping.

Score=2 When one forelimb is paralyzed (impossibility to grasp and the mouse turns around the paralyzed limb). At this time the head has also lost much of its muscle tone.

Score=3 Mouse cannot move, and food and water are unattainable.

—4— Bladder:

Score=0 A normal mouse has full control of his bladder.

Score=1 A mouse is considered incontinent when his lower body is soaked with urine.

—5— Death:

Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 106

Preparation of a Pharmaceutical Formulation

Formulation 1—Tablets:

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules:

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid:

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets:

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection:

A compound of formula (I) is dissolved in a buffered sterile saline injectable aqueous medium to a concentration of approximately 5 mg/mL.

The invention claimed is:

1. A compound of Formula (I)

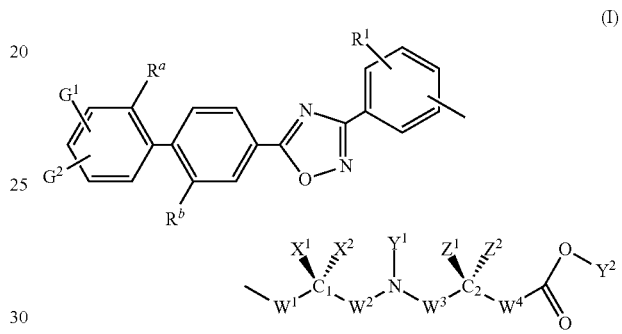

wherein $R^1$ denotes H, the group

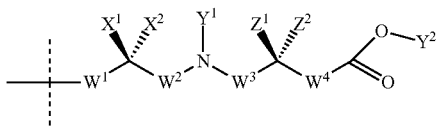

denotes one of the following groups:

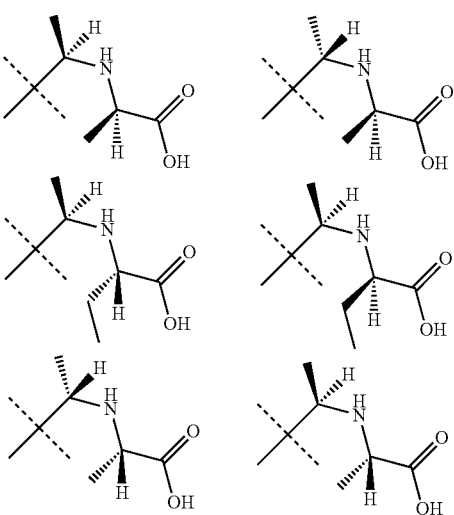

-continued

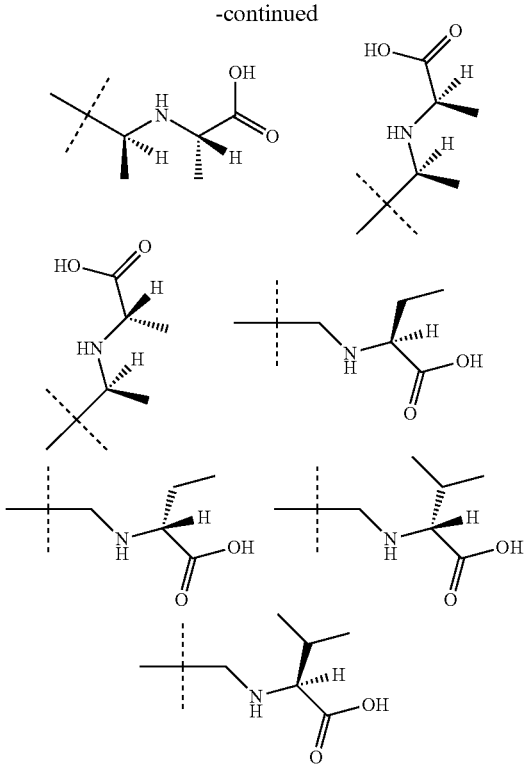

$R^a$ denotes Hal, $CH_3$ $CHF_2$, $CF_3$, and $CH_2CH_3$, $R^b$ denotes Hal, or a linear or branched alkyl having 1 to 3 carbon atoms wherein 1 to 3 H atoms are each optionally replaced by Hal, —$OCH_3$, or —$OCH_2CH_3$, $G^1$, $G^2$ independently from one another denote H, Hal, or A, A denotes a linear or branched alkyl having 1 to 3 carbon atoms wherein 1 to 3 H atoms are each optionally replaced by Hal, $OCH_3$, or OH, and Hal F, Cl or Br, or the oxidized form thereof wherein the group

is oxidized to

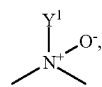

or a pharmaceutically acceptable solvate, tautomer, salt, enantiomer, or diastereoisomer thereof, including mixtures thereof in all ratios.

2. A compound according to claim 1, wherein said compound is selected from the following compounds:

| Compound No | Formula |
|---|---|
| 2 | ![structure] |
| 3 | ![structure] |
| 4 | ![structure] |

-continued

| Compound No | Formula |
|---|---|
| 5 | |
| 6 | |
| 10 | |
| 11 | |
| 17 | |
| 18 | |

-continued

| Compound No | Formula |
|---|---|
| 19 | |
| 20 | |
| 24 | |
| 25 | |
| 26 | |
| 27 | | and pharmaceutically acceptable solvates, tautomers, salts and stereoisomers thereof, including mixtures thereof in all ratios.

3. A process for the preparation of a compound of formula (I) according to claim 1, or a salt thereof, said process comprising:
reacting a compound of formula A

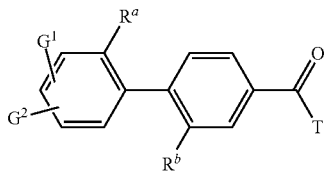

wherein $G_1$, $G_2$, $R^a$ and $R^b$ have the meanings given in claim 1, and T is OH, or a leaving group, wherein T is OH, with
a compound of formula B or its diasteromeric and/or enantiomeric mixture,

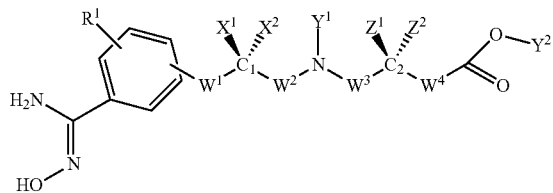

wherein $R^1$, $W_1$-$W_4$, $C_1$, $C_2$, $X_1$, $X_2$, $Y_1$, $Y_2$, $Z_1$ and $Z_2$ have the meanings given in claim 1 in the presence of a suitable base, or in case where T is OH, in the presence of a suitable condensation reagent;
cyclizing the resulting product; and
optionally a base or acid of the formula (I) is converted into one of its salts or any pharmaceutically acceptable solvates, tautomers, enantiomers, diastereoisomers thereof, including mixtures thereof in all ratios;
and optionally separating the resulting products mixture.

4. A pharmaceutical composition comprising at least one compound according to claim 1, and optionally excipients and/or adjuvants.

5. A pharmaceutical composition comprising at least one compound according to claim 1, and at least one further active ingredient.

6. A kit consisting of separate packs of
(a) an amount of a compound according to claim 1, and
(b) an amount of a further medicament active ingredient.

7. A method for treating a sphingosine 1-phosphate associated disorder, comprising administering to a patient a compound according to claim 1.

8. The method according to claim 7, wherein the sphingosine 1-phosphate-(1) associated disorder is an autoimmune disorder or condition associated with an overactive immune response.

9. A method for treating an immunoregulatory abnormality, comprising administering to a patient a compound according to claim 1.

10. The method according to claim 9, wherein the immunoregulatory abnormality is an autoimmune or chronic inflammatory disease selected from the group consisting of: systemic lupus erythematosis, chronic rheumatoid arthritis, inflammatory bowel disease, multiple sclerosis, amyotrophic lateral sclerosis (ALS), arteriosclerosis, atherosclerosis, scleroderma, or autoimmune hepatitis.

11. A compound according to claim 1, wherein $R^b$ is $CF_3$ or $CH_2OCH_3$ and $R^a$ is $CF_3$ or $CH_3$.

12. A compound according to claim 1, wherein $R^b$ is $CF_3$ and $R^a$ is $CH_3$.

13. A compound according to claim 1, wherein $R^b$ is $CF_3$ and $R^a$ is $CH_3$.

14. A compound according to claim 1, wherein one of $R^a$ and $R^b$ is —$CF_3$.

* * * * *